(12) United States Patent
Davison

(10) Patent No.: US 7,241,293 B2
(45) Date of Patent: *Jul. 10, 2007

(54) ELECTRODE SCREEN ENHANCED ELECTROSURGICAL APPARATUS AND METHODS FOR ABLATING TISSUE

(75) Inventor: Terry S. Davison, Redwood City, CA (US)

(73) Assignee: ArthroCare Corporation, Austin, TX (US)

( * ) Notice: Subject to any disclaimer, the term of this patent is extended or adjusted under 35 U.S.C. 154(b) by 25 days.

This patent is subject to a terminal disclaimer.

(21) Appl. No.: 10/713,643

(22) Filed: Nov. 13, 2003

(65) Prior Publication Data
US 2004/0153057 A1 Aug. 5, 2004

Related U.S. Application Data

(63) Continuation of application No. 09/836,940, filed on Apr. 17, 2001, now Pat. No. 6,746,447, which is a continuation-in-part of application No. 09/197,013, filed on Nov. 20, 1998, now Pat. No. 6,296,638.

(51) Int. Cl.
*A61B 18/14* (2006.01)
(52) U.S. Cl. .................. 606/41; 606/45; 606/46; 604/35; 604/114; 607/105; 607/113
(58) Field of Classification Search ............ 606/41, 606/45, 46, 48–50; 607/99, 105, 113; 604/35, 604/114
See application file for complete search history.

(56) References Cited
U.S. PATENT DOCUMENTS
2,056,377 A 10/1936 Wappler .................. 125/303
3,633,425 A 1/1972 Sanford .................... 73/356
3,815,604 A 6/1974 O'Malley et al. ......... 128/305
3,828,780 A 8/1974 Morrison, Jr. et al. .... 128/275

(Continued)

FOREIGN PATENT DOCUMENTS
DE 3930451 A1 3/1991

(Continued)

OTHER PUBLICATIONS

PCT International Search Report for PCT/US04/03614, 1 page, mailed Sep. 14, 2004.

(Continued)

*Primary Examiner*—Lee S. Cohen
(74) *Attorney, Agent, or Firm*—Richard R. Batt; John Raffle

(57) ABSTRACT

Electrosurgical methods and apparatus for the controlled ablation of tissue from a target site of a patient. The instrument includes a shaft having proximal and distal end portion and an active screen electrode on the distal end portion; a return electrode arranged on the shaft spaced from the screen electrode; at least one electrical connector extending through the shaft that connects the active electrode with a high frequency power supply; at least one electrical coupling member (such as a ball wire) adapted to secure the active screen electrode to the shaft and to electrically couple the screen electrode to the at least one electrical connector; and an aspiration lumen within the shaft having a distal opening coupled to the single active electrode wherein the screen electrode inhibits clogging of the aspiration lumen.

25 Claims, 71 Drawing Sheets

U.S. PATENT DOCUMENTS

| | | | |
|---|---|---|---|
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,970,088 A | 7/1976 | Morrison | 128/303 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,248,231 A | 2/1981 | Herczog et al. | 128/303 |
| 4,326,529 A | 4/1982 | Doss et al. | 128/303 |
| 4,381,007 A | 4/1983 | Doss | 128/303 |
| 4,474,179 A | 10/1984 | Koch | 606/40 |
| 4,476,862 A | 10/1984 | Pao | 128/303 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,590,934 A | 5/1986 | Malis et al. | 128/303 |
| 4,593,691 A | 6/1986 | Lindstrom et al. | 128/303 |
| 4,658,817 A | 4/1987 | Hardy | 606/14 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,727,874 A | 3/1988 | Bowers et al. | 128/303 |
| 4,765,331 A | 8/1988 | Petruzzi et al. | 128/303 |
| 4,785,823 A | 11/1988 | Eggers et al. | 128/692 |
| 4,805,616 A | 2/1989 | Pao | 128/303 |
| 4,823,791 A | 4/1989 | D'Amello et al. | 123/303 |
| 4,832,048 A | 5/1989 | Cohen | 606/41 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 600/439 |
| 4,936,301 A | 6/1990 | Rexroth et al. | 606/45 |
| 4,943,290 A | 7/1990 | Rexroth et al. | 606/45 |
| 4,966,597 A | 10/1990 | Cosman | 606/50 |
| 4,967,765 A | 11/1990 | Turner et al. | 128/785 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,908 A | 4/1991 | Rydell | 606/47 |
| 5,009,656 A | 4/1991 | Reimels | 606/48 |
| 5,035,696 A | 7/1991 | Rydell | 606/47 |
| 5,047,026 A | 9/1991 | Rydell | 606/48 |
| 5,047,027 A | 9/1991 | Rydell | 606/48 |
| 5,078,717 A | 1/1992 | Parins et al. | 606/48 |
| 5,080,660 A | 1/1992 | Buelna | 606/45 |
| 5,084,044 A | 1/1992 | Quint | 606/27 |
| 5,085,659 A | 2/1992 | Rydell | 606/47 |
| 5,088,997 A | 2/1992 | Delahuerga et al. | 606/42 |
| 5,098,431 A | 3/1992 | Rydell | 606/48 |
| 5,099,840 A | 3/1992 | Goble | 128/422 |
| 5,102,410 A | 4/1992 | Dressel | 606/15 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,156,151 A | 10/1992 | Imran | 600/375 |
| 5,167,659 A | 12/1992 | Ohtomo et al. | 606/40 |
| 5,171,311 A | 12/1992 | Rydell et al. | 606/48 |
| 5,178,620 A | 1/1993 | Eggers et al. | 606/41 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,207,675 A | 5/1993 | Canady | 606/40 |
| 5,217,457 A | 6/1993 | Delahuerga et al. | 606/42 |
| 5,217,459 A | 6/1993 | Kamerling | 606/48 |
| 5,261,410 A | 11/1993 | Alfano et al. | 600/475 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,290,282 A | 3/1994 | Casscells | 606/29 |
| 5,300,069 A | 4/1994 | Hunsberger et al. | 606/37 |
| 5,306,238 A | 4/1994 | Fleenor | 606/42 |
| 5,312,400 A | 5/1994 | Bales et al. | 606/41 |
| 5,314,406 A | 5/1994 | Arias et al. | 604/21 |
| 5,324,254 A | 6/1994 | Phillips | 604/21 |
| 5,330,470 A | 7/1994 | Hagen | 606/42 |
| 5,334,140 A | 8/1994 | Philips | 604/35 |
| 5,342,357 A | 8/1994 | Nardella | 606/40 |
| 5,366,443 A | 11/1994 | Eggers et al. | 252/511 |
| 5,370,675 A | 12/1994 | Edwards et al. | 607/101 |
| 5,374,261 A | 12/1994 | Yoon | 604/385.01 |
| 5,375,588 A | 12/1994 | Yoon | 128/4 |
| 5,380,277 A | 1/1995 | Phillips | 604/33 |
| 5,380,316 A | 1/1995 | Aita | 606/7 |
| 5,383,876 A | 1/1995 | Nardella | 606/49 |
| 5,383,917 A | 1/1995 | Desai et al. | 607/702 |
| 5,389,096 A | 2/1995 | Aita | 606/15 |
| 5,395,312 A | 3/1995 | Desai | 604/22 |
| 5,400,267 A | 3/1995 | Denen et al. | 702/59 |
| 5,401,272 A | 3/1995 | Perkins | 606/15 |
| 5,417,687 A | 5/1995 | Nardella et al. | 606/32 |
| 5,419,767 A | 5/1995 | Eggers et al. | 604/114 |
| 5,423,810 A | 6/1995 | Goble et al. | 606/40 |
| 5,423,882 A | 6/1995 | Jackman et al. | 607/122 |
| 5,436,566 A | 7/1995 | Thompson et al. | 324/713 |
| 5,437,662 A | 8/1995 | Nardella | 606/40 |
| 5,438,302 A | 8/1995 | Goble | 331/167 |
| 5,441,499 A | 8/1995 | Fritzsch | 606/45 |
| 5,451,224 A | 9/1995 | Goble et al. | 606/48 |
| 5,454,809 A | 10/1995 | Janssen | 606/41 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,514,130 A | 5/1996 | Baker | 606/41 |
| 5,554,152 A | 9/1996 | Aita | 606/7 |
| 5,556,397 A | 9/1996 | Long et al. | 606/48 |
| 5,569,242 A | 10/1996 | Lax et al. | 606/42 |
| 5,571,100 A | 11/1996 | Goble et al. | 606/41 |
| 5,584,872 A | 12/1996 | LaFontaine et al. | 607/117 |
| 5,609,151 A | 3/1997 | Mulier et al. | 128/642 |
| 5,633,578 A | 5/1997 | Eggers | 323/301 |
| 5,647,869 A | 7/1997 | Goble et al. | 606/37 |
| 5,662,680 A | 9/1997 | Desai | 606/210 |
| 5,676,693 A | 10/1997 | LaFontaine et al. | 607/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,700,262 A | 12/1997 | Acosta et al. | 606/48 |
| 5,725,524 A | 3/1998 | Mulier et al. | 606/41 |
| 5,766,153 A | 6/1998 | Eggers et al. | 604/114 |
| 5,807,395 A | 9/1998 | Mulier et al. | 606/41 |
| 5,810,764 A | 9/1998 | Eggers et al. | 604/23 |
| 5,810,809 A | 9/1998 | Rydell | 606/49 |
| 5,836,875 A | 11/1998 | Webster, Jr. | 600/374 |
| 5,843,019 A | 12/1998 | Eggers et al. | 604/22 |
| 5,860,951 A | 1/1999 | Eggers | 604/510 |
| 5,860,974 A | 1/1999 | Abele | 606/41 |
| 5,860,975 A | 1/1999 | Goble et al. | 606/45 |

| | | | |
|---|---|---|---|
| 5,871,469 A | 2/1999 | Eggers et al. | 604/114 |
| 5,873,855 A | 2/1999 | Eggers | 604/114 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,897,553 A | 4/1999 | Mulier et al. | 606/41 |
| 5,902,272 A | 5/1999 | Eggers et al. | 604/114 |
| 5,944,715 A * | 8/1999 | Goble et al. | 606/41 |
| 5,954,716 A | 9/1999 | Sharkey et al. | 606/32 |
| 6,004,319 A | 12/1999 | Goble et al. | 606/48 |
| 6,013,076 A | 1/2000 | Goble et al. | 606/41 |
| 6,015,406 A | 1/2000 | Goble et al. | 606/41 |
| 6,024,733 A | 2/2000 | Eggers et al. | 604/500 |
| 6,027,501 A | 2/2000 | Goble et al. | 606/41 |
| 6,039,734 A | 3/2000 | Goble | 606/41 |
| 6,047,700 A | 4/2000 | Eggers et al. | 128/898 |
| 6,056,746 A | 5/2000 | Goble et al. | 606/48 |
| 6,063,079 A | 5/2000 | Hovda et al. | 606/41 |
| 6,066,134 A | 5/2000 | Eggers et al. | 606/32 |
| 6,068,628 A | 5/2000 | Fanton et al. | 606/41 |
| 6,074,386 A | 6/2000 | Goble et al. | 606/34 |
| 6,090,106 A | 7/2000 | Goble et al. | 606/41 |
| 6,093,186 A | 7/2000 | Goble et al. | 606/34 |
| 6,102,046 A | 8/2000 | Weinstein et al. | 128/898 |
| 6,105,581 A | 8/2000 | Eggers et al. | 128/898 |
| 6,109,268 A | 8/2000 | Thapliyal et al. | 128/898 |
| 6,117,109 A | 9/2000 | Eggers et al. | 604/114 |
| 6,126,682 A | 10/2000 | Sharkey et al. | 607/96 |
| 6,142,992 A | 11/2000 | Cheng et al. | 606/34 |
| 6,149,620 A | 11/2000 | Baker et al. | 604/22 |
| 6,159,194 A | 12/2000 | Eggers et al. | 604/500 |
| 6,159,208 A | 12/2000 | Hovda et al. | 606/41 |
| 6,168,593 B1 | 1/2001 | Sharkey et al. | 606/34 |
| 6,174,309 B1 | 1/2001 | Wrublewski et al. | 606/45 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,203,542 B1 | 3/2001 | Ellsberry et al. | 606/41 |
| 6,210,402 B1 | 4/2001 | Olsen et al. | 606/32 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,234,178 B1 | 5/2001 | Goble et al. | 128/898 |
| 6,235,020 B1 | 5/2001 | Cheng et al. | 606/34 |
| 6,237,604 B1 | 5/2001 | Burnside et al. | 128/897 |
| 6,238,391 B1 | 5/2001 | Olsen et al. | 606/41 |
| 6,254,600 B1 | 7/2001 | Willink et al. | 606/41 |
| 6,261,286 B1 | 7/2001 | Goble et al. | 606/34 |
| 6,264,652 B1 | 7/2001 | Eggers et al. | 606/41 |
| 6,270,460 B1 | 8/2001 | McCartan et al. | 600/459 |
| 6,277,112 B1 * | 8/2001 | Underwood et al. | 606/32 |
| 6,280,441 B1 | 8/2001 | Ryan | 606/45 |
| 6,293,942 B1 * | 9/2001 | Goble et al. | 606/45 |
| 6,296,636 B1 | 10/2001 | Cheng et al. | 606/32 |
| 6,296,638 B1 * | 10/2001 | Davison et al. | 606/41 |
| 6,306,134 B1 | 10/2001 | Goble et al. | 606/42 |
| 6,308,089 B1 | 10/2001 | von der Rur et al. | 600/338 |
| 6,309,387 B1 | 10/2001 | Eggers et al. | 606/41 |
| 6,312,408 B1 | 11/2001 | Eggers et al. | 604/114 |
| 6,322,549 B1 | 11/2001 | Eggers et al. | 604/500 |
| 6,355,032 B1 | 3/2002 | Hovda et al. | 606/32 |
| 6,363,937 B1 | 4/2002 | Hovda et al. | 128/898 |
| 6,364,877 B1 | 4/2002 | Goble et al. | 606/34 |
| 6,379,351 B1 | 4/2002 | Thapliyal et al. | 606/41 |
| 6,391,025 B1 | 5/2002 | Weinstein et al. | 606/41 |
| 6,416,507 B1 | 7/2002 | Eggers et al. | 606/32 |
| 6,416,508 B1 | 7/2002 | Eggers et al. | 606/32 |
| 6,416,509 B1 | 7/2002 | Goble et al. | 606/37 |
| 6,432,103 B1 | 8/2002 | Ellsberry et al. | 606/41 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |
| 6,517,498 B1 | 2/2003 | Burbank et al. | 600/564 |
| 6,530,922 B2 | 3/2003 | Cosman | 606/34 |
| 6,578,579 B2 | 6/2003 | Burnside | 128/897 |
| 6,589,237 B2 | 7/2003 | Woloszko et al. | 606/41 |
| 6,602,248 B1 | 8/2003 | Sharps et al. | 606/32 |
| 6,620,156 B1 | 9/2003 | Garito et al. | 606/50 |
| 6,632,193 B1 | 10/2003 | Davison et al. | 604/22 |
| 6,632,220 B1 | 10/2003 | Eggers et al. | 606/41 |
| 6,749,608 B2 | 6/2004 | Garito et al. | 606/45 |
| 6,780,178 B2 | 8/2004 | Palanker et al. | 600/41 |
| 6,780,180 B1 | 8/2004 | Goble et al. | 606/41 |
| 6,802,842 B2 | 10/2004 | Ellman et al. | 606/45 |
| 6,920,883 B2 | 7/2005 | Bessette et al. | 128/898 |
| 6,929,640 B1 | 8/2005 | Underwood et al. | 606/32 |
| 6,949,096 B2 | 9/2005 | Davison et al. | 606/41 |
| 6,960,204 B2 | 11/2005 | Eggers et al. | 606/32 |
| 6,974,453 B2 | 12/2005 | Woloszko et al. | 606/41 |
| 6,991,631 B2 | 1/2006 | Woloszko et al. | 606/41 |
| 7,004,941 B2 | 2/2006 | Tvinnereim et al. | 606/41 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,104,986 B2 | 9/2006 | Hovda et al. | 606/32 |
| 7,131,969 B1 | 11/2006 | Hovda et al. | 606/45 |
| 2003/0013986 A1 | 1/2003 | Saadat | 600/549 |

FOREIGN PATENT DOCUMENTS

| | | |
|---|---|---|
| EP | 0703461 A2 | 3/1996 |
| EP | 0740926 A2 | 11/1996 |
| EP | 0 754 437 | 1/1997 |
| EP | 0 694 290 | 11/2000 |
| FR | 2313949 | 1/1977 |
| GB | 2 308 980 | 7/1997 |
| GB | 2 308 981 | 7/1997 |
| GB | 2 309 979 | 7/1997 |
| GB | 2 237 351 | 1/1999 |
| GB | 2 327 350 | 1/1999 |
| GB | 2 327 352 | 1/1999 |
| JP | 57-57802 | 4/1982 |
| JP | 57-117843 | 7/1982 |
| WO | 90 03152 | 4/1990 |
| WO | 90/07303 | 7/1990 |
| WO | 92/21278 | 12/1992 |
| WO | 93/13816 | 7/1993 |
| WO | 93/20747 | 10/1993 |
| WO | 94/04220 | 3/1994 |
| WO | 94/08654 | 4/1994 |
| WO | 95/34259 | 12/1995 |
| WO | 96/00042 | 1/1996 |
| WO | 97/00646 | 1/1997 |
| WO | 97/00647 | 1/1997 |
| WO | 97/24073 | 7/1997 |
| WO | 97/24074 | 7/1997 |
| WO | 97/24993 | 7/1997 |
| WO | 97/24994 | 7/1997 |
| WO | 97/48345 | 12/1997 |
| WO | 97/48346 | 12/1997 |
| WO | 98/07468 | 2/1998 |
| WO | 98/27879 | 7/1998 |
| WO | 98/27880 | 7/1998 |
| WO | 99/51155 | 10/1999 |
| WO | 99/51158 | 10/1999 |
| WO | 01/87154 | 5/2001 |
| WO | 02/36028 | 5/2002 |

OTHER PUBLICATIONS

Pearce, John A. "Electrosurgery", pp. 17, 69-75, 87, John Wiley & Sons, New York, 1986.

J.W. Ramsey et al., "A Comparison of Bipolar and Monopolar Diathermy Probes in Experimental Animals", *Urological Research* vol. 13, pp. 99-102, 1985.

V.E. Elsasser et al., "An Instrument for Transurethral Resection without Leakage of Current" *Acta Medicotechnica* vol. 24, No. 4, pp. 129-134, 1976.

P.C. Nardella *SPIE* 1068:42-49 Radio Frequency Energy and Impedance Feedback, 1989.

R. Tucker et al., Abstract P14-11, p. 248, "A Bipolar Electrosurgical Turp Loop", Nov. 1989.

R. Tucker et al. "A Comparison of Urologic Application of Bipolar Versus Monopolar Five French Electrosurgical Probes" *J. of Urology* vol. 141, pp. 662-665, 1989.

R. Tucker et al. "In vivo effect of 5 French Bipolar and Monopolar Electrosurgical Probes on the Porcine Bladder" *Urological Research* vol. 18, pp. 291-294, 1990.

Kramolowsky et al. "Use of 5F Bipolar Electrosurgical Probe in Endoscopic Urological Procedures" *J. of Urology* vol. 143, pp. 275-277, 1990.

Kramolowsky et al. "The Urological App of Electrosurgery" *J. of Urology* vol. 146, pp. 669-674, 1991.

Slager et al. "Spark Erosion of Arteriosclerotic Plaques" *Z. Kardiol.* 76:Suppl. 6, 67-71, 1987.

Slager et al. "Vaporization of Atheroscleroice Plaques by Spark Erosion" *JACC* 5(6):1382-6, Jun. 1985.

Olsen MD, Bipolar Laparoscopic Cholecstectomy Lecture (marked confidential), 12 pgs, Oct. 7, 1991.

Codman & Shurtleff, Inc. "The Malis Bipolar Electrosurgical System CMC-III Instruction Manual", 15 pgs, Jul. 1991.

Valley Forge's New Products, CLINICA, 475, 5, Nov. 6, 1991.

Valley Forge Scientific Corp., "Summary of Safety and Effective Information from 510K", 2 pgs, 1991.

Codman & Shurtleff, Inc. "The Malis Bipolar Coagulating and Bipolar Cutting System CMC-II" brochure, early, 2 pgs, 1991.

L. Malis, "The Value of Irrigation During Bipolar Coagulation" See ARTC 21602, 1 pg, Apr. 9, 1993.

L. Malis, "Excerpted from a seminar by Leonard I. Malis, M.D. at the 1995 American Association of Neurological Surgeons Meeting," 1 pg, 1995.

L. Malis, "Electrosurgery, Technical Note," *J. Neursurg.*, vol. 85, 970-975, Nov. 1996.

Ian E. Shuman, "Bipolar Versus Monopolar Electrosurgery: Clinical Applications," *Dentistry Today*, vol. 20, No. 12, 7 pgs, Dec. 2001.

Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.

Cook et al., "Therapeutic Medical Devices: Application and Design", Prentice Hall, Inc., 3 pgs, 1982.

Valleylab SSE2L Instruction Manual, 11 pgs, Jan. 6, 1983.

Robert D. Tucker et al., "Demodulated Low Frequency Currents from Electrosurgical Procedures," *Surgery, Gynecology and Obstetrics*, 159:39-43, 1984.

Lu, et al., "Electrical Thermal Angioplasty: Catheter Design Features, In Vitro Tissue Ablation Studies and In Vitro Experimental Findings," *Am J. Cardiol* vol. 60, pp. 1117-1122, Nov. 1, 1987.

Selikowitz et al., "Electric Current and Voltage Recordings on the Myocardium During Electrosurgical Procedures in Canines," *Surgery, Gynecology & Obstetrics*, vol. 164, 219-224, Mar. 1987.

J. O'Malley, Schaum's Outline of Theory and Problems of Basic Circuit Analysis, McGraw-Hill, 2$^{nd}$ Ed., pp. 3-5, 1992.

Arnaud Wattiez et al., "Electrosurgery in Operative Endoscopy," Electrosurgical Effects, Blackwell Science, pp. 85-93, 1995.

Leslie A. Geddes, "Medical Device Accidents: With Illustrative Cases" CRC Press, 3 pgs, 1998.

Wyeth, "Electrosurgical Unit" pp. 1181-1202.

C.P. Swain, et al., "Which Electrode, A Comparison of four endoscopic methods of electrocoagulation in experimental bleeding ulcers" *Gut* vol. 25, pp. 1424-1431, 1987.

Piercey et al., "Electrosurgical Treatment of Experimental Bleeding Canine Gastric Ulcers" *Gastroenterology* vol. 74(3), pp. 527-534, 1978.

A.K. Dobbie, "The Electrical Aspects of Surgical Diathermy, Bio Medical Engineering" *Bio-Medical Engineering* vol. 4, pp. 206-216, May 1969.

B. Lee et al. "Thermal Compression and Molding of Artherosclerotic Vascular Tissue with Use" *JACC* vol. 13(5), pp. 1167-1171, 1989.

K. Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.

W. Honig, "The Mechanism of Cutting in Electrosurgery" *IEEE* pp. 58-65, 1975.

Pearce, John C., "Electrosurgery", Handbook of Biomedical Engineering, chapter 3, Academic Press Inc., N.Y., pp. 98-113, 1988.

M.B. Dennis et al. "Evolution of Electrofulguration in Control of Bleeding of Experimental Gastric Ulcers," Digestive Diseases and Sciences, vol. 24, No. 11, 845-848, Nov. 1979.

Letter from Department of Health to Jerry Malis dated Jul. 25, 1985, 1 pg.

Letter from Jerry Malis to FDA dated Jul. 25, 1985, 2 pgs.

Letter from Department of Health to Jerry Malis dated Jan. 24, 1991, 3 pgs.

Leonard Malis, "Instrumentation for Microvascular Neurosurgery" *Cerebrovascular Surgery*, vol. 1, 245-260, 1985.

Valleylab, Inc. "Valleylab Part No. 945 100 102 A" Surgistat Service Manual, pp. 1-46, Jul. 1988.

Leonard I. Malis, "New Trends in Microsurgery and Applied Technology," *Advanced Technology in Neurosurgery*, 1-16, 1988.

* cited by examiner

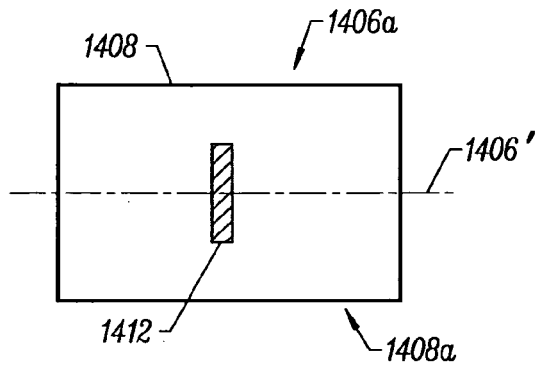
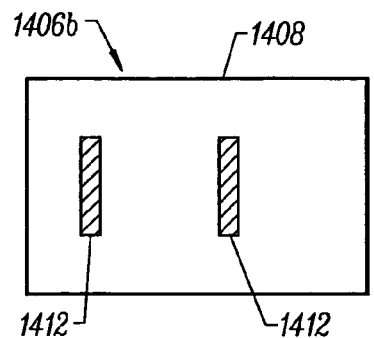
FIG. 36A    FIG. 36B
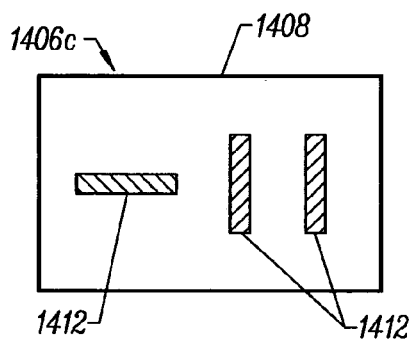
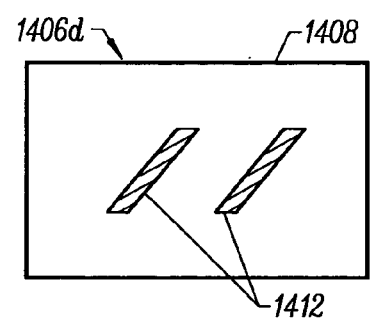
FIG. 36C    FIG. 36D
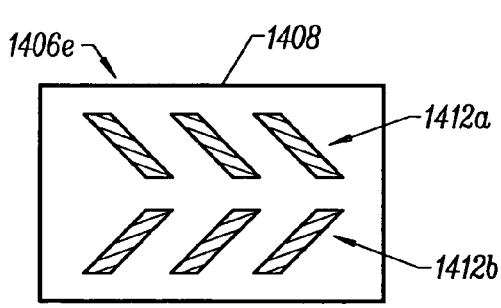
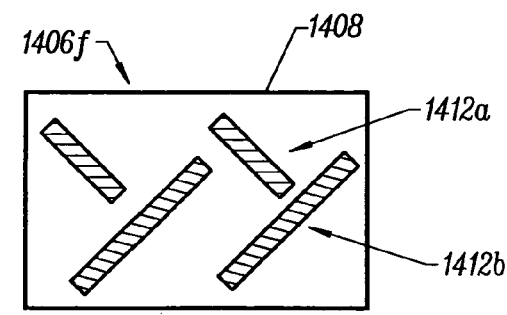
FIG. 36E    FIG. 36F

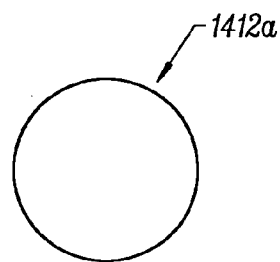
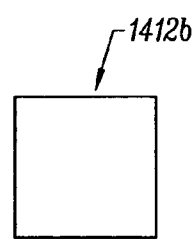
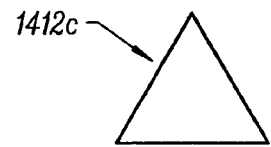
FIG. 39A　　　　FIG. 39B　　　　FIG. 39C
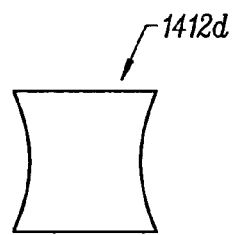
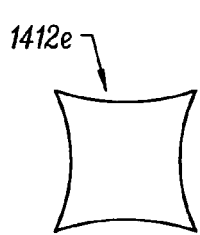
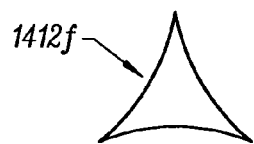
FIG. 39D　　　　FIG. 39E　　　　FIG. 39F
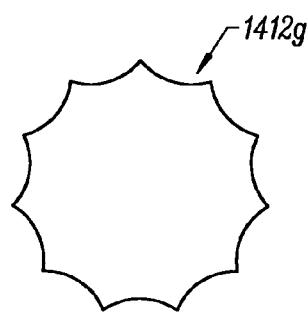
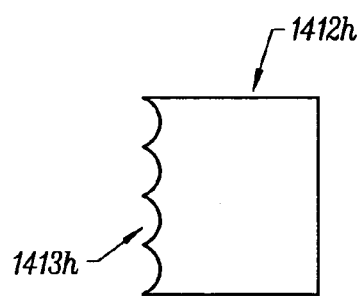
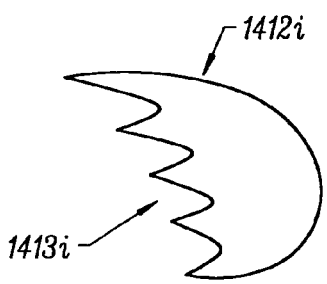
FIG. 39G　　　　FIG. 39H　　　　FIG. 39I

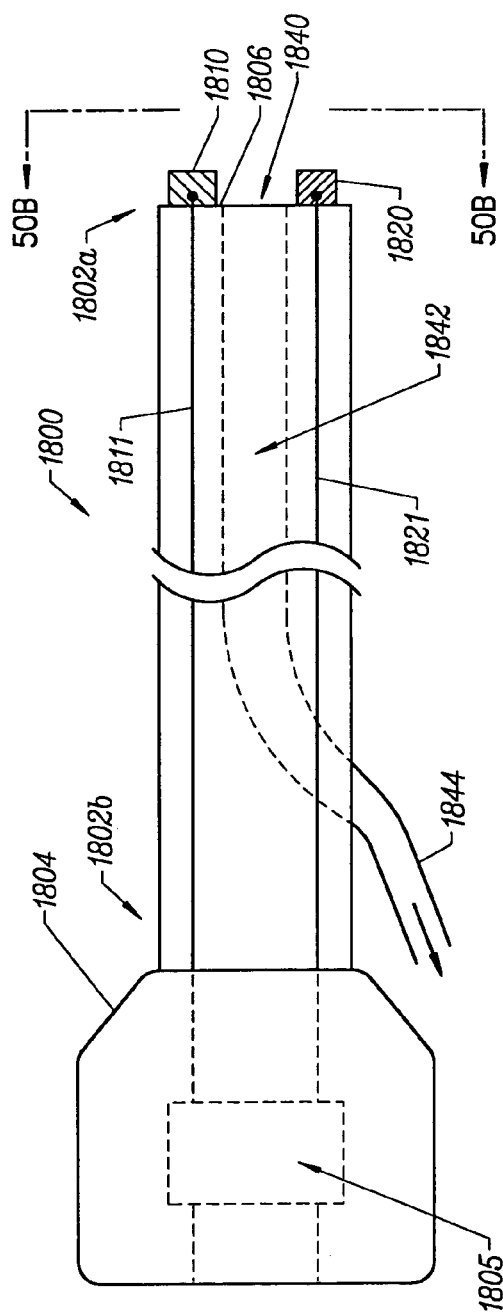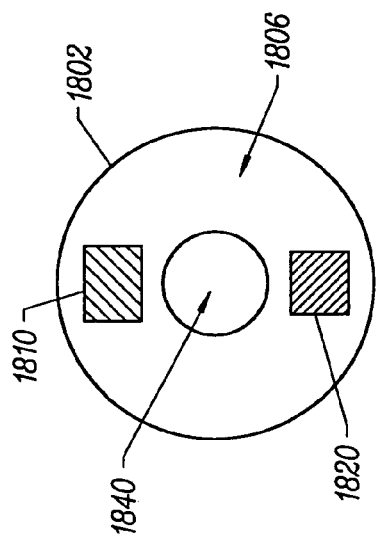
FIG. 50A
FIG. 50B

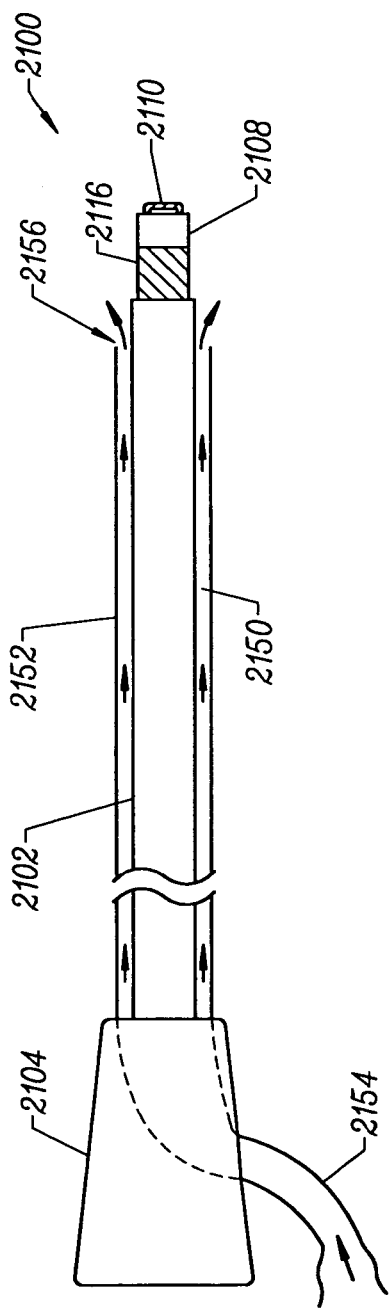
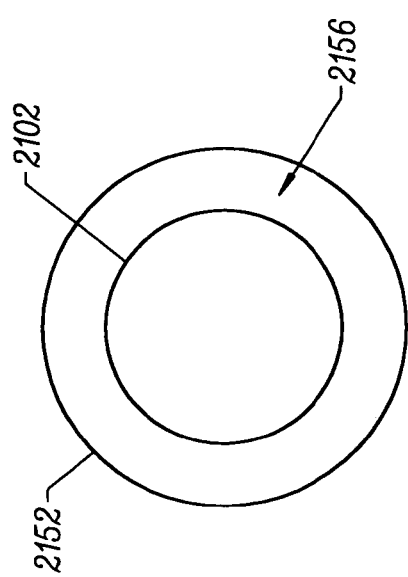
FIG. 64A
FIG. 64B

ELECTRODE SCREEN ENHANCED ELECTROSURGICAL APPARATUS AND METHODS FOR ABLATING TISSUE

RELATED APPLICATIONS

The present invention is a continuation of U.S. patent application Ser. No. 09/836,940, filed Apr. 17, 2001 now U.S. Pat. No. 6,746,447, which is a continuation-in-part of U.S. patent application Ser. No. 09/197,013, now U.S. Pat. No. 6,296,638, filed Nov. 20, 1998, the complete disclosure of each is incorporated herein by reference for all purposes.

BACKGROUND OF THE INVENTION

The present invention relates generally to the field of electrosurgery, and more particularly to surgical devices and methods which employ high frequency electrical energy to resect, coagulate, ablate, and aspirate cartilage, bone and other tissue, such as sinus tissue, adipose tissue, or meniscus, cartilage, and synovial tissue in a joint. The present invention also relates to apparatus and methods for aggressively removing tissue at a target site by a low temperature ablation procedure, and efficiently aspirating products of ablation from the target site. The present invention further relates to an electrosurgical probe having a plurality of working zones distinguishable from each other on the basis of their aspiration and/or ablation rate.

Conventional electrosurgical-methods generally reduce patient bleeding associated with tissue cutting operations and improve the surgeon's visibility. These electrosurgical devices and procedures, however, suffer from a number of disadvantages. For example, monopolar electrosurgery methods generally direct electric current along a defined path from the exposed or active electrode through the patient's body to the return electrode, which is externally attached to a suitable location on the patient's skin. In addition, since the defined path through the patient's body has a relatively high electrical impedance, large voltage differences must typically be applied between the active and return electrodes to generate a current suitable for cutting or coagulation of the target tissue. This current, however, may inadvertently flow along localized pathways in the body having less impedance than the defined electrical path. This situation will substantially increase the current flowing through these paths, possibly causing damage to or destroying tissue along and surrounding this pathway.

Bipolar electrosurgical devices have an inherent advantage over monopolar devices because the return current path does not flow through the patient beyond the immediate site of application of the bipolar electrodes. In bipolar devices, both the active and return electrode are typically exposed so that they may both contact tissue, thereby providing a return current path from the active to the return electrode through the tissue. One drawback with this configuration, however, is that the return electrode may cause tissue desiccation or destruction at its contact point with the patient's tissue.

Another limitation of conventional bipolar and monopolar electrosurgery devices is that they are not suitable for the precise removal (ablation) of tissue. For example, conventional electrosurgical cutting devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. The tissue is parted along the pathway of vaporized cellular fluid, inducing undesirable collateral tissue damage in regions surrounding the target tissue site.

In addition, conventional electrosurgical methods are generally ineffective for ablating certain types of tissue, and in certain types of environments within the body. For example, loose or elastic connective tissue, such as the synovial tissue in joints, is extremely difficult (if not impossible) to remove with conventional electrosurgical instruments because the flexible tissue tends to move away from the instrument when it is brought against this tissue. Since conventional techniques rely mainly on conducting current through the tissue, they are not effective when the instrument cannot be brought adjacent to or in contact with the elastic tissue for a long enough period of time to energize the electrode and conduct current through the tissue.

The use of electrosurgical procedures (both monopolar and bipolar) in electrically conductive environments can be further problematic. For example, many arthroscopic procedures require flushing of the region to be treated with isotonic saline, both to maintain an isotonic environment and to keep the field of view clear. However, the presence of saline, which is a highly conductive electrolyte, can cause shorting of the active electrode(s) in conventional monopolar and bipolar electrosurgery. Such shorting causes unnecessary heating in the treatment environment and can further cause nonspecific tissue destruction.

Conventional electrosurgical cutting or resecting devices also tend to leave the operating field cluttered with tissue fragments that have been removed or resected from the target tissue. These tissue fragments make visualization of the surgical site extremely difficult. Removing these tissue fragments can also be problematic. Similar to synovial tissue, it is difficult to maintain contact with tissue fragments long enough to ablate the tissue fragments in situ with conventional devices. To solve this problem, the surgical site is periodically or continuously aspirated during the procedure. However, the tissue fragments often clog the aspiration lumen of the suction instrument, forcing the surgeon to remove the instrument to clear the aspiration lumen or to introduce another suction instrument, which increases the length and complexity of the procedure.

During certain electrosurgical procedures, for example in procedures which involve aspiration of relatively large volumes of fluid from a target site, generating and maintaining a plasma from an electrically conductive fluid in the vicinity of the active electrode can be problematic. This situation may be exacerbated by splitting power from the power supply between two different types of active electrode, e.g. a distal ablation electrode adapted for tissue removal and a proximal digestion electrode adapted for disintegrating resected tissue fragments. The present invention overcomes problems related to splitting electric power between the two types of electrodes by having the ablation and digestion electrodes alternate between serving as active electrode and serving as return electrode.

Furthermore, in certain electrosurgical procedures of the prior art, for example, removal or resection of the meniscus during arthroscopic surgery to the knee, it is customary to employ two different tissue removal devices, namely an arthroscopic punch and a shaver. There is a need for an electrosurgical apparatus which enables the aggressive removal of relatively hard tissues (e.g. fibrocartilaginous tissue) as well as soft tissue, and which is adapted for aspirating resected tissue, excess fluids, and ablation by-products from the surgical site. The instant invention provides a single device which can replace the punch and the shaver of the prior art, wherein tissue may be aggressively removed according to a low temperature ablation procedure, and resected tissue can be efficiently removed by a combination of aspiration from the site of tissue resection and digestion of resected tissue fragments, wherein the resected tissue fragments are ablated in an aspiration stream by a cool ablation mechanism. The instant invention provides an electrosurgical suction apparatus and methods for the controlled removal of tissue targeted for treatment, to produce a smooth, contoured tissue surface.

There is also a need for an electrosurgical instrument for the controlled removal of a target tissue, wherein the instrument includes a plurality of working zones, and the working zones are adapted to possess dissimilar ablation rates and dissimilar aspiration rates. The instant invention provides a single instrument including a first working zone having a relatively low aspiration rate and a high ablation rate, and a second working zone having a relatively low ablation rate and a high aspiration rate, wherein the second zone works in concert with the first zone to ablate resected tissue fragments and to aspirate ablation by-products.

SUMMARY OF THE INVENTION

The present invention provides systems, apparatus, kits, and methods for selectively applying electrical energy to target tissue of a patient. In particular, methods and apparatus are provided for resecting, cutting, partially ablating, aspirating or otherwise removing tissue from a target site, and ablating the tissue in situ.

In one aspect, the present invention provides an electrosurgical instrument for treating tissue at a target site. The instrument comprises a shaft having a proximal portion and a distal end portion. One or more active loop electrodes are disposed at the distal end of the shaft. The loop electrodes preferably have one or more edges that promote high electric fields. A connector is disposed near the proximal end of the shaft for electrically coupling the active loop electrodes to a high frequency source.

The active loop electrodes typically have an exposed semicircular shape that facilitates the removing or ablating of tissue at the target site. During the procedure, bodily fluid, non-ablated tissue fragments and/or air bubbles are aspirated from the target site to improve visualization.

At least one return electrode is preferably spaced from the active electrode(s) a sufficient distance to prevent arcing therebetween at the voltages suitable for tissue removal and or heating, and to prevent contact of the return electrode(s) with the tissue. The current flow path between the active and return electrodes may be generated by immersing the target site within electrically conductive fluid (as is typical in arthroscopic procedures), or by directing an electrically conductive fluid along a fluid path past the return electrode and to the target site (e.g., in open procedures). Alternatively, the electrodes may be positioned within a viscous electrically conductive fluid, such as a gel, at the target site, and submersing the active and return electrode(s) within the conductive gel. The electrically conductive fluid will be selected to have sufficient electrical conductivity to allow current to pass therethrough from the active to the return electrode(s), and such that the fluid ionizes into a plasma when subject to sufficient electrical energy, as discussed below. In the exemplary embodiment, the conductive fluid is isotonic saline, although other fluids may be selected, as described in co-pending Provisional Patent Application No. 60/098,122, filed Aug. 27, 1998, the complete disclosure of which is incorporated herein by reference.

In a specific embodiment, tissue ablation results from molecular dissociation or disintegration processes. Conventional electrosurgery ablates or cuts through tissue by rapidly heating the tissue until cellular fluids explode, producing a cutting effect along the pathway of localized heating. The present invention volumetrically removes tissue, e.g., cartilage tissue, in a cool ablation process known as Coblation®, wherein thermal damage to surrounding tissue is minimized. During this process, a high frequency voltage applied to the active electrode(s) is sufficient to vaporize an electrically conductive fluid (e.g., gel or saline) between the electrode(s) and the tissue. Within the vaporized fluid, an ionized plasma is formed and charged particles (e.g., electrons) cause the molecular breakdown or disintegration of tissue components in contact with the plasma. This molecular dissociation is accompanied by the volumetric removal of the tissue. This process can be precisely controlled to effect the volumetric removal of tissue as thin as 10 to 50 microns with minimal heating of, or damage to, surrounding or underlying tissue structures. A more complete description of this Coblation® phenomenon is described in commonly assigned U.S. Pat. No. 5,683,366, the complete disclosure of which is incorporated herein by reference.

The present invention offers a number of advantages over conventional electrosurgery, microdebrider, shaver and laser techniques for removing soft tissue in arthroscopic, sinus or other surgical procedures. The ability to precisely control the volumetric removal of tissue results in a field of tissue ablation or removal that is very defined, consistent and predictable. In one embodiment, the shallow depth of tissue heating also helps to minimize or completely eliminate damage to healthy tissue structures, e.g., cartilage, bone and/or cranial nerves that are often adjacent the target sinus tissue. In addition, small blood vessels at the target site are simultaneously cauterized and sealed as the tissue is removed to continuously maintain hemostasis during the procedure. This increases the surgeon's field of view, and shortens the length of the procedure. Moreover, since the present invention allows for the use of electrically conductive fluid (contrary to prior art bipolar and monopolar electrosurgery techniques), isotonic saline may be used during the procedure. Saline is the preferred medium for irrigation because it has the same concentration as the body's fluids and, therefore, is not absorbed into the body as much as certain other fluids.

Systems according to the present invention generally include an electrosurgical instrument having a shaft with proximal and distal end portions, one or more active loop electrode(s) at the distal end of the shaft and one or more return electrode(s). The system can further include a high frequency power supply for applying a high frequency voltage difference between the active electrode(s) and the return electrode(s). The instrument typically includes an aspiration lumen within the shaft having an opening positioned proximal of the active electrode(s) so as to draw bodily fluids and air bubbles into the aspiration lumen under vacuum pressure.

In another aspect, the present invention provides an electrosurgical probe having a fluid delivery element for delivering electrically conductive fluid to the active electrode(s) and the target site. The fluid delivery element may be located on the instrument, e.g., a fluid lumen or tube, or it may be part of a separate instrument. In an exemplary configuration the fluid delivery element includes at least one opening that is positioned around the active electrodes. Such a configuration provides an improved flow of electrically conductive fluid and promotes more aggressive generation of the plasma at the target site.

Alternatively, an electrically conductive fluid, such as a gel or liquid spray, e.g., saline, may be applied to the tissue. In arthroscopic procedures, the target site will typically already be immersed in a conductive irrigant, i.e., saline. In these embodiments, the apparatus may lack a fluid delivery element. In both embodiments, the electrically conductive fluid will preferably generate a current flow path between the active electrode(s) and the return electrode(s). In an exemplary embodiment, a return electrode is located on the instrument and spaced a sufficient distance from the active electrode(s) to substantially avoid or minimize current shorting therebetween and to shield the tissue from the return electrode at the target site.

In another aspect, the present invention provides a method for applying electrical energy to a target site within or on a patient's body. The method comprises positioning one or more active electrodes into at least close proximity with the target site. An electrically conductive fluid is provided to the target site and a high frequency voltage is applied between the active electrodes and a return electrode to generate relatively high, localized electric field intensities between the active electrode(s) and the target site, wherein an electrical current flows from the active electrode(s) through tissue at the target site. The active electrodes are moved in relation to the targeted tissue to resect or ablate the tissue at the target site.

In another aspect, the present invention provides an electrosurgical system for removing tissue from a target site to be treated. The system includes a probe and a power supply for supplying high frequency alternating current to the probe. The probe includes a shaft, an ablation electrode, and a digestion electrode, wherein the ablation electrode and the digestion electrode are independently coupled to opposite poles of the power supply. Typically, the probe and electrosurgical system lack a dedicated return electrode. Instead, the ablation and digestion electrodes can alternate between serving as active electrode and serving as return electrode, i.e., the power supply can alternate between preferentially supplying electric power to the ablation electrode and preferentially supplying electric power to the digestion electrode. When power is preferentially supplied to the ablation electrode, the ablation electrode functions as an active electrode and is capable of ablating tissue, while the digestion electrode serves as a return electrode. When power is preferentially supplied to the digestion electrode, the digestion electrode functions as an active electrode and is capable of ablating tissue, while the ablation electrode serves as a return electrode. Thus, both the ablation electrode and the digestion electrode are adapted for ablating tissue, albeit under different circumstances. Namely, the ablation electrode is adapted for removing tissue from a site targeted for treatment, whereas the digestion electrode is adapted for digesting tissue fragments resected from the target site by the ablation electrode. Thus, the two electrode types (ablation and digestion electrodes) operate in concert to conveniently remove, ablate, or digest tissue targeted for treatment. It should be noted that the mechanism involved in removing tissue by the ablation electrode and in digesting tissue fragments by the digestion electrode may be essentially the same, e.g., a cool ablation process involving the molecular dissociation of tissue components to yield low molecular weight ablation by-products.

By the term "return electrode" is meant an electrode which serves to provide a current flow path from an active electrode back to a power supply, and/or an electrode of an electrosurgical device which does not produce an electrically-induced tissue-altering effect on tissue targeted for treatment. By the term "active electrode" is meant an electrode of an electrosurgical device which is adapted for producing an electrically-induced tissue-altering effect when brought into contact with, or close proximity to, a tissue targeted for treatment.

In another aspect, the invention provides an apparatus and method for treating tissue at a target site with an electrosurgical system having a probe including an ablation electrode and a digestion electrode, wherein the electrosurgical system lacks a dedicated return electrode. The ablation electrode and the digestion electrode are independently coupled to opposite poles of a power supply for supplying power to the ablation electrode and to the digestion electrode. Typically, during operation of the electrosurgical system of the invention the power supply does not supply power equally to the ablation electrode and to the digestion electrode. Instead, at a given time point during operation of the electrosurgical system, one of the two electrode types (the ablation electrode(s) or the digestion electrode(s)) may receive up to about 100% of the available power from the power supply.

According to one embodiment, the probe is positioned adjacent to a tissue to be treated, and power is supplied from the power supply preferentially to the ablation electrode at the expense, or to the exclusion, of the digestion electrode. In this manner the ablation electrode may receive up to about 100% of the power from the power supply, resulting in efficient generation of a plasma in the vicinity of the ablation electrode, and removal of tissue from the target site. During this phase of the procedure, the ablation electrode obviously has a tissue-altering effect on the tissue and functions as the active electrode, while the digestion electrode serves as the return electrode and is incapable of a tissue-altering effect. During a different phase of the procedure, power from the power supply is preferentially supplied to the digestion electrode at the expense of the ablation electrode. In this manner the digestion electrode may receive up to about 100% of the power from the power supply, resulting in efficient generation of a plasma in the vicinity of the digestion electrode, and digestion of tissue fragments resected by the ablation electrode. During the latter phase of the procedure, the digestion electrode obviously has a tissue-altering effect and functions as the active electrode, while the ablation electrode serves as the return electrode and is incapable of a tissue-altering effect.

Shifting power delivery from the ablation electrode to the digestion electrode, and vice versa, may be effected by the presence or absence of tissue (including whole tissue and resected tissue fragments) in contact with, or in the vicinity of, the ablation and digestion electrodes. For example, when only the ablation electrode is in contact with tissue (i.e., the digestion electrode is not in contact with tissue): a) the ablation electrode receives most of the available electric power from the power supply, and the ablation electrode functions as an active electrode (i.e., ablates tissue); and b) current density at the digestion electrode decreases, and the digestion electrode functions as a return electrode (i.e., has no tissue effect, and completes a current flow path from the ablation electrode back to the power supply). Conversely, when only the digestion electrode is in contact with tissue (i.e., the ablation electrode is not in contact with tissue):

a) the digestion electrode receives most of the available electric power from the power supply, and the digestion electrode functions as an active electrode; and b) current density at the ablation electrode decreases, and the ablation electrode functions as a return electrode (i.e., has no tissue effect, and completes a current flow path from the digestion electrode back to the power supply).

Thus, according to certain aspects of the invention, there is provided an electrosurgical probe having a first electrode type and a second electrode type, wherein both the first and second electrode types are capable of serving as an active electrode and are adapted for ablating tissue, and both the first and second electrode type are capable of serving as a return electrode. The probe is designed to operate in different modes according to whether i) only the first electrode type is in contact with tissue, ii) only the second electrode type is in contact with tissue, or iii) both the first electrode type and the second electrode type are in contact with tissue at the same time. Typically, the electrosurgical probe is configured such that a first electrode type can be brought into contact with tissue at a target site while a second electrode type does not contact the tissue at the target site. Indeed, in some embodiments the electrosurgical probe is configured such that one type of electrode can be brought into contact with tissue at a target site while the other electrode type remains remote from the tissue at the target site.

In one mode of operation, both the first electrode type (ablation electrode) and second electrode type (digestion electrode) may be in contact with tissue simultaneously. Under these circumstances, by arranging for an appropriate ablation electrode:digestion electrode surface area ratio, the available power from the power supply may be supplied preferentially to the digestion electrode. When tissue is in contact with, or in the vicinity of, the digestion electrode, the electrical impedance in the vicinity of the digestion electrode changes. Such a change in electrical impedance typically results from the presence of one or more tissue fragments flowing towards the digestion electrode in an aspiration stream comprising an electrically conductive fluid, and the change in electrical impedance may trigger a shift from the ablation electrode serving as active electrode to the digestion electrode serving as active electrode. The ablation electrode may be located distal to an aspiration port on the shaft. The digestion electrode may be arranged in relation to an aspiration device, so that the aspiration stream contacts the digestion electrode.

In another aspect, the present invention provides an electrosurgical suction apparatus adapted for coupling to a high frequency power supply and for removing tissue from a target site to be treated. The apparatus includes an aspiration channel terminating in a distal opening or aspiration port, and a plurality of active electrodes in the vicinity of the distal opening. The plurality of active electrodes may be structurally similar or dissimilar. In one embodiment, a plurality of active electrodes are arranged substantially parallel to each other on an electrode support, and each of the plurality of active electrodes traverses a void in the electrode support.

Typically, each of the plurality of active electrodes includes a first free end, a second connected end, and a loop portion having a distal face, the loop portion extending from a treatment surface of the electrode support and spanning the aspiration port. In one embodiment, the orientation of an active electrode with respect to the treatment surface may change from a first direction in the region of the connected end to a second direction in the region of the loop portion.

According to another aspect of the invention, the loop portion of each of the plurality of active electrodes may be oriented in a plurality of different directions with respect to the treatment surface. In one embodiment, the loop portion of each of the plurality of active electrodes is oriented in a different direction with respect to the treatment surface. In one embodiment, the orthogonal distance from the treatment surface to the distal face of each active electrode is substantially the same.

According to one aspect of the invention, a baffle or screen is provided at the distal end of the apparatus. In one embodiment the baffle is recessed within the void to impede the flow of solid material into the aspiration channel, and to trap the solid material in the vicinity of at least one of the plurality of active electrodes, whereby the trapped material may be readily digested.

In use, the plurality of active electrodes are coupled to a first pole of the high frequency power supply, and a return electrode is coupled to a second pole of the high frequency power supply for supplying high frequency alternating current to the device. Each of the plurality of active electrodes is capable of ablating tissue via a controlled ablation mechanism involving molecular dissociation of tissue components to yield low molecular weight ablation by-products. During this process, tissue fragments may be resected from the target site. Such resected tissue fragments may be digested by one or more of the plurality of active electrodes via essentially the same cool ablation mechanism as described above (i.e., involving molecular dissociation of tissue components), to form smaller tissue fragments and/or low molecular weight ablation by-products. The smaller tissue fragments and low molecular weight ablation by-products, together with any other unwanted materials (e.g., bodily fluids, extraneous saline) may be aspirated from the target site via the aspiration channel.

In another aspect, the present invention provides a method for removing tissue from a target site via an electrosurgical suction device, wherein the plurality of active electrodes are juxtaposed with the target tissue, and a high frequency voltage is applied to the plurality of active electrodes sufficient to ablate the tissue via localized molecular dissociation of tissue components. The apparatus is adapted for efficiently ablating tissue and for rapidly removing unwanted materials, including resected tissue fragments, from the target site. The apparatus is further adapted for providing a relatively smooth, even contour to a treated tissue.

According to another aspect of the invention, there is provided an electrosurgical probe having an aspiration unit including a plurality of aspiration ports, a plurality of active electrodes, and a working portion arranged at the distal end of the probe, wherein the working portion includes a plurality of working zones. The plurality of active electrodes are disposed on an electrically insulating electrode support. The working zones may be spaced from each other, either axially or laterally, on the electrode support. The working zones may be distinguished from each other by their ablation rate and/or their aspiration rate. Typically, each working zone has at least one aspiration port and at least one active electrode. Each active electrode is capable of generating a plasma, in the presence of an electrically conductive fluid, and upon the application of a high frequency voltage between that active electrode and a return electrode. The return electrode may be disposed on the shaft distal end, at a location proximal or inferior to the electrode support. Generally, a working zone having a relatively high aspiration rate has a relatively low ablation rate, and vice versa. In general, a working zone having a relatively high aspiration rate is less suited to the initiation and maintenance of a plasma, as compared with a working zone having a relatively low aspiration rate.

In one embodiment, all of a plurality of working zones are arranged on a single plane of an electrode support. In another embodiment, the electrode support includes a plurality of planes, and a working portion of the probe occupies at least two of the plurality of planes. In another embodiment, each of a plurality of working zones occupies a different plane of the electrode support. According to one aspect of the invention, one or more of the active electrodes is in the form of a wire loop. The active electrodes may be strategically arranged with respect to the aspiration ports. In one embodiment, an electrode loop at least partially extends across (traverses) one or more aspiration ports. In another embodiment, at least a portion of the aspiration ports are located towards the periphery of a working zone of the electrode support.

According to another aspect of the invention, there is provided an electrosurgical probe having a first working zone and a second working zone, wherein the first working zone has a relatively low aspiration rate and is adapted for aggressively ablating tissue from a target site. In contrast, the second working zone includes at least one aspiration port, has a relatively high aspiration rate, and is adapted for rapidly aspirating fluids therefrom. The second working zone has a relatively low ablation rate, which is, nevertheless, sufficient to vaporize tissue fragments resected by the first working zone, whereby blockage of the at least one aspiration port of the second working zone is avoided. In one aspect of the invention, the relative ablation rate of the first and second working zones can be "tuned" by the appropriate selection of the number, size, and distribution of aspiration ports for each zone.

In another embodiment, there is provided a method for ablating a target tissue using an electrosurgical probe having a working portion which includes a plurality of working zones. Each of the plurality of working zones may differ with respect to one or more of the following characteristics: axial placement on the probe, number and/or size of aspiration ports, aspiration rate, propensity to initiate and maintain a plasma, and ablation rate. The method involves advancing the probe distal end towards the target tissue, such that at least a first working zone is in at least close proximity to the target tissue. Thereafter, a high frequency voltage is applied between at least one active electrode of the working portion and a return electrode, whereby at least a portion of the target tissue is ablated. Typically, the ablation of target tissue in this manner occurs via plasma-induced molecular dissociation of target tissue components to produce low molecular weight or gaseous ablation by-products. In one embodiment, at least a portion of the ablation by-products are aspirated from the surgical site via one or more aspiration ports located on a second working zone of the probe. The ablation of target tissue by the first working zone may result in the resection of fragments of the target tissue. Such resected tissue fragments may be ablated (vaporized) by one or more active electrodes of the second working zone to once again form low molecular weight ablation by-products, whereby blockage of the aspiration ports is prevented.

A further understanding of the nature and advantages of the invention will become apparent by reference to the remaining portions of the specification and drawings.

BRIEF DESCRIPTION OF THE DRAWINGS

FIGS. 36A–F each show a resection unit having at least one resection electrode head arranged on a resection electrode support, according to various embodiments of the invention;

FIGS. 39A–I each show a cross-section of a resection electrode head, according to one embodiment of the invention, as seen along the lines 39A–I of FIG. 38B;

FIG. 50A shows a longitudinal section of a probe showing detail of the shaft and handle;

FIG. 50B is an end view of the distal terminus of the electrosurgical probe of FIG. 50A;

FIG. 64A shows an electrosurgical suction apparatus having an outer sheath, according to another embodiment of the invention;

FIG. 64B shows a transverse cross-section of the apparatus of FIG. 64A;

DESCRIPTION OF SPECIFIC EMBODIMENTS

Figure 1:
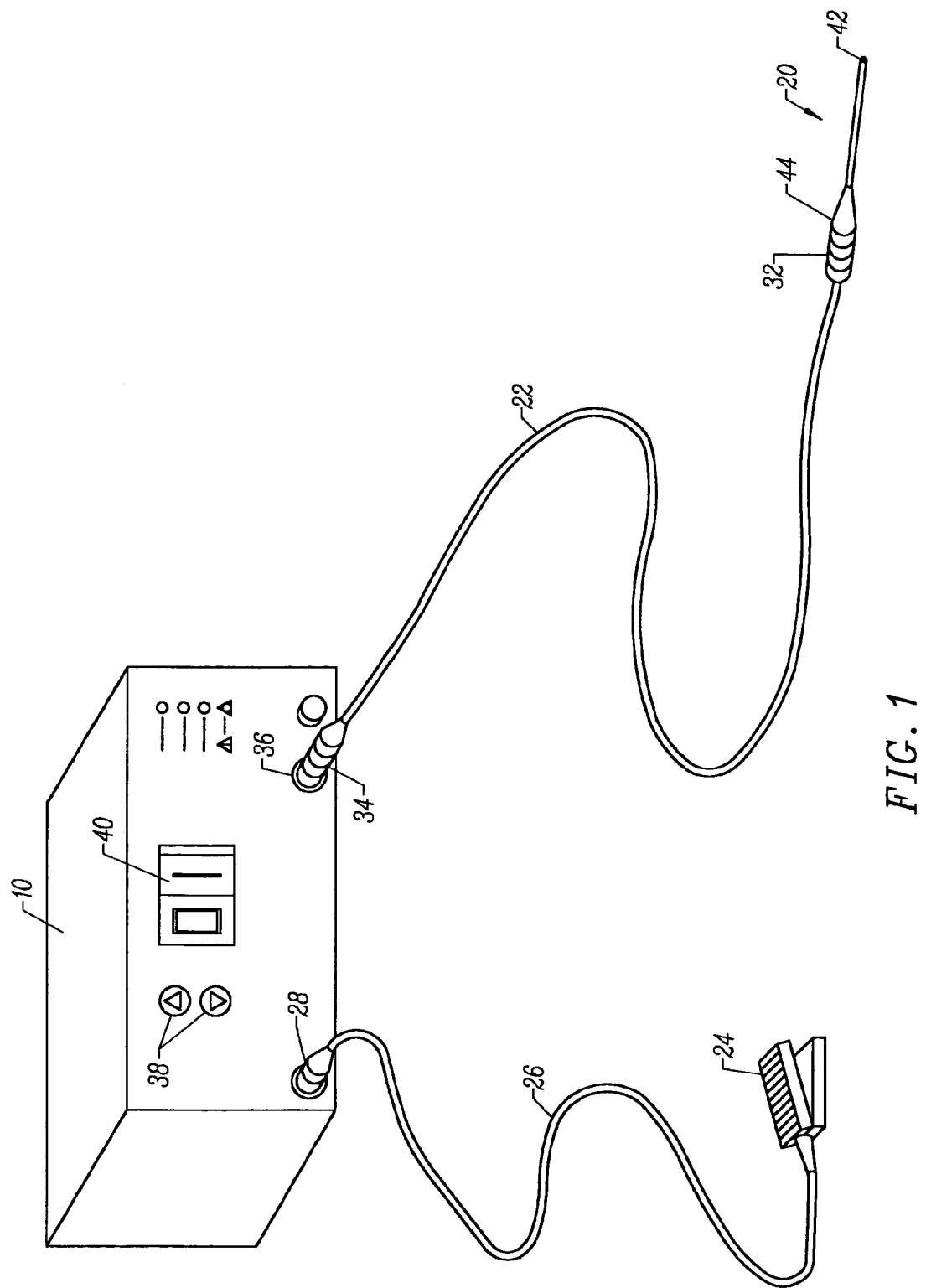
FIG. 1 is a perspective view of an electrosurgical system incorporating a power supply and an electrosurgical probe for tissue ablation, resection, incision, contraction and for vessel hemostasis according to the present invention.

The present invention provides systems and methods for selectively applying electrical energy to a target location within or on a patient's body. The present invention is particularly useful in procedures where the tissue site is flooded or submerged with an electrically conductive fluid, such as arthroscopic surgery of the knee, shoulder, ankle, hip, elbow, hand or foot. In addition, tissues which may be treated by the system and method of the present invention include, but are not limited to, prostate tissue and leiomyomas (fibroids) located within the uterus, gingival tissues and mucosal tissues located in the mouth, tumors, scar tissue, myocardial tissue, collagenous tissue within the eye or epidermal and dermal tissues on the surface of the skin. Other procedures for which the present invention may be used include laminectomy/discetomy procedures for treating herniated disks, decompressive laminectomy for stenosis in the lumbosacral and cervical spine, posterior lumbosacral and cervical spine fusions, treatment of scoliosis associated with vertebral disease, foraminotomies to remove the roof of the intervertebral foramina to relieve nerve root compression, as well as anterior cervical and lumbar discectomies. The present invention is also useful for resecting tissue within accessible sites of the body that are suitable for electrode loop resection, such as the resection of prostate tissue, leiomyomas (fibroids) located within the uterus, and other diseased tissue within the body.

The present invention is also useful for procedures in the head and neck, such as the ear, mouth, pharynx, larynx, esophagus, nasal cavity and sinuses. These procedures may be performed through the mouth or nose using speculae or gags, or using endoscopic techniques, such as functional endoscopic sinus surgery (FESS). These procedures may include the removal of swollen tissue, chronically-diseased inflamed and hypertrophic mucus linings, polyps and/or neoplasms from the various anatomical sinuses of the skull, the turbinates and nasal passages, in the tonsil, adenoid, epi-glottic and supra-glottic regions, and salivary glands, submucus resection of the nasal septum, excision of diseased tissue and the like. In other procedures, the present invention may be useful for collagen shrinkage, ablation and/or hemostasis in procedures for treating snoring and obstructive sleep apnea (e.g., soft palate, such as the uvula, or tongue/pharynx stiffening, and midline glossectomies), for gross tissue removal, such as tonsillectomies, adenoidectomies, tracheal stenosis and vocal cord polyps and lesions, or for the resection or ablation of facial tumors or tumors within the mouth and pharynx, such as glossectomies, laryngectomies, acoustic neuroma procedures and nasal ablation procedures. In addition, the present invention is useful for procedures within the ear, such as stapedotomies, tympanostomies or the like.

The present invention may also be useful for cosmetic and plastic surgery procedures in the head and neck. For example, the present invention is particularly useful for ablation and sculpting of cartilage tissue, such as the cartilage within the nose that is sculpted during rhinoplasty procedures. The present invention may also be employed for skin tissue removal and/or collagen shrinkage in the epidermis or dermis tissue in the head and neck, e.g., the removal of pigmentations, vascular lesions (e.g., leg veins), scars, tattoos, etc., and for other surgical procedures on the skin, such as tissue rejuvenation, cosmetic eye procedures (blepharoplasties), wrinkle removal, tightening muscles for facelifts or browlifts, hair removal and/or transplant procedures, etc.

For convenience, certain embodiments of the invention will be described primarily with respect to the resection and/or ablation of the meniscus and the synovial tissue within a joint during an arthroscopic procedure and to the ablation, resection and/or aspiration of sinus tissue during an endoscopic sinus surgery procedure, but it will be appreciated that the systems and methods can be applied equally well to procedures involving other tissues of the body, as well as to other procedures including open procedures, intravascular procedures, urology, laparoscopy, arthroscopy, thoracoscopy or other cardiac procedures, dermatology, orthopedics, gynecology, otorhinolaryngology, spinal and neurologic procedures, oncology, and the like.

In the present invention, high frequency (RF) electrical energy is applied to one or more active electrodes in the presence of electrically conductive fluid to remove and/or modify the structure of tissue structures. Depending on the specific procedure, the present invention may be used to: (1) volumetrically remove tissue, bone or cartilage (i.e., ablate or effect molecular dissociation of the tissue structure); (2) cut or resect tissue; (3) shrink or contract collagen connective tissue; and/or (4) coagulate severed blood vessels.

In one aspect of the invention, systems and methods are provided for the volumetric removal or ablation of tissue structures. In these procedures, a high frequency voltage difference is applied between one or more active electrode(s) and one or more return electrode(s) to develop high electric field intensities in the vicinity of the target tissue site. The high electric field intensities lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxides of carbon, hydrocarbons and nitrogen compounds. This molecular disintegration completely removes the tissue structure, as opposed to dehydrating the tissue material by the removal of liquid from within the cells of the tissue, as is typically the case with electrosurgical desiccation and vaporization.

The high electric field intensities may be generated by applying a high frequency voltage that is sufficient to vaporize an electrically conductive fluid over at least a portion of the active electrode(s) in the region between the distal tip of the active electrode(s) and the target tissue. The electrically conductive fluid may be a gas or liquid, such as isotonic saline, delivered to the target site, or a viscous fluid, such as a gel, that is located at the target site. In the latter embodiment, the active electrode(s) are submersed in the electrically conductive gel during the surgical procedure. Since the vapor layer or vaporized region has a relatively high electrical impedance, it minimizes the current flow into the electrically conductive fluid. This ionization, under optimal conditions, induces the discharge of energetic electrons and photons from the vapor layer to the surface of the target tissue. A more detailed description of this cold ablation phenomenon, termed Coblation®, can be found in commonly assigned U.S. Pat. No. 5,683,366 the complete disclosure of which is incorporated herein by reference.

The present invention applies high frequency (RF) electrical energy in an electrically conductive fluid environment to remove (i.e., resect, cut, or ablate) or contract a tissue structure, and to seal transected vessels within the region of the target tissue. The present invention is particularly useful for sealing larger arterial vessels, e.g., on the order of 1 mm in diameter or greater. In some embodiments, a high frequency power supply is provided having an ablation mode, wherein a first voltage is applied to an active electrode sufficient to effect molecular dissociation or disintegration of the tissue, and a coagulation mode, wherein a second, lower voltage is applied to an active electrode (either the same or a different electrode) sufficient to achieve hemostasis of severed vessels within the tissue. In other embodiments, an electrosurgical probe is provided having one or more coagulation electrode(s) configured for sealing a severed vessel, such as an arterial vessel, and one or more active electrodes configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to coagulate tissue with the coagulation electrode(s), and to ablate or contract the tissue with the active electrode(s). In other embodiments, the power supply is combined with the probe such that the coagulation electrode receives power when the power supply is in the coagulation mode (low voltage), and the active electrode(s) receive power when the power supply is in the ablation mode (higher voltage).

In the method of the present invention, one or more active electrodes are brought into close proximity to tissue at a target site, and the power supply is activated in the ablation mode such that sufficient voltage is applied between the active electrodes and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply and to convert the system into the coagulation mode. In this mode, the active electrodes may be pressed against the severed vessel to provide sealing and/or coagulation of the vessel. Alternatively, a coagulation electrode located on the same or a different probe may be pressed against the severed vessel. Once the vessel is adequately sealed, the surgeon activates a control (e.g., another foot pedal) to increase the voltage of the power supply and convert the system back into the ablation mode.

The present invention is particularly useful for removing or ablating tissue around nerves, such as spinal or cranial nerves, e.g., the olfactory nerve on either side of the nasal cavity, the optic nerve within the optic and cranial canals, and the palatine nerve within the nasal cavity, soft palate, uvula and tonsil, etc. One of the significant drawbacks with prior art microdebriders and lasers is that these devices do not differentiate between the target tissue and the surrounding nerves or bone. Therefore, the surgeon must be extremely careful during these procedures to avoid damage to the bone or nerves within and around the nasal cavity. In the present invention, the Coblation® process for removing tissue results in extremely small depths of collateral tissue damage as discussed above. This allows the surgeon to remove tissue close to a nerve without causing collateral damage to the nerve fibers.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Peripheral nerves usually comprise a connective tissue sheath, or epineurium, enclosing the bundles of nerve fibers to protect these nerve fibers. This protective tissue sheath typically comprises a fatty tissue (e.g., adipose tissue) having substantially different electrical properties than the normal target tissue, such as the turbinates, polyps, mucus tissue or the like, that are, for example, removed from the nose during sinus procedures. The system of the present invention measures the electrical properties of the tissue at the tip of the probe with one or more active electrode(s). These electrical properties may include electrical conductivity at one, several or a range of frequencies (e.g., in the range from 1 kHz to 100 MHz), dielectric constant, capacitance or combinations of these. In this embodiment, an audible signal may be produced when the sensing electrode(s) at the tip of the probe detects the fatty tissue surrounding a nerve, or direct feedback control can be provided to only supply power to the active electrode (s), either individually or to the complete array of electrodes, if and when the tissue encountered at the tip or working end of the probe is normal tissue based on the measured electrical properties.

In one embodiment, the current limiting elements (discussed in detail below) are configured such that the active electrodes will shut down or turn off when the electrical impedance of tissue at the tip of the probe reaches a threshold level. When this threshold level is set to the impedance of the fatty tissue surrounding nerves, the active electrodes will shut off whenever they come in contact with, or in close proximity to, nerves. Meanwhile, the other active electrodes, which are in contact with or in close proximity to nasal tissue, will continue to conduct electric current to the return electrode. This selective ablation or removal of lower impedance tissue in combination with the Coblation® mechanism of the present invention allows the surgeon to precisely remove tissue around nerves or bone.

In addition to the above, applicant has discovered that the Coblation® mechanism of the present invention can be manipulated to ablate or remove certain tissue structures, while having little effect on other tissue structures. As discussed above, the present invention uses a technique of vaporizing electrically conductive fluid to form a plasma layer or pocket around the active electrode(s), and then inducing the discharge of energy from this plasma or vapor layer to break the molecular bonds of the tissue structure. Based on initial experiments, applicants believe that the free electrons within the ionized vapor layer are accelerated in the high electric fields near the electrode tip(s). When the density of the vapor layer (or within a bubble formed in the electrically conductive liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Energy evolved by the energetic electrons (e.g., 4 to 5 eV) can subsequently bombard a molecule and break its bonds, dissociating a molecule into free radicals, which then combine to form gaseous or liquid Coblation® by-products.

The energy evolved by the energetic electrons may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, components of adipose tissue have double bonds that require a substantially higher energy level than 4 to 5 eV to break. Accordingly, the present invention in its current configuration generally does not ablate or remove such fatty tissue. However, the present invention may be used to effectively ablate cells to release the inner fat content in a liquid form. Of course, factors may be changed such that these double bonds can be broken (e.g., increasing the voltage or changing the electrode configuration to increase the current density at the electrode tips).

In another aspect of the invention, a loop electrode is employed to resect, shape or otherwise remove tissue fragments from the treatment site, and one or more active electrodes are employed to ablate (i.e., break down the tissue by processes including molecular dissociation or disintegration) the non-ablated tissue fragments in situ. Once a tissue fragment is cut, partially ablated or resected by the loop electrode, one or more active electrodes will be brought into close proximity to these fragments (either by moving the probe into position, or by drawing the fragments to the active electrodes with a suction lumen). Voltage is applied between the active electrodes and the return electrode to volumetrically remove the fragments through molecular dissociation, as described above. The loop electrode and the active electrodes are preferably electrically isolated from each other such that, for example, current can be limited (passively or actively) or completely interrupted to the loop electrode as the surgeon employs the active electrodes to ablate tissue fragments (and vice versa).

In another aspect of the invention, the loop electrode(s) are employed to ablate tissue using the Coblation® mechanisms described above. In these embodiments, the loop electrode(s) provides a relatively uniform smooth cutting or ablation effect across the tissue. In addition, loop electrodes generally have a larger surface area exposed to electrically conductive fluid (as compared to the smaller active electrodes described above), which increases the rate of ablation of tissue. Preferably, the loop electrode(s) extend a sufficient distance from the electrode support member selected to achieve a desirable ablation rate, while minimizing power dissipation into the surrounding medium (which could cause undesirable thermal damage to surrounding or underlying tissue). In an exemplary embodiment, the loop electrode has a length from one end to the other end of about 0.5 to 20 mm, usually about 1 to 8 mm. The loop electrode usually extends about 0.25 to 10 mm from the distal end of the support member, preferably about 1 to 4 mm.

The loop electrode(s) may have a variety of cross-sectional shapes. Electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. For example, material can be removed along the length of a solid or hollow wire electrode to form D or C shaped wires, respectively, with edges facing in the cutting direction. Alternatively, material can be removed at closely spaced intervals along the electrode length to form transverse grooves, slots, threads or the like along the electrodes.

In some embodiments, the loop electrode(s) will have a "non-active" portion or surface to selectively reduce undesirable current flow from the non-active portion or surface into tissue or surrounding electrically conductive liquids (e.g., isotonic saline, blood or blood/non-conducting irrigant mixtures). Preferably, the "non-active" electrode portion will be coated with an electrically insulating material. This can be accomplished, for example, with plasma deposited coatings of an insulating material, thin-film deposition of an insulating material using evaporative or sputtering techniques (e.g., $SiO_2$ or $Si_3N_4$), dip coating, or by providing an electrically insulating support member to electrically insulate a portion of the external surface of the electrode. The electrically insulated non-active portion of the active electrode(s) allows the surgeon to selectively resect and/or ablate tissue, while minimizing necrosis or ablation of surrounding non-target tissue or other body structures.

In addition, the loop electrode(s) may comprise a single electrode extending from first and second ends to an insulating support in the shaft, or multiple, electrically isolated electrodes extending around the loop. One or more return electrodes may also be positioned along the loop portion. Further descriptions of these configurations can be found in U.S. application Ser. No. 08/687792, filed on Jul. 18, 1996, now U.S. Pat. No. 5,843,019, which as already been incorporated herein by reference.

The electrosurgical probe will comprise a shaft or a handpiece having a proximal end and a distal end which supports one or more active electrode(s). The shaft or handpiece may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. The distal portion of the shaft may comprise a flexible material, such as plastics, malleable stainless steel, etc, so that the physician can mold the distal portion into different configurations for different applications. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft. Thus, the shaft will typically have a length of at least 5 cm for oral procedures and at least 10 cm, more typically being 20 cm, or longer for endoscopic procedures. The shaft will typically have a diameter of at least 0.5 mm and frequently in the range of from about 1 to 10 mm. Of course, for dermatological procedures on the outer skin, the shaft may have any suitable length and diameter that would facilitate handling by the surgeon.

For procedures within the nose and joints, the shaft will have a suitable diameter and length to allow the surgeon to reach the target by delivering the probe shaft through an percutaneous opening in the patient (e.g., a portal formed in the joint in arthroscopic surgery, or through one of the patient's nasal passages in FESS). Thus, the shaft will usually have a length in the range of from about 5 to 25 cm, and a diameter in the range of from about 0.5 to 5 mm. For procedures requiring the formation of a small hole or channel in tissue, such as treating swollen turbinates, the shaft diameter will usually be less than 3 mm, preferably less than about 1 mm. Likewise, for procedures in the ear, the shaft should have a length in the range of about 3 to 20 cm, and a diameter of about 0.3 to 5 mm. For procedures in the mouth or upper throat, the shaft will have any suitable length and diameter that would facilitate handling by the surgeon. For procedures in the lower throat, such as laryngectomies, the shaft will be suitably designed to access the larynx. For example, the shaft may be flexible, or have a distal bend to accommodate the bend in the patient's throat. In this regard, the shaft may be a rigid shaft having a specifically designed bend to correspond with the geometry of the mouth and throat, or it may have a flexible distal end, or it may be part of a catheter. In any of these embodiments, the shaft may also be introduced through rigid or flexible endoscopes. Specific shaft designs will be described in detail in connection with the figures hereinafter.

The current flow path between the active electrode(s) and the return electrode(s) may be generated by submerging the tissue site in an electrically conductive fluid (e.g., a viscous fluid, such as an electrically conductive gel), or by directing an electrically conductive fluid along a fluid path to the target site (i.e., a liquid, such as isotonic saline, or a gas, such as argon). This latter method is particularly effective in a dry environment (i.e., the tissue is not submerged in fluid) because the electrically conductive fluid provides a suitable current flow path from the active electrode to the return electrode. A more complete description of an exemplary method of directing electrically conductive fluid between the active and return electrodes is described in parent application Ser. No. 08/485,219, filed Jun. 7, 1995, now U.S. Pat. No. 5,697,281, previously incorporated herein by reference.

In some procedures, it may also be necessary to retrieve or aspirate the electrically conductive fluid after it has been directed to the target site. For example, in procedures in the nose, mouth or throat, it may be desirable to aspirate the fluid so that it does not flow down the patient's throat. In addition, it may be desirable to aspirate small pieces of tissue that are not completely disintegrated by the high frequency energy, air bubbles, or other fluids at the target site, such as blood, mucus, the gaseous products of ablation, etc. Accordingly, the system of the present invention can include a suction lumen in the probe, or on another instrument, for aspirating fluids from the target site.

In some embodiments, the probe will include one or more aspiration electrode(s) coupled to the distal end of the suction lumen for ablating, or at least reducing the volume of, tissue fragments that are aspirated into the lumen. The aspiration electrode(s) function mainly to inhibit clogging of the lumen that may otherwise occur as larger tissue fragments are drawn therein. The aspiration electrode(s) may be different from the ablation active electrode(s), or the same electrode(s) may serve both functions. In some embodiments, the probe will be designed to use suction force to draw loose tissue, such as synovial tissue to the aspiration or ablation electrode(s) on the probe, which are then energized to ablate the loose tissue.

In other embodiments, the aspiration lumen can be positioned proximal of the active electrodes a sufficient distance such that the aspiration lumen will primarily aspirate air bubbles and body fluids such as blood, mucus, or the like. Such a configuration allows the electrically conductive fluid to dwell at the target site for a longer period. Consequently, the plasma can be created more aggressively at the target site and the tissue can be treated in a more efficient manner. Additionally, by positioning the aspiration lumen opening somewhat distant from the active electrodes, it may not be necessary to have ablation electrodes at the lumen opening since, in this configuration, tissue fragments will typically not be aspirated through the lumen.

The present invention may use a single active electrode or an electrode array distributed over a contact surface of a probe. In the latter embodiment, the electrode array usually includes a plurality of independently current-limited and/or power-controlled active electrodes to apply electrical energy selectively to the target tissue while limiting the unwanted application of electrical energy to the surrounding tissue and environment. Such unwanted application of electrical energy results from power dissipation into surrounding electrically conductive liquids, such as blood, normal saline, electrically conductive gel and the like. The active electrodes may be independently current-limited by isolating the terminals from each other and connecting each terminal to a separate power source that is isolated from the other active electrodes. Alternatively, the active electrodes may be connected to each other at either the proximal or distal ends of the probe to form a single connector that couples to a power source.

In one configuration, each individual active electrode in the electrode array is electrically insulated from all other active electrodes in the array within the probe and is connected to a power source which is isolated from each of the other active electrodes in the array or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the probe, connectors, cable, controller or along the conductive path from the controller to the distal tip of the probe. Alternatively, the resistance and/or capacitance may occur on the surface of the active electrode(s) due to oxide layers which form selected active electrodes (e.g., titanium or a resistive coating on the surface of metal, such as platinum).

The tip region of the probe may comprise many independent active electrodes designed to deliver electrical energy in the vicinity of the tip. The selective application of electrical energy to the conductive fluid is achieved by connecting each individual active electrode and the return electrode to a power source having independently controlled or current limited channels. The return electrode(s) may comprise a single tubular member of conductive material proximal to the electrode array at the tip which also serves as a conduit for the supply of the electrically conductive fluid between the active and return electrodes. Alternatively, the probe may comprise an array of return electrodes at the distal tip of the probe (together with the active electrodes) to maintain the electric current at the tip. The application of high frequency voltage between the return electrode(s) and the electrode array results in the generation of high electric field intensities at the distal tips of the active electrodes with conduction of high frequency current from each individual active electrode to the return electrode. The current flow from each individual active electrode to the return electrode (s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the active electrode(s) for appropriate time intervals effects cutting, removing, ablating, shaping, contracting or otherwise modifying the target tissue. The tissue volume over which energy is dissipated (i.e., over which a high current density exists) may be precisely controlled, for example, by the use of a multiplicity of small active electrodes whose effective diameters or principal dimensions range from about 5 mm to 0.01 mm, preferably from about 2 mm to 0.05 mm, and more preferably from about 1 mm to 0.1 mm. In these embodiments, electrode areas for both circular and non-circular terminals will have a contact area (per active electrode) below 25 $mm^2$, preferably being in the range from 0.0001 $mm^2$ to 1 $mm^2$, and more preferably from 0.005 $mm^2$ to 0.5 $mm^2$. The circumscribed area of the electrode array is in the range from 0.25 $mm^2$ to 75 $mm^2$, preferably from 0.5 $mm^2$ to 40 $mm^2$, and will usually include at least two isolated active electrodes, preferably at least five active electrodes, often greater than 10 active electrodes and even 50 or more active electrodes, disposed over the distal contact surfaces on the shaft. The use of small diameter active electrodes increases the electric field intensity and reduces the extent or depth of tissue heating as a consequence of the divergence of current flux lines which emanate from the exposed surface of each active electrode.

The area of the tissue treatment surface can vary widely, and the tissue treatment surface can assume a variety of geometries, with particular areas and geometries being selected for specific applications. Active electrode surfaces can have areas in the range from 0.25 $mm^2$ to 75 $mm^2$, usually being from about 0.5 $mm^2$ to 40 $mm^2$. The geometries can be planar, concave, convex, hemispherical, conical, linear "in-line" array or virtually any other regular or irregular shape. Most commonly, the active electrode(s) or active electrode(s) will be formed at the distal tip of the electrosurgical probe shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical probe shaft (e.g., in the manner of a spatula), facilitating access to certain body structures in endoscopic procedures.

The electrically conductive fluid should have a threshold conductivity to provide a suitable conductive path between the active electrode(s) and the return electrode(s). The electrical conductivity of the fluid (in units of millisiemens per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm.

In some embodiments, the electrode support and the fluid outlet may be recessed from an outer surface of the probe or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the active electrode(s) and the return electrode (s) to maintain the conductive path therebetween. In addition, this will help to maintain a vapor or plasma layer between the active electrode(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

The voltage applied between the return electrode(s) and the electrode array will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the active electrode size, the operating frequency and the operation mode of the particular procedure or desired effect on the tissue (i.e., contraction, coagulation or ablation). Typically, the peak-to-peak voltage will be in the range of 10 to 2000 volts, preferably in the range of 20 to 1200 volts and more preferably in the range of about 40 to 800 volts (again, depending on the electrode size, the operating frequency and the operation mode).

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed at about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, and/or the maximum allowed temperature selected for the probe tip. The power source allows the user to select the voltage level according to the specific requirements of a particular FESS procedure, arthroscopic surgery, dermatological procedure, ophthalmic procedures, open surgery or other endoscopic surgery procedure. A description of a suitable power source can be found in U.S. patent application Ser. No. 60/062,997 filed Oct. 23, 1997, the complete disclosure of which has been incorporated herein by reference.

The power source may be current limited or otherwise controlled so that undesired heating of the target tissue or surrounding (non-target) tissue does not occur. In one embodiment of the present invention, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual active electrode in contact with a low resistance medium (e.g., saline irrigant or conductive gel), the resistance of the current limiting resistor increases significantly, thereby minimizing the power delivery from the active electrode into the low resistance medium (e.g., saline irrigant or conductive gel).

It should be clearly understood that the invention is not limited to electrically isolated active electrodes, or even to a plurality of active electrodes. For example, the array of active electrodes may be connected to a single lead that extends through the probe shaft to a power source of high frequency current. Alternatively, the probe may incorporate a single electrode that extends directly through the probe shaft or is connected to a single lead that extends to the power source. The active electrode may have a ball shape (e.g., for tissue vaporization and desiccation), a twizzle shape (for vaporization and needle-like cutting), a spring shape (for rapid tissue debulking and desiccation), a twisted metal shape, an annular or solid tube shape or the like. Alternatively, the electrode may comprise a plurality of filaments, a rigid or flexible brush electrode (for debulking a tumor, such as a fibroid, bladder tumor or a prostate adenoma), a side-effect brush electrode on a lateral surface of the shaft, a coiled electrode or the like. In one embodiment, the probe comprises a single active electrode that extends from an insulating member, e.g., ceramic, at the distal end of the probe. The insulating member is preferably a tubular structure that separates the active electrode from a tubular or annular return electrode positioned proximal to the insulating member and the active electrode.

Referring now to FIG. 1, an exemplary electrosurgical system 5 for resection, ablation, coagulation and/or contraction of tissue will now be described in detail. As shown, electrosurgical system 5 generally includes an electrosurgical probe 20 connected to a power supply 10 for providing high frequency voltage to one or more active electrodes and a loop electrode (not shown in FIG. 1) on probe 20. Probe 20 includes a connector housing 44 at its proximal end, which can be removably connected to a probe receptacle 32 of a probe cable 22. The proximal portion of cable 22 has a connector 34 to couple probe 20 to power supply 10. Power supply 10 has an operator controllable voltage level adjustment 38 to change the applied voltage level, which is observable at a voltage level display 40. Power supply 10 also includes one or more foot pedals 24 and a cable 26 which is removably coupled to a receptacle 30 with a cable connector 28. The foot pedal 24 may also include a second pedal (not shown) for remotely adjusting the energy level applied to active electrodes 104 (FIG. 2), and a third pedal (also not shown) for switching between an ablation mode and a coagulation mode.

Figure 2:
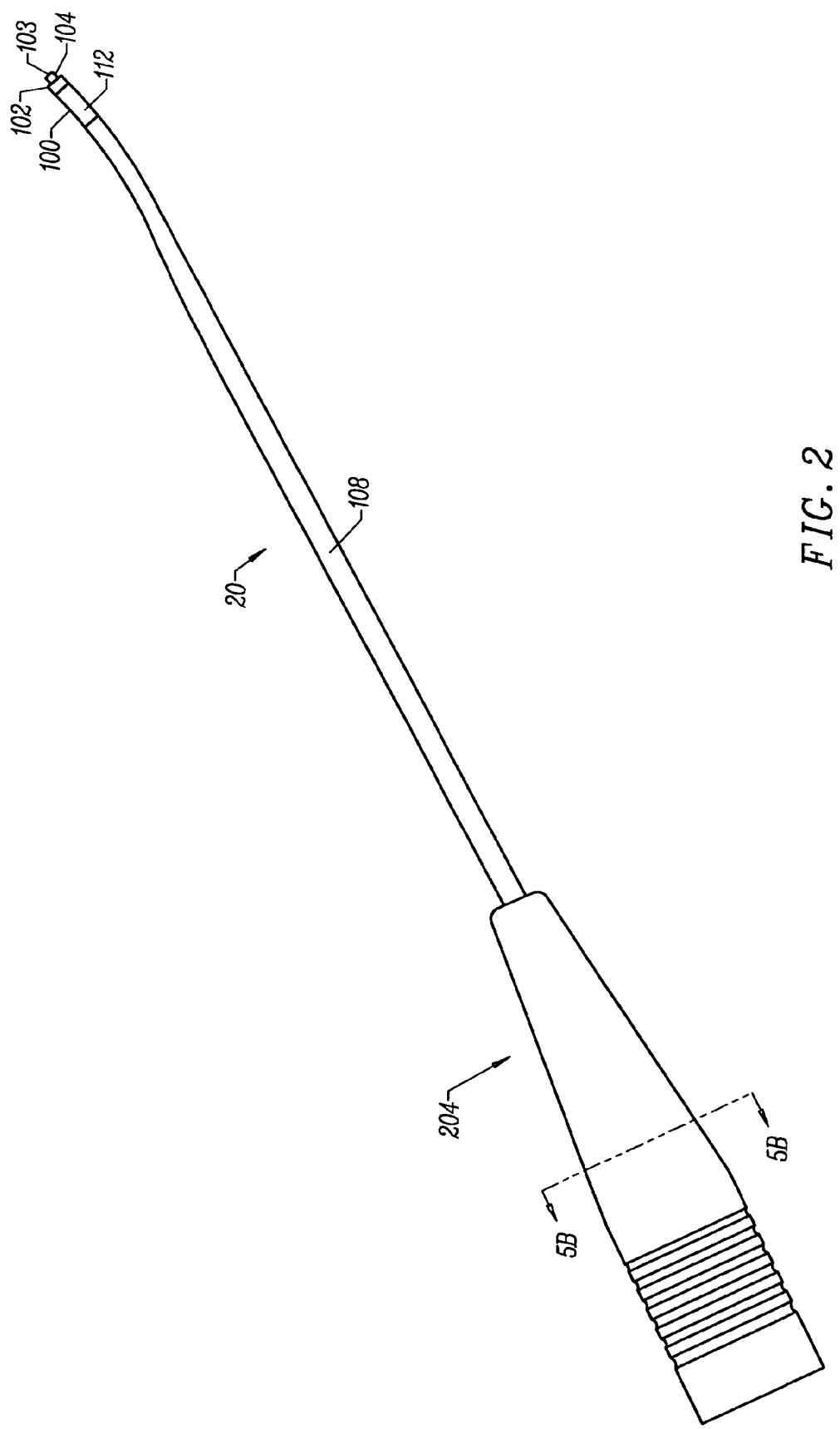
FIG. 2 is a side view of an electrosurgical probe according to the present invention incorporating a loop electrode for resection and ablation of tissue.

FIGS. 2–5 illustrate an exemplary electrosurgical probe 20 constructed according to the principles of the present invention. As shown in FIG. 2, probe 20 generally includes an elongated shaft 100 which may be flexible or rigid, a handle 204 coupled to the proximal end of shaft 100 and an electrode support member 102 coupled to the distal end of shaft 100. Shaft 100 preferably comprises an electrically conducting material, usually metal, which is selected from the group consisting of tungsten, stainless steel alloys, platinum or its alloys, titanium or its alloys, molybdenum or its alloys, and nickel or its alloys. Shaft 100 includes an electrically insulating jacket 108, which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating of the structure at the point of contact causing necrosis.

Figure 3:
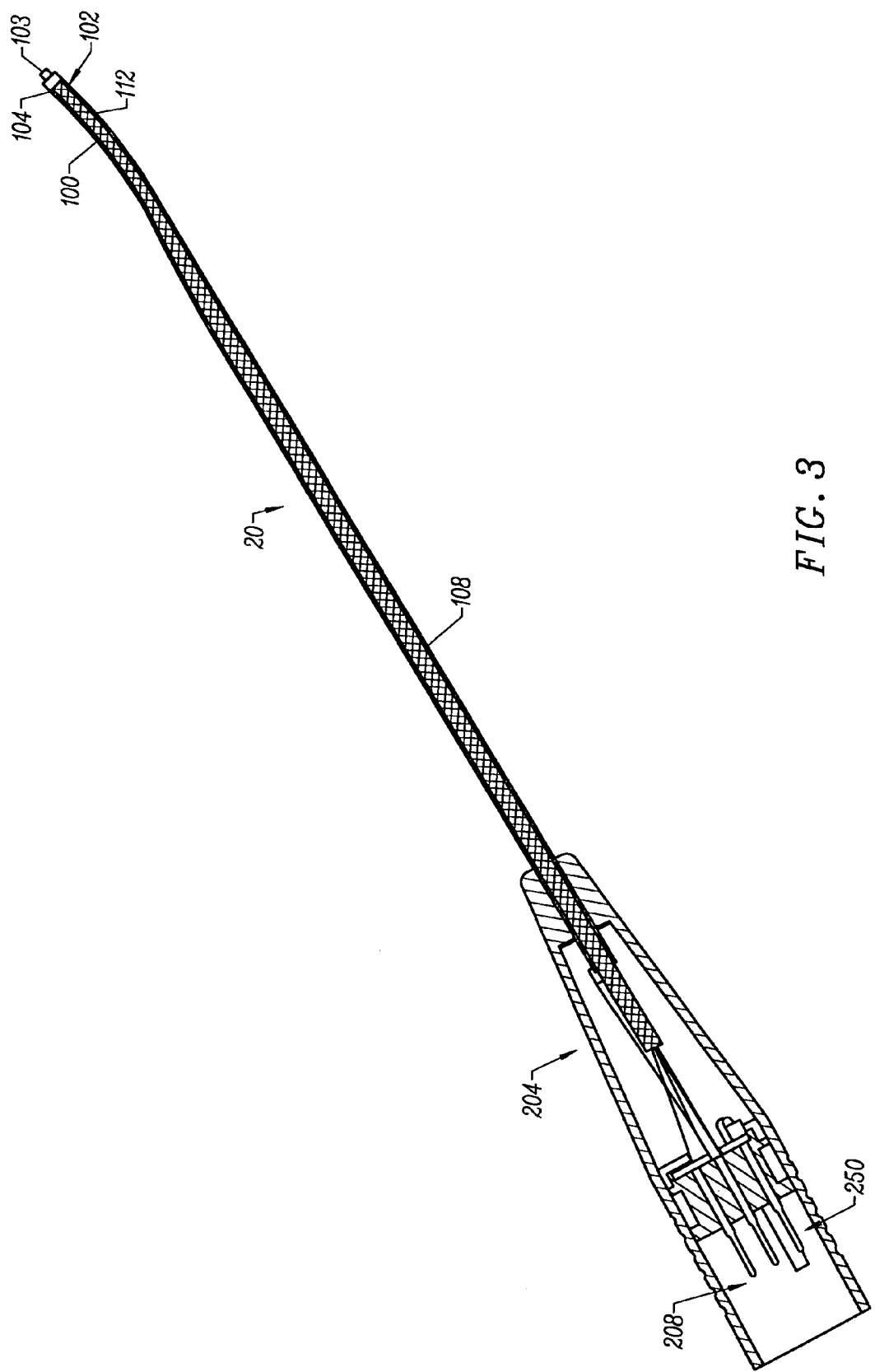
FIG. 3 is a cross-sectional view of the electrosurgical probe of FIG. 2.

Handle 204 typically comprises a plastic material that is easily molded into a suitable shape for handling by the surgeon. As shown in FIG. 3, handle 204 defines an inner cavity 208 that houses electrical connections 250 (discussed below), and provides a suitable interface for connection to an electrical connecting cable 22 (see FIG. 1). As shown in FIG. 5B, the probe will also include a coding resistor 400 having a value selected to program different output ranges and modes of operation for the power supply. This allows a single power supply to be used with a variety of different probes in different applications (e.g., dermatology, cardiac surgery, neurosurgery, arthroscopy, etc). Electrode support member 102 extends from the distal end of shaft 100 (usually about 1 to 20 mm), and provides support for a loop electrode 103 and a plurality of electrically isolated active electrodes 104 (see FIG. 4).

As shown in FIG. 3, the distal portion of shaft 100 is preferably bent to improve access to the operative site of the tissue being treated (e.g., contracted). Electrode support member 102 has a substantially planar tissue treatment surface 212 (see FIG. 4) that is usually at an angle of about 10 to 90 degrees relative to the longitudinal axis of shaft 100, preferably about 10 to 30 degrees and more preferably about 15-18 degrees. In addition, the distal end of the shaft may have a bevel, as described in commonly-assigned patent application Ser. No. 08/562,332 filed Nov. 22, 1995, now U.S. Pat. No. 6,024,733. In alternative embodiments, the distal portion of shaft 100 comprises a flexible material which can be deflected relative to the longitudinal axis of the shaft. Such deflection may be selectively induced by mechanical tension of a pull wire, for example, or by a shape memory wire that expands or contracts by externally applied temperature changes. A more complete description of this embodiment can be found in PCT International Application, U.S. National Phase Serial No. PCT/US94/05168.

The bend in the distal portion of shaft 100 is particularly advantageous in arthroscopic treatment of joint tissue as it allows the surgeon to reach the target tissue within the joint as the shaft 100 extends through a cannula or portal. Of course, it will be recognized that the shaft may have different angles depending on the procedure. For example, a shaft having a 90° bend angle may be particularly useful for accessing tissue located in the back portion of a joint compartment and a shaft having a 10° to 30° bend angle may be useful for accessing tissue near or in the front portion of the joint compartment.

Figure 4:
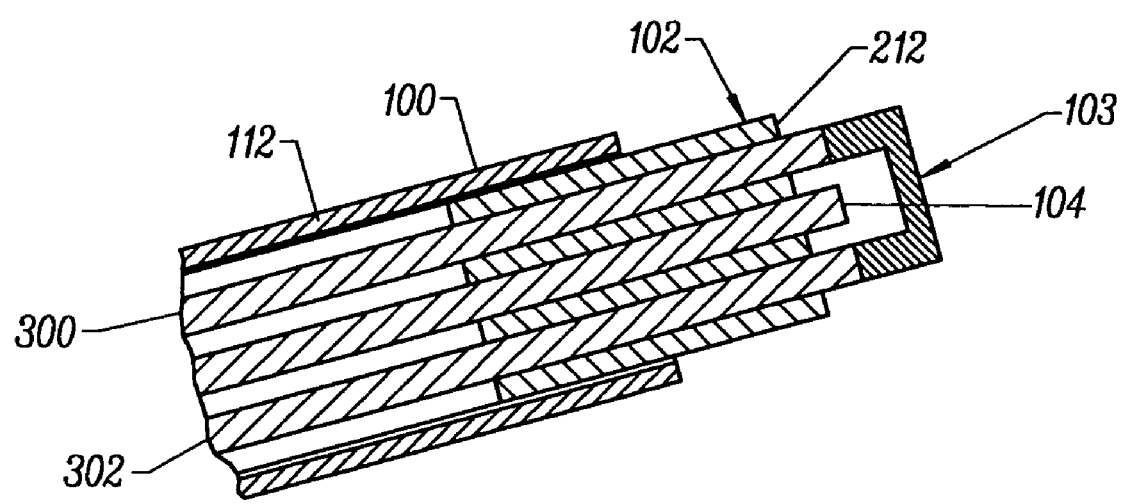
FIG. 4 is an exploded sectional view of a distal portion of the electrosurgical probe.
Figure 5B:
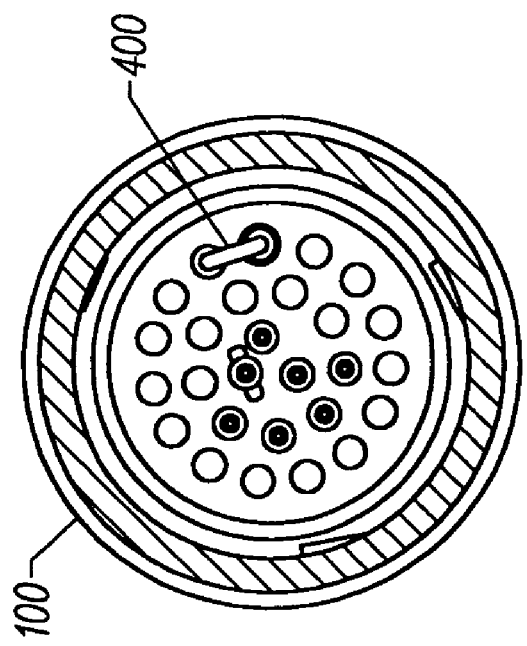
FIGS. 5A and 5B are end and cross-sectional views, respectively, of the proximal portion of the probe.
Figure 5A:
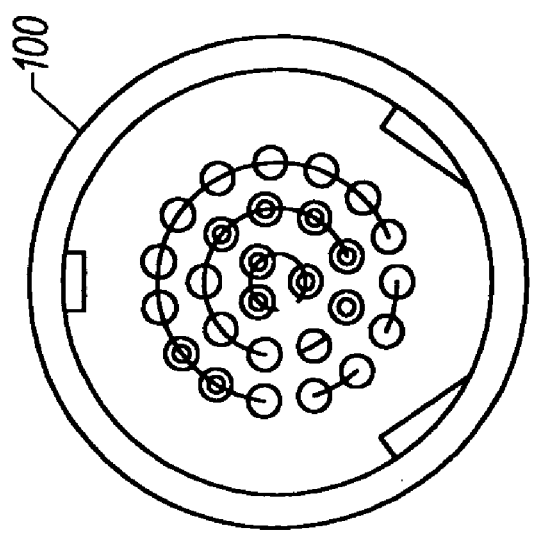

As shown in FIG. 4, loop electrode 103 has first and second ends extending from the electrode support member 102. The first and second ends are coupled to, or integral with, a pair of connectors 300, 302, e.g., wires, that extend through the shaft of the probe to its proximal end for coupling to the high frequency power supply. The loop electrode usually extends about 0.5 to about 10 mm from the distal end of support member 102, preferably about 1 to 2 mm. In the representative embodiment, the loop electrode has a solid construction with a substantially uniform cross-sectional area, e.g., circular, square, etc. Of course, it will be recognized that the loop or ablation electrode may have a wide variety of cross-sectional shapes, such as annular, square, rectangular, L-shaped, V-shaped, D-shaped, C-shaped, star-shaped and crossed-shaped, as described in commonly-assigned patent application Ser. No. 08/687792. In addition, it should be noted that loop electrode 103 may have a geometry other than that shown in FIGS. 2–5, such as a semi-circular loop, a V-shaped loop, a straight wire electrode extending between two support members, and the like. Also, loop electrode may be positioned on a lateral surface of the shaft, or it may extend at a transverse angle from the distal end of the shaft, depending on the particular surgical procedure.

Loop electrode 103 usually extends further away from the support member than the active electrodes 104 to facilitate resection and ablation of tissue. As discussed below, loop electrode 103 is especially configured for resecting fragments or pieces of tissue, while the active electrodes ablate or cause molecular dissociation or disintegration of the removed pieces from the fluid environment. In the presently preferred embodiment, the probe will include 3 to 7 active electrodes positioned on either side of the loop electrode. The probe may further include a suction lumen (not shown) for drawing the pieces of tissue toward the active electrodes after they have been removed from the target site by the loop electrode 103.

Referring to FIG. 4, the electrically isolated active electrodes 104 are preferably spaced apart over tissue treatment surface 212 of electrode support member 102. The tissue treatment surface and individual active electrodes 104 will usually have dimensions within the ranges set forth above. In the representative embodiment, the tissue treatment surface 212 has an oval cross-sectional shape with a length L in the range of 1 mm to 20 mm and a width W in the range from 0.3 mm to 7 mm. The oval cross-sectional shape accommodates the bend in the distal portion of shaft 202. The active electrodes 104 preferably extend slightly outward from surface 212, typically by a distance from 0.2 mm to 2. However, it will be understood that electrodes 104 may be flush with this surface, or even recessed, if desired. In one embodiment of the invention, the active electrodes are axially adjustable relative to the tissue treatment surface so that the surgeon can adjust the distance between the surface and the active electrodes.

In the embodiment shown in FIGS. 2–5, probe 20 includes a return electrode 112 for completing the current path between active electrodes 104, loop electrode 103 and a high frequency power supply 10 (see FIG. 1). As shown, return electrode 112 preferably comprises an annular exposed region of shaft 102 slightly proximal to tissue treatment surface 212 of electrode support member 102. Return electrode 112 typically has a length of about 0.5 to 10 mm and more preferably about 1 to 10 mm. Return electrode 112 is coupled to a connector 250 that extends to the proximal end of probe 10, where it is suitably connected to power supply 10 (FIG. 1).

As shown in FIG. 2, return electrode 112 is not directly connected to active electrodes 104 and loop electrode 103. To complete a current path from active electrodes 104 or loop electrodes 103 to return electrode 112, electrically conductive fluid (e.g., isotonic saline) is caused to flow therebetween. In the representative embodiment, the electrically conductive fluid is delivered from a fluid delivery element (not shown) that is separate from probe 20. In arthroscopic surgery, for example, the joint cavity will be flooded with isotonic saline and the probe 20 will be introduced into this flooded cavity. Electrically conductive fluid will be continually re-supplied to maintain the conduction path between return electrode 112 and active electrodes 104 and loop electrode 103.

In alternative embodiments, the fluid path may be formed in probe 20 by, for example, an inner lumen or an annular gap (not shown) between the return electrode and a tubular support member within shaft 100. This annular gap may be formed near the perimeter of the shaft 100 such that the electrically conductive fluid tends to flow radially inward towards the target site, or it may be formed towards the center of shaft 100 so that the fluid flows radially outward. In both of these embodiments, a fluid source (e.g., a bag of fluid elevated above the surgical site or having a pumping device), is coupled to probe 20 via a fluid supply tube (not shown) that may or may not have a controllable valve. A more complete description of an electrosurgical probe incorporating one or more fluid lumen(s) can be found in commonly assigned, patent application Ser. No. 08/485,219, filed on Jun. 7, 1995, now U.S. Pat. No. 5,697,281, the complete disclosure of which is incorporated herein by reference.

In addition, probe 20 may include an aspiration lumen (not shown) for aspirating excess conductive fluid, other fluids, such as blood, and/or tissue fragments from the target site. The probe may also include one or more aspiration electrode(s), such as those described below in reference to FIGS. 8–12, for ablating the aspirated tissue fragments. Alternatively, the aspiration electrode(s) may comprise the active electrodes described above. For example, the probe may have an aspiration lumen with a distal opening positioned adjacent one or more of the active electrodes at the distal end of the probe. As tissue fragments are drawn into the aspiration lumen, the active electrodes are energized to ablate at least a portion of these fragments to prevent clogging of the lumen.

Figure 6:
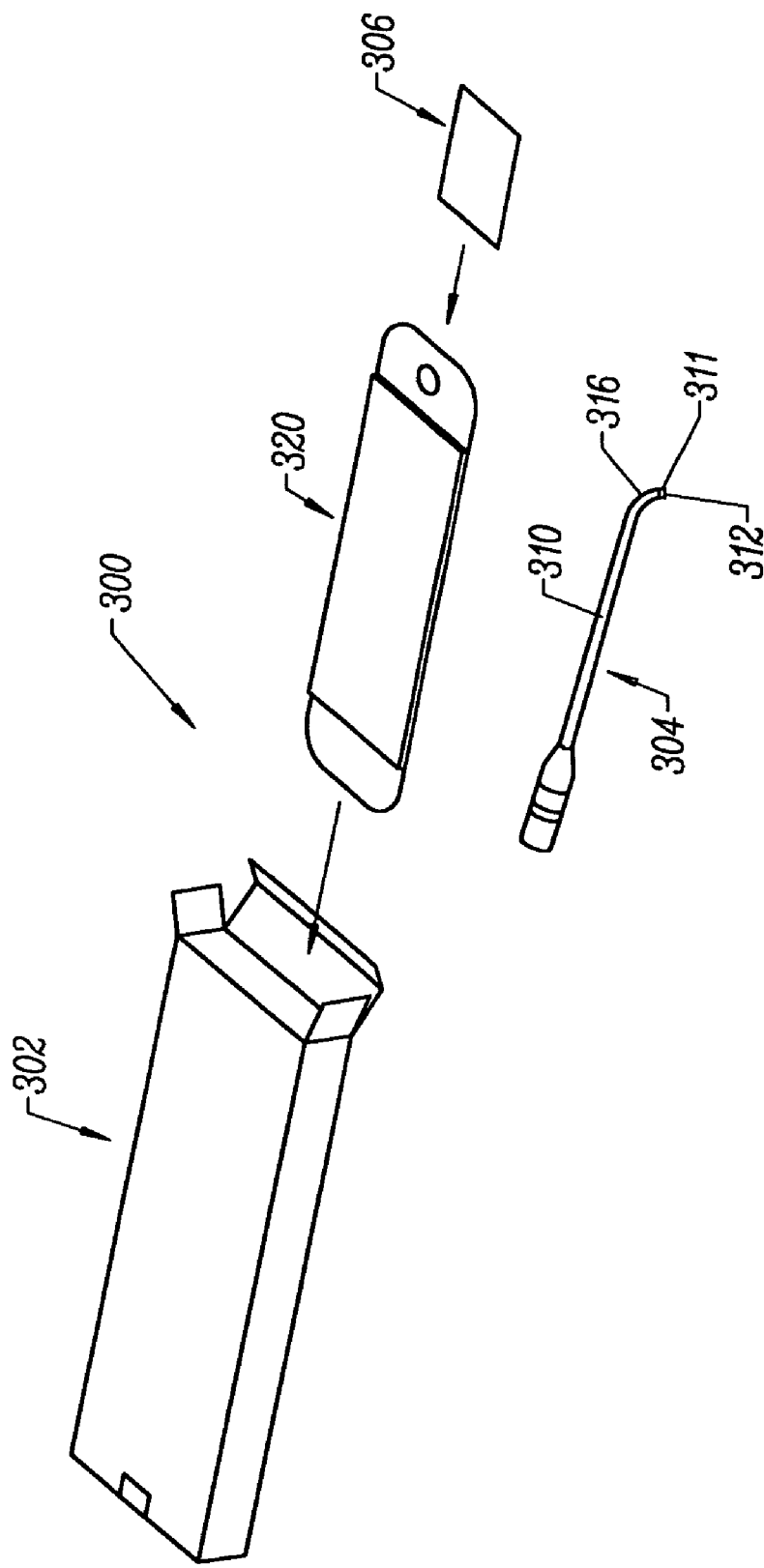
FIG. 6 illustrates a surgical kit for removing and ablating tissue according to the present invention.

Referring now to FIG. 6, a surgical kit 300 for resecting and/or ablating tissue within a joint according to the invention will now be described. As shown, surgical kit 300 includes a package 302 for housing a surgical instrument 304, and an instructions for use 306 of instrument 304. Package 302 may comprise any suitable package, such as a box, carton, wrapping, etc. In the exemplary embodiment, kit 300 further includes a sterile wrapping 320 for packaging and storing instrument 304. Instrument 304 includes a shaft 310 having at least one loop electrode 311 and at least one active electrode 312 at its distal end, and at least one connector (not shown) extending from loop electrode 311 and active electrode 312 to the proximal end of shaft 310. The instrument 304 is generally disposable after a single procedure. Instrument 304 may or may not include a return electrode 316.

The instructions for use 306 generally includes the steps of adjusting a voltage level of a high frequency power supply (not shown) to effect resection and/or ablation of tissue at the target site, connecting the surgical instrument 304 to the high frequency power supply, positioning the loop electrode 311 and the active electrode 312 within electrically conductive fluid at or near the tissue at the target site, and activating the power supply. The voltage level is usually about 40 to 400 volts RMS for operating frequencies of about 100 to 200 kHz. In a preferred embodiment, the positioning step includes introducing at least a distal portion of the instrument 304 through a portal into a joint.

The present invention is particularly useful for lateral release procedures, or for resecting and ablating a bucket-handle tear of the medial meniscus. In the latter technique, the probe is introduced through a medial port and the volume which surrounds the working end of the probe is filled with an electrically conductive fluid which may, by way of example, be isotonic saline or other biocompatible, electrically conductive irrigant solution. When a voltage is applied between the loop electrode and the return electrode, electrical current flows from the loop electrode, through the irrigant solution to the return electrode. The anterior horn is excised by pressing the exposed portion of the loop electrode into the tear and removing one or more tissue fragments. The displaced fragments are then ablated with the active electrodes as described above.

Through a central patellar splitting approach, the probe is then placed within the joint through the intercondylar notch, and the attached posterior horn insertion is resected by pressing the loop electrode into the attached posterior fragment. The fragment is then removed with the active electrodes and the remnant is checked for stability.

Figure 7:
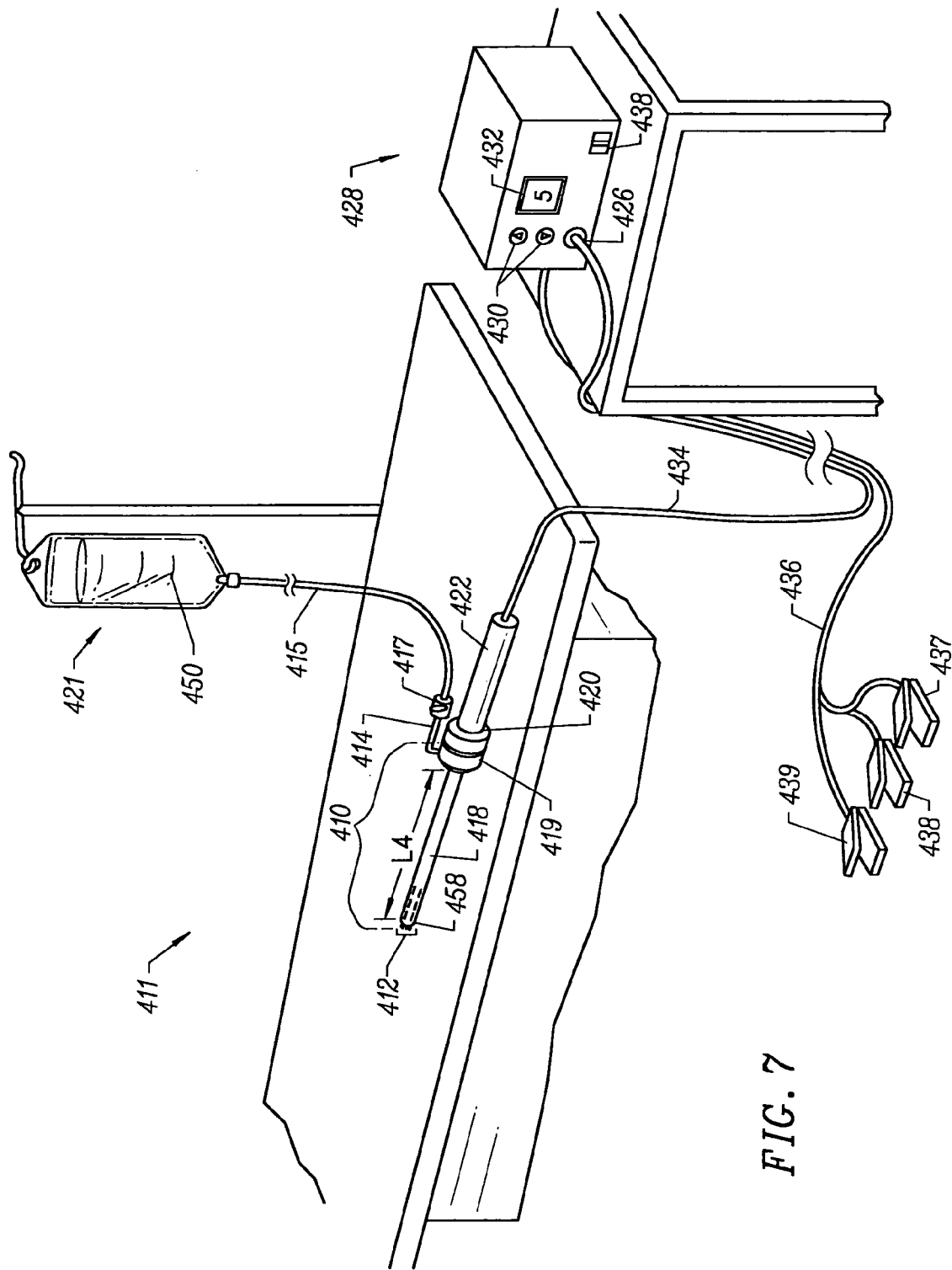
FIG. 7 is a perspective view of another electrosurgical system incorporating a power supply, an electrosurgical probe and a supply of electrically conductive fluid for delivering the fluid to the target site.

Referring now to FIG. 7, an exemplary electrosurgical system 411 for treatment of tissue in 'dry fields' will now be described in detail. Of course, system 411 may also be used in a 'wet field', i.e., the target site is immersed in electrically conductive fluid. However, this system is particularly useful in 'dry fields' where the fluid is preferably delivered through an electrosurgical probe to the target site. As shown, electrosurgical system 411 generally comprises an electrosurgical handpiece or probe 410 connected to a power supply 428 for providing high frequency voltage to a target site and a fluid source 421 for supplying electrically conductive fluid 450 to probe 410. In addition, electrosurgical system 411 may include an endoscope (not shown) with a fiber optic head light for viewing the surgical site, particularly in sinus procedures or procedures in the ear or the back of the mouth. The endoscope may be integral with probe 410, or it may be part of a separate instrument. The system 411 may also include a vacuum source (not shown) for coupling to a suction lumen or tube in the probe 410 for aspirating the target site.

As shown, probe 410 generally includes a proximal handle 419 and an elongate shaft 418 having an array 412 of active electrodes 458 at its distal end. A connecting cable 434 has a connector 426 for electrically coupling the active electrodes 458 to power supply 428. The active electrodes 458 are electrically isolated from each other and each of the terminals 458 is connected to an active or passive control network within power supply 428 by means of a plurality of individually insulated conductors (not shown). A fluid supply tube 415 is connected to a fluid tube 414 of probe 410 for supplying electrically conductive fluid 450 to the target site.

Similar to the above embodiment, power supply 428 has an operator controllable voltage level adjustment 430 to change the applied voltage level, which is observable at a voltage level display 432. Power supply 428 also includes first, second and third foot pedals 437, 438, 439 and a cable 436 which is removably coupled to power supply 428. The foot pedals 437, 438, 439 allow the surgeon to remotely adjust the energy level applied to active electrodes 458. In an exemplary embodiment, first foot pedal 437 is used to place the power supply into the ablation mode and second foot pedal 438 places power supply 428 into the "coagulation" mode. The third foot pedal 439 allows the user to adjust the voltage level within the "ablation" mode. In the ablation mode, a sufficient voltage is applied to the active electrodes to establish the requisite conditions for molecular dissociation of the tissue (i.e., vaporizing a portion of the electrically conductive fluid, ionizing charged particles within the vapor layer, and accelerating these charged particles against the tissue). As discussed above, the requisite voltage level for ablation will vary depending on the number, size, shape and spacing of the electrodes, the distance to which the electrodes extend from the support member, etc. Once the surgeon places the power supply in the ablation mode, voltage level adjustment 430 or third foot pedal 439 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the coagulation mode, the power supply 428 applies a low enough voltage to the active electrodes (or the coagulation electrode) to avoid vaporization of the electrically conductive fluid and subsequent molecular dissociation of the tissue. The surgeon may automatically toggle the power supply between the ablation and coagulation modes by alternately stepping on foot pedals 437, 438, respectively. This allows the surgeon to quickly move between coagulation and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulate small severed vessels within the tissue. However, larger vessels, or vessels with high fluid pressures (e.g., arterial vessels) may not be sealed in the ablation mode. Accordingly, the surgeon can simply actuate foot pedal 438, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by actuating foot pedal 437. A specific design of a suitable power supply for use with the present invention can be found in U.S. Provisional Patent Application No. 60/062,997 filed Oct. 23, 1997, previously incorporated herein by reference.

Figure 8:
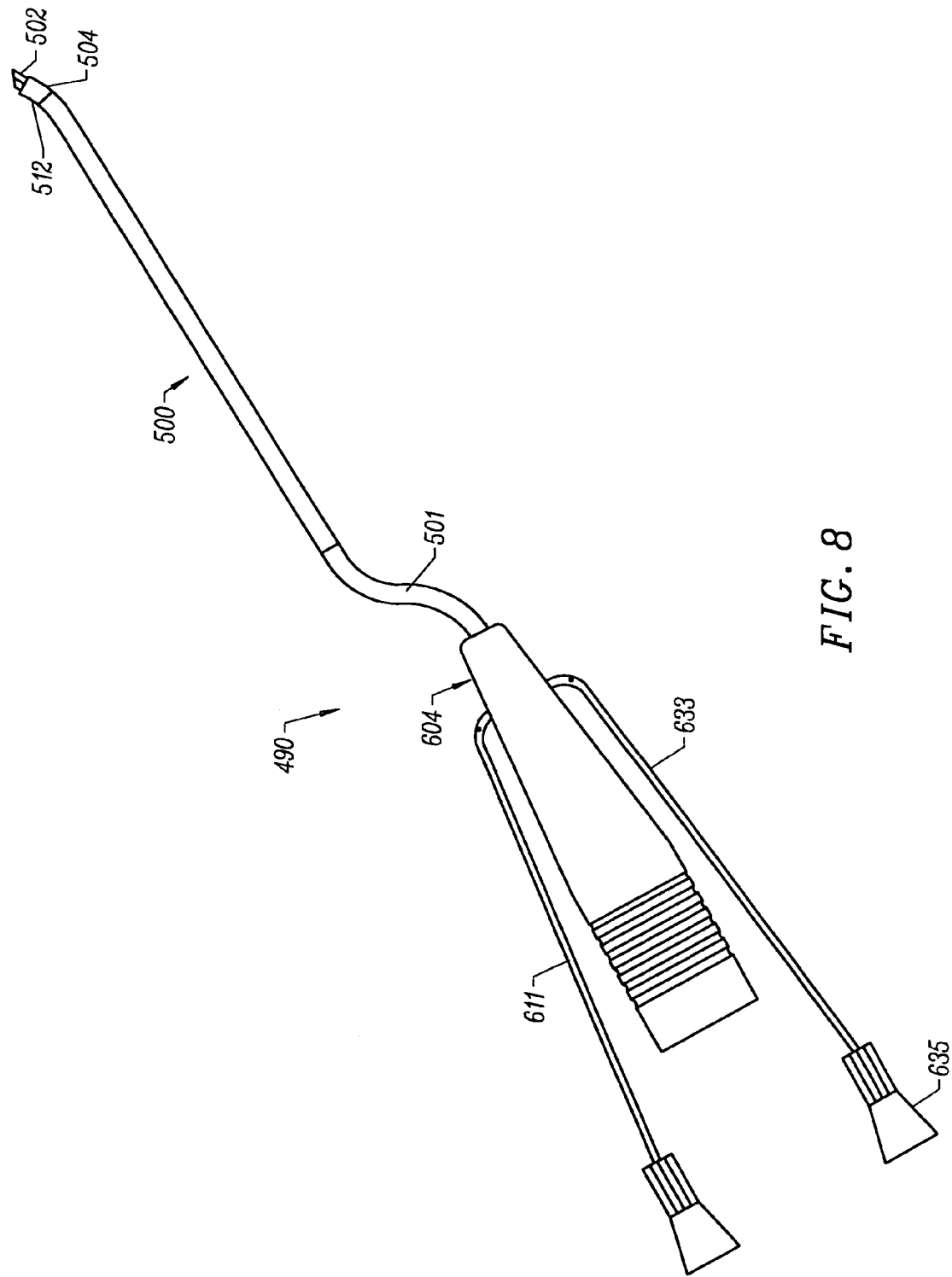
FIG. 8 is a side view of another electrosurgical probe according to the present invention incorporating aspiration electrodes for ablating aspirated tissue fragments and/or tissue strands, such as synovial tissue.
Figure 9:
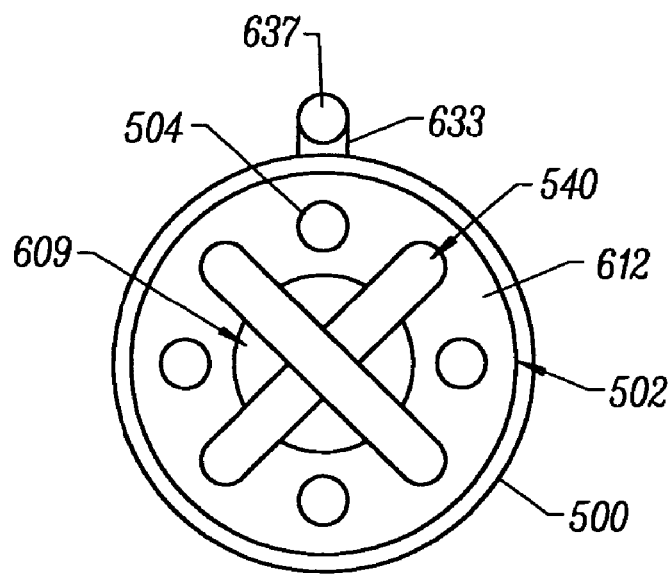
FIG. 9 is an end view of the probe of FIG. 8.
Figure 10:
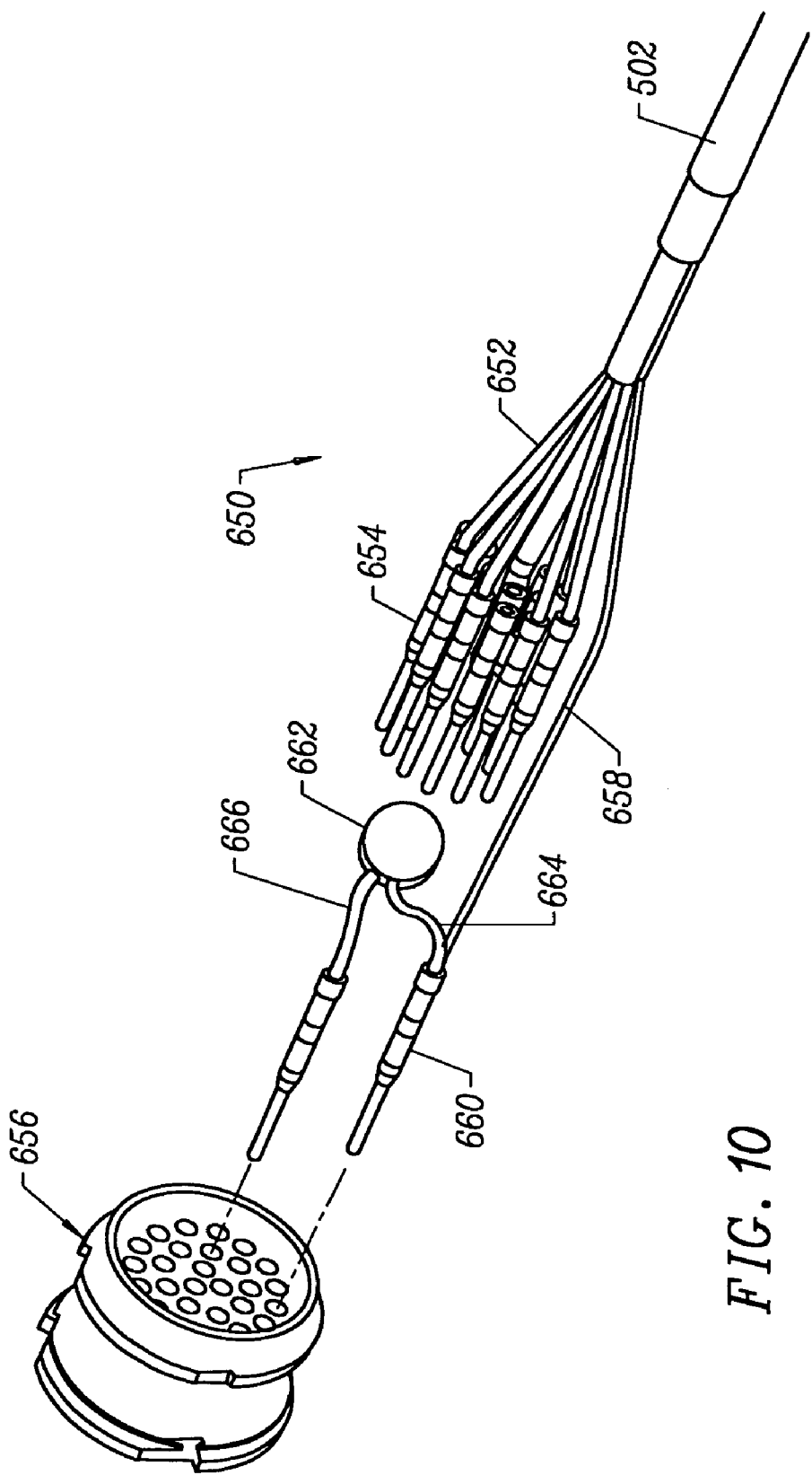
FIG. 10 is an exploded view of a proximal portion of the electrosurgical probe.

FIGS. 8–10 illustrate an exemplary electrosurgical probe 490 constructed according to the principles of the present invention. As shown in FIG. 8, probe 490 generally includes an elongated shaft 500 which may be flexible or rigid, a handle 604 coupled to the proximal end of shaft 500 and an electrode support member 502 coupled to the distal end of shaft 500. Shaft 500 preferably includes a bend 501 that allows the distal section of shaft 500 to be offset from the proximal section and handle 604. This offset facilitates procedures that require an endoscope, such as FESS, because the endoscope can, for example, be introduced through the same nasal passage as the shaft 500 without interference between handle 604 and the eyepiece of the endoscope (see FIG. 16). In one embodiment, shaft 500 preferably comprises a plastic material that is easily molded into the desired shape.

In an alternative embodiment (not shown), shaft 500 comprises an electrically conducting material, usually metal, which is selected from the group comprising tungsten, stainless steel alloys, platinum or its alloys, titanium or its alloys, molybdenum or its alloys, and nickel or its alloys. In this embodiment, shaft 500 includes an electrically insulating jacket 508 which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating and necrosis of the structure at the point of contact.

Handle 604 typically comprises a plastic material that is easily molded into a suitable shape for handling by the surgeon. Handle 604 defines an inner cavity (not shown) that houses the electrical connections 650 (FIG. 10), and provides a suitable interface for connection to an electrical connecting cable 422 (see FIG. 7). Electrode support member 502 extends from the distal end of shaft 500 (usually about 1 to 20 mm), and provides support for a plurality of electrically isolated active electrodes 504 (see FIG. 9). As shown in FIG. 8, a fluid tube 633 extends through an opening in handle 604, and includes a connector 635 for connection to a fluid supply source, for supplying electrically conductive fluid to the target site. Depending on the configuration of the distal surface of shaft 500, fluid tube 633 may extend through a single lumen (not shown) in shaft 500, or it may be coupled to a plurality of lumens (also not shown) that extend through shaft 500 to a plurality of openings at its distal end. In the representative embodiment, fluid tube 633 extends along the exterior of shaft 500 to a point just proximal of return electrode 512 (see FIG. 9). In this embodiment, the fluid is directed through an opening 637 past return electrode 512 to the active electrodes 504. Probe 490 may also include a valve 417 (FIG. 8) or equivalent structure for controlling the flow rate of the electrically conductive fluid to the target site.

As shown in FIG. 8, the distal portion of shaft 500 is preferably bent to improve access to the operative site of the tissue being treated. Electrode support member 502 has a substantially planar tissue treatment surface 612 that is usually at an angle of about 10 to 90 degrees relative to the longitudinal axis of shaft 600, preferably about 30 to 60 degrees and more preferably about 45 degrees. In alternative embodiments, the distal portion of shaft 500 comprises a flexible material which can be deflected relative to the longitudinal axis of the shaft. Such deflection may be selectively induced by mechanical tension of a pull wire, for example, or by a shape memory wire that expands or contracts by externally applied temperature changes. A more complete description of this embodiment can be found in PCT International Application, U.S. National Phase Serial No. PCT/US94/05168, filed on May 10, 1994, now U.S. Pat. No. 5,697,909, the complete disclosure of which has is incorporated herein by reference.

The bend in the distal portion of shaft 500 is particularly advantageous in the treatment of sinus tissue as it allows the surgeon to reach the target tissue within the nose as the shaft 500 extends through the nasal passage. Of course, it will be recognized that the shaft may have different angles depending on the procedure. For example, a shaft having a 90° bend angle may be particularly useful for accessing tissue located in the back portion of the mouth and a shaft having a 10° to 30° bend angle may be useful for accessing tissue near or in the front portion of the mouth or nose In the embodiment shown in FIGS. 8–10, probe 490 includes a return electrode 512 for completing the current path between active electrodes 504 and a high frequency power supply (e.g., power supply 428, FIG. 8). As shown, return electrode 512 preferably comprises an annular conductive band coupled to the distal end of shaft 500 slightly proximal to tissue treatment surface 612 of electrode support member 502, typically about 0.5 to 10 mm and more preferably about 1 to 10 mm from support member 502. Return electrode 512 is coupled to a connector 658 that extends to the proximal end of probe 409, where it is suitably connected to power supply 428 (FIG. 7).

As shown in FIG. 8, return electrode 512 is not directly connected to active electrodes 504. To complete this current path so that active electrodes 504 are electrically connected to return electrode 512, electrically conductive fluid (e.g., isotonic saline) is caused to flow therebetween. In the representative embodiment, the electrically conductive fluid is delivered through fluid tube 633 to opening 637, as described above. Alternatively, the fluid may be delivered by a fluid delivery element (not shown) that is separate from probe 490. In arthroscopic surgery, for example, the joint cavity will be flooded with isotonic saline and the probe 490 will be introduced into this flooded cavity. Electrically conductive fluid will be continually re-supplied to maintain the conduction path between return electrode 512 and active electrodes 504.

In alternative embodiments, the fluid path may be formed in probe 490 by, for example, an inner lumen or an annular gap between the return electrode and a tubular support member within shaft 500. This annular gap may be formed near the perimeter of the shaft 500 such that the electrically conductive fluid tends to flow radially inward towards the target site, or it may be formed towards the center of shaft 500 so that the fluid flows radially outward. In both of these embodiments, a fluid source (e.g., a bag of fluid elevated above the surgical site or having a pumping device), is coupled to probe 490 via a fluid supply tube (not shown) that may or may not have a controllable valve. A more complete description of an electrosurgical probe incorporating one or more fluid lumen(s) can be found in parent patent application Ser. No. 08/485,219, filed on Jun. 7, 1995, now U.S. Pat. No. 5,697,281, the complete disclosure of is incorporated herein by reference.

Referring to FIG. 9, the electrically isolated active electrodes 504 are spaced apart over tissue treatment surface 612 of electrode support member 502. The tissue treatment surface and individual active electrodes 504 will usually have dimensions within the ranges set forth above. As shown, the probe includes a single, larger opening 609 in the center of tissue treatment surface 612, and a plurality of active electrodes (e.g., about 3–15) around the perimeter of surface 612 (see FIG. 9). Alternatively, the probe may include a single, annular, or partially annular, active electrode at the perimeter of the tissue treatment surface. The central opening 609 is coupled to a suction lumen (not shown) within shaft 500 and a suction tube 611 (FIG. 8) for aspirating tissue, fluids and/or gases from the target site. In this embodiment, the electrically conductive fluid generally flows radially inward past active electrodes 504 and then back through the opening 609. Aspirating the electrically conductive fluid during surgery allows the surgeon to see the target site, and it prevents the fluid from flowing into the patient's body, e.g., through the sinus passages, down the patient's throat or into the ear canal.

As shown, one or more of the active electrodes 504 comprise loop electrodes 540 that extend across distal opening 609 of the suction lumen within shaft 500. In the representative embodiment, two of the active electrodes 504 comprise loop electrodes 540 that cross over the distal opening 609. Of course, it will be recognized that a variety of different configurations are possible, such as a single loop electrode, or multiple loop electrodes having different configurations than shown. In addition, the electrodes may have shapes other than loops, such as the coiled configurations shown in FIGS. 11 and 12. Alternatively, the electrodes may be formed within the suction lumen proximal to the distal opening 609, as shown in FIG. 13. The main function of loop electrodes 540 is to ablate portions of tissue that are drawn into the suction lumen to prevent clogging of the lumen.

Loop electrodes 540 are electrically isolated from the other active electrodes 504, which can be referred to hereinafter as the ablation electrodes 504. Loop electrodes 540 may or may not be electrically isolated from each other. Loop electrodes 540 will usually extend only about 0.05 to 4 mm, preferably about 0.1 to 1 mm from the tissue treatment surface of electrode support member 504.

Of course, it will be recognized that the distal tip of the probe may have a variety of different configurations. For example, the probe may include a plurality of openings 609 around the outer perimeter of tissue treatment surface 612. In this embodiment, the active electrodes 504 extend from the center of tissue treatment surface 612 radially inward from openings 609. The openings are suitably coupled to fluid tube 633 for delivering electrically conductive fluid to the target site, and a suction tube 611 for aspirating the fluid after it has completed the conductive path between the return electrode 512 and the active electrodes 504. In this embodiment, the ablation active electrodes 504 are close enough to openings 609 to ablate most of the large tissue fragments that are drawn into these openings.

FIG. 10 illustrates the electrical connections 650 within handle 604 for coupling active electrodes 504 and return electrode 512 to the power supply 428. As shown, a plurality of wires 652 extend through shaft 500 to couple terminals 504 to a plurality of pins 654, which are plugged into a connector block 656 for coupling to a connecting cable 422 (FIG. 7). Similarly, return electrode 512 is coupled to connector block 656 via a wire 658 and a plug 660.

In use, the distal portion of probe 490 is introduced to the target site (either endoscopically, through an open procedure, or directly onto the patient's skin) and active electrodes 504 are positioned adjacent to tissue at the target site. Electrically conductive fluid is delivered through tube 633 and opening 637 to the tissue. The fluid flows past the return electrode 512 to the active electrodes 504 at the distal end of the shaft. The rate of fluid flow is controlled with valve 417 (FIG. 7) such that the zone between the tissue and electrode support 502 is constantly immersed in the fluid. The power supply 428 is then turned on and adjusted such that a high frequency voltage difference is applied between active electrodes 504 and return electrode 512. The electrically conductive fluid provides the conduction path between active electrodes 504 and the return electrode 512.

In the representative embodiment, the high frequency voltage is sufficient to convert the electrically conductive fluid (not shown) between the target tissue and active electrodes 504 into an ionized vapor layer or plasma (not shown). As a result of the applied voltage difference between active electrode(s) 504 and the target tissue (i.e., the voltage gradient across the plasma layer), charged particles in the plasma (e.g., electrons) are accelerated towards the tissue. At sufficiently high voltage differences, these charged particles gain sufficient energy to cause dissociation of the molecular bonds within tissue structures. This molecular dissociation is accompanied by the volumetric removal (i.e., ablative sublimation) of tissue and the production of low molecular weight gases, such as oxygen, nitrogen, carbon dioxide, hydrogen and methane. The short range of the accelerated charged particles within the tissue confines the molecular dissociation process to the surface layer to minimize damage and necrosis to the underlying tissue.

During the process, the gases will be aspirated through opening 609 and suction tube 611 to a vacuum source or collection reservoir (not shown). In addition, excess electrically conductive fluid and other fluids (e.g., blood) will be aspirated from the target site to facilitate the surgeon's view. Applicant has also found that tissue fragments are also aspirated through opening 609 into suction lumen and tube 611 during the procedure. These tissue fragments are ablated or dissociated with loop electrodes 540 with a similar mechanism described above. Namely, as electrically conductive fluid and tissue fragments are aspirated towards loop electrodes 540, these electrodes are activated so that a high frequency voltage is applied to loop electrodes 540 and return electrode 512 (of course, the probe may include a different, separate return electrode for this purpose). The voltage is sufficient to vaporize the fluid, and create a plasma layer between loop electrodes 540 and the tissue fragments so that portions of the tissue fragments are ablated or removed. This reduces the volume of the tissue fragments as they pass through suction lumen to minimize clogging of the lumen.

In addition, the present invention is particularly useful for removing elastic tissue, such as the synovial tissue found in joints. In arthroscopic procedures, this elastic synovial tissue tends to move away from instruments within the conductive fluid, making it difficult for conventional instruments to remove this tissue. With the present invention, the probe is moved adjacent the target synovial tissue, and the vacuum source is activated to draw the synovial tissue towards the distal end of the probe. The aspiration and/or active electrodes are then energized to ablate this tissue. This allows the surgeon to quickly and precisely ablate elastic tissue with minimal thermal damage to the treatment site.

In one embodiment, loop electrodes 540 are electrically isolated from the other active electrodes 504, and electrodes 540 must be separately activated by power supply 428. In other embodiments, loop electrodes 540 will be activated at the same time that active electrodes 504 are activated. In this case, applicant has found that the plasma layer typically forms when tissue is drawn adjacent to loop electrodes 540.

Figure 11:
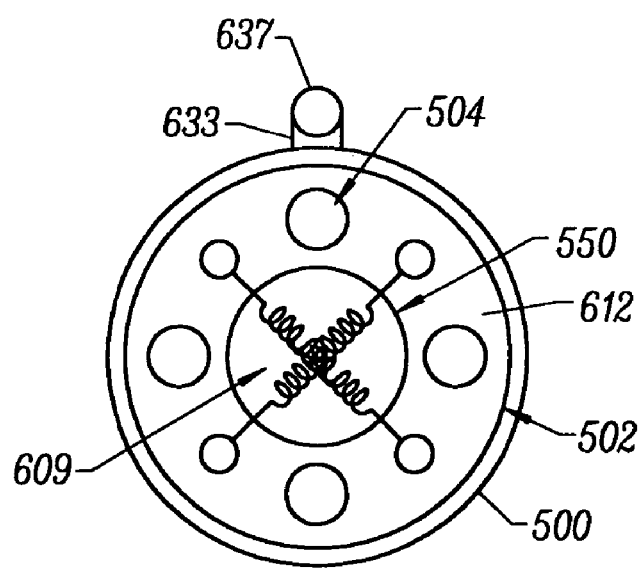
FIGS. 11–13 illustrate alternative probes according to the present invention, incorporating aspiration electrodes.
Figure 12:
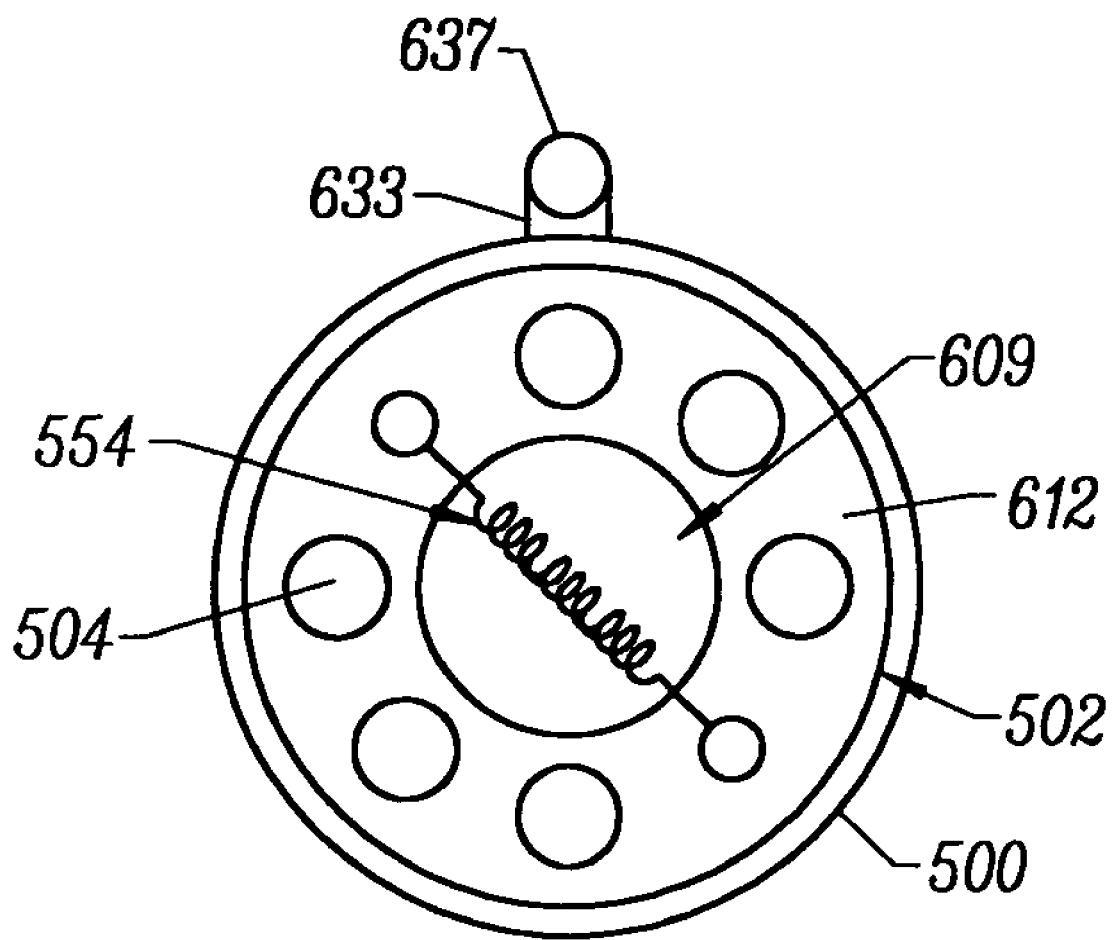
Figure 13:
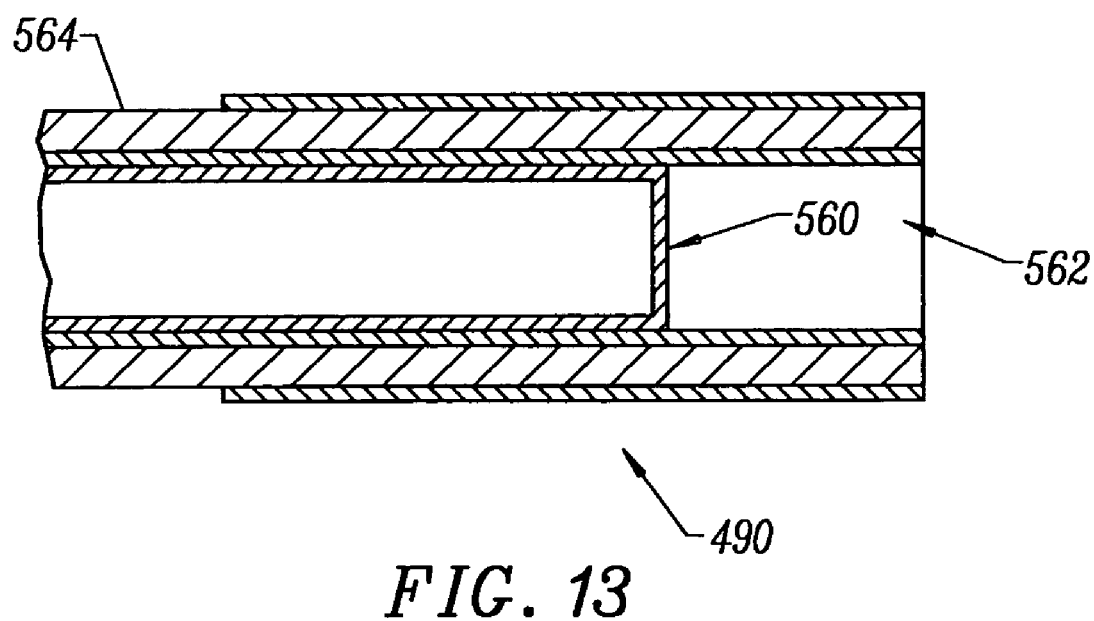

Referring now to FIGS. 11 and 12, alternative embodiments for aspiration electrodes will now be described. As shown in FIG. 11, the aspiration electrodes may comprise a pair of coiled electrodes 550 that extend across distal opening 609 of the suction lumen. The larger surface area of the coiled electrodes 550 usually increases the effectiveness of the electrodes 550 in ablating tissue fragments passing through opening 609. In FIG. 12, the aspiration electrode comprises a single coiled electrode 552 passing across the distal opening 609 of suction lumen. This single electrode 552 may be sufficient to inhibit clogging of the suction lumen. Alternatively, the aspiration electrodes may be positioned within the suction lumen proximal to the distal opening 609. Preferably-, these electrodes are close to opening 609 so that tissue does not clog the opening 609 before it reaches electrode(s) 554. In this embodiment, a separate return electrode 556 may be provided within the suction lumen to confine the electric currents therein.

Referring to FIG. 13, another embodiment of the present invention incorporates an aspiration electrode 560 within the aspiration lumen 562 of the probe. As shown, the electrode 560 is positioned just proximal of distal opening 609 so that the tissue fragments are ablated as they enter lumen 562. In the representative embodiment, the aspiration electrode 560 comprises a loop electrode that extends across the aspiration lumen 562. However, it will be recognized that many other configurations are possible. In this embodiment, the return electrode 564 is located on the exterior of the probe, as in the previously described embodiments. Alternatively, the return electrode(s) may be located within the aspiration lumen 562 with the aspiration electrode 560. For example, the inner insulating coating 563 may be exposed at portions within the lumen 562 to provide a conductive path between this exposed portion of return electrode 564 and the aspiration electrode 560. The latter embodiment has the advantage of confining the electric currents to within the aspiration lumen. In addition, in dry fields in which the conductive fluid is delivered to the target site, it is usually easier to maintain a conductive fluid path between the active and return electrodes in the latter embodiment because the conductive fluid is aspirated through the aspiration lumen 562 along with the tissue fragments.

FIGS. 14–17 illustrate a method for treating nasal or sinus blockages, e.g., chronic sinusitis, according to the present invention. In these procedures, the polyps, turbinates or other sinus tissue may be ablated or reduced (e.g., by tissue contraction) to clear the blockage and/or enlarge the sinus cavity to reestablish normal sinus function. For example, in chronic rhinitis, which is a collective term for chronic irritation or inflammation of the nasal mucosa with hypertrophy of the nasal mucosa, the inferior turbinate may be reduced by ablation or contraction. Alternatively, a turbinectomy or mucotomy may be performed by removing a strip of tissue from the lower edge of the inferior turbinate to reduce the volume of the turbinate. For treating nasal polypi, which comprises benign pedicled or sessile masses of nasal or sinus mucosa caused by inflammation, the nasal polypi may be contracted or shrunk, or ablated by the method of the present invention. For treating severe sinusitis, a frontal sinus operation may be performed to introduce the electrosurgical probe to the site of blockage. The present invention may also be used to treat diseases of the septum, e.g., ablating or resecting portions of the septum for removal, straightening or reimplantation of the septum.

The present invention is particularly useful in functional endoscopic sinus surgery (FESS) in the treatment of sinus disease. In contrast to prior art microdebriders, the electrosurgical probe of the present invention effects hemostasis of severed blood vessels, and allows the surgeon to precisely remove tissue with minimal or no damage to surrounding tissue, bone, cartilage or nerves. By way of example and not limitation, the present invention may be used for the following procedures: (1) uncinectomy or medial displacement or removal of portions of the middle turbinate; (2) maxillary, sphenoid or ethmoid sinusotomies or enlargement of the natural ostium of the maxillary, sphenoid, or ethmoid sinuses, respectively; (3) frontal recess dissections, in which polypoid or granulation tissue are removed; (4) polypectomies, wherein polypoid tissue is removed in the case of severe nasal polyposis; (5) concha bullosa resections or the thinning of polypoid middle turbinate; (6) septoplasty; and the like.

Figure 14:
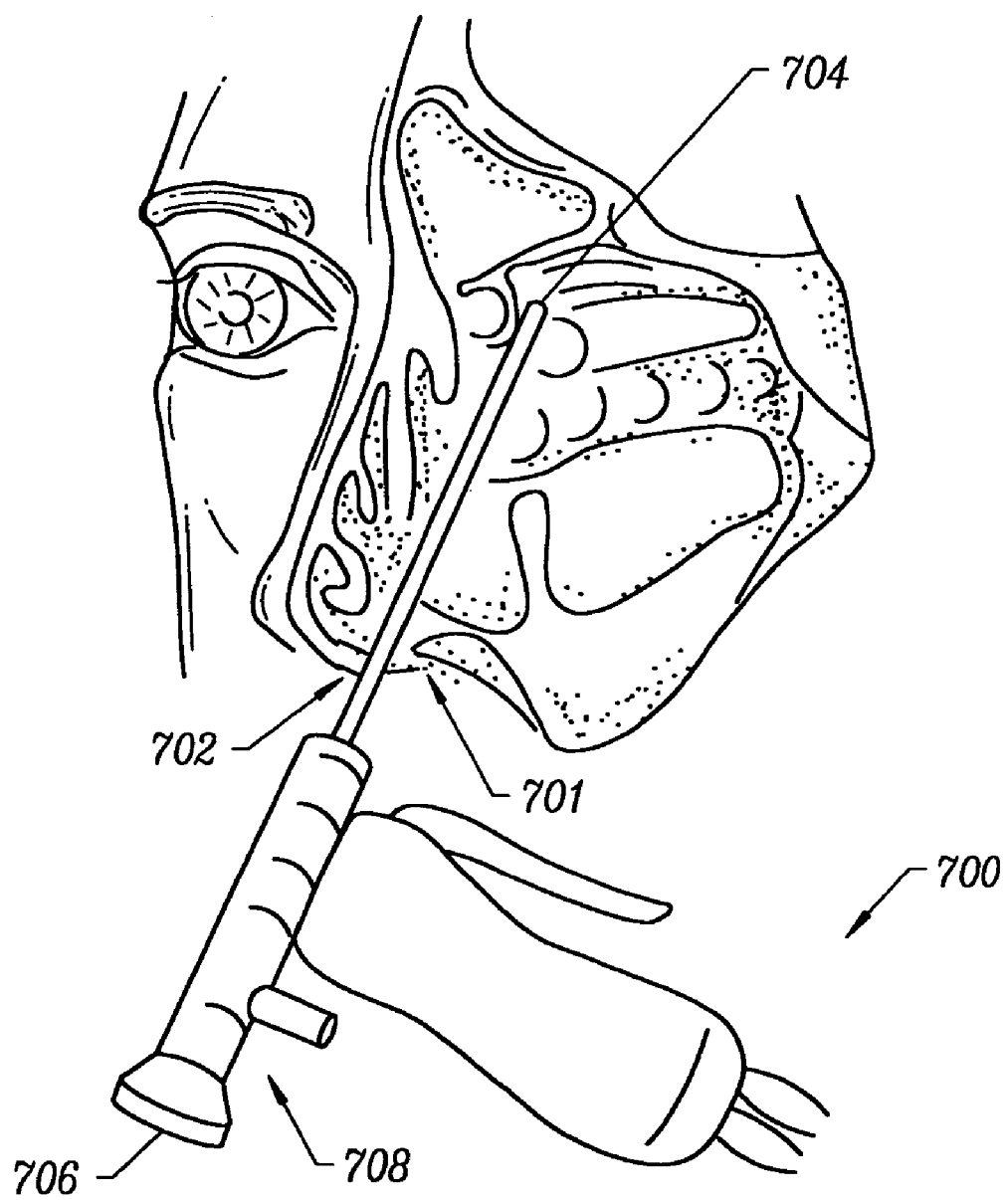
FIG. 14 illustrates an endoscopic sinus surgery procedure, wherein an endoscope is delivered through a nasal passage to view a surgical site within the nasal cavity of the patient.

FIGS. 14–17 schematically illustrate an endoscopic sinus surgery (FESS) procedure according to the present invention. As shown in FIG. 14, an endoscope 700 is first introduced through one of the nasal passages 701 to allow the surgeon to view the target site, e.g., the sinus cavities. As shown, the endoscope 700 will usually comprise a thin metal tube 702 with a lens (not shown) at the distal end 704, and an eyepiece 706 at the proximal end 708. As shown in FIG. 8, the probe shaft 500 has a bend 501 to facilitate use of both the endoscope and the probe 490 in the same nasal passage (i.e., the handles of the two instruments do not interfere with each other in this embodiment). Alternatively, the endoscope may be introduced transorally through the inferior soft palate to view the nasopharynx. Suitable nasal endoscopes for use with the present invention are described in U.S. Pat. Nos. 4,517,962, 4,844,052, 4,881,523 and 5,167,220, the complete disclosures of which are incorporated herein by reference for all purposes.

Alternatively, the endoscope 700 may include a sheath (not shown) having an inner lumen for receiving the electrosurgical probe shaft 500. In this embodiment, the shaft 500 will extend through the inner lumen to a distal opening in the endoscope. The shaft will include suitable proximal controls for manipulation of its distal end during the surgical procedure.

Figure 15:
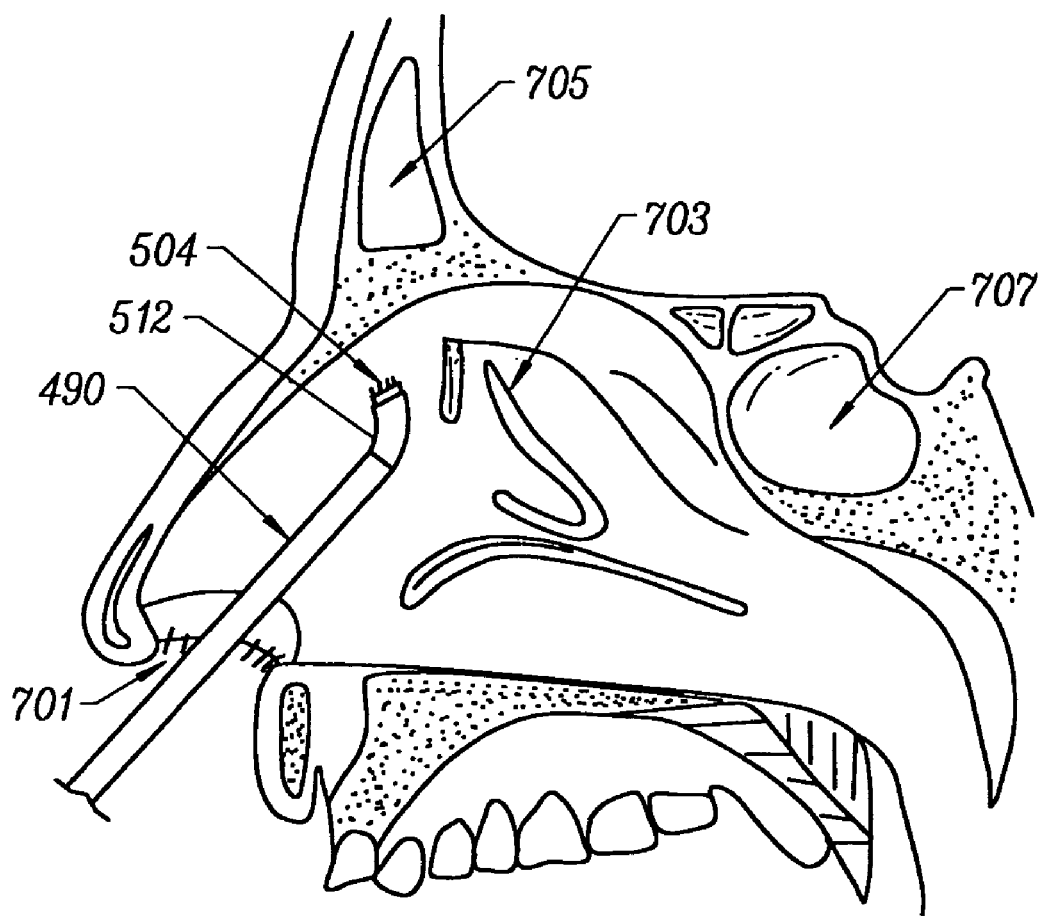
FIG. 15 illustrates an endoscopic sinus surgery procedure with one of the probes described above according to the present invention.

As shown in FIG. 15, the distal end of probe 490 is introduced through nasal passage 701 into the nasal cavity 703 (endoscope 700 is not shown in FIG. 15). Depending on the location of the blockage, the active electrodes 504 will be positioned adjacent the blockage in the nasal cavity 703, or in one of the paranasal sinuses 705, 707. Note that only the frontal sinus 705 and the sphenoidal sinus 707 are shown in FIG. 15, but the procedure is also applicable to the ethmoidal and maxillary sinuses. Once the surgeon has reached the point of major blockage, electrically conductive fluid is delivered through tube 633 and opening 637 to the tissue (see FIG. 8). The fluid flows past the return electrode 512 to the active electrodes 504 at the distal end of the shaft. The rate of fluid flow is controlled by valve 417 (FIG. 8) such that the zone between the tissue and electrode support 502 is constantly immersed in the fluid. The power supply 428 is then turned on and adjusted such that a high frequency voltage difference is applied between active electrodes 504 and return electrode 512. The electrically conductive fluid provides the conduction path between active electrodes 504 and the return electrode 512.

Figure 16A:
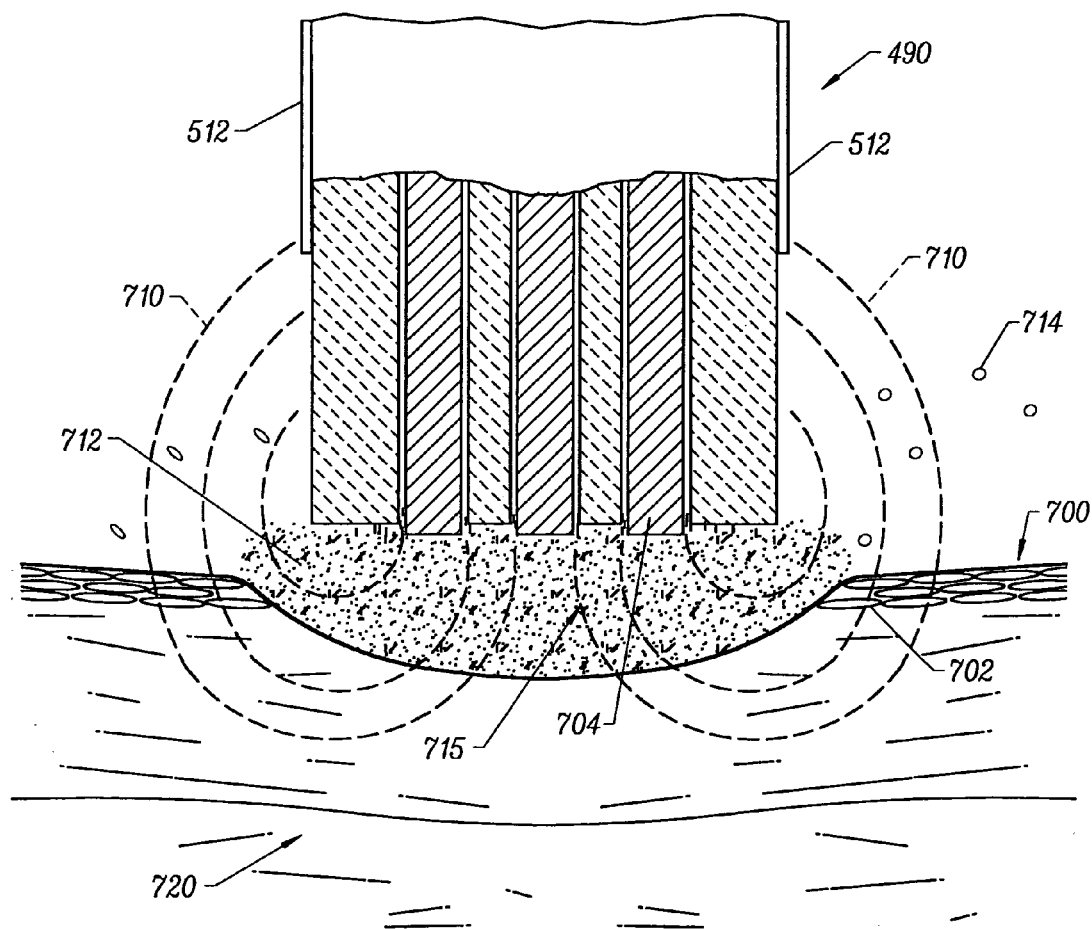
FIGS. 16A and 16B illustrate a detailed view of the sinus surgery procedure, illustrating ablation of tissue according to the present invention.
Figure 16B:
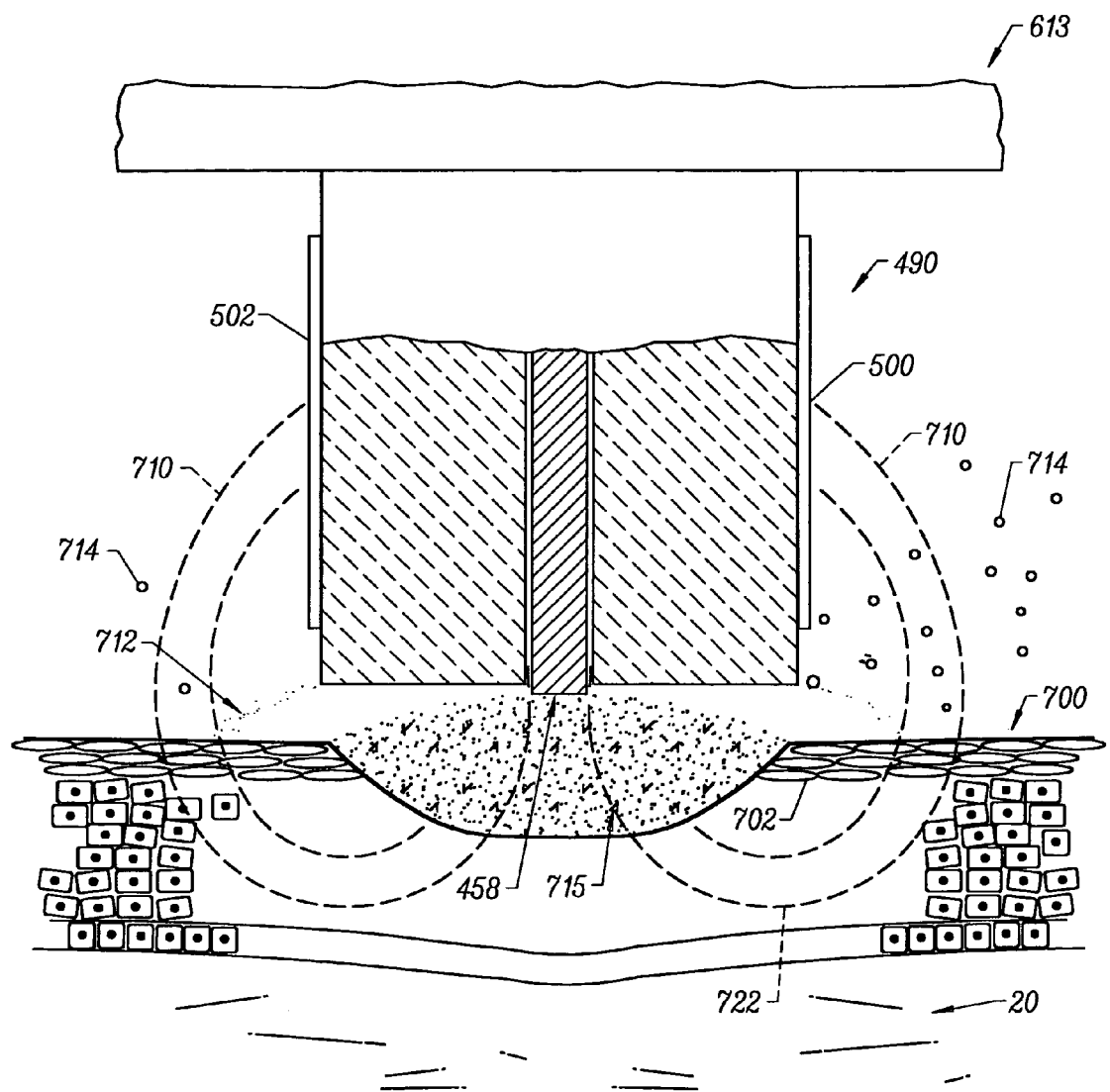

FIGS. 16A and 16B illustrate the removal of sinus tissue in more detail As shown, the high frequency voltage is sufficient to convert the electrically conductive fluid (not shown) between the target tissue 702 and active electrode(s) 504 into an ionized vapor layer 712 or plasma. As a result of the applied voltage difference between active electrode(s) 504 (or active electrode 458) and the target tissue 702 (i.e., the voltage gradient across the plasma layer 712), charged particles 715 in the plasma (e.g., electrons) are accelerated. At sufficiently high voltage differences, these charged particles 715 gain sufficient energy to cause dissociation of the molecular bonds within tissue structures in contact with the plasma field. This molecular dissociation is accompanied by the volumetric removal (i.e., ablative sublimation) of tissue and the production of low molecular weight gases 714, such as oxygen, nitrogen, carbon dioxide, hydrogen and methane. The short range of the accelerated charged particles 715 within the tissue confines the molecular dissociation process to the surface layer to minimize damage and necrosis to the underlying tissue 720.

During the process, the gases 714 will be aspirated through opening 609 and suction tube 611 to a vacuum source. In addition, excess electrically conductive fluid, and other fluids (e.g., blood) will be aspirated from the target site 700 to facilitate the surgeon's view. During ablation of the tissue, the residual heat generated by the current flux lines, will usually be sufficient to coagulate any severed blood vessels at the site. Typically, the temperature of the treated tissue is less than 150° C. If the residual heat is not sufficient to coagulate severed blood vessels, the surgeon may switch the power supply 428 into the coagulation mode by lowering the voltage to a level below the threshold for fluid vaporization, as discussed above. This simultaneous hemostasis results in less bleeding and facilitates the surgeon's ability to perform the procedure. Once the blockage has been removed, aeration and drainage are reestablished to allow the sinuses to heal and return to their normal function.

Figure 18:
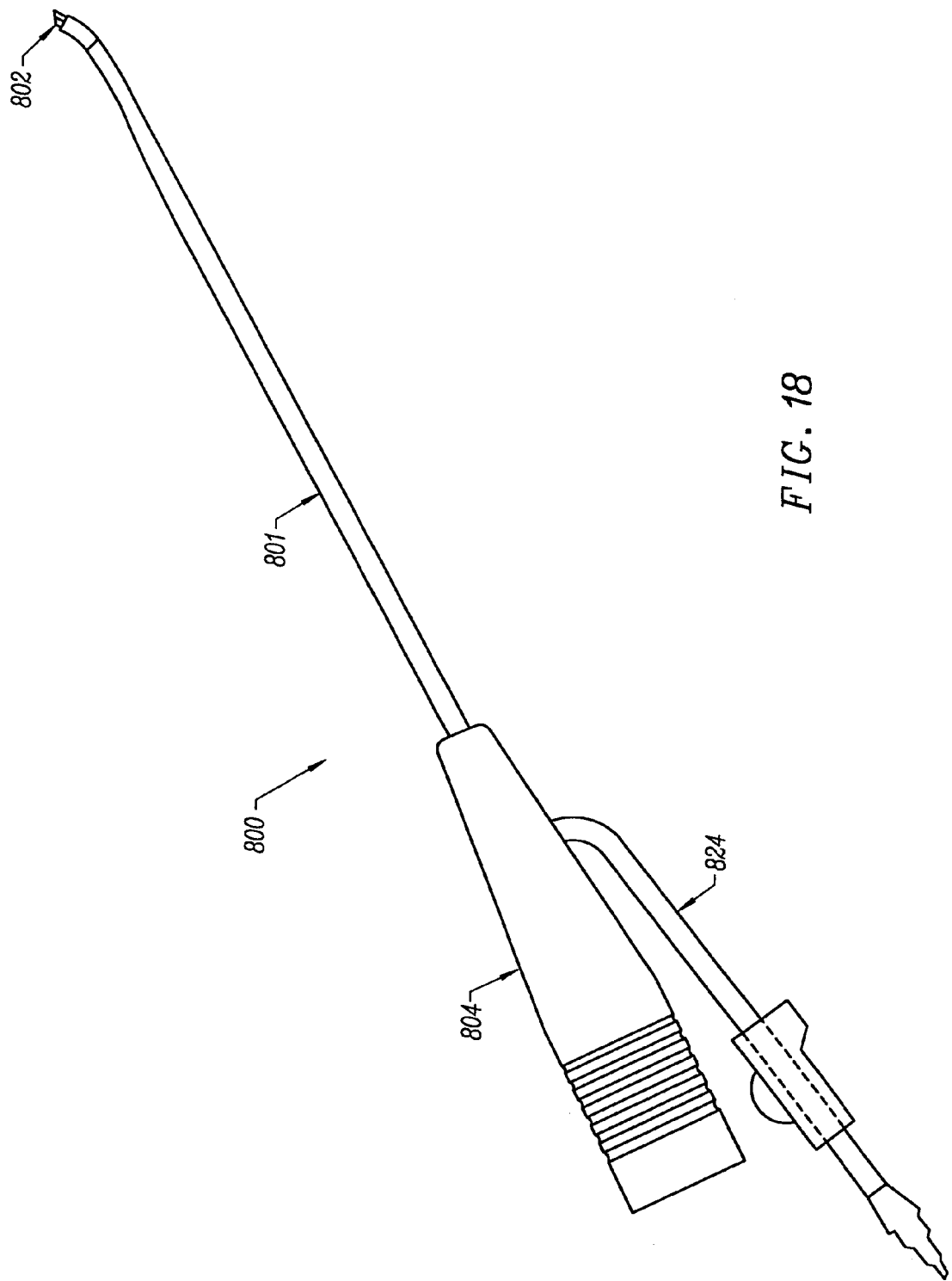
FIG. 18 is a perspective view of another embodiment of the present invention.
Figure 19:
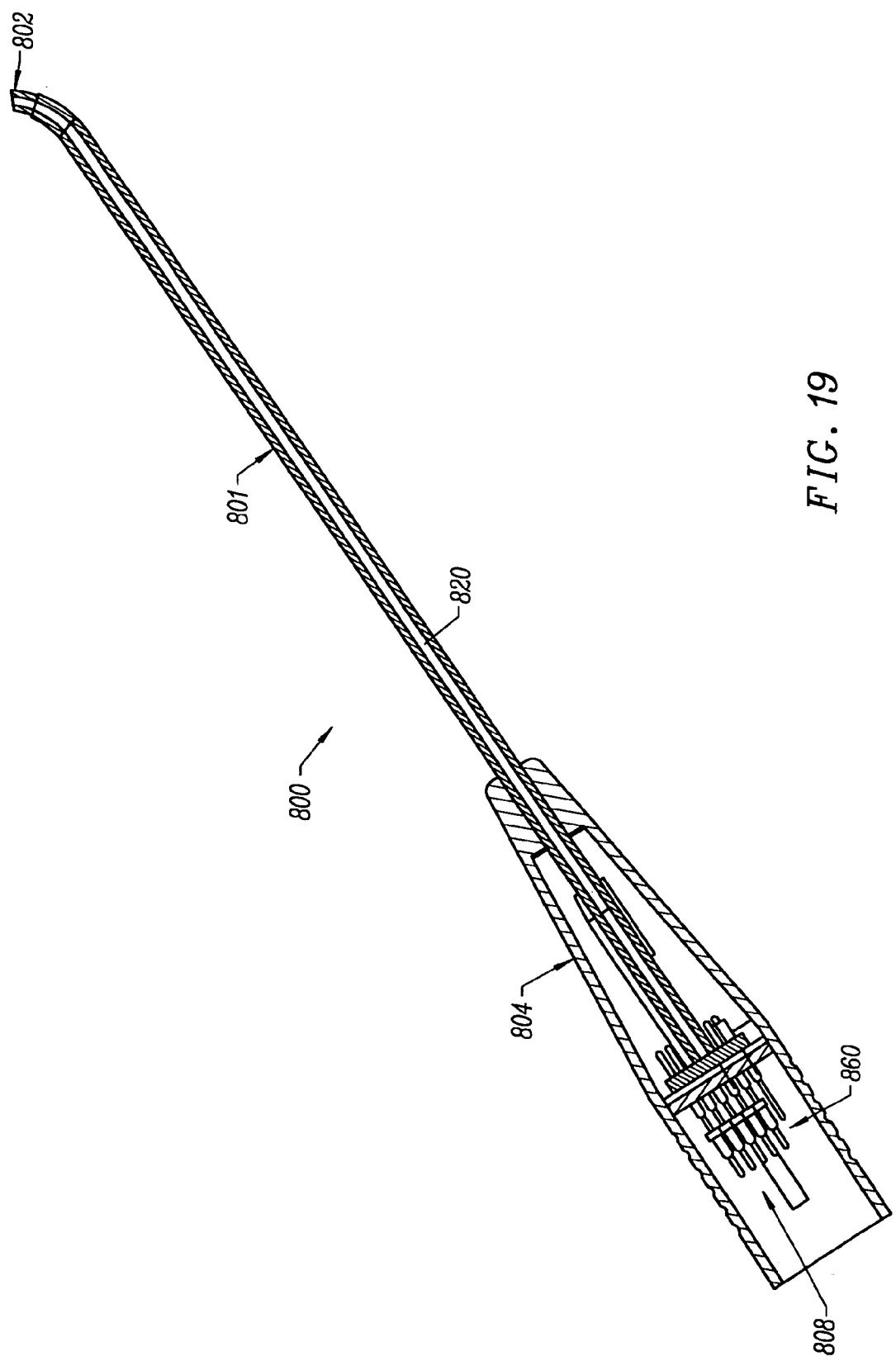
FIG. 19 is a side-cross-sectional view of the electrosurgical probe of FIG. 18.
Figure 20:
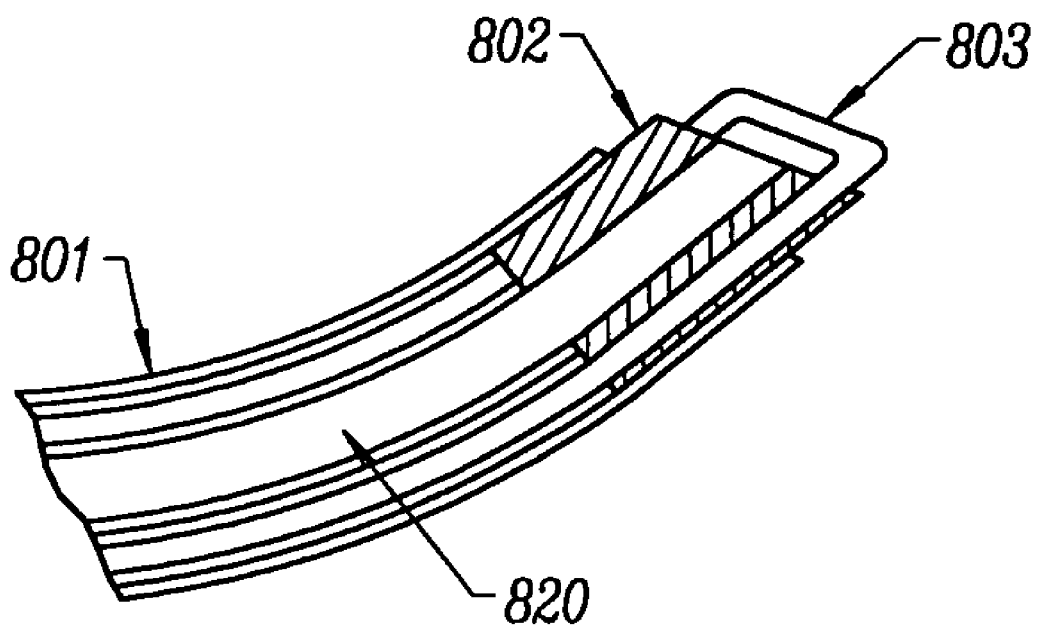
FIG. 20 is an enlarged detailed cross-sectional view of the distal end portion of the probe of FIG. 18.
Figure 21:
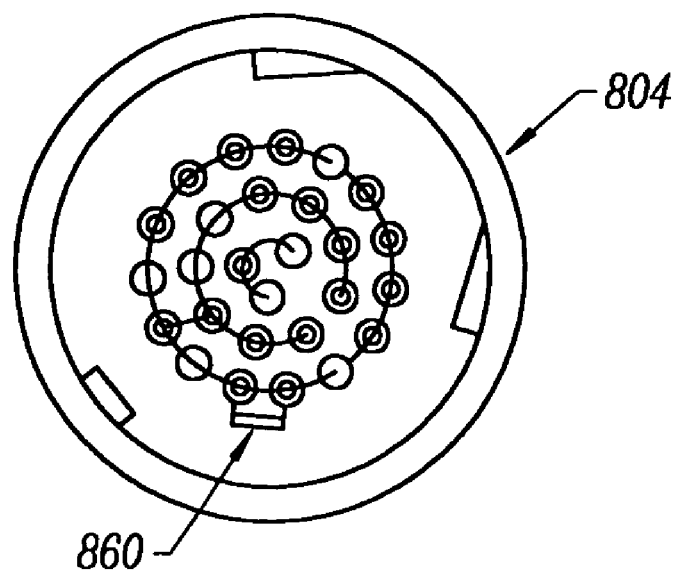
FIGS. 21 and 22 show the proximal end and the distal end, respectively, of the probe of FIG. 18.
Figure 22:
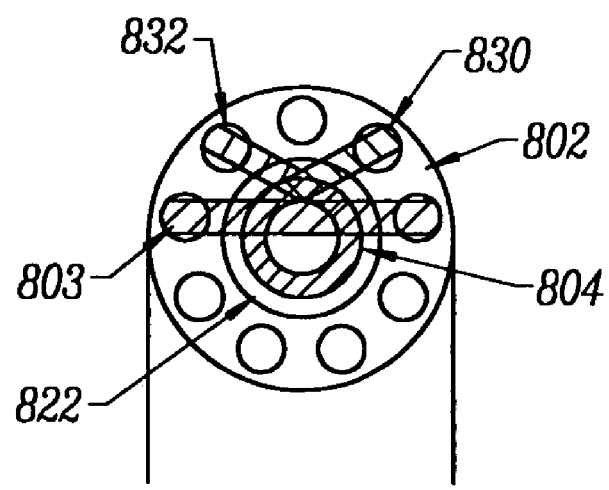

FIGS. 18–22 illustrate another embodiment of the present invention. As shown in FIG. 18, an electrosurgical probe 800 includes an elongated shaft 801 which may be flexible or rigid, a handle 804 coupled to the proximal end of shaft 801 and an electrode support member 802 coupled to the distal end of shaft 801. As in previous embodiments, probe 800 includes an active loop electrode 803 (e.g., FIG. 20) and a return electrode 812 (not shown), the latter spaced proximally from active loop electrode 803. The probe 800 further includes a suction lumen 820 (FIG. 19) for aspirating excess fluids, bubbles, tissue fragments, and/or products of ablation from the target site. As shown in FIGS. 19 and 22, suction lumen 820 extends through support member 802 to a distal opening 822, and extends through shaft 801 and handle 804 to an external connector 824 for coupling to a vacuum source. Typically, the vacuum source is a standard hospital pump that provides suction pressure to connector 824 and lumen 820.

As shown in FIG. 19, handle 804 defines an inner cavity 808 that houses the electrical connections 850 (discussed above), and provides a suitable interface for connection to an electrical connecting cable 22 (see FIG. 1). As shown in FIG. 21, the probe will also include a coding resistor 860 having a value selected to program different output ranges and modes of operation for the power supply. This allows a single power supply to be used with a variety of different probes in different applications (e.g., dermatology, cardiac surgery, neurosurgery, arthroscopy, etc).

Electrode support member 802 extends from the distal end of shaft 801 (usually about 1 to 20 mm), and provides support for loop electrode 803 and a ring electrode 804 (see FIG. 22). As shown in FIG. 20, loop electrode 803 has first and second ends extending from the electrode support member 802. The first and second ends are each coupled to, or integral with, one or more connectors, e.g., wires (not shown), that extend through the shaft of the probe to its proximal end for coupling to the high frequency power supply. The loop electrode usually extends about 0.5 to about 10 mm from the distal end of support member, preferably about 1 to 2 mm. Loop electrode 803 usually extends further away from the support member than the ring electrode 804 to facilitate ablation of tissue. As discussed below, loop electrode 803 is especially configured for tissue ablation, while the ring electrode 804 ablates tissue fragments that are aspirated into suction lumen 820.

Referring to FIG. 22, ring electrode 804 preferably comprises a tungsten or titanium wire having two ends 830, 832 coupled to electrical connectors (not shown) within support member 802. The wire is bent to form one-half of a figure eight, thereby forming a ring positioned over opening 822 of suction lumen 820. This ring inhibits passage of tissue fragments large enough to clog suction lumen 820. Moreover, voltages applied between ring electrode 804 and return electrode 812 provide sufficient energy to ablate these tissue fragments into smaller fragments that are then aspirated through lumen 820. In a presently preferred embodiment, ring electrode 804 and loop electrode 803 are electrically isolated from each other. However, electrodes 804, 803 may be electrically coupled to each other in some applications.

Figure 25:
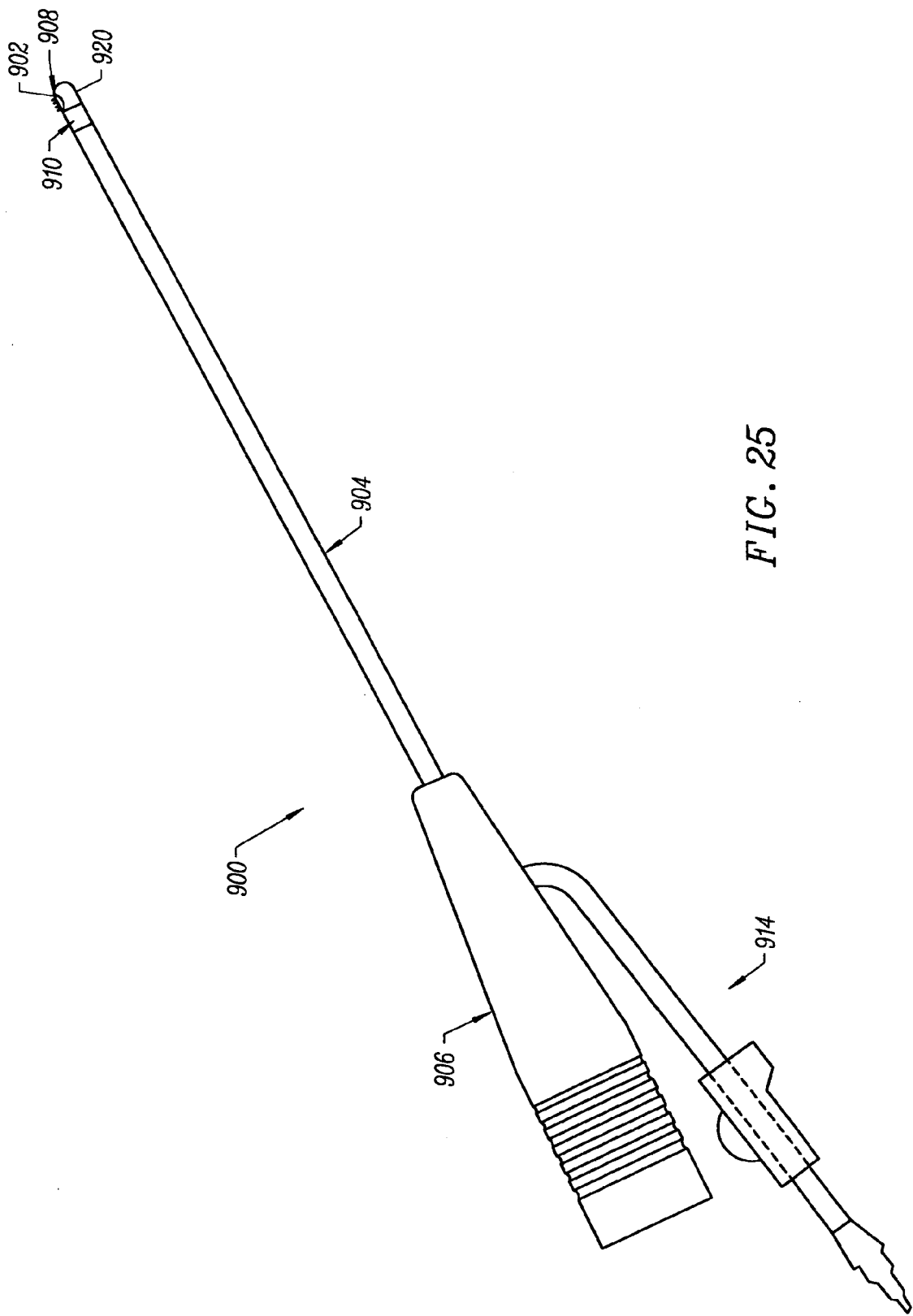
FIG. 25 is a perspective view of yet another embodiment of the present invention.

FIGS. 25–31 illustrate another embodiment of the present invention including an electrosurgical probe 900 incorporating an active screen electrode 902. As shown in FIG. 25, probe 900 includes an elongated shaft 904 which may be flexible or rigid, a handle 906 coupled to the proximal end of shaft 904 and an electrode support member 908 coupled to the distal end of shaft 904. Probe 900 further includes an active screen electrode 902 and a return electrode 910 spaced proximally from active screen electrode 902. In this embodiment, active screen electrode 902 and support member 908 are configured such that the active electrode 902 is positioned on a lateral side of the shaft 904 (e.g., 90 degrees from the shaft axis) to allow the physician to access tissue that is offset from the axis of the portal or arthroscopic opening into the joint cavity in which the shaft 904 passes during the procedure. To accomplish this, probe 900 includes an electrically insulating cap 920 coupled to the distal end of shaft 904 and having a lateral opening 922 for receiving support member 908 and screen electrode 902.

Figure 26:
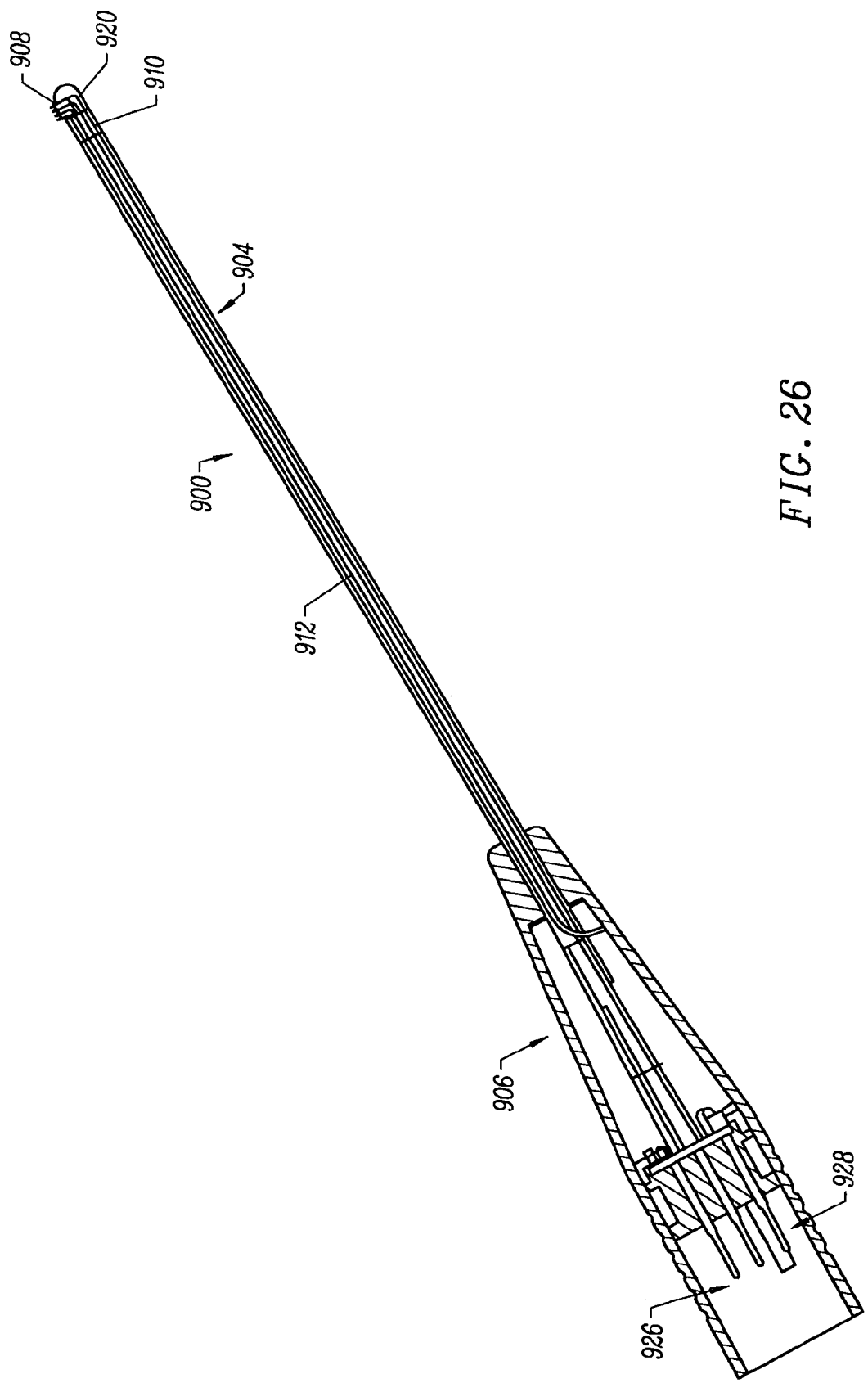
FIG. 26 is a side cross-sectional view of the electrosurgical probe of FIG. 25.
Figure 27:
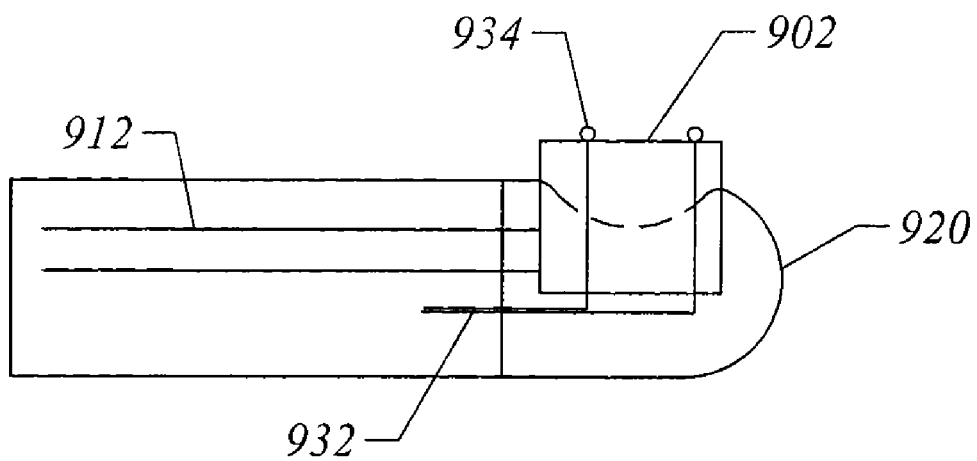
FIG. 27 is an enlarged detailed view of the distal end portion of the probe of FIG. 25.
Figure 30:
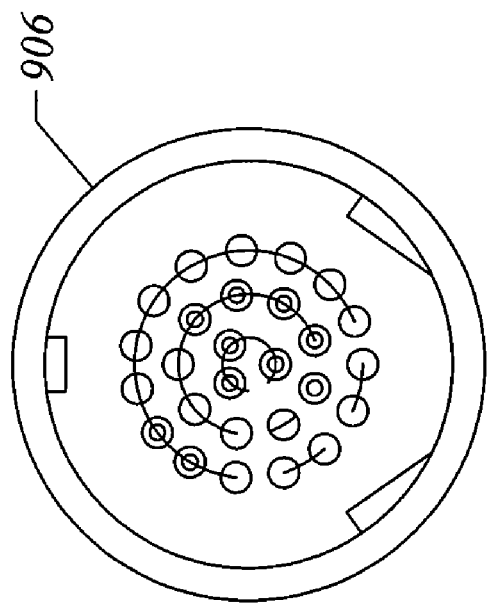
FIG. 30 illustrates the proximal end of the probe of FIG. 25.

The probe 900 further includes a suction connection tube 914 for coupling to a source of vacuum, and an inner suction lumen 912 (FIG. 26) for aspirating excess fluids, tissue fragments, and/or products of ablation (e.g., bubbles) from the target site. In addition, suction lumen 912 allows the surgeon to draw loose tissue, e.g., synovial tissue, towards the screen electrode 902, as discussed above. Typically, the vacuum source is a standard hospital pump that provides suction pressure to connection tube 914 and lumen 912. However, a pump may also be incorporated into the high frequency power supply. As shown in FIGS. 26, 27 and 30, internal suction lumen 912, which preferably comprises peek tubing, extends from connection tube 914 in handle 906, through shaft 904 to an axial opening 916 in support member 908, through support member 908 to a lateral opening 918. Lateral opening 918 contacts screen electrode 902, which includes a plurality of holes 924 (FIG. 28) for allowing aspiration therethrough, as discussed below.

As shown in FIG. 26, handle 906 defines an inner cavity 926 that houses the electrical connections 928 (discussed above), and provides a suitable interface for connection to an electrical connecting cable 22 (see FIG. 1). An end view of the handle 906 is shown in FIG. 30.

Figure 28:
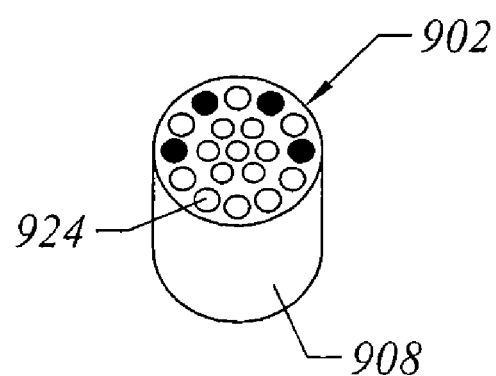
FIG. 28 is a perspective view of the distal portion of the probe of FIG. 25.
Figure 29:
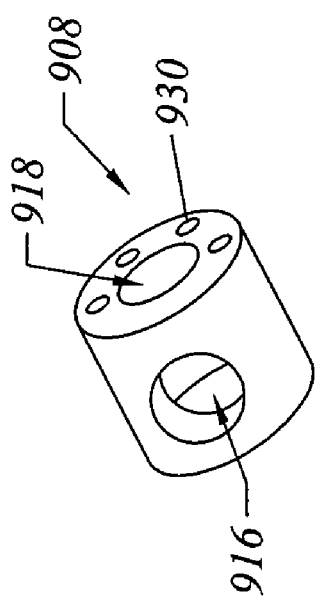
FIG. 29 is a perspective view of an electrode support member of the probe of FIG. 25.
Figure 31:
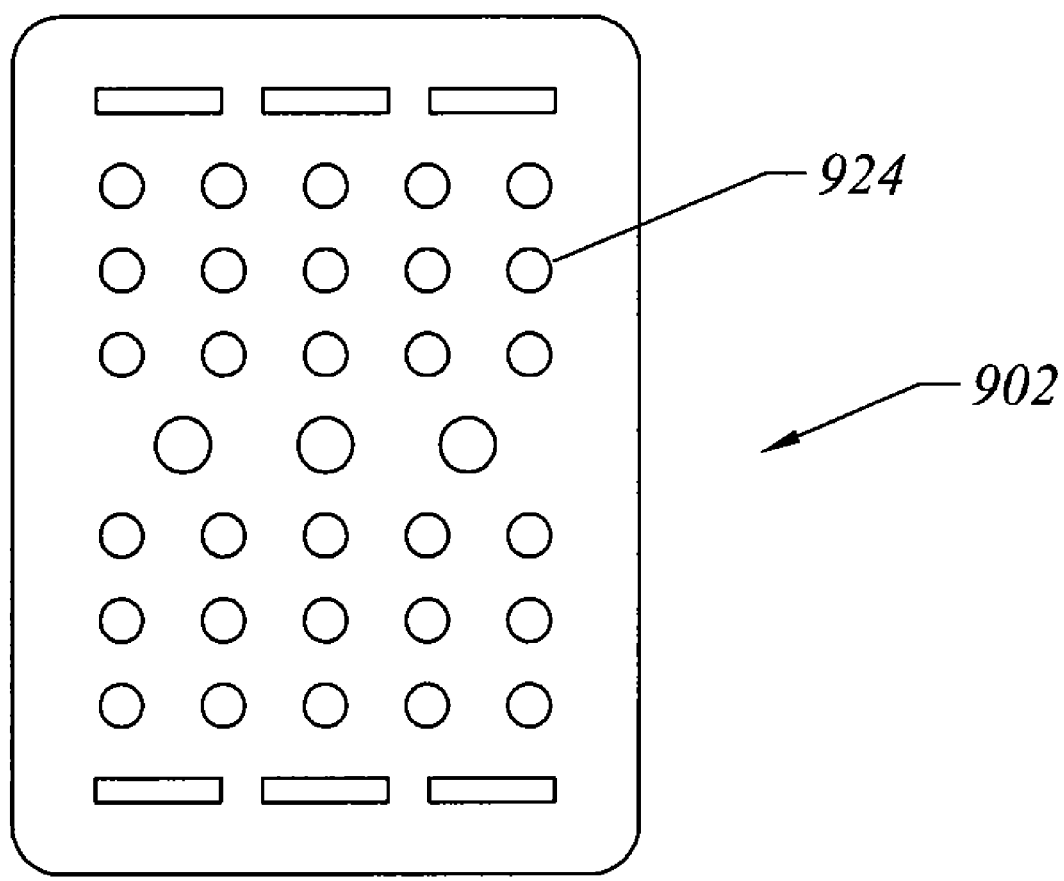
FIG. 31 is an alternative embodiment of the active electrode for the probe of FIG. 25.

Referring to FIG. 29, electrode support member 908 preferably comprises an inorganic material, such as glass, ceramic, silicon nitride, alumina or the like, that has been formed with lateral and axial openings 918, 916 for suction, and with one or more smaller holes 930 for receiving electrical connectors 932. In the representative embodiment, support member 908 has a cylindrical shape for supporting a circular screen electrode 902. Of course, screen electrode 902 may have a variety of different shapes, such as the rectangular shape shown in FIG. 31, which may change the associated shape of support member 908. Various types of smaller holes or apertures 924 are shown in the screen 902 of FIG. 31 including circular apertures, and rectangular apertures. The rectangular apertures comprise corners. As shown in FIGS. 27–29, electrical connectors 932 extend from connections 928, through shaft 904 and holes 930 in support member 908 to screen electrode 902 to couple the active electrode 902 to a high frequency power supply. In the representative embodiment, screen electrode 902 is mounted to support member 908 by ball wires 934 that extend through holes 924 in screen electrode 902 and holes 930 in support member 908. Ball wires 934 function to electrically couple the screen 902 to connectors 932 and to secure the screen 902 onto the support member 908. Of course, a variety of other methods may be used to accomplish these functions, such as nailhead wires, adhesive and standard wires, a channel in the support member, etc.

The screen electrode 902 will comprise a conductive material, such as tungsten, titanium, molybdenum, stainless steel, aluminum, gold, copper or the like. In some embodiments, it may be advantageous to construct the active and return electrodes of the same material to eliminate the possibility of DC currents being created by dissimilar metal electrodes. Screen electrode 902 will usually have a diameter in the range of about 0.5 to 8 mm, preferably about 1 to 4 mm, and a thickness of about 0.05 to about 2.5 mm, preferably about 0.1 to 1 mm. Electrode 902 will comprise a plurality of holes 924 having sizes that may vary depending on the particular application and the number of holes (usually from one to 50 holes, and preferably about 3 to 20 holes). Holes 924 will typically be large enough to allow ablated tissue fragments to pass through into suction lumen 912, typically being about 2 to 30 mils in diameter, preferably about 5 to 20 mils in diameter. In some applications, it may be desirable to only aspirate fluid and the gaseous products of ablation (e.g., bubbles) so that the holes may be much smaller, e.g., on the order of less than 10 mils, often less than 5 mils.

In the representative embodiment, probe 900 is manufactured as follows: screen electrode 902 is placed on support member 908 so that holes 924 are lined up with holes 930. One or more ball wires 934 are inserted through these holes, and a small amount of adhesive (e.g., epotek) is placed around the outer face of support member 908. The ball wires 934 are then pulled until screen 902 is flush with support member 908, and the entire sub-assembly is cured in an oven or other suitable heating mechanism. The electrode-support member sub-assembly is then inserted through the lateral opening in cap 920 and adhesive is applied to the peek tubing suction lumen 912. The suction lumen 912 is then placed through axial hole 916 in support member 908 and this sub-assembly is cured. The return electrode 910 (which is typically the exposed portion of shaft 904) is then adhered to cap 920.

Another advantage of the present invention is the ability to precisely ablate layers of sinus tissue without causing necrosis or thermal damage to the underlying and surrounding tissues, nerves (e.g., the optic nerve) or bone. In addition, the voltage can be controlled so that the energy directed to the target site is insufficient to ablate bone or adipose tissue (which generally has a higher impedance than the target sinus tissue). In this manner, the surgeon can literally clean the tissue off the bone, without ablating or otherwise effecting significant damage to the bone.

Figure 17:
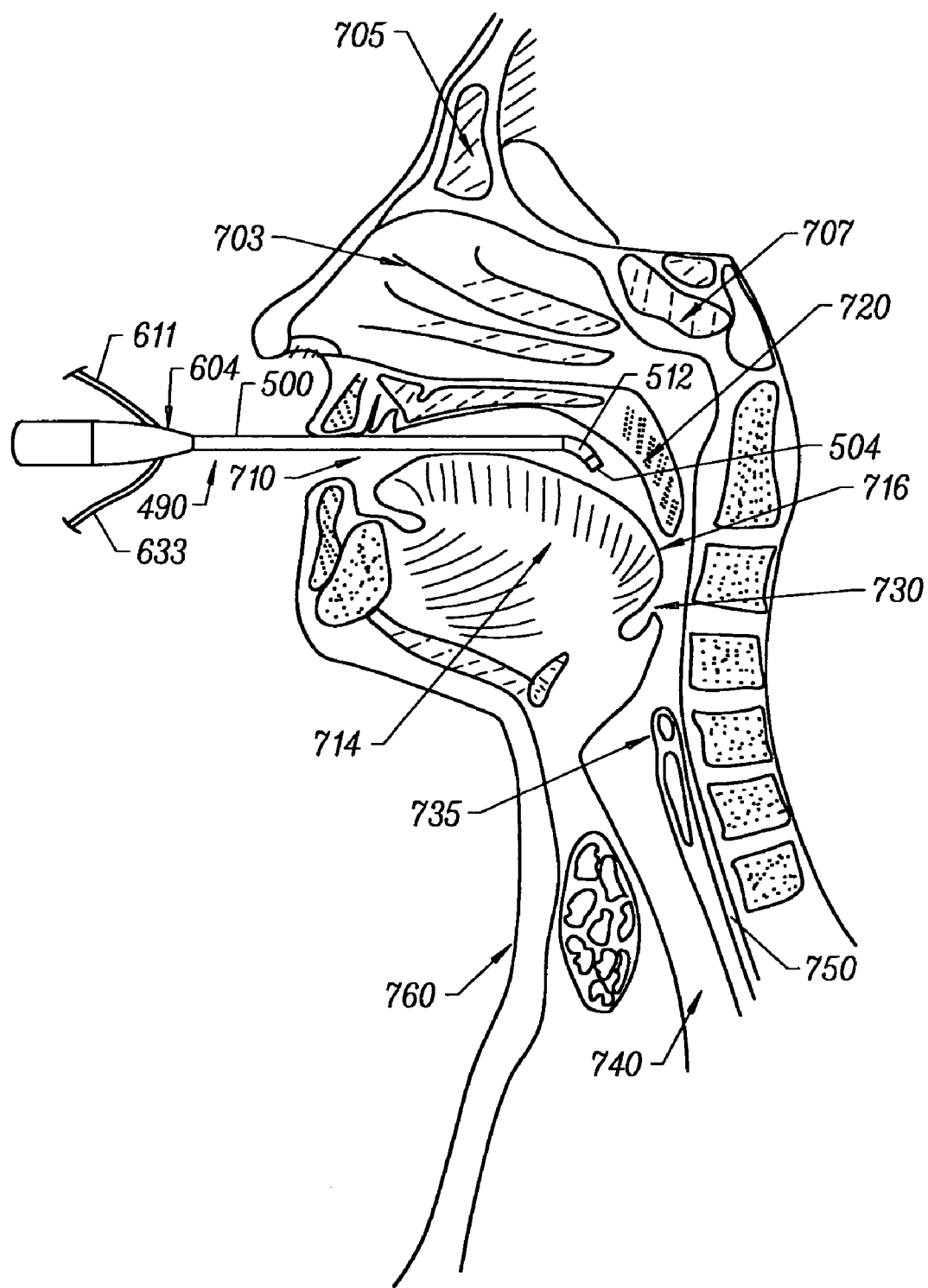
FIG. 17 illustrates a procedure for treating obstructive sleep disorders, such as sleep apnea, according to the present invention.

Methods for treating air passage disorders according to the present invention will now be described. In these embodiments, an electrosurgical probe such as one described above can be used to ablate targeted masses including, but not limited to, the tongue, tonsils, turbinates, soft palate tissues (e.g., the uvula), hard tissue and mucosal tissue. In one embodiment, selected portions of the tongue 714 are removed to treat sleep apnea. In this method, the distal end of an electrosurgical probe 490 is introduced into the patient's mouth 710, as shown in FIG. 17. An endoscope (not shown), or other type of viewing device, may also be introduced, or partially introduced, into the mouth 710 to allow the surgeon to view the procedure (the viewing device may be integral with, or separate from, the electrosurgical probe). The active electrodes 504 are positioned adjacent to or against the back surface 716 of the tongue 714, and electrically conductive fluid is delivered to the target site, as described above. The power supply 428 is then activated to remove selected portions of the back of the tongue 714, as described above, without damaging sensitive structures, such as nerves, and the bottom portion of the tongue 714.

In another embodiment, the electrosurgical probe of the present invention can be used to ablate and/or contract soft palate tissue to treat snoring disorders. In particular, the probe is used to ablate or shrink sections of the uvula 720 without causing unwanted tissue damage under and around the selected sections of tissue. For tissue contraction, a sufficient voltage difference is applied between the active electrodes 504 and the return electrode 512 to elevate the uvula tissue temperature from normal body temperatures (e.g., 37° C.) to temperatures in the range of 45° C. to 90° C., preferably in the range from 60° C. to 70° C. This temperature elevation causes contraction of the collagen connective fibers within the uvula tissue.

In addition to the above procedures, the system and method of the present invention may be used for treating a variety of disorders in the mouth 710, pharynx 730, larynx 735, hypopharynx, trachea 740, esophagus 750 and the neck 760. For example, tonsillar hyperplasia or other tonsil disorders may be treated with a tonsillectomy by partially ablating the lymphoepithelial tissue. This procedure is usually carried out under intubation anesthesia with the head extended. An incision is made in the anterior faucial pillar, and the connective tissue layer between the tonsillar parenchyma and the pharyngeal constrictor muscles is demonstrated. The incision may be made with conventional scalpels, or with the electrosurgical probe of the present invention. The tonsil is then freed by ablating through the upper pole to the base of the tongue, preserving the faucial pillars. The probe ablates the tissue, while providing simultaneous hemostasis of severed blood vessels in the region. Similarly, adenoid hyperplasia, or nasal obstruction leading to mouth breathing difficulty, can be treated in an adenoidectomy by separating (e.g., resecting or ablating) the adenoid from the base of the nasopharynx.

Other pharyngeal disorders can be treated according to the present invention. For example, hypopharyngeal diverticulum involves small pouches that form within the esophagus immediately above the esophageal opening. The sac of the pouch may be removed endoscopically according to the present invention by introducing a rigid esophagoscope, and isolating the sac of the pouch. The cricopharyngeus muscle is then divided, and the pouch is ablated according to the present invention. Tumors within the mouth and pharynx, such as hemangiomas, lymphangiomas, papillomas, lingual thyroid tumors, or malignant tumors, may also be removed according to the present invention.

Other procedures of the present invention include removal of vocal cord polyps and lesions and partial or total laryngectomies. In the latter procedure, the entire larynx is removed from the base of the tongue to the trachea, if necessary with removal of parts of the tongue, the pharynx, the trachea and the thyroid gland.

Tracheal stenosis may also be treated according to the present invention. Acute and chronic stenoses within the wall of the trachea may cause coughing, cyanosis and choking.

Figure 23:
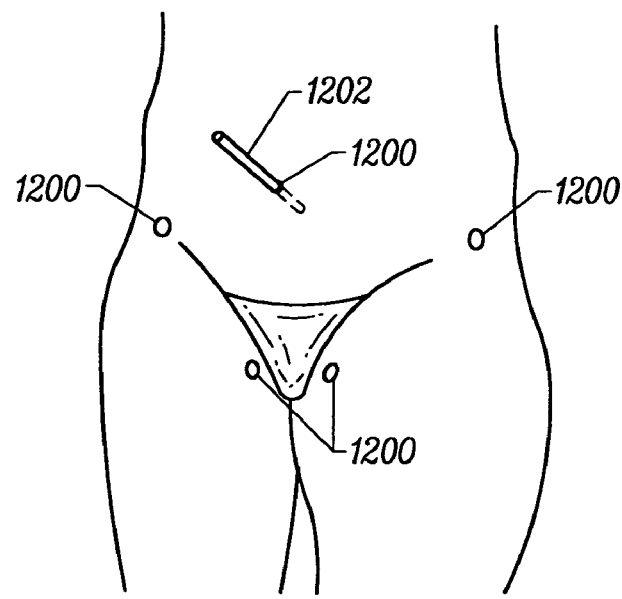
FIG. 23 illustrates a method for removing fatty tissue from the abdomen, groin or thigh region of a patient according to the present invention.

FIG. 23 schematically illustrates a lipectomy procedure in the abdomen according to the present invention. In a conventional liposuction procedure according to the prior art, multiple incisions are made to allow cross-tunneling, and the surgeon will manipulate the suction cannula in a linear piston-like motion during suction to remove the adipose tissue to avoid clogging of the cannula, and to facilitate separation of the fatty tissue from the remaining tissue. The present invention mostly solves these two problems and, therefore, minimizes the need for the surgeon to manipulate the probe in such a fashion.

Liposuction in the abdomen, lower torso and thighs according to the present invention removes the subcutaneous fat in these regions while leaving the fascial, neurovascular and lymphatic network intact or only mildly compromised. As shown, access incisions 1200 are typically positioned in natural skin creases remote from the areas to be liposuctioned. As shown in FIG. 23, the distal portion (not shown) of an electrosurgical instrument 1202 is introduced through one or more of the incisions 1200 and one or more active electrode(s) 1004 (FIG. 33) are positioned adjacent the fatty tissue. Electrically conductive fluid, e.g., isotonic saline, is delivered through tube 1133 and opening 1137 to the tissue. The fluid flows past the return electrode 1012 to the active electrodes 1004 at the distal end of the shaft. The rate of fluid flow is controlled by a valve such that the zone between the tissue and electrode support 1002 is constantly immersed in the fluid. The power supply 928 is then turned on and adjusted such that a high frequency voltage difference is applied between active electrodes 1004 and return electrode 1012. The electrically conductive fluid provides the conduction path between active electrodes 1004 and the return electrode 1012.

In the representative embodiment, the high frequency voltage is sufficient to convert the electrically conductive fluid (not shown) between the target tissue and active electrodes 1004 into an ionized vapor layer or plasma (not shown). As a result of the applied voltage difference between active electrode(s) 1004 and the target tissue (i.e., the voltage gradient across the plasma layer), charged particles in the plasma (e.g., electrons) are accelerated towards the fatty tissue. At sufficiently high voltage differences, these charged particles gain sufficient energy to cause dissociation of the molecular bonds within tissue structures. This molecular dissociation is accompanied by the volumetric removal (i.e., ablative sublimation) of tissue and the production of low molecular weight gases, such as oxygen, nitrogen, carbon dioxide, hydrogen and methane. The short range of the accelerated charged particles within the tissue confines the molecular dissociation process to the surface layer to minimize damage and necrosis to the underlying tissue.

In alternative embodiments, the high frequency voltage is sufficient to heat and soften or separate portions of the fatty tissue from the surrounding tissue. Suction is then applied from a vacuum source (not shown) through lumen 962 to aspirate or draw away the heated fatty tissue. A temperature of about 45° C. softens fatty tissue, and a temperature of about 50° C. normally liquefies mammalian adipose tissue. This heating and softening of the fatty tissue reduces the collateral damage created when the heated tissue is then removed through aspiration. Alternatively, the present invention may employ a combination of ablation through molecular dissociation, as described above, and heating or softening of the fatty tissue. In this embodiment, some of the fatty tissue is ablated in situ, while other portions are softened to facilitate removal through suction.

During the process, the gases will be aspirated through the suction tube to a vacuum source. In addition, excess electrically conductive fluid, and other fluids (e.g., blood) will be aspirated from the target site to facilitate the surgeon's view. Applicant has also found that tissue fragments are also aspirated through opening 1109 into suction lumen and tube 1111 during the procedure. These tissue fragments are ablated or dissociated with loop electrodes 1040 in a similar mechanism to that described above. That is, as electrically conductive fluid and tissue fragments are aspirated towards loop electrodes 1040, these electrodes 1040 are activated so that a high frequency voltage is applied between loop electrodes 1040 and return electrode 1012 (of course, the probe may include a different, separate return electrode for this purpose). The voltage is sufficient to vaporize the fluid, and create a plasma layer between loop electrodes 1040 and the tissue fragments so that portions of the tissue fragments are ablated or removed. This reduces the volume of the tissue fragments as they pass through suction lumen to minimize clogging of the lumen.

In one embodiment, loop electrodes 1040 are electrically isolated from the other active electrodes 1004, and electrodes 1040 must be separately activated at the power supply 928. In other embodiments, loop electrodes 1040 will be activated at the same time that active electrodes 1004 are activated. In this case, applicant has found that the plasma layer typically forms when tissue is drawn adjacent to loop electrodes 1040.

Figure 24:
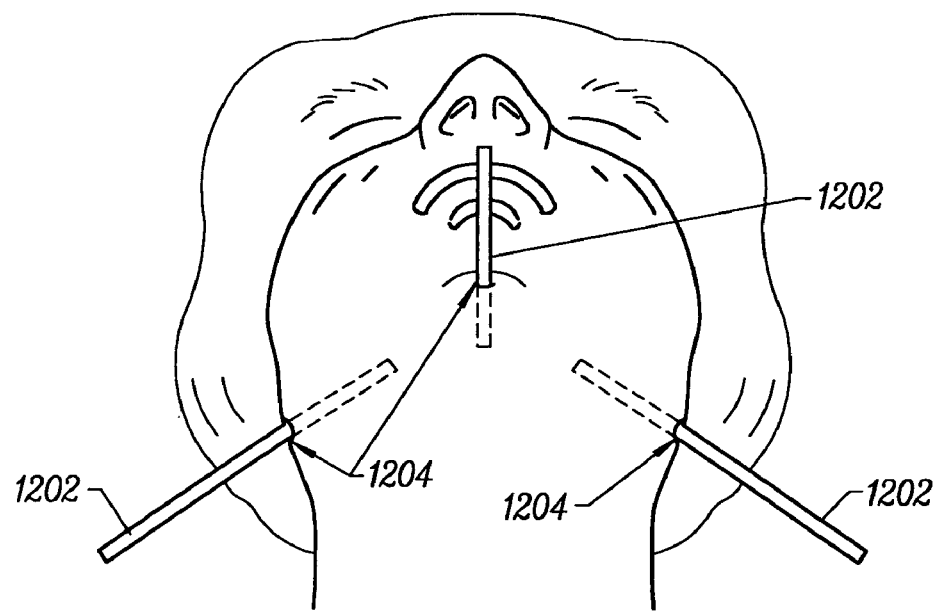
FIG. 24 illustrates a method for removing fatty tissue in the head and neck region of a patient according to the present invention.

FIG. 24 illustrates a cervical liposuction procedure in the face and neck according to the present invention. As shown, the distal portion of the electrosurgical probe 1202 may be inserted in either submental or retroauricular incisions 1204 in the face and neck. In this procedure, the probe 1202 is preferably passed through a portion of the fatty tissue with the power supply 928 activated, but without suction to establish a plane of dissection at the most superficial level of desired fat removal. This plane of dissection allows a smooth, supple, re-draping of the region after liposuction has been completed. If this "pre-tunneling" is not performed in this region, the cannula has a tendency to pull the skin inward, creating small pockets and indentations in the skin, which become evident as superficial irregularities after healing. Pre-tunneling also enables accurate, safe and proper removal of fat deposits while preserving a fine cushion of sub-dermal fat.

The present invention may also be used to perform lipectomies in combination with face and neck lifts to facilitate the latter procedures. After the cervical liposuction is complete, the skin flaps are elevated in the temporal, cheek and lateral regions. The lateral neck skin flap dissection is greatly facilitated by the previous suction lipectomy in that region, and the medial and central skin flap elevation may be virtually eliminated.

In another embodiment, the present invention comprises an electrified shaver or microdebrider. Powered instrumentation, such as microdebrider devices and shavers, has been used to remove polyps or other swollen tissue in functional endoscopic sinus surgery and synovial and meniscus tissue and articular cartilage I arthroscopic procedures. These powered instruments are disposable motorized cutters having a rotating shaft with a serrated distal tip for cutting and resecting tissue. The handle of the microdebrider is typically hollow, and it accommodates a small vacuum, which serves to aspirate debris. In this procedure, the distal tip of the shaft is endoscopically delivered to a target site of the patient's body, and an external motor rotates the shaft and the serrated tip, allowing the tip to cut tissue, which is then aspirated through the instrument.

While microdebriders and shavers of the prior art have shown some promise, these devices suffer from a number of disadvantages. For one thing, these devices sever blood vessels within the tissue, usually causing profuse bleeding that obstructs the surgeon's view of the target site. Controlling this bleeding can be difficult since the vacuuming action tends to promote hemorrhaging from blood vessels disrupted during the procedure. In addition, usually the microdebrider or shaver of the prior art must be periodically removed from the patient to cauterize severed blood vessels, thereby lengthening the procedure. Moreover, the serrated edges and other fine crevices of the microdebrider and shaver can easily become clogged with debris, which requires the surgeon to remove and clean the microdebrider during the surgery, further increasing the length of the procedure.

The present invention solves the above problems by providing one or more active electrodes at the distal tip of the aspiration instrument to effect hemostasis of severed blood vessels at the target site. This minimizes bleeding to clear the surgical site, and to reduce postoperative swelling and pain. In addition, by providing an aspiration electrode on or near the suction lumen, as described above, the present invention avoids the problems of clogging inherent with these devices.

The systems of the present invention may include a bipolar arrangement of electrodes designed to ablate tissue at the target site, and then aspirate tissue fragments, as described above. Alternatively, the instrument may also include a rotating shaft with a cutting tip for cutting tissue in a conventional manner. In this embodiment, the electrode(s) serve to effect hemostasis at the target site and to reduce clogging of the aspiration lumen, while the rotating shaft and cutting tip do the bulk of tissue removal by cutting the tissue in a conventional manner.

The system and method of the present invention may also be useful to efficaciously ablate (i.e., disintegrate) cancer cells and tissue containing cancer cells, such as cancer on the surface of the epidermis, eye, colon, bladder, cervix, uterus and the like. The present invention's ability to completely disintegrate the target tissue can be advantageous in this application because simply vaporizing and fragmenting cancerous tissue may lead to spreading of viable cancer cells (i.e., seeding) to other portions of the patient's body or to the surgical team in close proximity to the target tissue. In addition, the cancerous tissue can be removed to a precise depth while minimizing necrosis of the underlying tissue.

In another aspect of the invention, systems and methods are provided for treating articular cartilage defects, such as chondral fractures or chondromalicia. The method comprises positioning a distal end of an electrosurgical instrument, such as a probe or a catheter, into close proximity to an articular cartilage surface, either arthroscopically or through an open procedure. High frequency voltage is then applied between an active electrode on the instrument and a return electrode such that electric current flows therebetween and sufficient energy is imparted to the articular cartilage to smooth its surface or to reduce a level of fibrillation in the cartilage. In treating chondromalicia, the voltage between the electrodes is sufficient to heat (e.g., shrink) or ablate (i.e., remove) cartilage strands extending from the articular cartilage surface. In treating chondral fractures, lesions or other defects, the voltage is typically sufficient to ablate or heat at least a portion of the diseased tissue while leaving behind a smooth, contoured surface. In both cases, the method preferably includes forming a substantially continuous matrix layer on the surface of the tissue to seal the tissue, insulating the fracturing and fissuring within the articular cartilage that can cause further degeneration.

The present invention provides a highly controlled application of energy across the articular cartilage, confining the effect to the surface to produce precise and anatomically optimal tissue sculpting that stabilizes the articular cartilage and minimizes collateral tissue injury. Results to date demonstrate that cultures of post-treated chondrocytes within the cartilage tissue remain viable for at least one month, confirming that remaining chrondrocytes remain viable after this procedure. Moreover, minimal to no collagen abnormalities have been detected in post-operative cartilage tissue, and diseased areas are smoothed without further evidence of fibrillation. In addition, the bipolar configuration of the present invention controls the flow of current to the immediate region around the distal end of the probe, which minimizes tissue necrosis and the conduction of current through the patient. The residual heat from the electrical energy also provides simultaneous hemostasis of severed blood vessels, which increases visualization of the surgical field for the surgeon, and improves recovery time for the patient. The techniques of the present invention produce significantly less thermal energy than many conventional techniques, such as lasers and conventional RF devices, which reduces collateral tissue damage and minimizes pain and postoperative scarring. Patients generally experience less pain and swelling, and consequently achieve their range of motion earlier. A more complete description of exemplary systems and methods for treating articular cartilage can be found in co-pending commonly assigned U.S. patent application Ser. Nos. 09/183,838, filed Oct. 30, 1998 and 09/177,861, filed Oct. 23, 1998, the complete disclosures of which are incorporated herein by reference.

In another aspect, the present invention provides an electrosurgical probe having at least one active loop electrode for resecting and ablating tissue. In comparison to the planar electrodes, ball electrodes, or the like, the active loop electrodes provide a greater current concentration to the tissue at the target site. The greater current concentration can be used to aggressively create a plasma within the electrically conductive fluid, and hence a more efficient resection of the tissue at the target site. In use, the loop electrode(s) are typically employed to ablate tissue using the Coblation® mechanisms as described above. Voltage is applied between the active loop electrodes and a return electrode to volumetrically loosen fragments from the target site through molecular dissociation. Once the tissue fragments are loosened from the target site, the tissue fragments can be ablated in situ within the plasma (i.e., break down the tissue by processes including molecular dissociation or disintegration).

In some embodiments, the loop electrode(s) provide a relatively uniform smooth cutting or ablation effect across the tissue. The loop electrodes generally have a larger surface area exposed to electrically conductive fluid (as compared to the smaller active electrodes described above), which increases the rate of ablation of tissue.

Applicants have found that the current concentrating effects of the loop electrodes further provide reduced current dissipation into the surrounding tissue, and consequently improved patient comfort through the reduced stimulation of surrounding nerves and muscle. Preferably, the loop electrode(s) extend a sufficient distance from the electrode support member to achieve current concentration and an improved ablation rate while simultaneously reducing current dissipation into the surrounding medium (which can cause undesirable muscle stimulation, nerve stimulation, or thermal damage to surrounding or underlying tissue). In an exemplary embodiment, the loop electrode has a length from one end to the other end of about 0.5 mm to 20 mm, usually about 1 mm to 8 mm. The loop electrode usually extends about 0.25 mm to 10 mm from the distal end of the support member, preferably about 1 mm to 4 mm.

The loop electrode(s) may have a variety of cross-sectional shapes. Electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. For example, material can be removed along the length of a solid or hollow wire electrode to form D or C shaped wires, respectively, with edges facing in the cutting direction. Alternatively, material can be removed at closely spaced intervals along the electrode length to form transverse grooves, slots, threads or the like along the electrodes.

In yet another aspect, the present invention provides an electrosurgical probe having an aspiration lumen with an opening that is spaced proximally from the active electrodes. Applicants have found that by spacing the suction lumen opening proximal of the active electrodes that a more aggressive plasma can be created. In use, the saline is delivered to the target site and allowed to remain in contact with the electrodes and tissue for a longer period of time. By increasing the distance between the aspiration lumen and the conductive fluid, the dwell time of the conductive fluid is increased and the plasma can be aggressively created. Advantageously, by moving the aspiration lumen out of the target area, the suction will primarily aspirate blood and gas bubbles from the target site, while leaving the conductive fluid in the target area. Consequently, less conductive fluid and tissue fragments are aspirated from the target site and less clogging of the aspiration lumen occurs.

In a further aspect, the present invent provides an electrosurgical probe having a conductive fluid delivery lumen that has at least one distal opening positioned at least partially around the active electrodes. The configuration of the openings can be completely around the active electrodes (e.g., 0 configuration or annular shaped) or partially around the active electrodes (e.g., U configuration or C configuration) such that delivery of the conductive fluid immerses the active electrodes with conductive fluid during the ablation or resection procedure. Because the conductive fluid can be delivered from a plurality of directions, the dwell time of the conductive fluid is increased, and consequently the creation of the plasma can be improved.

In a preferred embodiment, the conductive fluid lumen comprises a plurality of openings that are positioned so as to substantially surround the active electrode array. As above, by "substantially surround", is meant that the openings are at least partially around the active electrodes. In some configurations, the openings will be equally spaced around the active electrodes. However, it will be appreciated that in other alternative embodiments, the openings will only partially surround the active electrodes or can be unevenly spaced about the active electrodes.

With reference to FIGS. 32–45 there follows a description of an electrosurgical probe 1400 including a resection unit 1406, according to various embodiments of the instant invention. Probe 1400 is adapted for aggressive ablation, for resection, or for combined ablation and resection of tissue. Probe 1400 may be used in a broad range of surgical procedures including, without limitation, those listed or described hereinabove with reference to the apparatus of FIGS. 1–31. In some embodiments, resection unit 1406 may be used to resect tissue by mechanical abrasion, cutting, or severing of tissue. In some embodiments, resection unit 1406 may be used to ablate tissue, e.g., via a Coblation® (cool ablation) mechanism. The Coblation® mechanism has been described hereinabove. Briefly, and without being bound by theory, Coblation® involves the localized generation of a plasma by the application of a high frequency voltage between at least one active electrode and a return electrode in the presence of an electrically conductive fluid. The plasma thus generated causes the breakdown of tissues, e.g., via molecular dissociation, to form low molecular weight ablation by-products. Such low molecular weight ablation by-products may be easily removed from a target site, e.g., via aspiration. Coblation® allows the controlled removal of tissue, in which both the quantity and quality of tissue removed can be accurately determined. In some embodiments, resection unit 1406 may be used for combined resection and ablation: to resect tissue by application of a mechanical force to the tissue and, concurrently therewith, to electrically ablate ("Coblate") the tissue contacted by resection unit 1406. Applicants have found that a combination of mechanical resection and electrical ablation by resection unit 1406 provides advantageous tissue removal, as compared with mechanical resection or electrical ablation alone. Advantages of tissue removal by combined resection and ablation by resection unit 1406 include a more rapid and aggressive tissue removal, as compared with ablation alone; and a more controlled and less traumatic tissue removal, as compared with mechanical resection alone.

Figure 32:
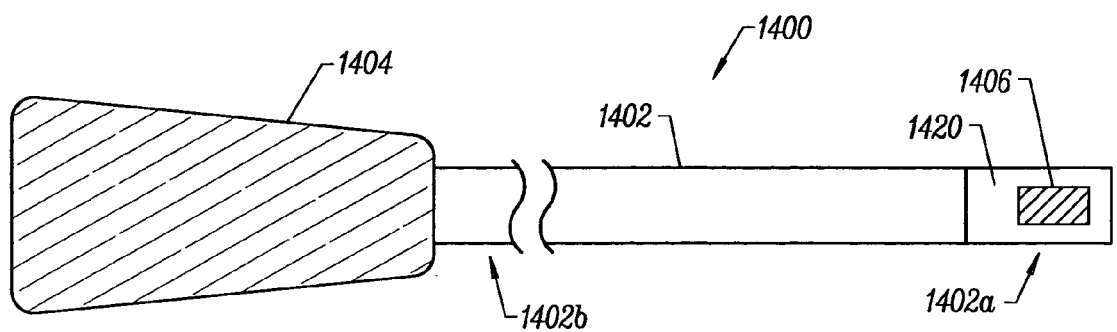
FIG. 32 shows an electrosurgical probe including a resection unit, according to another embodiment of the invention.
Figure 33:
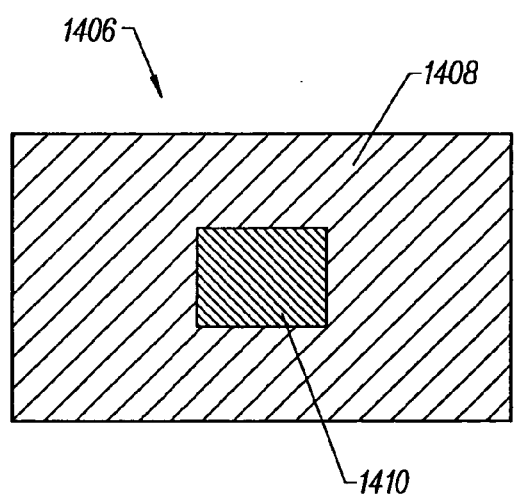
FIG. 33 shows a resection unit of an electrosurgical probe, the resection unit including a resection electrode on a resection electrode support.

FIG. 32 shows probe 1400 including a shaft 1402 affixed at shaft proximal end portion 1402*b* to a handle 1404. Resection unit 1406 is disposed on shaft distal end portion 1402*a*. Although FIG. 32 shows only a single resection unit 1406 on shaft 1402, certain embodiments of the instant invention may include a plurality of resection units 1406 which may be alike or dissimilar in various respects (for example, the size and shape of electrode support 1408, and the number, arrangement, and type of resection electrodes 1410) (FIG. 33). In the embodiment of FIG. 32, a return electrode 1420 is located at shaft distal end portion 1402a. Return electrode 1420 may be in the form of an annular band. Resection unit 1406 is shown in FIG. 32 as being arranged within, or surrounded by, return electrode 1420. In other embodiments, resection unit 1406 may be arranged adjacent to return electrode 1420. Under the invention, shaft 1402 may be provided in a range of different lengths and diameters. Preferably, shaft 1402 has a length in the range of from about 5 cm to about 30 cm; more preferably in the range of from about 10 cm to about 25 cm. Preferably, shaft 1402 has a diameter in the range of from about 1 mm to about 20 mm; more preferably in the range of from about 2 mm to about 10 mm.

FIG. 33 schematically represents resection unit 1406 of probe 1400, wherein resection unit 1406 includes a resection electrode 1410 on a resection electrode support member 1408. In FIG. 33 resection electrode 1410 is represented as a single "box" located within support 1408, however, other arrangements and numbers of resection electrode 1410 are contemplated and are within the scope of the invention (see, for example, FIGS. 36A–F, FIGS. 41A–C). Resection electrode support 1408 may comprise an electrically insulating, and durable or refractory material, such as a glass, a ceramic, a silicone rubber, a polyurethane, a urethane, a polyimide, silicon nitride, teflon, or alumina, and the like. Resection electrode support 1408 is shown in FIG. 33 as being substantially square in outline, however, a broad range of other shapes are also possible. The size of resection electrode support 1408 may depend on a number of factors, including the diameter or width of shaft 1402. In one embodiment, support 1408 may be mounted laterally on shaft 1402 as an annular band, i.e., support 1408 may completely encircle shaft 1402. Typically support 1408 represents or occupies from about 2% to 100% of the circumference of shaft 1402. More typically, support 1408 occupies from about 50% to 80% of the circumference of shaft 1402, most typically from about 10% to 50% of the circumference of shaft 1402. In embodiments wherein support 1408 is mounted terminally on shaft 1402, support 1408 typically occupies from about 5% to 100% of the cross-sectional area of shaft 1402, more typically from about 10% to 95% of the cross-sectional area of shaft 1402.

FIGS. 34A–D each show an electrosurgical probe 1400, according to certain embodiments of the invention. Probe 1400 is depicted in FIGS. 34A–D as being linear, however, according to various embodiments of the invention, shaft 1402 may include one or more curves or bends therein (see, for example, FIG. 43B). Resection electrodes 1410 are omitted from FIGS. 34A–D for the sake of clarity. However, as described elsewhere herein, each resection unit 1406 includes at least one resection electrode 1410 (see, for example, FIGS. 36A–F, 38A–D, 41A–C).

Figure 34A:
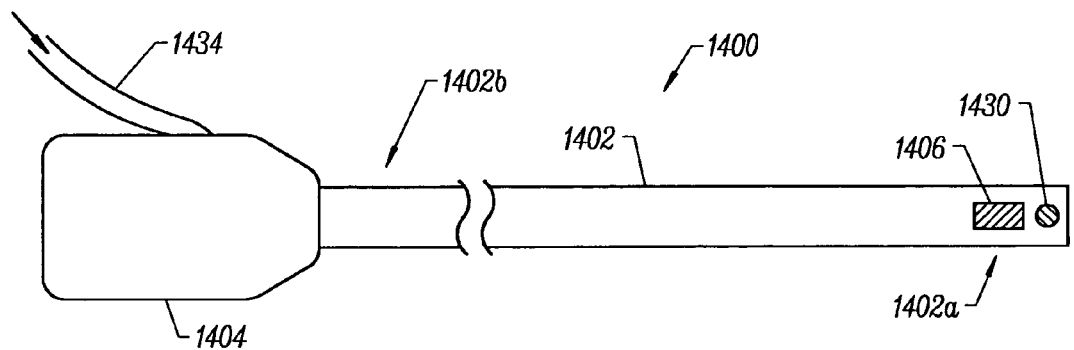
FIGS. 34A–D each show an electrosurgical probe including a resection unit, according to various embodiments of the invention.
Figure 35A:
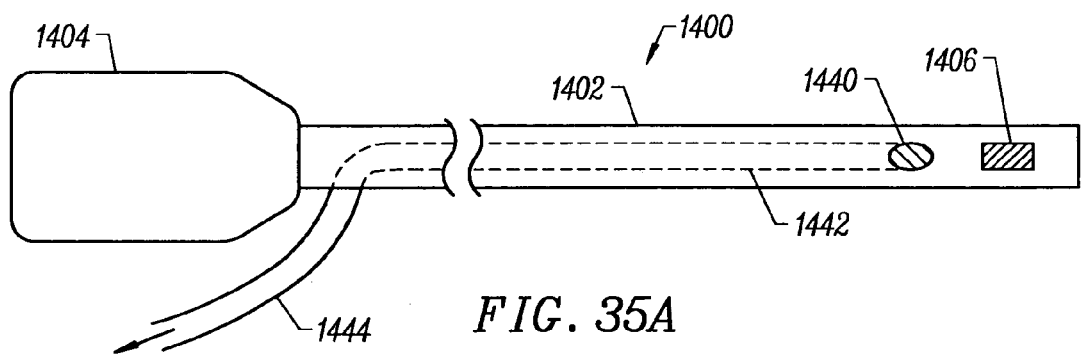
FIG. 35A shows an electrosurgical probe including a resection unit and an aspiration device, according to the invention.
Figure 35B:
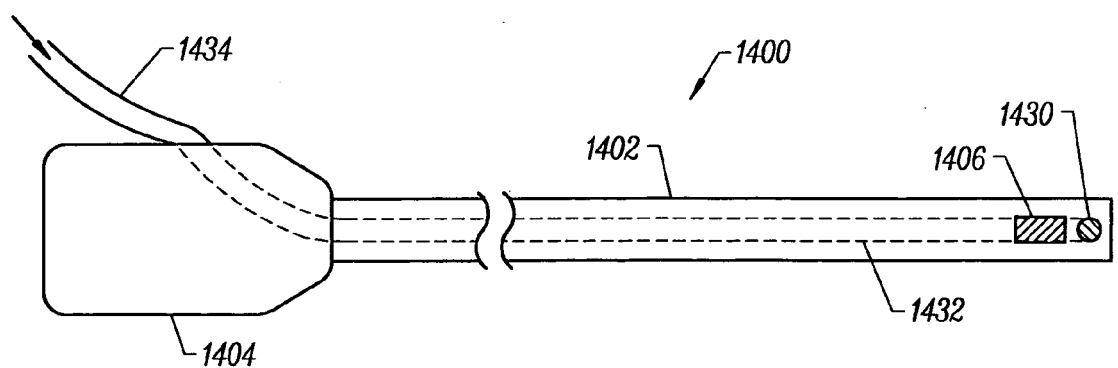
FIG. 35B shows an electrosurgical probe including a resection unit and a fluid delivery device, according to one embodiment of the invention.

With reference to FIG. 34A, probe 1400 includes a fluid delivery tube 1434, and a fluid delivery port 1430 located distal to resection unit 1406 on shaft distal end portion 1402a. Fluid delivery port 1430 is coupled to fluid delivery tube 1434 via a fluid delivery lumen 1432 (FIG. 35B). Fluid delivery tube 1434 is, in turn, coupled to a source of an electrically conductive fluid (see, e.g., FIG. 7). Fluid delivery port 1430 is adapted to provide a quantity of an electrically conductive fluid to shaft distal end portion 1402a during a procedure, as is described elsewhere herein in enabling detail.

Figure 34B:
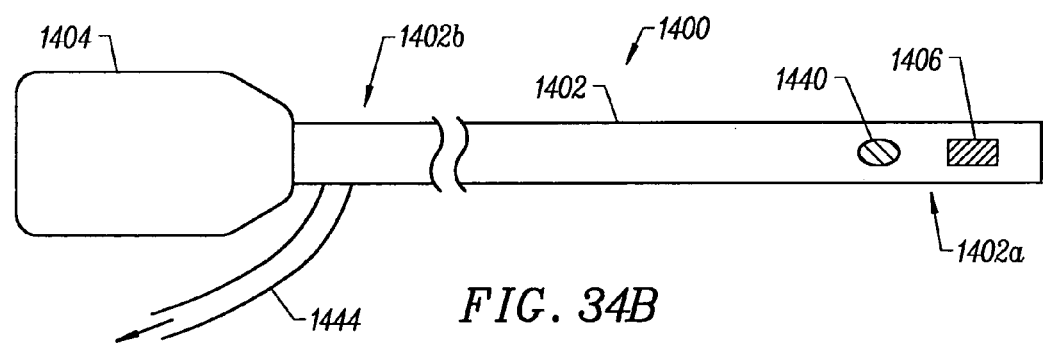
Figure 34C:
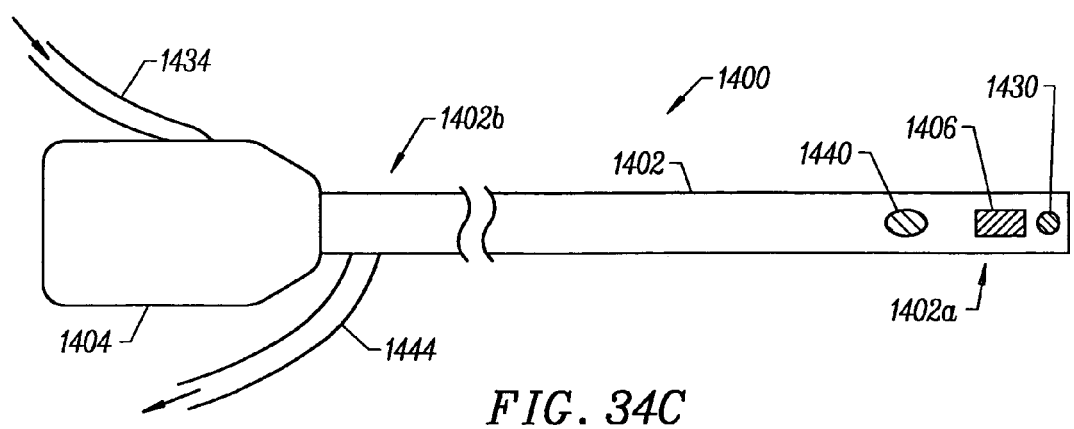

FIG. 34B shows probe 1400 including an aspiration tube 1444 and an aspiration port 1440 located proximal to resection unit 1406. In the embodiment depicted in FIG. 34B, aspiration tube 1444 is shown as being connected to probe 1400 at shaft proximal end 1402b, however other arrangements for coupling aspiration tube 1444 to probe 1400 are possible under the invention. FIG. 34C shows probe 1400 including both an aspiration tube 1444 and a fluid delivery tube 1434; and both a fluid delivery port 1430 and an aspiration port 1440. Although fluid delivery port 1430 is depicted in FIG. 34A, 34C as a single port located distal to resection unit 1406, other arrangements of fluid delivery port(s) 1430/1430' with respect to resection unit 1406, are contemplated according to various embodiments of the invention. Aspiration port 1440 is located proximal to resection unit 1406. Preferably, aspiration port 1440 is located a distance of at least 2 mm proximal to resection unit 1406. More preferably, aspiration port 1440 is located a distance in the range of from about 4 mm to about 50 mm proximal to resection unit 1406. In one embodiment, aspiration port 1440 may have a screen (not shown) to prevent relatively large fragments of resected tissue from entering aspiration lumen 1442 (FIG. 35A). Such a screen may serve as an active electrode and cause ablation of tissue fragments which contact the screen. Alternatively, the screen may serve as a mechanical sieve or filter to exclude entry of relatively large tissue fragments into lumen 1442.

Figure 34D:
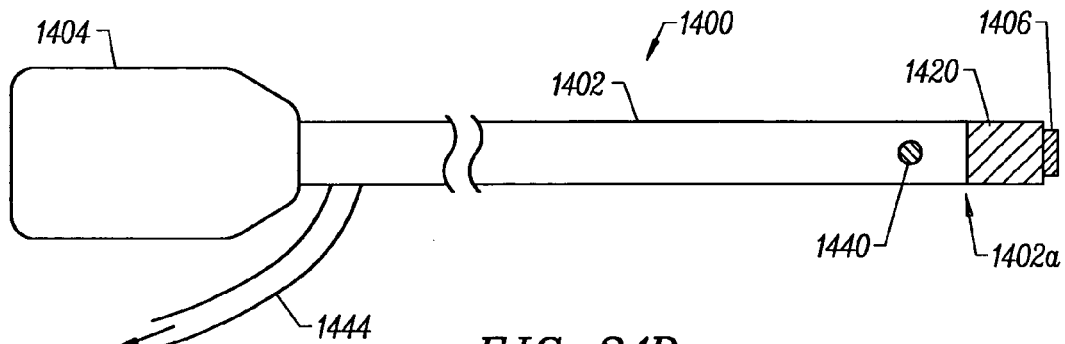

FIG. 34D shows probe 1400 in which resection unit 1406 is located at the distal terminus of shaft 1402. In this embodiment, return electrode 1420 is located at shaft distal end 1402a, and aspiration port 1440 is located proximal to return electrode 1420. The embodiment of FIG. 34D may further include one or more fluid delivery ports 1430 (see, for example, FIGS. 44A–D) for delivering an electrically conductive fluid to, at least, resection unit 1406. In certain embodiments, fluid delivery port(s) 1430 deliver a quantity of an electrically conductive fluid to shaft distal end 1402a sufficient to immerse resection unit 1406 and return electrode 1420. In some embodiments, fluid delivery port(s) 1430 deliver a quantity of an electrically conductive fluid from shaft distal end 1402a sufficient to immerse the tissue at a site targeted for ablation and/or resection.

FIG. 35A shows electrosurgical probe 1400 including resection unit 1406 and aspiration port 1440 proximal to resection unit 1406, according to one embodiment of the invention. Aspiration port 1440 is coupled to aspiration tube 1444 via an aspiration lumen 1442. Aspiration tube 1444 may be coupled to a vacuum source, as is well known in the art. Aspiration lumen 1442 serves as a conduit for removal of unwanted materials (e.g., excess fluids and resected tissue fragments) from the surgical field or target site of an ablation and/or resection procedure, essentially as described hereinabove with reference to other embodiments of an electrosurgical probe. The embodiment of FIG. 35A may further include a fluid delivery device (see, for example, FIG. 35B).

FIG. 35B shows electrosurgical probe 1400 including resection unit 1406 and fluid delivery port 1430 located distal to resection unit 1406, according to one embodiment of the invention. Fluid delivery port 1430 is coupled to fluid delivery tube 1434 via a fluid delivery lumen 1432. Fluid delivery lumen 1432 serves as a conduit for providing a quantity of an electrically conductive fluid to resection unit 1406 and/or the target site of an ablation and resection procedure. The embodiment of FIG. 35B may further include an aspiration device (see, for example, FIG. 35A). In the embodiment of FIG. 35B, tube 1434 is coupled to probe 1400 at handle 1404, however other arrangements for coupling tube 1434 to probe 1400 are also within the scope of the invention.

FIGS. 36A–F each show a resection unit 1406a–f as seen in plan view, wherein each resection unit 1406a–f includes a resection electrode support 1408 and at least one resection electrode head 1412, according to various embodiments of the invention. Each resection electrode 1410 (e.g., FIG. 33), may have a single terminal or resection electrode head 1412, such that each resection electrode head 1412 is independently coupled to a power supply (e.g., power supply 428 of FIG. 7). Alternatively, each resection electrode 1410 may have a plurality of terminals or resection electrode heads 1412. Each resection electrode 1410 may be coupled to a power supply unit (not shown in FIGS. 36A–F) via a connection block and connector cable, essentially as described hereinabove (e.g., with reference to FIGS. 7 & 10).

FIG. 36A indicates the longitudinal axis 1406' of resection units 1406a–f, as well as electrode support distal end 1408a (indication of longitudinal axis 1406' and support distal end 1408a are omitted from FIGS. 36B–F for the sake of clarity, however the orientation of resection units 1406b–f is the same as that of resection unit 1406a). In each of FIGS. 36A–F, resection electrode heads 1412 are depicted as having an elongated, substantially rectangular shape in plan view. However, other shapes and arrangements for resection electrode heads 1412 are also within the scope of the invention.

FIGS. 36A–F show just some of the arrangements of resection electrode head(s) 1412 on each resection electrode support 1408, according to various embodiments. Briefly, FIG. 36A shows a single resection electrode head 1412 located substantially centrally within support 1408 and aligned approximately perpendicular to longitudinal axis 1406'. FIG. 36B shows a plurality of resection electrode heads 1412 arranged substantially parallel to each other and aligned substantially perpendicular to axis 1406'. FIG. 36C shows a plurality of resection electrode heads 1412 arranged substantially parallel to each other and aligned substantially perpendicular to axis 1406', and an additional resection electrode head 1412 arranged substantially parallel to axis 1406'. FIG. 36D shows a plurality of resection electrode heads 1412 arranged substantially parallel to each other and aligned at an angle intermediate between parallel to axis 1406' and perpendicular to axis 1406'. FIG. 36E shows a plurality of resection electrode heads 1412 including a first substantially parallel array 1412a aligned at a first angle with respect to axis 1406' and a second substantially parallel array 1412b aligned at a second angle with respect to axis 1406'. FIG. 36F shows a plurality of resection electrode heads 1412 having an arrangement similar to that described for FIG. 36E, wherein resection electrode heads 1412 are of different sizes.

Figure 37:
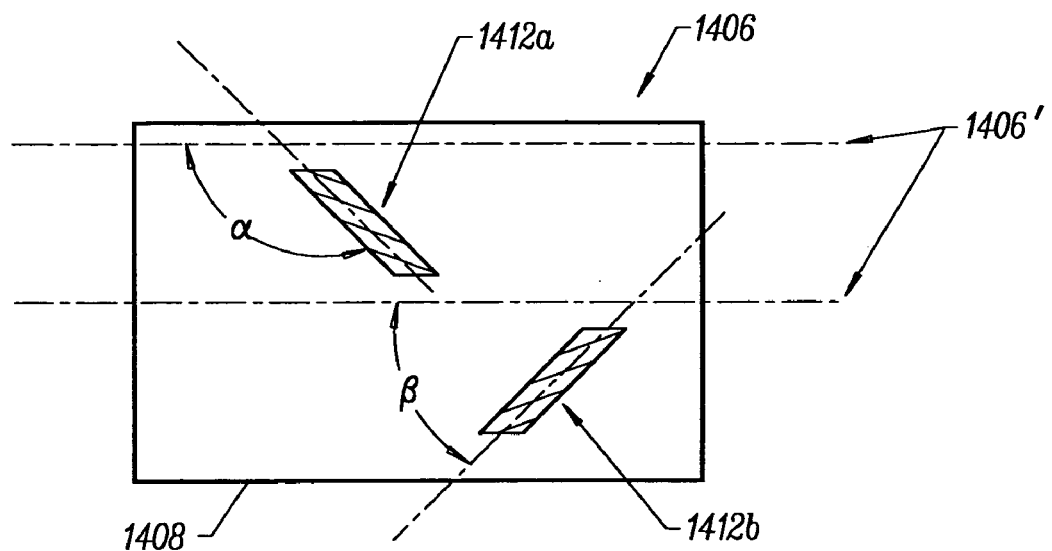
FIG. 37 illustrates an arrangement of a resection electrode head with respect to the longitudinal axis of a resection unit.

FIG. 37 illustrates an angle at which a resection electrode head 1412 may be arranged on electrode support 1408 with respect to the longitudinal axis 1406' of resection unit 1406. According to certain embodiments, resection electrode heads 1412 may be arranged on electrode support 1408 at an angle in the range of from 0° to about 175° with respect to longitudinal axis 1406'. In embodiments having first and second parallel arrays of resection electrode heads 1412, e.g., FIG. 36E, first array 1412a is preferably arranged at an angle α in the range of from about 90° to 170°, and more preferably from about 105° to 165°. Second array 1412b is preferably arranged at an angle β in the range of from about 10° to 90°, and more preferably from about 15° to 75°.

Figure 38A:
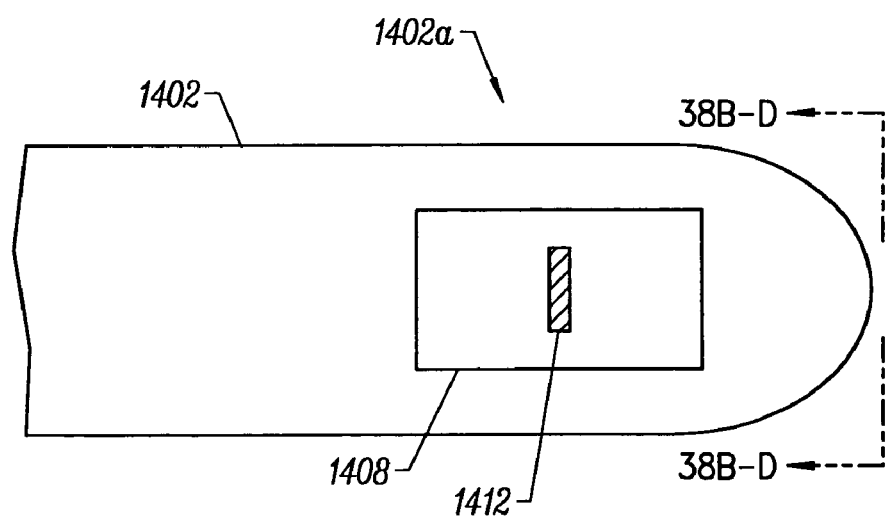
FIG. 38A shows, in plan view, a resection electrode support disposed on a shaft distal end of an electrosurgical probe.
Figure 38B:
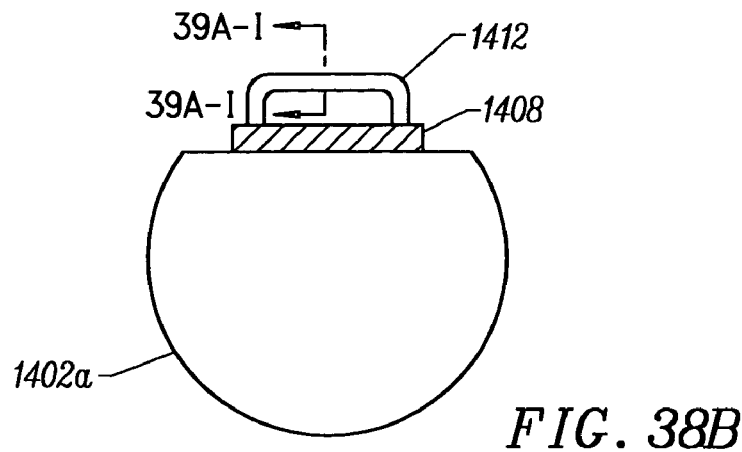
FIGS. 38B–D each show a profile of a resection electrode head on a resection electrode support.
Figure 38C:
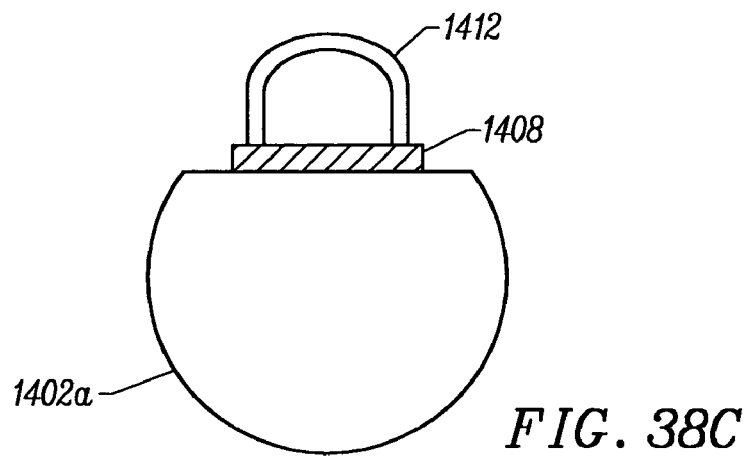
Figure 38D:
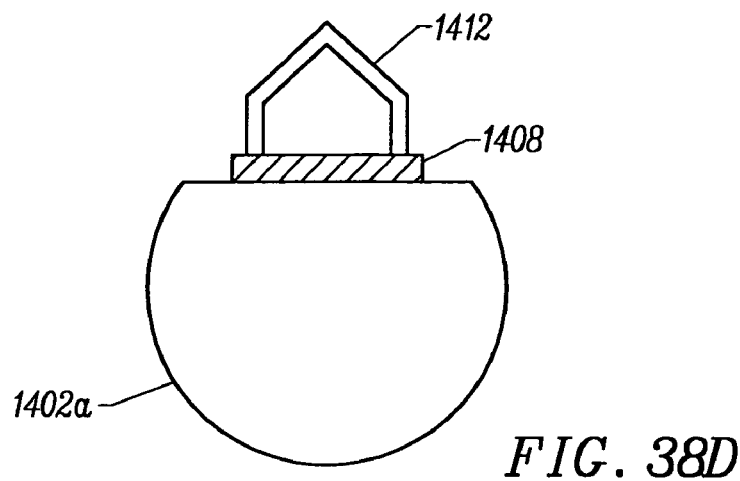

FIG. 38A shows in plan view a resection electrode support 1408 arranged on shaft distal end portion 1402a, wherein electrode support 1408 includes resection electrode head 1412. FIGS. 38B–D each show a profile of a resection electrode head 1412 on an electrode support 1408 as seen along the line 38B–D of FIG. 38A. From an examination of FIGS. 38B–D it can be readily seen that, according to certain embodiments of the invention, resection electrode head 1412 may protrude a significant distance from the external surface of shaft 1402. Typically, each resection electrode head 1412 protrudes from resection electrode support 1408 by a distance in the range of from about 0.1 to 20 mm, and preferably by a distance in the range of from about 0.2 to 10 mm. Resection electrode head 1412 may have a profile which is substantially square or rectangular; arched or semi-circular; or angular and pointed, as represented by FIGS. 38B–D, respectively. Other profiles and shapes for resection electrode head 1412 are also within the scope of the invention. Only one resection electrode head 1412 is depicted per electrode support 1408 in FIGS. 38A–D. However, according to the invention, each electrode support 1408 may have a plurality of resection electrode heads 1412 arranged thereon in a variety of arrangements (see, e.g., FIGS. 36A–F).

In the embodiments of FIGS. 38B–D, each electrode head 1412 is in the form of a filament or wire of electrically conductive material. In one embodiment, the filament or wire comprises a metal. Such a metal is preferably a durable, corrosion resistant metal. Suitable metals for construction of resection electrode head 1412 include, without limitation, tungsten, stainless steel alloys, platinum or its alloys, titanium or its alloys, molybdenum or its alloys, and nickel or its alloys. In embodiments wherein each electrode head 1412 is in the form of a filament or wire, the diameter of the wire is preferably in the range of from about 0.05 mm to about 5 mm, more preferably in the range of from about 0.1 to about 2 mm.

FIGS. 39A–I each show a cross-section of the filament or wire of resection electrode head 1412 as seen, for example, along the lines 39A–I of FIG. 38B. Evidently, a variety of different cross-sectional shapes for resection electrode head 1412 are possible. For example, resection electrode head 1412 may be substantially round or circular, substantially square, or substantially triangular in cross-section, as depicted in FIGS. 39A–C, respectively. Resection electrode head 1412 may have a cross-section having at least one curved side. For example, head 1412d of FIG. 39D has two substantially parallel sides and two concave sides. Head 1412e of FIG. 39E has four concave sides forming four cusps, while head 1412f (FIG. 39F) includes three concave sides forming three cusps. FIGS. 39G–I each depict a cross-section of a wire or filament having serrations on at least one side thereof. Resection electrode head 1412g comprises a filament having a substantially circular cross-section, wherein the circumference of the filament is serrated. In another embodiment (not shown) a selected portion of the circumference of a substantially round filament may be serrated. Resection electrode head 1412h (FIG. 39H) comprises a filament having a substantially square cross-section, wherein a leading or cutting edge portion 1413h of the filament is serrated. FIG. 39I shows a head 1412i comprising a filament of an electrically conductive material having a substantially crescent-shaped or semi-circular cross-sectional shape, wherein cutting edge portion 1413i is serrated. In addition, other cross-sectional shapes for electrode head 1412 are contemplated and are within the scope of the invention. Preferably, the cross-sectional shape and other features of resection electrode head 1412 promote high current densities in the vicinity of resection electrode head 1412 following application of a high frequency voltage to resection electrode head 1412. More preferably, the cross-sectional shape and other features of resection electrode head 1412 promote high current densities in the vicinity of a leading or cutting edge, e.g., edge 1413*h*, 1413*i*, of resection electrode head 1412 following application of a high frequency voltage to resection electrode head 1412. As noted previously, high current densities promote generation of a plasma in the presence of an electrically conductive fluid, and the plasma in turn efficiently ablates tissue via the Coblation® procedure or mechanism. Preferably, the cross-sectional shape and other features of resection electrode head 1412 are also adapted for maintenance of the plasma in the presence of a stream of fluid passing over resection electrode head 1412. In one embodiment, the cross-sectional shape and other features of resection electrode head 1412 are also adapted for the efficient mechanical resection, abrading, or severing of, at least, soft tissue (such as skeletal muscle, skin, cartilage, etc.).

In one embodiment a cutting edge, e.g., edge 1413*h*, 1413*i*, is adapted for both ablating and resecting tissue. Depending on the embodiment, cutting edge 1413*h*, 1413*i* may be oriented, or point, in various directions relative to the longitudinal axis of shaft 1402. For example, depending on the particular embodiment of probe 1400, and on the particular surgical procedure(s) for which embodiments of probe 1400 are designed to perform, cutting edge 1413*h*, 1413*i* may be oriented distally, proximally, or laterally.

Figure 40:
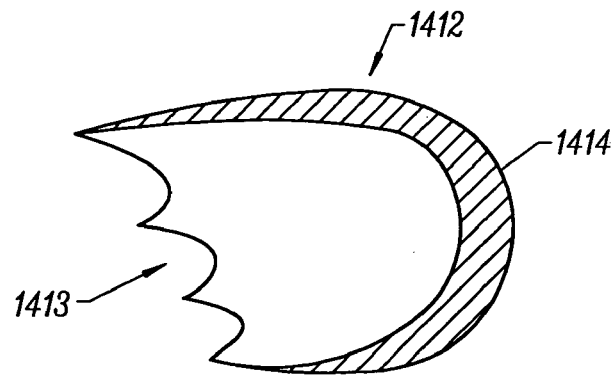
FIG. 40 shows a cross-section of a resection electrode head having an exposed cutting edge and a covered portion having an insulating layer, according to another embodiment of the invention.

FIG. 40 shows a cross-section of a resection electrode head 1412, according to another embodiment of the invention, wherein head 1412 includes a cutting edge 1413, and an insulating layer 1414 disposed on a covered portion of head 1412, and wherein cutting edge 1413 is free from insulating layer 1414. Cutting edge 1413 promotes high current densities in a region between resection electrode head 1412 and the target site upon application of a high frequency voltage to resection electrode head 1412. At the same time, insulating layer 1414 reduces undesirable current flow into tissue or surrounding electrically conducting liquids from covered (insulated) portion of resection electrode head 1412. The application or deposition of insulating layer 1414 to resection electrode head 1412 may be achieved by for example, thin-film deposition of an insulating material using evaporative or sputtering techniques, well known in the art. Insulating layer 1414 provides an electrically insulated non-active portion of resection electrode head 1412, thereby allowing the surgeon to selectively resect and/or ablate tissue, while minimizing necrosis or ablation of surrounding non-target tissue or other body structures.

Figure 41A:
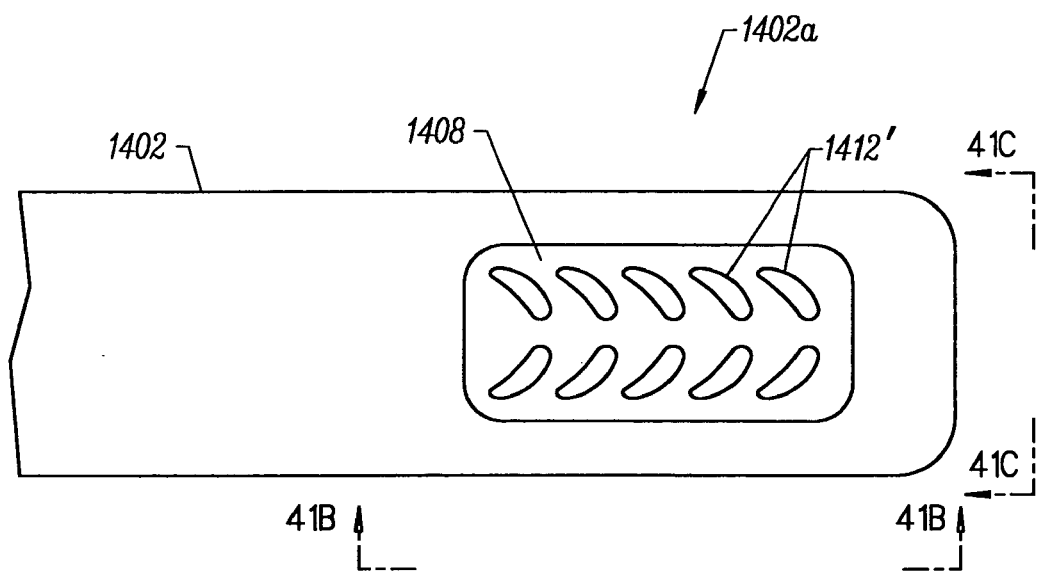
FIG. 41A illustrates a distal end of an electrosurgical probe including a plurality of resection electrode heads, according to another embodiment of the invention.
Figure 41B:
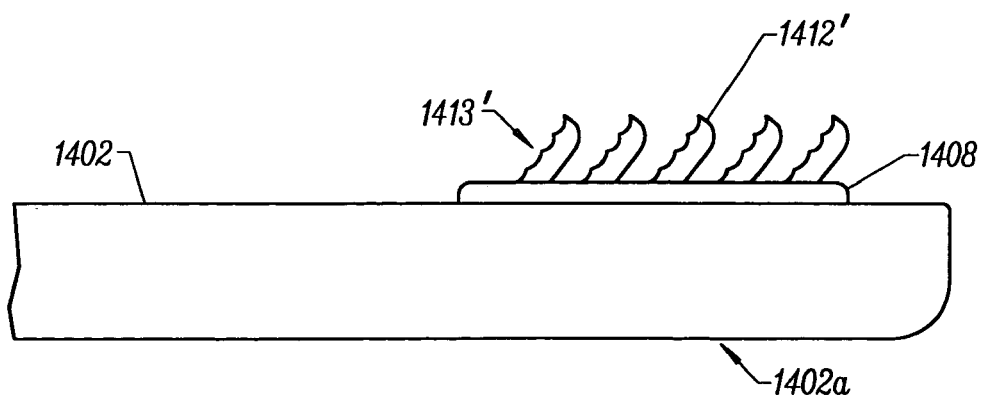
FIG. 41B illustrates the distal end of the electrosurgical probe of FIG. 41A taken along the lines 41B—41B.
Figure 41C:
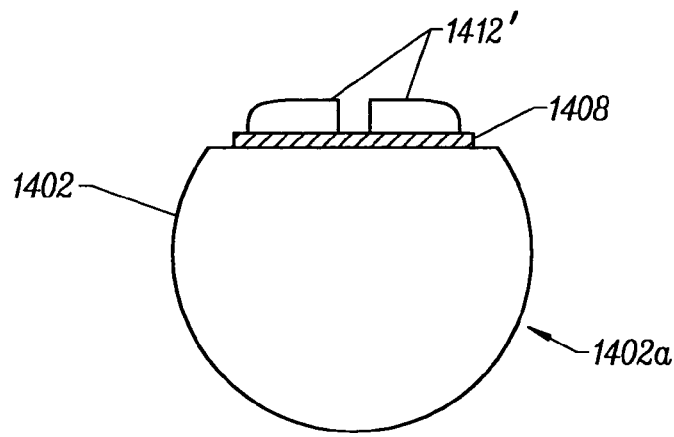
FIG. 41C illustrates the distal end of the electrosurgical probe of FIG. 41A taken along the lines 41C—41C.

FIG. 41A illustrates a distal end of an electrosurgical probe showing in plan view resection electrode support 1408 including a plurality of resection electrode heads 1412', according to another embodiment of the invention. In contrast to resection electrode heads 1412 described hereinabove, each resection electrode head 1412' in the embodiment of FIGS. 41A–C is in the form of a blade. In one embodiment, each resection electrode head 1412' may have a covered portion having an insulating layer thereon (analogous to insulating layer 1414 of resection electrode head 1412 of FIG. 40). Resection electrode heads 1412' are depicted in FIG. 41A as being arranged in a pair of angled parallel electrode head arrays. However, other arrangements for resection electrode heads 1412' are within the scope of the invention. FIG. 41B shows resection electrode heads 1412' as seen along the lines 41B—41B of FIG. 41A. Each resection electrode head 1412' may include a cutting edge 1413' adapted for promoting high current density in the vicinity of each resection electrode head 1412' upon application of a high frequency voltage thereto. In one embodiment, cutting edge 1413' is also adapted for severing or mechanical resection of tissue. In one embodiment, cutting edge 1413' is serrated. Cutting edge 1413' is shown in FIG. 41B as facing away from shaft distal end portion 1402*a*. However, in an analogous situation to that described hereinabove with reference to FIGS. 39H–I, various embodiments of probe 1400 may have cutting edge 1413' facing in any direction with respect to the longitudinal axis of shaft 1402, e.g., cutting edge 1413' may face distally, proximally, or laterally. Thus, probe 1400 may be provided in a form suitable for performing a broad range of resection and ablation procedures.

FIG. 41C illustrates shaft distal end 1402*a* of electrosurgical probe 1400, taken along the lines 41C—41C of FIG. 41A, showing resection electrode heads 1412' on resection electrode support 1408. From an examination of FIGS. 41B–C it can be readily appreciated that, according to certain embodiments of the invention, resection electrode heads 1412' may protrude a significant distance from the external surface of shaft 1402. Typically, each resection electrode head 1412' protrudes from resection electrode support 1408 by a distance in the range of from about 0.1 to 20 mm, and preferably by a distance in the range of from about 0.2 to 10 mm. Each resection electrode head 1412' may comprise a metal blade, wherein the metal blade comprises a metal such as tungsten, stainless steel alloys, platinum or its alloys, titanium or its alloys, molybdenum or its alloys, nickel or its alloys, and the like.

Figure 42A:
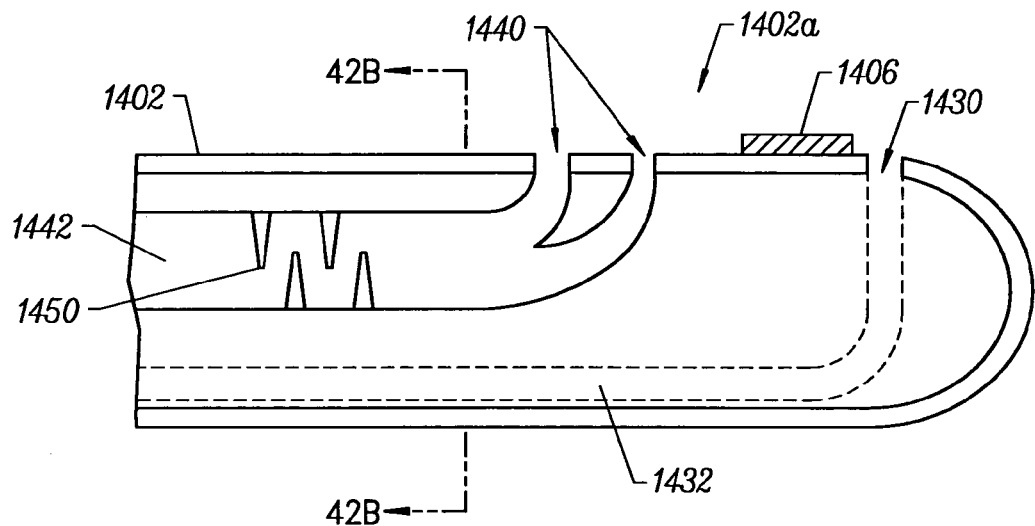
FIG. 42A is a sectional view of a distal end portion of an electrosurgical shaft, according to one embodiment of the invention.

FIG. 42A is a sectional view of shaft 1402 including distal end portion 1402*a*. Shaft 1402 includes resection unit 1406 and fluid delivery port 1430 for supplying electrically conductive fluid to resection unit 1406 via fluid delivery lumen 1432. A plurality of aspiration ports 1440 are located proximal to resection unit 1406. Aspiration ports 1440 lead to aspiration lumen 1442. Applicants have determined that positioning aspiration ports somewhat distant from resection unit 1406 and delivery port 1430, the dwell time of the electrically conductive fluid is increased, and a plasma can be created more aggressively and consistently. Advantageously, by moving the aspiration ports somewhat distant from the target site, suction will primarily aspirate excess or unwanted fluids (e.g., tissue fluids, blood, etc.) and gaseous ablation by-products from the target site, while the electrically conductive fluid, such as isotonic saline, remains at the target site. Consequently, less conductive fluid and tissue fragments are aspirated from the target site, and entry of resected tissue fragments into aspiration lumen 1442 is less likely to occur.

Figure 42B:
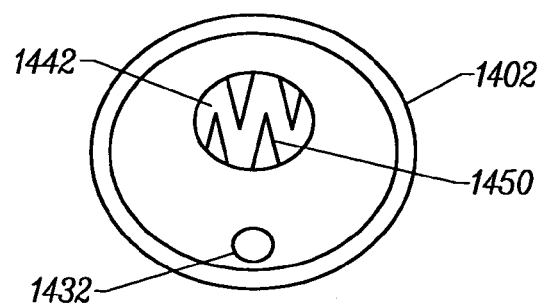
FIG. 42B illustrates the distal end of the shaft of FIG. 42A taken along the lines 42B—42B.

In the embodiments of FIGS. 42A–B, aspiration lumen 1442 includes at least one digestion electrode 1450. More preferably, aspiration lumen 1442 includes a plurality of digestion electrodes 1450. Each digestion electrode 1450 serves as an active (ablation) electrode and is coupled to a high frequency power supply (e.g. power supply 428 of FIG. 7). Each digestion electrode 1450 is adapted for rapidly breaking down any tissue fragments that may be drawn into aspiration lumen 1442 during a resection and ablation procedure. In this manner, lumen 1442 remains free from blockage, and allows a surgical procedure to be completed conveniently and efficiently without interruption to either unblock lumen 1442 or to replace probe 1400. The shape, arrangement, size, and number, of digestion electrodes 1450 is to some extent a matter of design choice. Preferably, each digestion electrode 1450 is adapted to provide a high current density upon application thereto of a high frequency voltage, thereby promoting rapid and efficient ablation of resected tissue fragments.

In one embodiment, a plurality of digestion electrodes 1450 of a suitable shape and size may be arranged within aspiration lumen 1442 such that digestion electrodes 1450 at least partially overlap or interweave. Such overlapping digestion electrodes 1450 may act, at least to some extent, as a screen to mechanically restrain tissue fragments thereat. While tissue fragments are restrained against one or more digestion electrodes 1450, the latter may efficiently ablate the former to yield low molecular weight ablation by-products which readily pass through lumen 1442 in the aspiration stream. FIG. 42B illustrates in transverse section shaft 1402 taken along the lines 42B—42B of FIG. 42A, and showing fluid delivery lumen 1432 and aspiration lumen 1442, the latter having digestion electrodes 1450 arranged therein. In this embodiment, digestion electrodes 1450 are shown as having pointed surfaces, such as are known to promote high current densities thereat, and digestion electrodes 1450 at least partially interweave with each other.

Figure 43A:
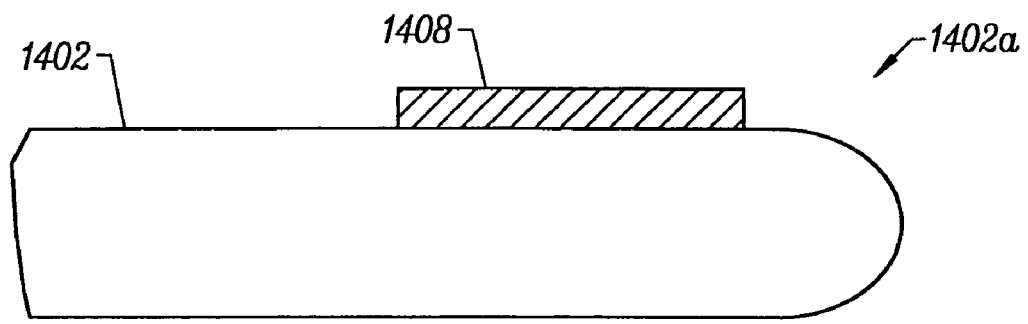
FIGS. 43A–D are side views of the shaft distal end portion of an electrosurgical probe, according to another embodiment of the invention.
Figure 43B:
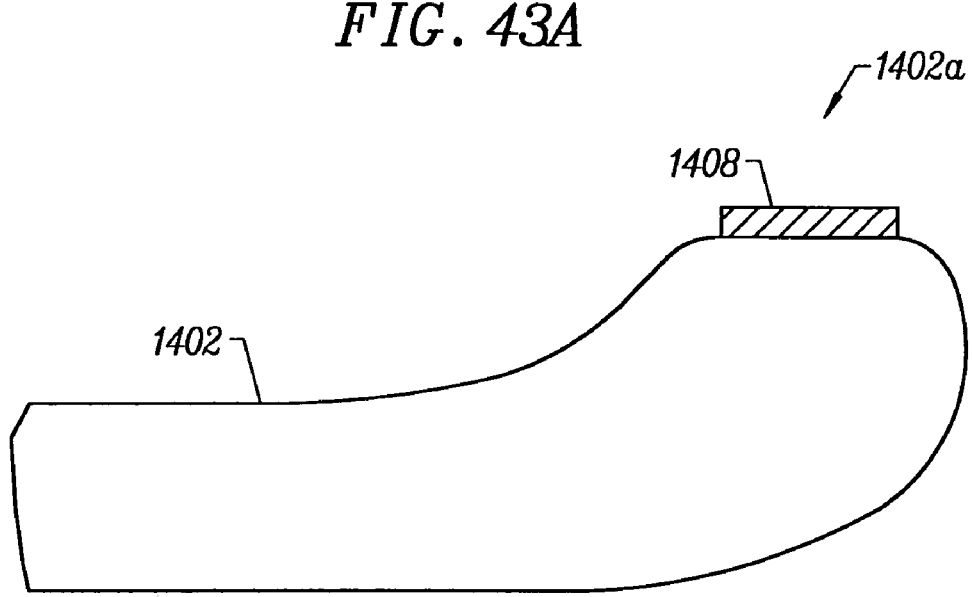

FIGS. 43A–D are side views of shaft distal end portion 1402*a* of an electrosurgical probe 1400. FIG. 43A shows resection electrode support 1408 disposed laterally on a linear or substantially linear shaft distal end 1402*a*. FIG. 43B shows resection electrode support 1408 disposed on the terminus of shaft 1402, wherein shaft distal end 1402*a* includes a bend or curve. In the embodiments of FIGS. 43A, 43B, electrode support 1408 protrudes from an external surface of shaft distal end portion 1402*a*. Typically, electrode support 1408 protrudes a distance in the range of from about 0 (zero) to about 20 mm from the external surface of shaft 1402. Each resection electrode support 1408 of the invention includes at least one resection electrode terminal or head 1412/1412'. Each resection electrode head 1412/1412' is coupled, e.g. via a connection block and connecting cable, to a high frequency power supply unit, essentially as described hereinabove. However, for the sake of clarity, resection electrode head(s) 1412/1412' are omitted from FIGS. 43A–D.

Figure 43C:
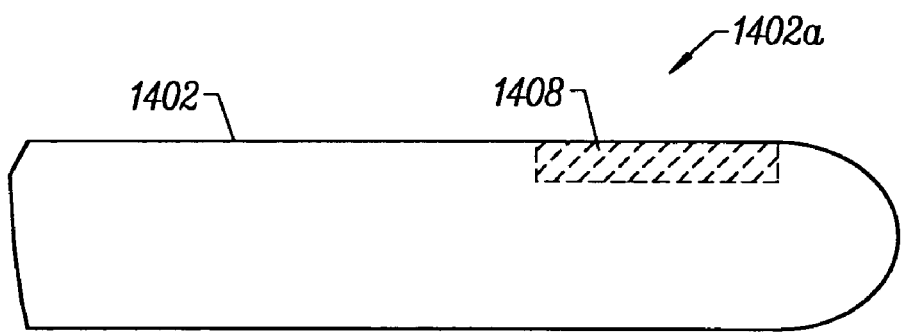
Figure 43D:
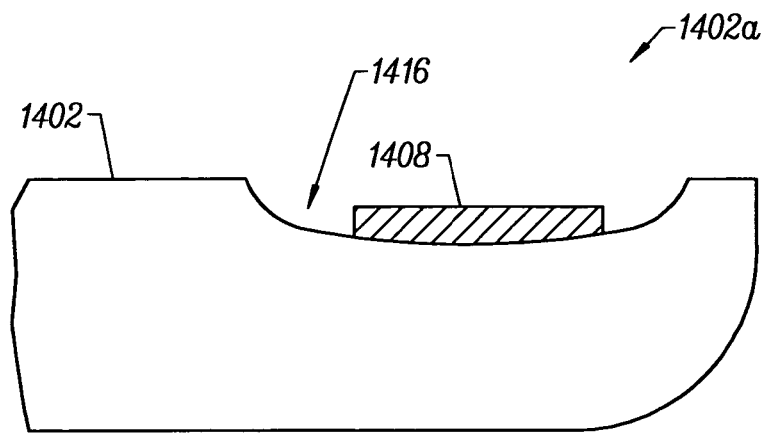

FIG. 43C shows shaft 1402 having resection electrode support 1408 countersunk or recessed within shaft distal end 1402*a*. In this embodiment, an external surface of resection electrode support 1408 may be aligned, or flush, with an external surface of shaft 1402. In this embodiment, resection electrode heads 1412/1412' (FIGS. 38B–D, 41A–C) may protrude from the external surface of shaft distal end 1402*a* to various extents, as described hereinabove. FIG. 43D shows a shaft distal end portion 1402 having a depression or cavity 1416 therein. In this embodiment, resection electrode support 1408 is housed within cavity 1416. In this embodiment, resection electrode heads 1412/1412' may, or may not, extend above cavity 1416 and from the shaft external surface. In this embodiment the extent, if any, to which resection electrode heads 1412/1412' extend above cavity 1416 is determined by the depth of cavity 1416, as well as by the height of resection electrode support 1408, and the height of resection electrode heads 1412/1412'. The embodiment of FIG. 43D serves to isolate non-target tissue from resection electrode heads 1412/1412', thereby minimizing collateral damage to such tissue during a resection and ablation procedure.

Figure 44A:
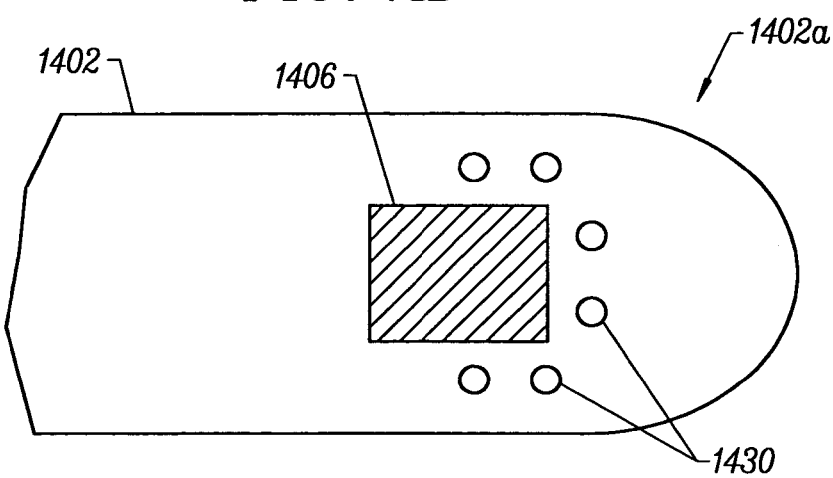
FIGS. 44A–D each show a resection unit in relation to a fluid delivery device, according to various embodiments of the invention.
Figure 44B:
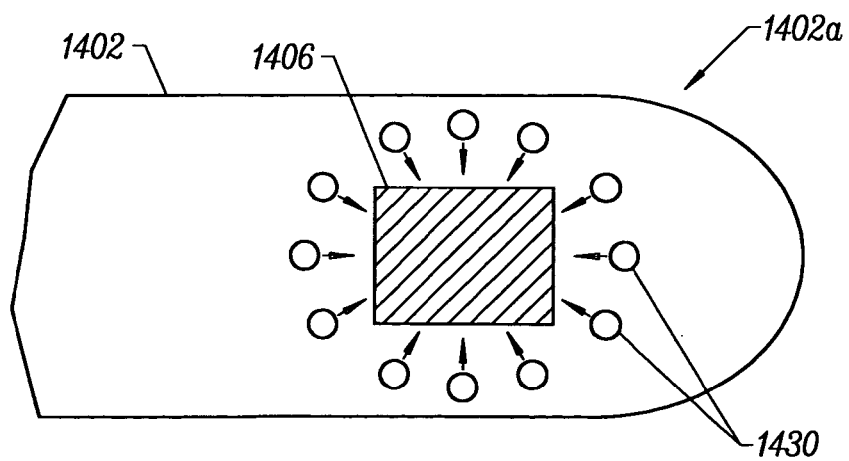

Referring now to FIGS. 44A–D, a fluid delivery device for delivering an electrically conductive fluid to resection unit 1406 or to tissue at a target site can include a single fluid delivery port 1430 (e.g., FIG. 34A) or a plurality of ports 1430. In exemplary embodiments of probe 1400, ports 1430 are disposed around a perimeter of resection unit 1406, and are positioned to deliver the conductive fluid to resection electrode head(s) 1412/1412'. As shown in FIG. 44A, a plurality of ports 1430 may be arranged around a distal portion of resection unit 1406. In the embodiment of FIG. 44B a plurality of ports 1430 are arranged around the entire perimeter of resection unit 1406. The arrows shown in FIG. 44B indicate a direction in which an electrically conductive fluid may be delivered from the plurality of fluid delivery ports 1430. In one embodiment, fluid delivery ports 1430 are rounded or substantially circular in outline.

Figure 44C:
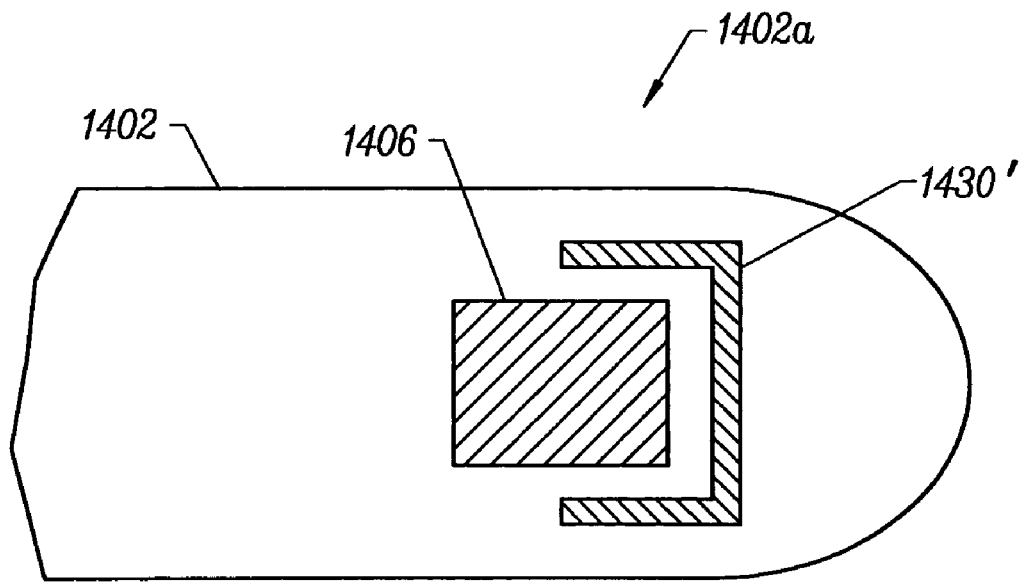
Figure 44D:
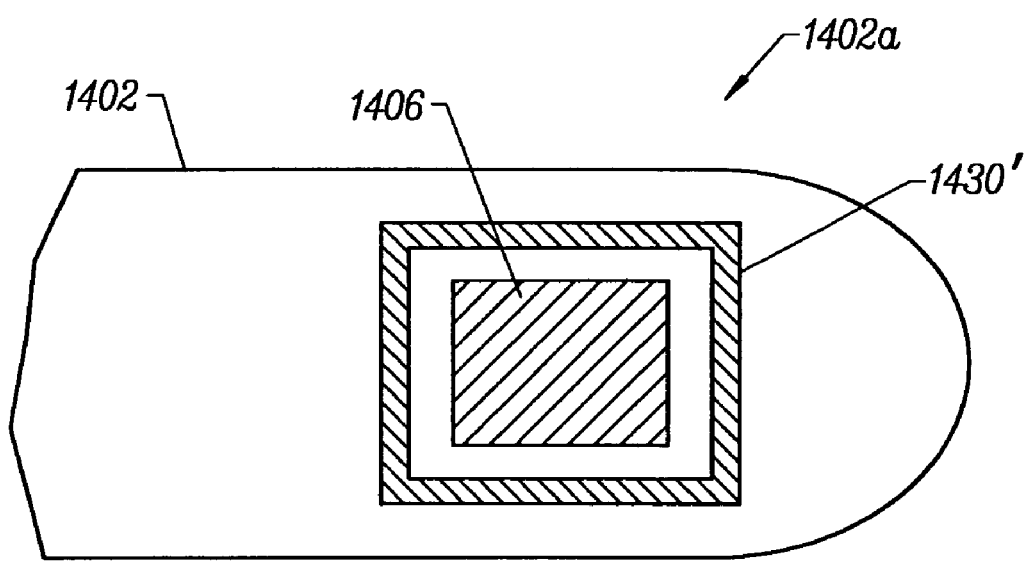

As shown in FIG. 44C, a fluid delivery port 1430' may be in the form of an elongated opening or slit extending around a distal portion of resection unit 1406. In the embodiment of FIG. 44D port 1430' is in the form of a single slit extending around the perimeter of resection unit 1406. In each embodiment (FIGS. 44A–D), delivery ports 1430/1430' preferably deliver electrically conductive fluid in the direction of resection unit 1406. The amount of electrically conductive fluid delivered to resection unit 1406, and the timing or periodicity of such fluid delivery, may be controlled by an operator (surgeon). In one embodiment, the amount of electrically conductive fluid delivered to resection unit 1406 is sufficient to, at least transiently, immerse resection electrode heads 1412/1412' in the electrically conductive fluid.

Figure 45:
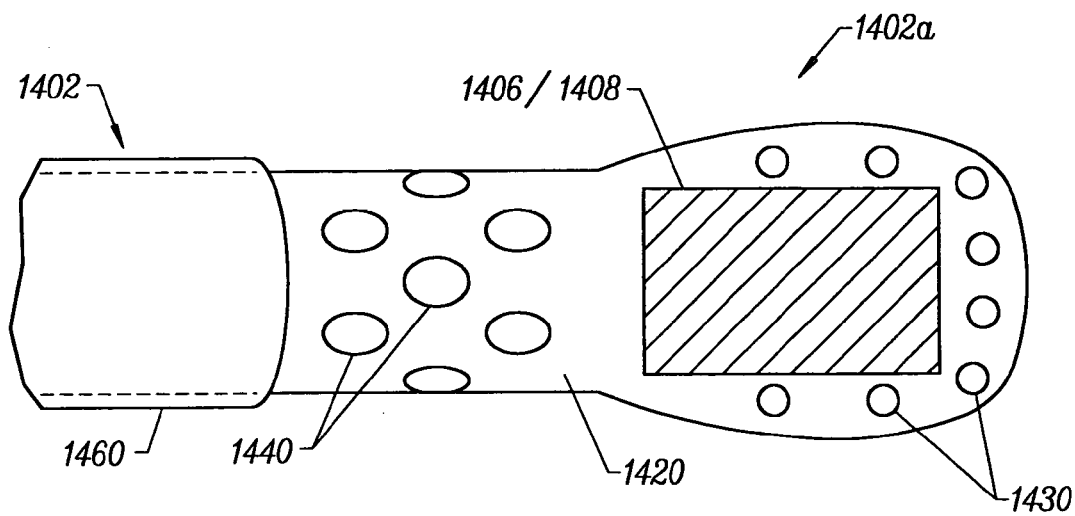
FIG. 45 shows a shaft distal end portion of an electrosurgical probe, according to one embodiment of the invention.

FIG. 45 shows a shaft distal end portion 1402*a* of shaft 1402, according to one embodiment of the invention. In this embodiment, resection unit 1406/resection electrode support 1408 is disposed on return electrode 1420, wherein return electrode 1420 comprises an exposed region of shaft 1402. By "exposed region" is meant a region of shaft distal end portion 1402*a* which is not covered by an insulating sleeve or sheath 1460. Insulating sleeve 1460 may comprise a layer or coating of a flexible insulating material, such as various plastics (e.g., a polyimide or polytetrafluoroethylene, and the like) as is well known in the art. In this embodiment, a plurality of fluid delivery ports 1430 are positioned within return electrode 1420 such that when the electrically conductive fluid contacts resection electrode heads 1412/1412' on resection electrode support 1408, an electrical circuit, or current flow path, is completed. A plurality of aspiration ports 1440 are spaced proximally from resection electrode support 1408 for removing unwanted fluids, such as ablation by-products, from the vicinity of resection unit 1406. Resection electrode support 1408 may be substantially square, rectangular, oval, circular, etc. Typically, resection electrode support 1408 has a dimension in the longitudinal direction of the shaft (i.e., a length) in the range of from about 1 mm to about 20 mm, more typically in the range of from about 2 mm to about 10 mm.

Figure 46:
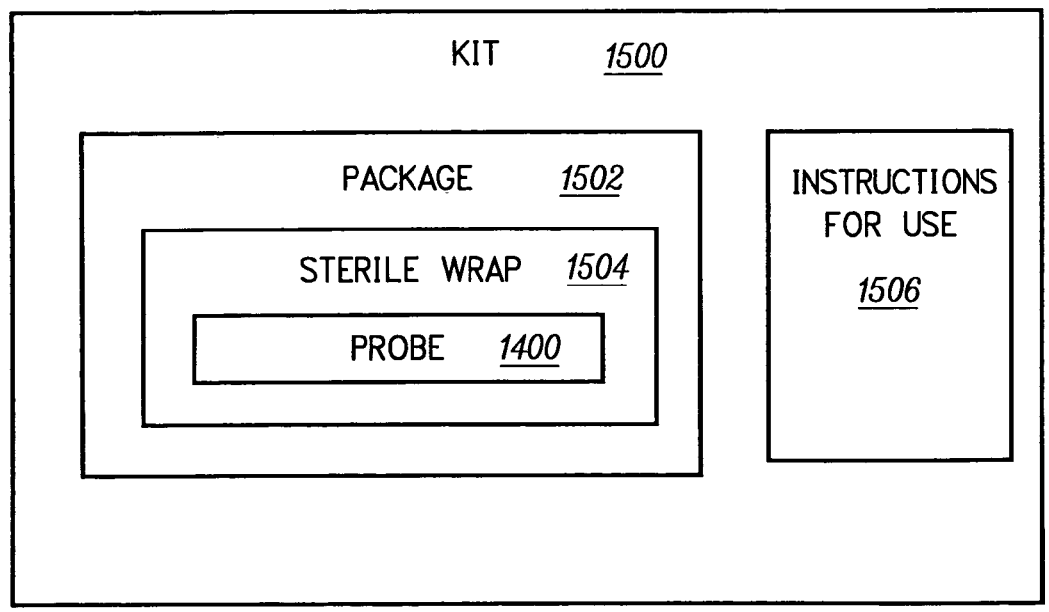
FIG. 46 schematically represents a surgical kit for resection and ablation of tissue, according to another embodiment of the invention.

Referring now to FIG. 46, a surgical kit 1500 for resecting and/or ablating tissue according to the invention will now be described. FIG. 46 schematically represents surgical kit 1500 including electrosurgical probe 1400, a package 1502 for housing probe 1400, a surgical instrument 1504, and an instructions for use 1506. Instructions for use 1506 include instructions for using probe 1400 in conjunction with apparatus ancillary to probe 1400, such as power supply 428 (FIG. 7). Package 1502 may comprise any suitable package, such as a box, carton, etc. In an exemplary embodiment, package 1502 includes a sterile wrap or wrapping 1504 for maintaining probe 1400 under aseptic conditions prior to performing a surgical procedure.

An electrosurgical probe 1400 of kit 1500 may comprise any of the embodiments described hereinabove. For example, probe 1400 of kit 1500 may include shaft 1402 having at least one resection electrode 1410 at shaft distal end 1402*a*, and at least one connector (not shown) extending from the at least one resection electrode 1410 to shaft proximal end 1402*b* for coupling resection electrode 1410 to a power supply. Probe 1400 and kit 1500 are disposable after a single procedure. Probe 1400 may or may not include a return electrode 1420.

Instructions for use 1506 generally includes, without limitation, instructions for performing the steps of: adjusting a voltage level of a high frequency power supply to effect resection and/or ablation of tissue at the target site; connecting probe 1400 to the high frequency power supply; positioning shaft distal end 1402a within an electrically conductive fluid at or near the tissue at the target site; and activating the power supply to effect resection and/or ablation of the tissue at the target site. An appropriate voltage level of the power supply is usually in the range of from about 40 to 400 volts RMS for operating frequencies of about 100 to 200 kHz. Instructions 1506 may further include instruction for advancing shaft 1402 towards the tissue at the target site, and for moving shaft distal end portion 1402a in relation to the tissue. Such movement may be performed with or without the exertion of a certain mechanical force on the target tissue via resection unit 1406, depending on parameters such as the nature of the procedure to be performed, the type of tissue at the target site, the rate at which the tissue is to be removed, and the particular design or embodiment of probe 1400/resection unit 1406.

Figure 47A:
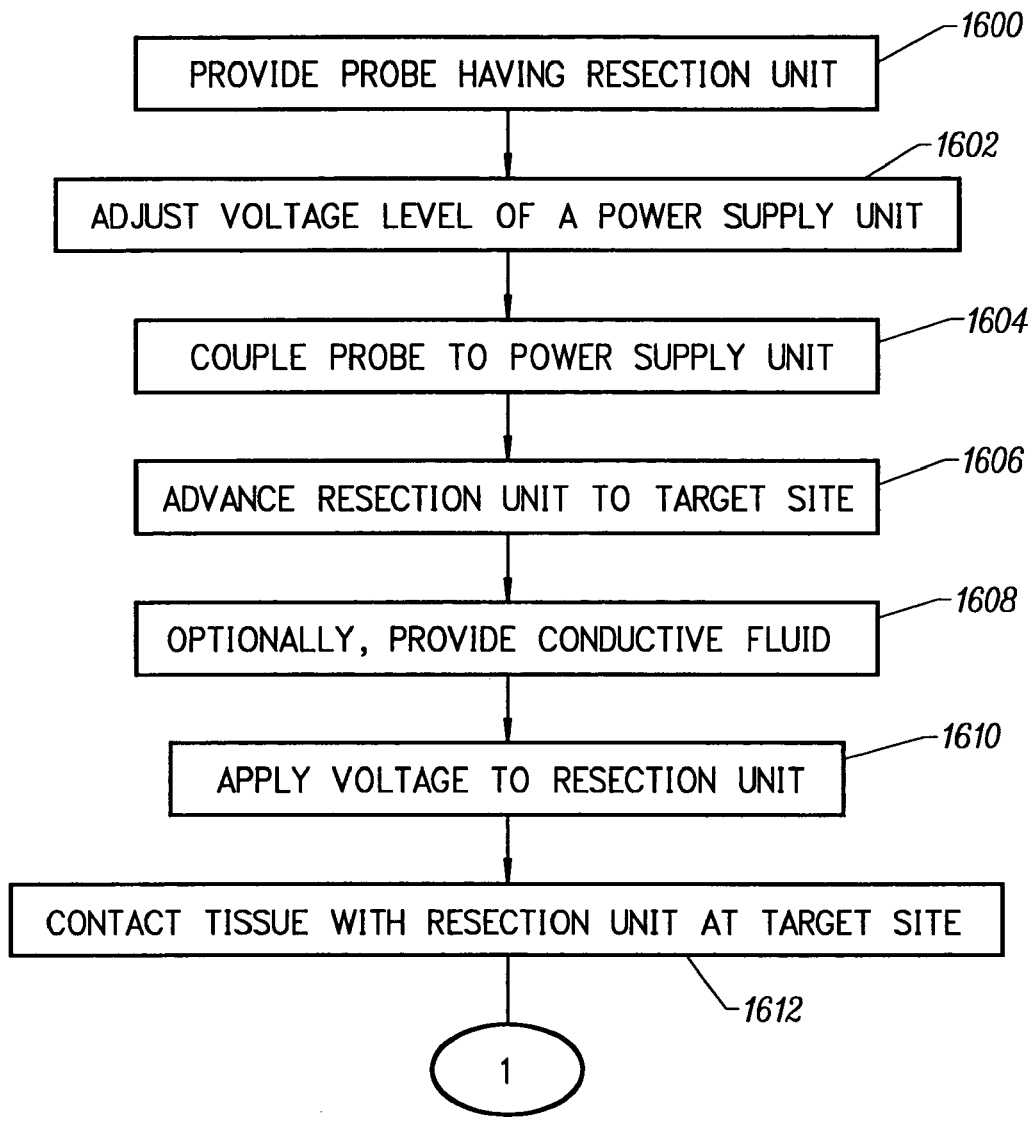
FIGS. 47A–B schematically represent a method of performing a resection and ablation electrosurgical procedure, according to another embodiment of the invention.
Figure 47B:
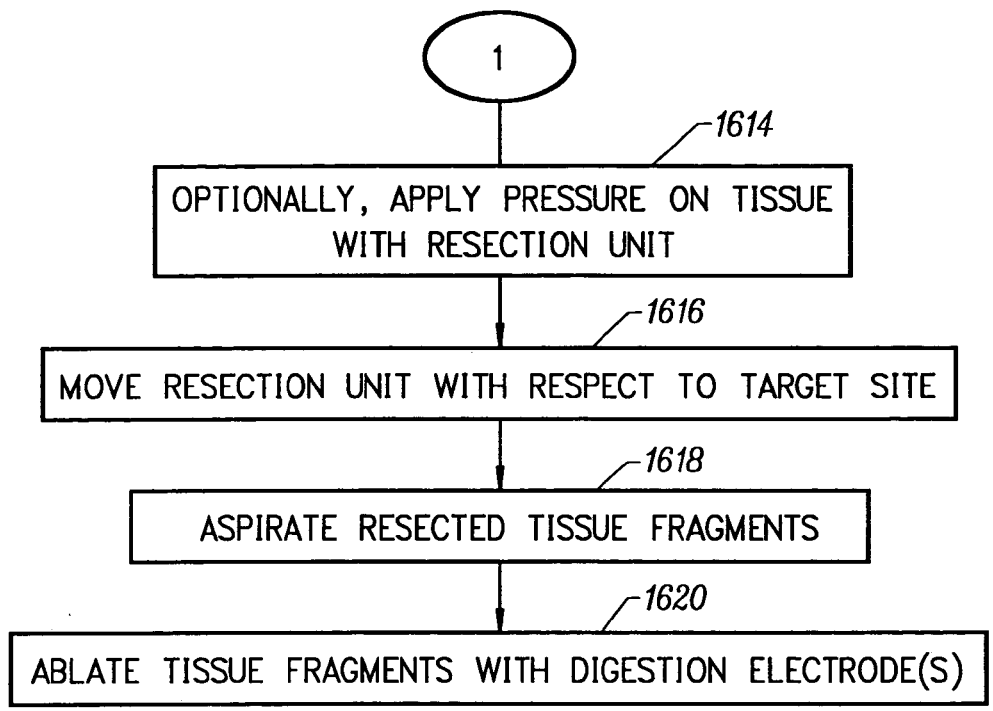

FIGS. 47A–B schematically represent a method of performing a resection and ablation electrosurgical procedure, according to another embodiment of the invention, wherein step 1600 (FIG. 47A) involves providing an electrosurgical probe having a resection unit. The probe provided in step 1600 includes a shaft distal end, wherein the resection unit is disposed at the shaft distal end, either laterally or terminally. The resection unit includes an electrode support comprising an insulating material and at least one resection electrode head arranged on the electrode support. Step 1602 involves adjusting a voltage level of a power supply, wherein the power supply is capable of providing a high frequency voltage of a selected voltage level and frequency. The voltage selected is typically between about 5 kHz and 20 MHz, essentially as described hereinabove. The RMS voltage will usually be in the range of from about 5 volts to 1000 volts, and the peak-to-peak voltage will be in the range of from about 10 to 2000 volts, again as described hereinabove. The actual or preferred voltage will depend on a number of factors, including the number and size of resection electrodes comprising the resection unit.

Step 1604 involves coupling the probe to the power supply unit. Step 1606 involves advancing the resection unit towards tissue at a target site whence tissue is to be removed. In optional step 1608, a quantity of an electrically conductive fluid may be applied to the resection unit and/or to the target site. For performance of a resection and ablation procedure in a dry field, optional step 1608 is typically included in the procedure. Step 1608 may involve the application of a quantity of an electrically conductive fluid, such as isotonic saline, to the target site. The quantity of an electrically conductive fluid may be controlled by the operator of the probe. The quantity of an electrically conductive fluid applied in step 1608 may be sufficient to completely immerse the resection unit and/or to completely immerse the tissue at the target site. Step 1610 involves applying a high frequency voltage to the resection unit via the power supply unit. Step 1612 involves contacting the tissue at the target site with the resection unit.

With reference to FIG. 47B, optional step 1614 involves exerting pressure on the tissue at the target site by applying a force to the probe, while the resection unit is in contact with the tissue at the target site, in order to effect resection of tissue. Typically, such a force is applied manually by the operator (surgeon), although mechanical application of a force to the probe, e.g., by a robotic arm under computer control, is also possible. The amount of any force applied in optional step 1614 will depend on factors such as the nature of the tissue to be removed, the design or embodiment of the probe, and the amount of tissue to be resected. For example, in the absence of any mechanical force applied to the tissue, tissue removal from the target site is primarily or solely by ablation. On the other hand, with the electrical power turned off, either transiently or for all or a portion of a procedure, the probe may be used for mechanical resection of tissue. Typically, however, the probe is used for the concurrent electrical ablation and mechanical resection of tissue.

Step 1616 involves moving the resection unit of the probe with respect to the tissue at the target site. Typically, step 1616 involves moving the resection unit and the at least one resection electrode head in a direction substantially perpendicular to a direction of any pressure exerted in step 1614, or in a direction substantially parallel to a surface of the tissue at the target site. Typically, step 1616 is performed concurrently with one or more of steps 1608 through 1614. In one embodiment, step 1616 involves repeatedly moving the resection unit with respect to the tissue at the target site until an appropriate quantity of tissue has been removed from the target site. Typically, a portion of the tissue removed from the target site is in the form of resected tissue fragments. Step 1618 involves aspirating the resected tissue fragments from the target site via at least one aspiration port on the shaft, wherein the at least one aspiration port is coupled to an aspiration lumen. In one embodiment, the probe includes at least one digestion electrode capable of aggressively ablating resected tissue fragments. Step 1620 involves ablating resected tissue fragments with the at least one digestion electrode. In one embodiment, the at least one digestion electrode is arranged within the aspiration lumen, and the resected tissue fragments are ablated within the aspiration lumen.

Figure 48:
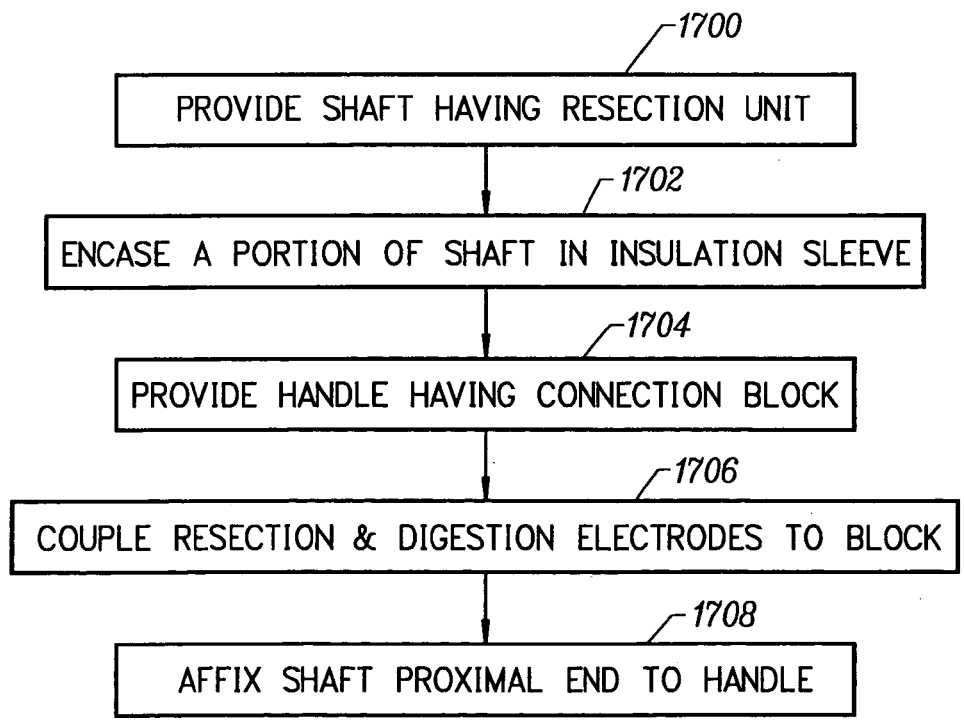
FIG. 48 schematically represents a method of making a resection and ablation electrosurgical probe, according to yet another embodiment of the invention.

FIG. 48 schematically represents a method of making a resection and ablation electrosurgical probe, according to the invention, wherein step 1700 involves providing a shaft having a resection unit. The shaft provided in step 1700 includes a shaft proximal end and a shaft distal end, wherein the resection unit is disposed at the shaft distal end, either laterally or terminally. In one embodiment, the shaft comprises an electrically conductive lightweight metal cylinder. The resection unit includes an electrode support comprising an insulating material and at least one resection electrode arranged on the electrode support. Each resection electrode includes a resection electrode head. Each resection electrode head typically comprises a wire, filament, or blade of a hard or rigid, electrically conductive solid material, such as tungsten, stainless steel alloys, platinum or its alloys, titanium or its alloys, molybdenum or its alloys, nickel or its alloys, and the like.

Typically, the shaft provided in step 1700 further includes at least one digestion electrode capable of aggressively ablating tissue fragments. In one embodiment, the at least one digestion electrode is arranged within the aspiration lumen. Each digestion electrode typically comprises an electrically conductive metal, such as tungsten, stainless steel alloys, platinum or its alloys, titanium or its alloys, molybdenum or its alloys, nickel or its alloys, aluminum, gold, or copper, and the like. Typically, the shaft provided in step 1700 further includes a return electrode.

In one embodiment, the method includes step 1702 which involves encasing a portion of the shaft within an insulating sleeve to provide an electrically insulated proximal portion of the shaft and an exposed distal portion of the shaft. The exposed distal portion of the shaft defines a return electrode of the probe. The insulating sleeve typically comprises a substantially cylindrical length of a flexible insulating material such as polytetrafluoroethylene, a polyimide, and the like. Such flexible insulating materials are well known in the art. In one embodiment, the resection electrode support is disposed on the return electrode. The resection electrode support typically comprises an electrically insulating material such as a glass, a ceramic, a silicone rubber, a polyurethane, a urethane, a polyimide, silicon nitride, teflon, alumina, or the like. The electrode support serves to electrically insulate the at least one resection electrode head from the return electrode. Step 1704 involves providing a handle having a connection block. Step 1706 involves coupling the resection electrodes and the digestion electrodes to the connection block. The connection block provides a convenient mechanism by which the resection and digestion electrodes may be coupled to a high frequency power supply. Step 1708 involves affixing the shaft proximal end to the handle.

There now follows a description, with reference to FIGS. 49–60B, of an electrosurgical probe 1800 and associated electrosurgical system adapted for the aggressive removal of tissue during a broad range of surgical procedures. According to one aspect of the invention, probe 1800 differs from certain other probes described hereinbelow, and from conventional probes of the prior art, in that probe 1800 lacks a dedicated or permanent return electrode. Furthermore, in use the electrosurgical system of which probe 1800 is a part is not operated in conjunction with a non-integral return electrode (e.g., a dispersive pad). Rather, probe 1800 includes a first electrode (or electrode type) and a second electrode (or electrode type), wherein each of the first electrode type and the second electrode type is designed and adapted for having a tissue-altering effect on a target tissue. That is to say, each of the first electrode type and the second electrode type can function as an active electrode. Each of the first electrode type and the second electrode type can also function as a return electrode. In particular, the first electrode and the second electrode can alternate between serving as an active electrode and serving as a return electrode. Typically, when the first electrode serves as the active electrode, the second electrode serves as the return electrode; and when the second electrode serves as the active electrode, the first electrode serves as the return electrode. In use, the first electrode and the second electrode are independently coupled to opposite poles of a high frequency power supply to enable current flow therebetween. For example, the first electrode and the second electrode may be independently coupled to opposite poles of power supply 428 (FIG. 7), for supplying alternating current to the first electrode and the second electrode.

Figure 49:
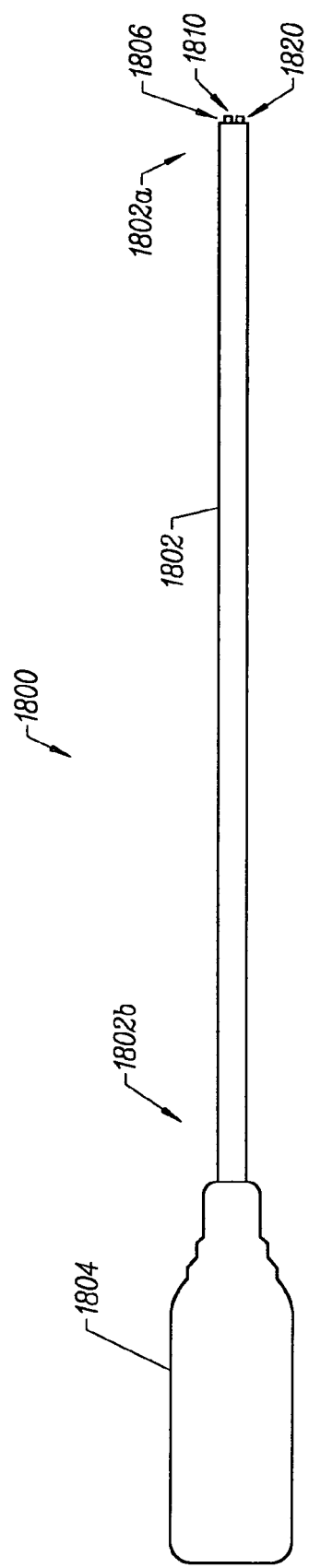
FIG. 49 is a side view of an electrosurgical probe having electrodes mounted on the distal terminus of the probe shaft, according to one embodiment of the invention.

Typically, the first electrode or electrode type comprises one or more ablation electrodes 1810, and the second electrode or electrode type comprises one or more digestion electrodes 1820 (e.g., FIG. 49). According to one embodiment, at any given time point electric power is generally supplied preferentially to the first electrode or to the second electrode. , That is to say, at any given time point the high frequency power supply alternatively supplies most of the power to either the first electrode or to the second electrode. In this manner, at any given time point either the first electrode or the second electrode may receive up to about 100% of the power from the power supply. Typically, an electrode or electrode type which receives most of the power from the power supply receives from about 60% to about 100% of the power; and more typically from about 70% to about 100% of the power. The actual percentage of power preferentially received by one of the two electrode types at any given time point may vary according to a number of factors, including: the power level or setting of the power supply, the electrical impedance of any tissue in the presence of the two electrode types, and the geometry of the two electrode types.

Typically, when only the ablation electrode is in contact with tissue, the ablation electrode preferentially receives electric power from the power supply such that the ablation electrode functions as the active electrode and ablates tissue, e.g., at a target site targeted for treatment. In this ablation mode, the digestion electrode normally serves as a return electrode. Conversely, when only the digestion electrode is in contact with tissue, the digestion electrode typically receives the majority of the electric power from the power supply such that the digestion electrode functions as the active electrode and is capable of ablating tissue (e.g., digesting tissue fragments resected from the target site during the ablation mode). In this digestion mode, the ablation electrode normally serves as a return electrode.

Typically, when one of the two electrode types encounters tissue such that the milieu of that electrode type undergoes a change in electrical impedance, while the other electrode type is not in contact with or adjacent to tissue in this manner, the former electrode type preferentially receives power from the power supply. Typically, the electrode type which preferentially receives power from the power supply functions as active electrode and is capable of having a tissue-altering effect. Usually, only one of the two electrode types can function as active electrode during any given time period. During that given time period, the other, non-active electrode functions as a return electrode and is incapable of having a tissue-altering effect. While not being bound by theory, Applicants believe that the preferential delivery of power to one electrode type in the presence of tissue, while the other electrode type is not in the presence of tissue, is due to the electrical impedance of the tissue causing relatively high current densities to be generated at the former electrode type.

In one mode of operation, both the first and second electrode types may be in contact with tissue simultaneously. For example, an ablation electrode of the probe may be in contact with tissue at a site targeted for treatment, and at the same time the digestion electrode may be in contact with one or more fragments of tissue resected from the target site. If the ablation and digestion electrodes are both in contact with tissue at the same time but the electrodes have different surface areas, the available power may be supplied preferentially to one of the two electrode types. In particular, by arranging for an appropriate ablation electrode:digestion electrode surface area ratio, when tissue is in contact with or in the vicinity of the digestion electrode, the digestion electrode may receive the majority of the available electric power and thus function as the active electrode. By arranging for an appropriate ablation electrode:digestion electrode surface area ratio, a shift from the ablation electrode serving as active electrode to the digestion electrode serving as active electrode can be triggered by a change in electrical impedance in the vicinity of the digestion electrode. Such a change in electrical impedance typically results from the presence of one or more tissue fragments, e.g. a tissue fragment flowing towards the digestion electrode in an aspiration stream. According to one aspect of the invention, the ablation electrode:digestion electrode surface area ratio is in the range of from about 3:1 to about 1.5:1.

According to the invention, the elimination of a conventional or dedicated return electrode from probe 1800 enables the active electrode, i.e., either the ablation electrode or the digestion electrode, to receive up to 100%, of the power or current supplied by the high frequency power supply. For convenience, the terms ablation electrode and digestion electrode may be used hereafter in the singular form, it being understood that such terms include one, or more than one, ablation electrode; and one, or more than one, digestion electrode, respectively. Ablation electrode 1810 is capable of aggressively removing tissue from a target site by a cool ablation mechanism (Coblation®), generally as described hereinabove. Typically, the temperature of tissue subjected to cool ablation according to the instant invention is in the range of from about 45° C. to 90° C., and more typically in the range of from about 60° C. to 70° C.

According to one embodiment, ablation electrode 1810 may be regarded as a default or primary active electrode, and as a back-up or secondary return electrode; while digestion electrode 1820 may be regarded as a default or primary return electrode and as a secondary active electrode. The active electrode (either electrode 1810 or electrode 1820, depending on the mode of operation of the electrosurgical system) generates a plasma from an electrically conductive fluid present in the vicinity of the active electrode, and the plasma causes breakdown of tissue in the region of the active electrode by molecular dissociation of tissue components to form low molecular weight Coblation® by-products, essentially as described hereinabove. The return electrode completes a current flow path from the active electrode via the electrically conductive fluid located therebetween, and has no significant tissue-altering effect while serving as the return electrode.

In one embodiment and according to one mode of operation of an electrosurgical system of the invention, probe 1800 is configured such that only one of the two electrode types is in contact with tissue at a target site. According to one aspect of the invention, probe 1800 is configured such that one of the two electrode types can be brought into contact with tissue at a target site while the other of the two electrode types remains remote from the tissue at the target site. Typically, probe 1800 is configured such that ablation electrode 1810 can be readily brought into contact with the tissue at the target site, while digestion electrode 1820 avoids contact with the tissue at the target site.

According to one aspect of the invention, when ablation electrode 1810 is in the presence of tissue (e.g., at a target site) and in the absence of tissue (e.g. resected tissue fragments) in the milieu of digestion electrode 1820, electrodes 1810, 1820 may serve as default active and return electrodes, respectively. However, when tissue is present in the milieu of digestion electrode 1820, power from the power supply may be switched from ablation electrode 1810 to digestion electrode 1820, such that electrode 1820 serves as an active electrode while ablation electrode 1810 serves as the return electrode. In one aspect, such an alternation, or reversal, of roles between electrodes 1810, 1820 may be a transient event. For example, in the presence of a resected tissue fragment, digestion electrode 1820 may preferentially receive power from the power supply and assume the role of active electrode, such that a plasma is generated in the vicinity of digestion electrode 1820, and the resected tissue fragment is broken down via Coblation® to form low molecular weight by-products. Thereafter, in the absence of tissue in the milieu of digestion electrode 1820, electrode 1820 may rapidly revert to its role of default return electrode. At the same time, ablation electrode 1810 reverts to its role of default active electrode. The respective roles of electrodes 1810 and 1820 as active and return electrodes, respectively, may then continue until digestion electrode 1820 again encounters tissue in its vicinity. In this manner, digestion electrode 1820 generally only receives most of the power from the power supply in the presence of tissue (e.g., a resected tissue fragment), while ablation electrode 1810 may preferentially receive power from the power supply at all times other than when digestion electrode 1820 preferentially receives power from the power supply.

While not being bound by theory, Applicants believe that the transformation or "switch" of digestion electrode 1820, from serving as return electrode to serving as active electrode, may be mediated by a change in electrical impedance in the vicinity of digestion electrode 1820, wherein the impedance change results from the presence of tissue in the electrically conductive fluid adjacent to electrode 1820. Again, while not being bound by theory, Applicants believe that the ratio of the surface area of the ablation electrode (Sa) to the surface area of the digestion electrode (Sd), Sa:Sd is a factor in causing electrodes 1810 and 1820 to alternate between active/return electrode mode. Generally, the Sa:Sd ratio is in the range of from about 3.5:1 to about 1:1, typically in the range of from about 2.5:1 to about 1.5:1, and usually about 2:1. By selecting a suitable Sa:Sd ratio for probe 1800, as has been achieved by Applicants, the feature of alternating between preferentially supplying power to ablation electrode 1810 and preferentially supplying power to digestion electrode 1820 becomes an inherent characteristic of an electrosurgical system according to the invention. An effective or optimum Sa:Sd ratio for bringing about a shift in preferentially supplying power to either ablation electrode 1810 or digestion electrode 1820 may vary according to a number of parameters including the volume of materials aspirated from a target site, and the velocity of an aspiration stream. Therefore, in some embodiments an aspiration stream control unit (not shown) may be used in conjunction with probe 1800 in order to quantitatively regulate the aspiration stream.

FIG. 49 shows a side view of an electrosurgical probe 1800 for use in conjunction with an electrosurgical system, according to one embodiment of the invention. Probe 1800 includes a handle 1804 and a shaft 1802 having shaft distal end 1802*a* and shaft proximal end 1802*b*. In this embodiment, ablation electrode 1810 and digestion electrode 1820 are mounted on the distal terminus 1806 of shaft 1802. However, lateral mounting of ablation electrode 1810 and digestion electrode 1820 is also possible under the invention. In light of the absence of a permanent or dedicated return electrode from probe 1800, shaft 1802 may comprise a rigid insulating material, for example, various synthetic polymers, plastics, and the like, well known in the art. Alternatively, shaft 1802 may comprise an electrically conducting solid material whose surface is entirely covered with an insulating material. Such electrically conducting solid materials include various metals such as stainless steel, tungsten and its alloys, and the like. An insulating material covering shaft 1802 may comprise a flexible, electrically insulating sleeve or jacket of a plastic material, such as a polyimide, and the like. Typically, shaft 1802 has a length in the region of from about 5 to 30 cm, more typically from about 7 to 25 cm, and most typically from about 10 to 20 cm. Generally, handle 1804 has a length in the range of from about 2 to 10 cm.

FIG. 50A is a longitudinal section of probe 1800 including shaft distal end 1802*a* having ablation electrode 1810 and digestion electrode 1820 mounted at shaft distal terminus

1806. Handle 1804 includes a connection block 1805. Ablation electrode 1810 and digestion electrode 1820 are connected to connection block 1805 via ablation electrode lead 1811 and digestion electrode lead 1821, respectively. Leads 1811, 1821 enable ablation electrode 1810 and digestion electrode 1820 to be coupled to a power supply independently of each other, such that ablation electrode 1810 and digestion electrode 1820 can independently receive power from the power supply. Connection block 1805 provides a convenient mechanism for coupling electrodes 1810, 1820 to the power supply, e.g., via one or more connecting cables (see, e.g., FIG. 7). Probe 1800 of FIG. 50A also includes an aspiration device, namely a terminal aspiration port 1840, an aspiration lumen 1842 leading proximally from port 1840, and an aspiration tube 1844 coupled to lumen 1842. Tube 1844 may be coupled to a vacuum source, for applying a vacuum or partial vacuum to port 1840, and to a collection reservoir for collecting aspirated materials, as is well known in the art.

FIG. 50B is an end view of shaft distal terminus 1806 of FIG. 50A, as seen along the lines 50B—50B of FIG. 50A. In FIG. 50B, ablation electrode 1810 and digestion electrode 18200 are each represented as a rectangular box located at approximately 12 o'clock and six o'clock, respectively, on either side of a substantially centrally located aspiration port 1840. However, various other shapes, number, arrangements, etc. for electrodes 1810, 1820 and aspiration port 1840 are contemplated under the invention, as is described in enabling detail hereinbelow. Each of ablation electrode 1810 and digestion electrode 1820 may be constructed from a material comprising a metal such as tungsten, stainless steel alloys, platinum or its alloys, titanium or its alloys, molybdenum or its alloys, nickel or its alloys, aluminum, gold, or copper, and the like. One material for construction of ablation electrode 1810 and digestion electrode 1820 is platinum, or various of its alloys.

Figure 51A:
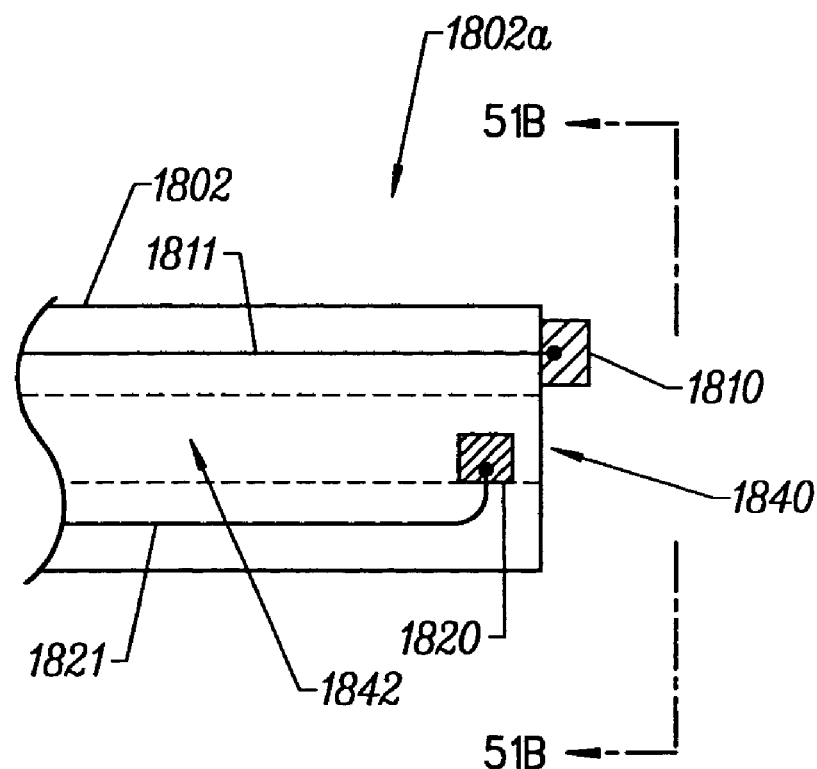
FIG. 51A shows a longitudinal section of a probe showing detail of the shaft distal end, according to another embodiment of the invention.

FIG. 51A shows a longitudinal section of shaft distal end 1802*a* of probe 1800, according to another embodiment of the invention, wherein ablation electrode 1810 is mounted on shaft distal terminus 1806. Shaft distal end 1402*a* includes port 1440 leading to aspiration lumen 1442. In this embodiment, digestion electrode 1820 is mounted proximal to ablation electrode 1810 within lumen 1442. Digestion electrode 1820 is shown in FIG. 51A as being mounted in the distal region of lumen 1442 adjacent to port 1440, however, according to certain embodiments of the invention, ablation electrode 1810 may be located within lumen 1442 more distant from port 1440. In this configuration, ablation electrode 1810 may be readily brought into contact with tissue at a site targeted for treatment, while digestion electrode 1820 does not contact the tissue at the target site and electrode 1820 remains remote from the target site.

Figure 51B:
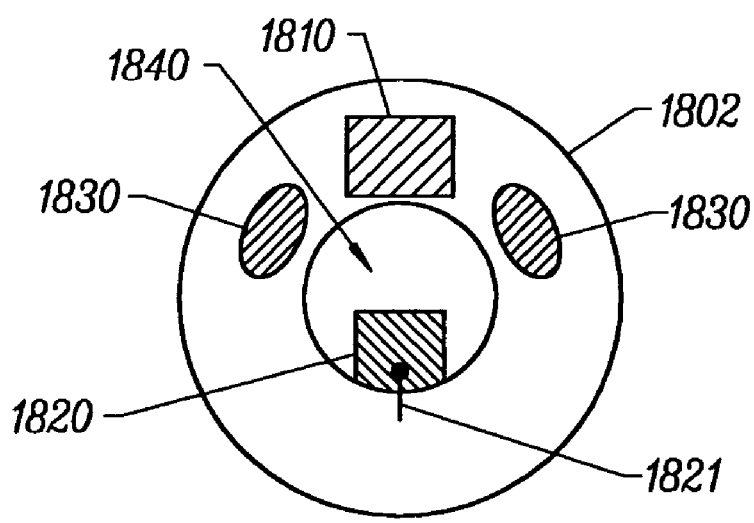
FIG. 51B is an end view of the distal terminus of the electrosurgical probe of FIG. 51A.

Ablation electrode 1810 and digestion electrode 1820 have ablation electrode lead 1811 and digestion electrode lead 1821, respectively. Ablation electrode lead 1811 and digestion electrode lead 1821 may be coupled to connection block 1805, substantially as described with reference to FIG. 50A. FIG. 51B shows an end view of distal terminus 1806 of electrosurgical probe 1800, taken along the lines 51B—51B of FIG. 51A. Ablation electrode 1810 and digestion electrode 1820 are each represented as a rectangular box, wherein digestion electrode 1820 is located at approximately six o'clock within aspiration lumen 1842. However, various other shapes, locations, etc. for electrodes 1810, 1820 are possible under the invention. A plurality of fluid delivery ports 1830 are also located on shaft distal terminus 1806 adjacent to ablation electrode 1810. Ports 1830 serve to deliver electrically conductive fluid to tissue at a target site, or to ablation electrode 1810 before or during a surgical procedure, e.g., as described hereinabove with reference to FIGS. 34A, 44A–D. Although two ports 1830 are shown in FIG. 51B as being substantially ovoid, other shapes, arrangements, and numbers of ports 1830 are also within the scope of the invention.

Figure 52A:
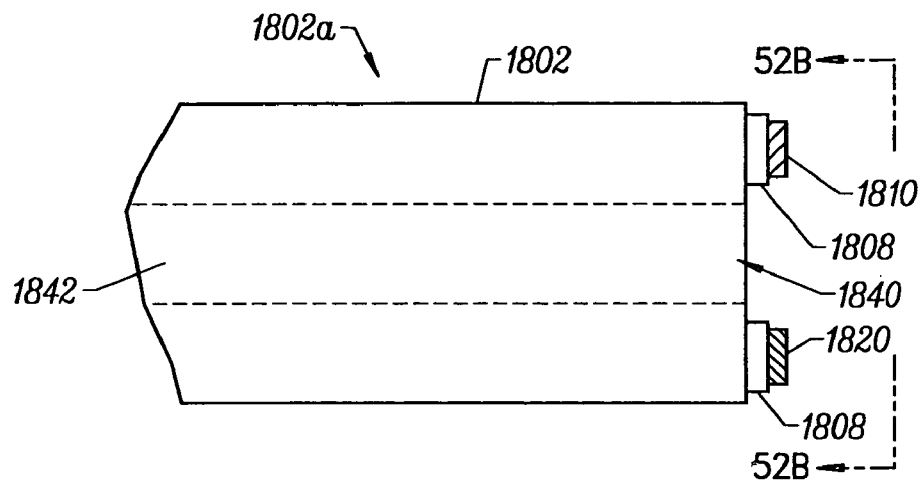
FIG. 52A shows a longitudinal section of a probe showing detail of the shaft distal end, according to another embodiment of the invention.
Figure 52B:
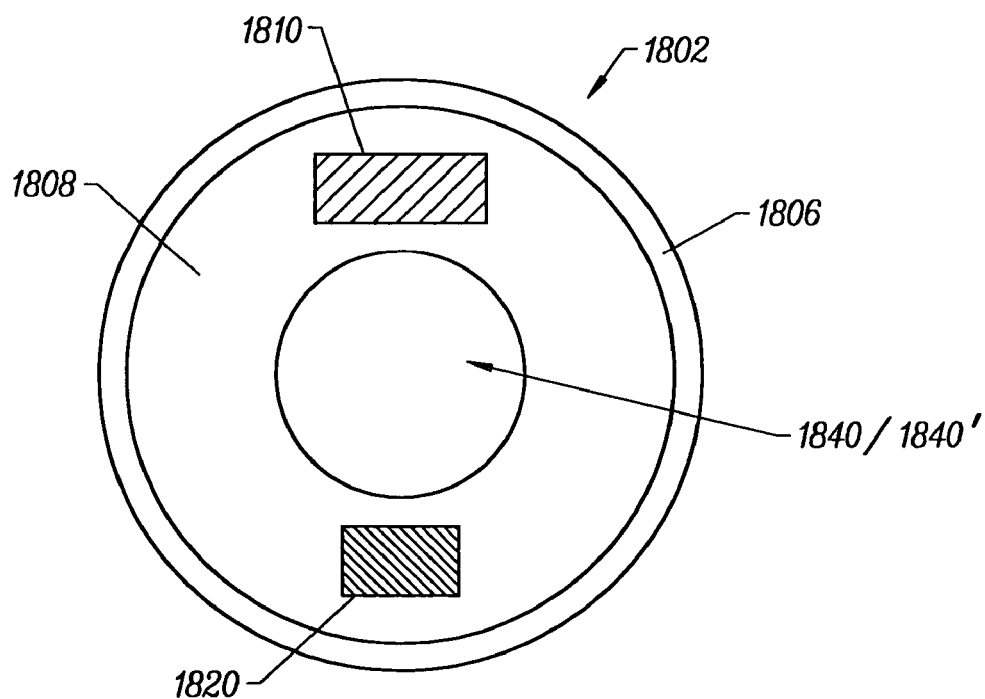
FIG. 52B is an end view of the distal terminus of the electrosurgical probe of FIG. 52A.

FIG. 52A is a longitudinal section of a probe 1800, according to another embodiment of the invention, in which ablation electrode 1810 and digestion 1820 are mounted on an electrode support 1808 at shaft distal terminus 1806. Ablation and digestion electrode leads 1811, 1821 are omitted for the sake of clarity. FIG. 52B is an end view of shaft distal terminus 1806, taken along the lines 52B—52B of FIG. 52A. Support 1808 includes a central bore or void 1840' (FIGS. 53B–D), wherein bore 1840' defines an opening to aspiration port 1840/lumen 1842. Ablation electrode 1810 and digestion electrode 1820 are shown in FIG. 52A as being in the same plane or substantially the same plane. However, according to various alternative embodiments of the invention, ablation and digestion electrodes 1810, 1820 may be in different planes. Typically, ablation and digestion electrodes 1810, 1820 are in the same plane, or digestion electrode 1820 is located proximal to ablation electrode 1810 In the former situation, (i.e., ablation and digestion electrodes 1810, 1820 are in the same plane) by advancing probe 1800 towards the target site at a suitable angle, ablation electrode 1810 may contact the tissue at the target site while digestion electrode 1820 avoids contact with the tissue. In the latter situation (i.e., digestion electrode 1820 is located proximal to ablation electrode 1810 (e.g., FIGS. 51A, 57A)), probe 1800 is configured such that digestion electrode 1820 easily avoids contact with tissue at a site targeted for resection by ablation electrode 1810, regardless of the angle at which probe 1800 approaches the tissue.

Figures 53A, 53B:
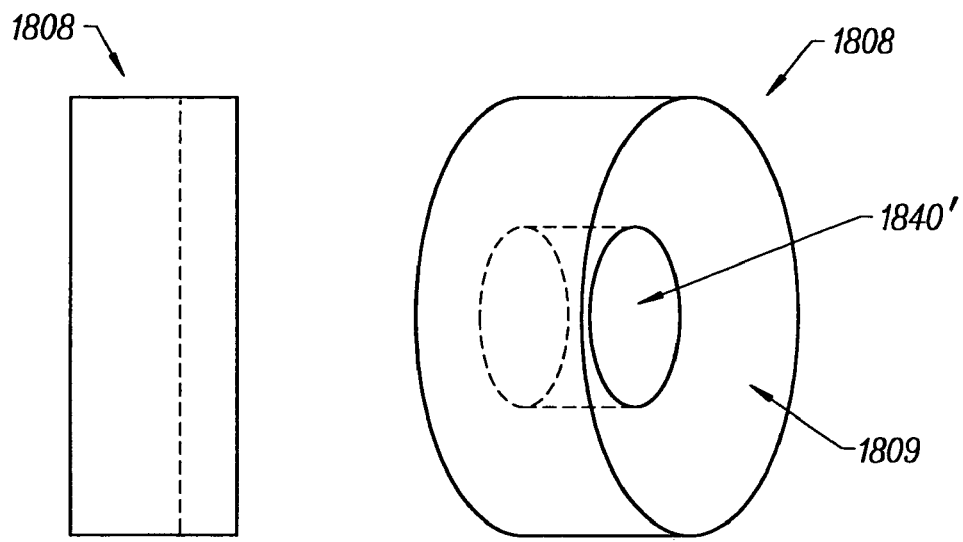
FIGS. 53A–D show side, perspective, face, and sectional views, respectively of an electrode support of an electrosurgical probe, according to another embodiment of the invention.
Figure 53C:
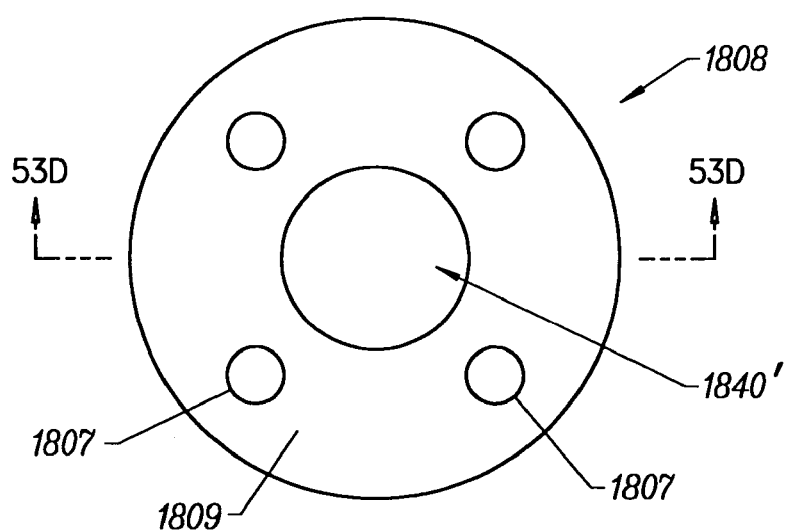
Figure 53D:
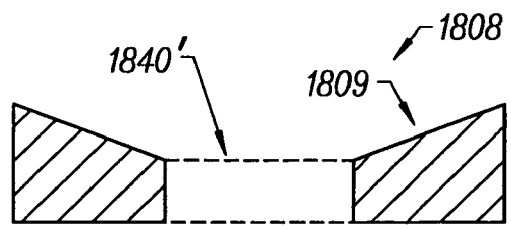

The structure of an electrode support 1808 according to one embodiment is perhaps best seen in FIGS. 53A–D. FIG. 53A shows support 1808, unmounted on shaft 1802, as seen from the side. FIG. 53B is a perspective view of support 1808, including bore 1840' and a frusto-conical distal surface 1809. FIG. 53C is a face or end view of support 1808 showing bore 1840', and frusto-conical distal surface 1809. Support 1808 may include one or more mounting holes 1807 adapted for mounting support 1808 to shaft 1802, or for mounting ablation and digestion electrodes 1810, 1820 to support 1808. Mounting holes 1807 may also be used for passing electrode leads 1811, 1821, therethrough. Although four mounting holes 1807 are shown substantially equidistant from each other in FIG. 53C, other numbers and arrangements of mounting holes 1807 are possible under the invention. In some embodiments, mounting holes 1807 are strategically located on support 1808, for example, to specifically accommodate the precise size, number, and arrangement of electrodes to be mounted or affixed thereto. FIG. 53D is a sectional view of support 1808 taken along the lines 53D—53D of FIG. 53C illustrating the geometry of support 1808 including surface 1809. In some embodiments, ablation electrode 1810 may be mounted on surface 1809. In certain embodiments, both ablation electrode 1810 and digestion electrode 1820 may be mounted on surface 1809. Support 1808 may comprise a rigid or substantially rigid, durable or refractory insulating material. In one embodiment, support 1808 comprises a material such as a ceramic, a glass, a silicone rubber, or the like.

Figure 54:
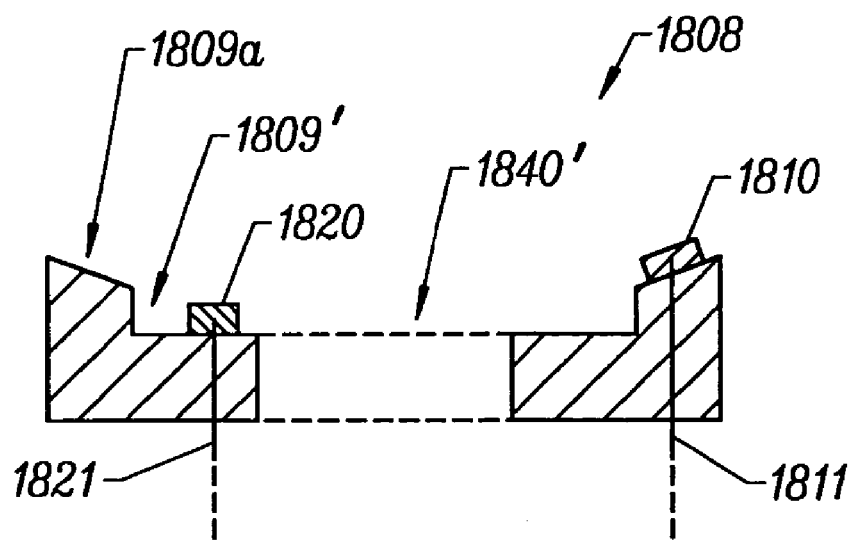
FIGS. 54 and 55 each show a sectional view of an electrode support of an electrosurgical probe, according to two different embodiments of the invention.

FIG. 54 shows a sectional view of electrode support 1808 of an electrosurgical probe 1800, in which a portion of frusto-conical surface 1809 (see, e.g., FIG. 53B) has been removed to provide a narrower frusto-conical surface 1809a and a recessed surface 1809'. In this embodiment, ablation electrode 1810 may be mounted on a distal portion of surface 1809 for making facile contact with tissue to be treated or removed. Such an arrangement for ablation electrode 1810 promotes rapid and aggressive tissue removal from a target site. Digestion electrode 1820, in contrast, may be disposed on recessed surface 1809' to avoid direct contact of electrode 1820 with tissue. As described hereinabove, the presence of tissue in the vicinity of digestion electrode 1820 may trigger the switching of electric power from ablation electrode 1810 to digestion electrode 1820. By avoiding direct contact of electrode 1820 with tissue at a site targeted for treatment, digestion electrode 1820 is prevented from preferentially receiving electric power from the power supply over an extended time period. This situation is undesirable in that when the digestion electrode 1820 preferentially receives electric power (i.e., functions as active electrode), there is concomitant transfer of electric power away from ablation electrode 1810. Under these circumstances, ablation electrode 1810 functions as return electrode, and consequently tissue at the target site is not efficiently removed via the cool ablation mechanism of the invention.

Figure 55:
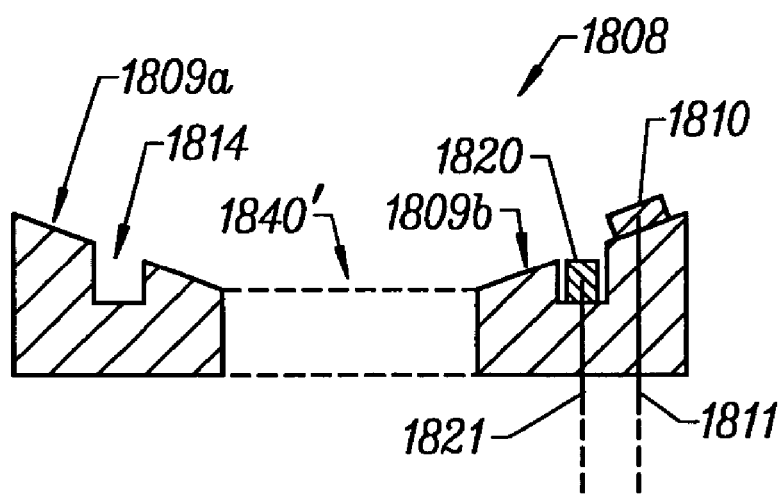

FIG. 55 shows a sectional view of electrode support 1808 of an electrosurgical probe 1800 in which a groove 1814 is formed in frusto-conical surface 1809 (see, e.g., FIG. 53B) to provide an outer surface 1809a and an inner surface 1809b. In this embodiment, ablation electrode 1810 may be mounted on outer surface 1809a for making facile contact with tissue and efficient tissue removal, essentially as described with reference to FIG. 54. In the embodiment of FIG. 55, however, digestion electrode 1820 is disposed within groove 1814. In this manner, electrode 1820 avoids routine contact with tissue, and probe 1800 of FIG. 55 enjoys the advantages expounded with respect to the embodiment of FIG. 54, namely the futile reversal of role of electrodes 1810, 1820 triggered by tissue in the presence of electrode 1820.

Figure 56A:
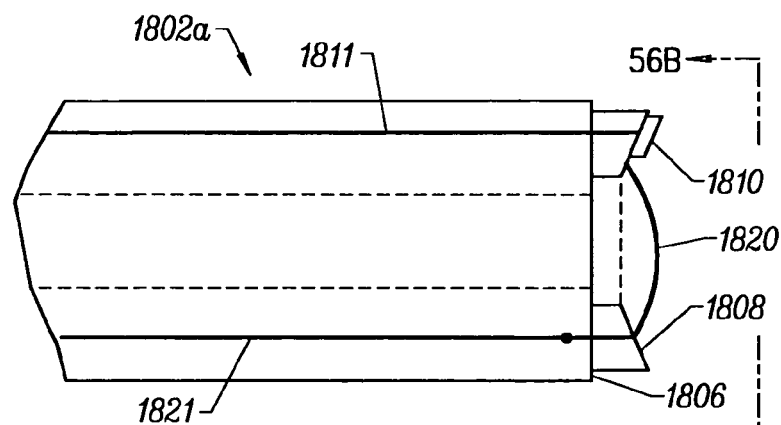
FIG. 56A shows a longitudinal section of the shaft distal end of an electrosurgical probe, according to another embodiment of the invention.
Figure 56B:
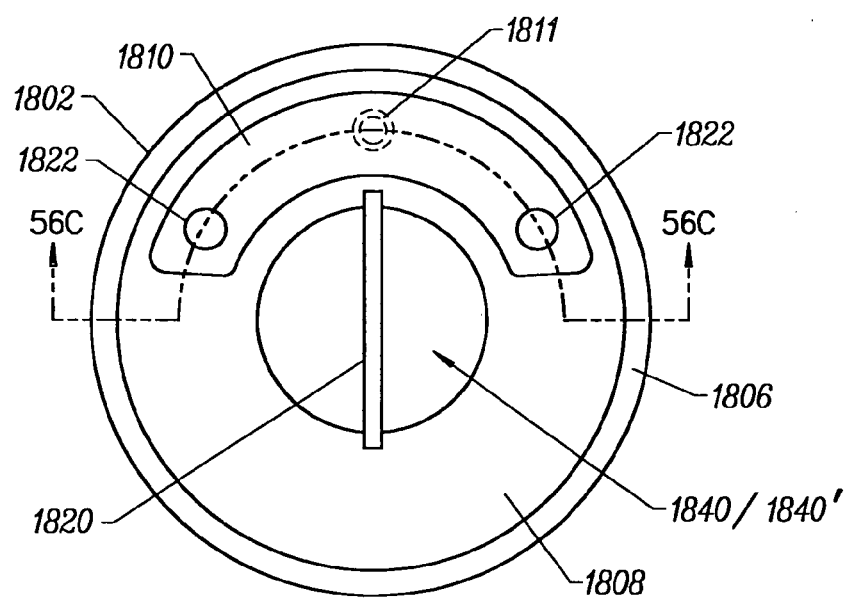
FIG. 56B is an end view of the distal terminus of the electrosurgical probe of FIG. 56A.
Figure 56C:
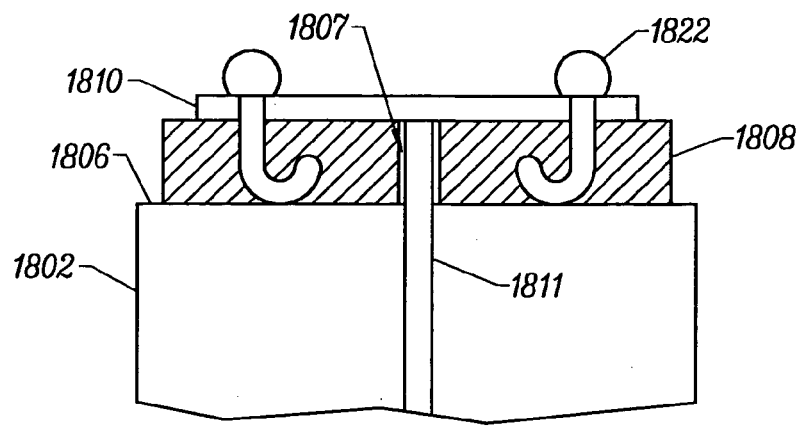
FIG. 56C shows attachment of an ablation electrode to an electrode support.

FIG. 56A shows, in longitudinal section, a shaft distal end 1802a of an electrosurgical probe 1800, according to another embodiment of the invention, wherein digestion electrode 1820 is disposed on support 1808 and extends across aspiration port 1840/bore 1840'. In one embodiment, digestion electrode 1820 has a first end attached to electrode lead 1821 (e.g., FIGS. 57A, 57B), and a second free end. In another embodiment, digestion electrode 1820 is in the form of a flat wire or metal ribbon (e.g., FIG. 58). Ablation electrode 1810 is located on surface 1809 of support 1808 distal to digestion electrode 1820. FIG. 56B shows the distal end of probe 1800, taken along the lines 56B—56B of FIG. 56A, illustrating a plurality of attachment units 1822 for affixing electrode 1810 to support 1808. In this embodiment, support 1808 occupies the majority of shaft distal terminus 1806. Ablation electrode 1810 is mounted on support 1808, has a substantially semi-circular shape, and partially surrounds aspiration port 1840. FIG. 56C is a side view of shaft distal end 1802a showing attachment of ablation electrode 1810 to electrode support 1808, according to one embodiment of the invention. Although FIG. 56C shows ablation electrode 1810 affixed to electrode support 1808 via ball wires, other attachment methods are also within the scope of the invention. Methods for attachment of electrically conductive solids (e.g., metals) to insulating solid supports are well known in the art. Ablation electrode 1810 is coupled to connection block 1805 via electrode lead 1811. Lead 1811 may pass through mounting hole 1807.

Figure 57A:
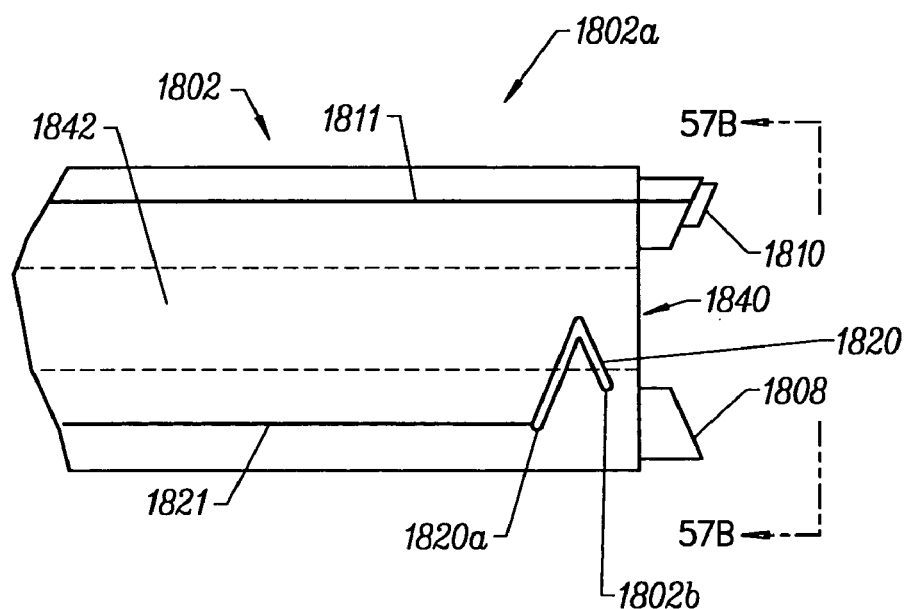
FIG. 57A shows a longitudinal section of the shaft distal end of an electrosurgical probe, according to another embodiment of the invention.
Figure 57B:
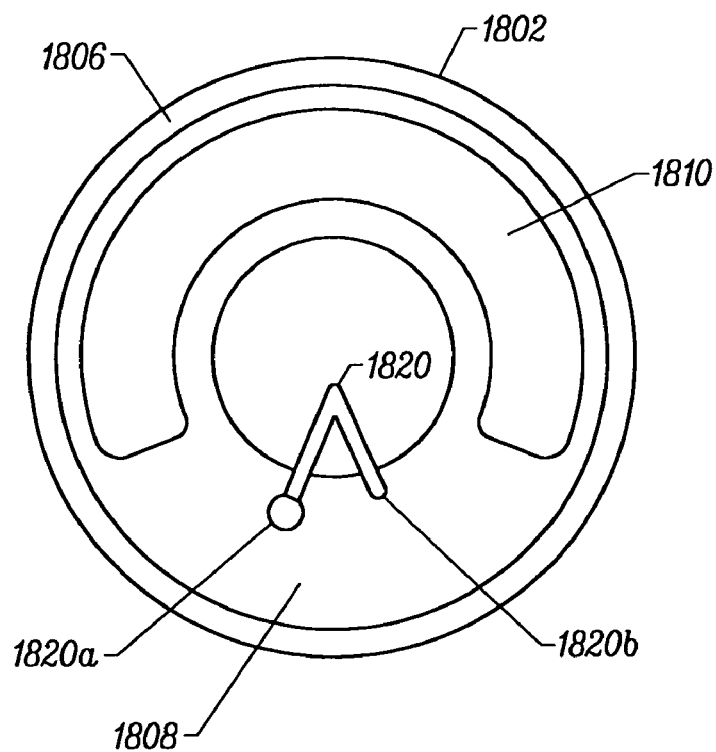
FIG. 57B is an end view of the distal terminus of the electrosurgical probe of FIG. 57A.

FIG. 57A shows a longitudinal section of shaft distal end 1802a of a probe 1800, according to another embodiment of the invention. In this embodiment, digestion electrode 1820 is arranged within aspiration lumen 1842. Ablation electrode 1810 is located distal to aspiration port 1840 and is coupled to lead 1811. FIG. 57B shows, in end view, the distal end portion 1802a of probe 1800, taken along the lines 57B—57B of FIG. 57A. Digestion electrode 1820 of FIGS. 57A, 57B is in the form of a flat wire or metal ribbon. Electrode 1820 has a first end 1820a and a second free end 1820b. First end 1820a is connected to lead 1821 (FIG. 57A). In contrast, in this embodiment, free end 1820b terminates without contacting an electrically conductive material, for example free end 1820b terminates in a wall of aspiration lumen 1842, wherein lumen 1842 comprises an electrically insulating material. As an example, lumen 1842 may comprise a plastic tube or cylinder having electrically insulating properties. By arranging for free end 1820b to dead-end or terminate without contacting an electrically conductive material, Applicants have found improved generation and maintenance of a plasma in the vicinity of electrode 1820 upon application of a suitable high frequency voltage thereto. As is described fully hereinabove, the presence of a plasma is a key factor in efficient ablation of tissues via the cool ablation (Coblation®) mechanism of the invention. Without intending to be bound in any way by theory, Applicants believe that by arranging for free end 1820b to terminate without contacting an electrically conductive material, when electric power is preferentially supplied to electrode 1820, distribution of power along the length of electrode 1820 is asymmetric and is highly concentrated at certain locations. In this way, localized high current densities are produced in the vicinity of some region(s) of electrode 1820, thereby promoting plasma formation.

Figure 58:
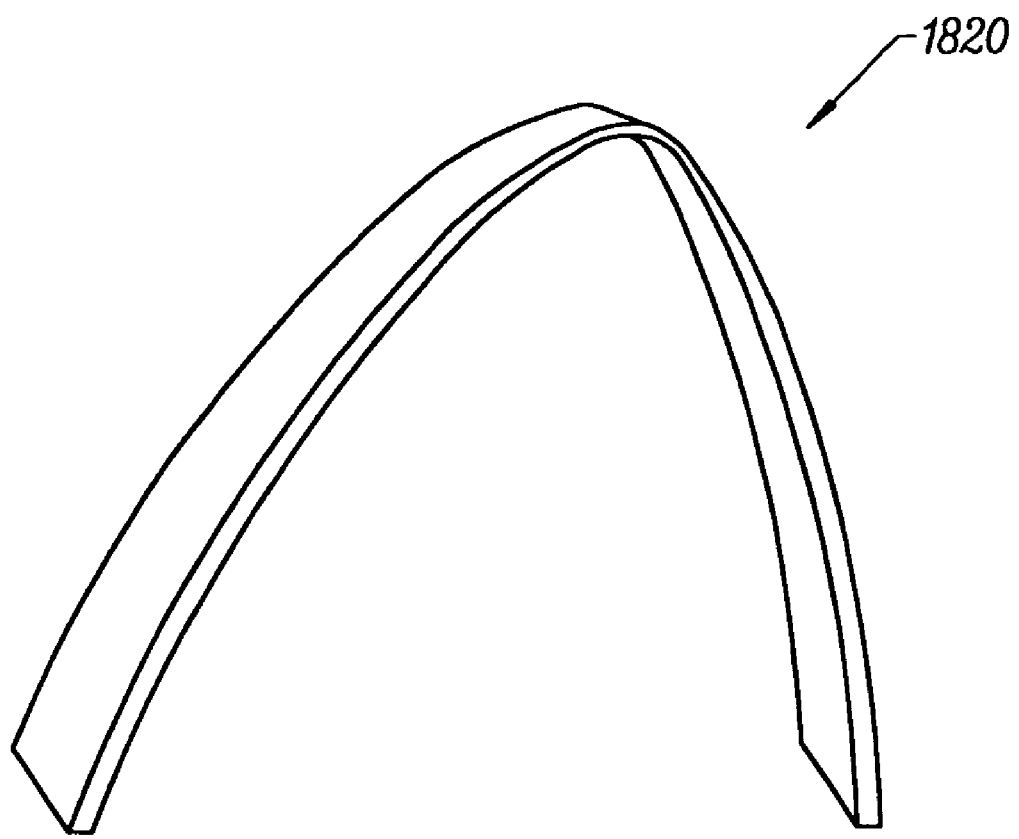
FIG. 58 is a perspective view of a digestion electrode of an electrosurgical probe, according to one embodiment of the invention.

FIG. 58 is a perspective view of a digestion electrode 1820, according to one embodiment of the invention. Although electrode 1820 is shown as having an arch shape, other shapes including planar or flat, circular or rounded, helical, etc., are also within the scope of the invention. Similarly, although electrode 1820 is shown as a flat wire or ribbon, i.e., as having a substantially rectangular cross-sectional shape, many other cross-sectional shapes for electrode 1820 are also possible under the invention. As an example, electrode 1820 may have one or more of the cross-sectional shapes described hereinabove, for example, with reference to FIGS. 39A–I.

Figure 59A:
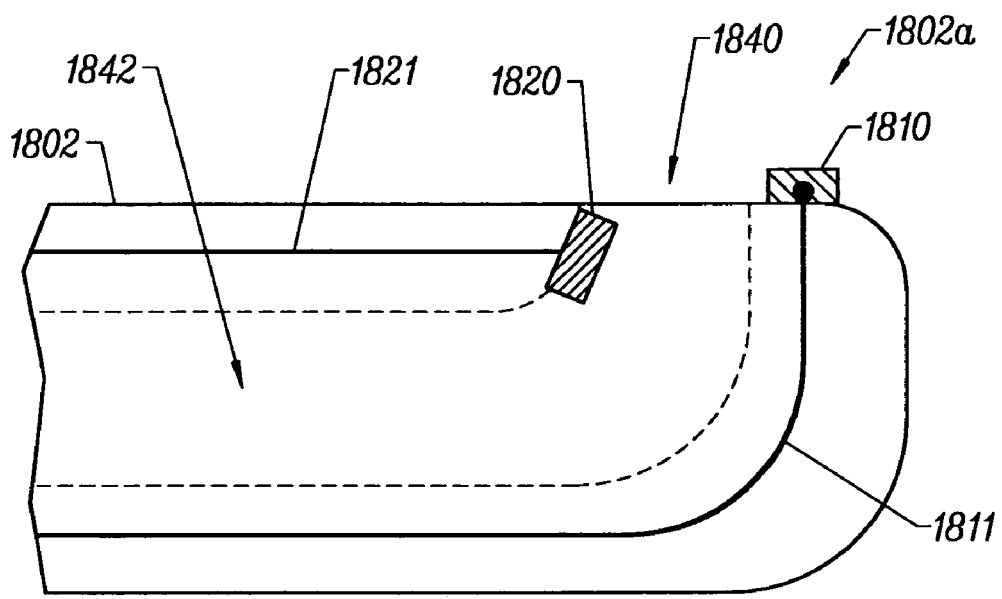
FIG. 59A shows a longitudinal section view of the shaft distal end of an electrosurgical probe, having an electrode mounted laterally on the shaft distal end, according to another embodiment of the invention.
Figure 59B:
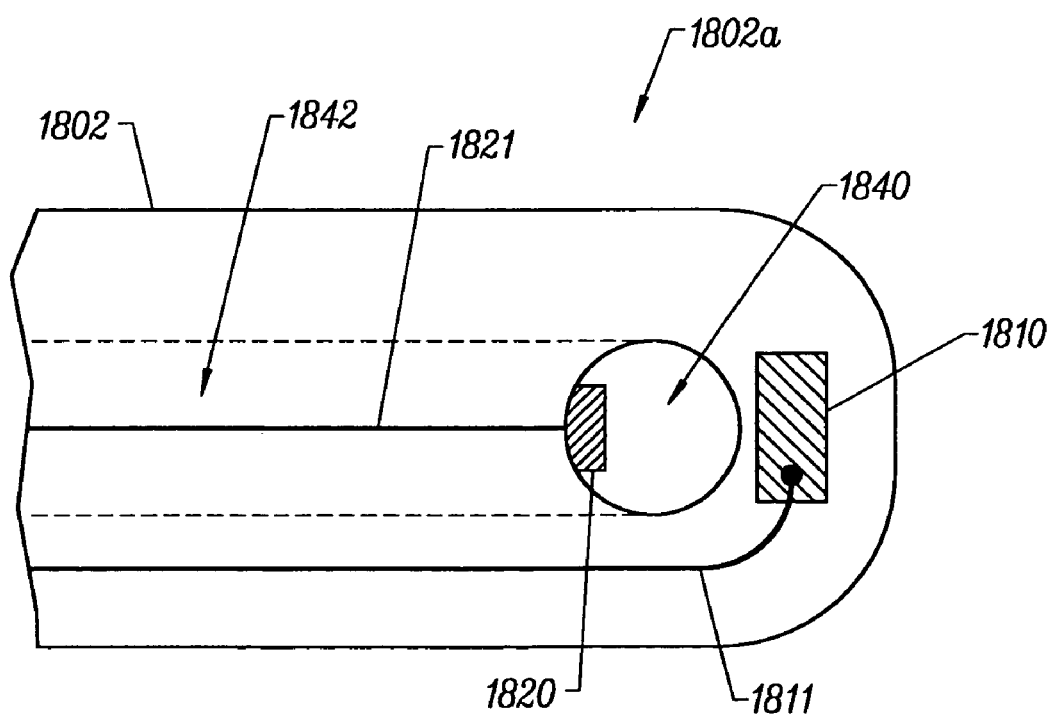
FIG. 59B is a plan view of the shaft distal end shown in FIG. 59A.

FIG. 59A shows, in longitudinal section, shaft distal end 1802a of an electrosurgical probe 1800, wherein ablation electrode 1810 is mounted laterally on shaft 1802. In this embodiment, shaft distal terminus 1806 may have a rounded shape. Ablation electrode 1810 is coupled to lead 1811 for connecting electrode 1810 to connection block 1805. Digestion electrode 1820 is disposed proximal to ablation electrode 1810 within aspiration lumen 1842. FIG. 59B shows shaft distal end 1802a of FIG. 59A in plan view. Ablation electrode 1810 may be mounted on an electrode support (e.g., FIGS. 60A–B). Ablation electrode 1810 and digestion electrode 1820 are each represented in FIGS. 52A–B as a rectangular box. However, various other shapes, locations, etc. for electrodes 1810, 1820 are possible under the invention.

Figure 60A:
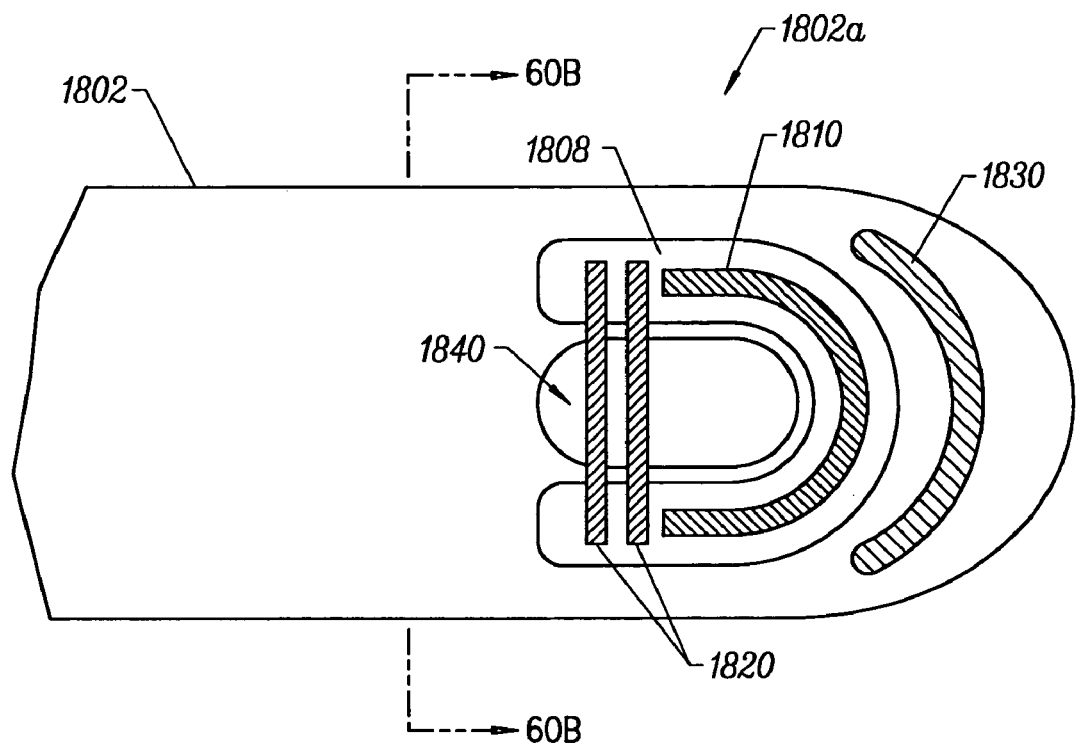
FIG. 60A shows a plan view of the shaft distal end of an electrosurgical probe, having ablation and digestion electrodes mounted laterally on the shaft distal end, according to another embodiment of the invention.
Figure 60B:
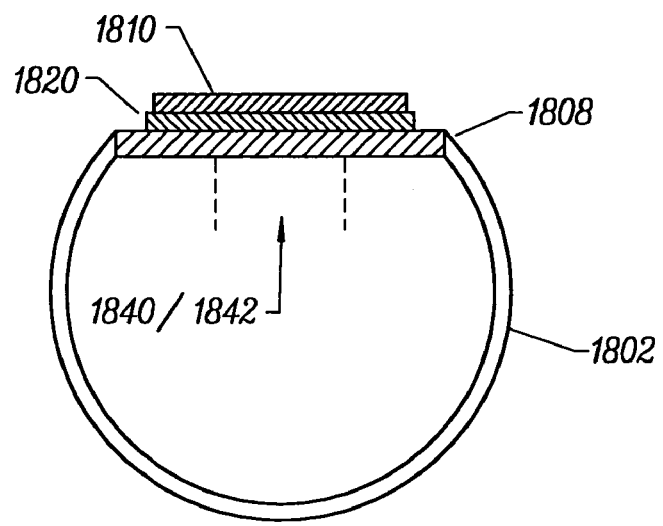
FIG. 60B shows a transverse cross-section of the shaft distal end of FIG. 60A.

FIG. 60A shows a plan view of shaft distal end 1802a of an electrosurgical probe 1800, having ablation and digestion electrodes 1810, 1820 mounted laterally on shaft distal end 1802a, according to another embodiment of the invention. Ablation electrode 1810 partially encircles aspiration port 1840, and is mounted on electrode support 1808. Electrode support 1808 may be a hard or durable electrically insulating material of the type described hereinabove. A pair of digestion electrodes 1820 are disposed proximal to ablation electrode 1810 and extend across port 1840. FIG. 60B shows a transverse cross-section of shaft distal end 1802a taken along the lines 60B—60B of FIG. 60A. Ablation electrode 1810 may be in the form of a metal screen, a metal plate, a wire, or a metal ribbon. In one embodiment, ablation electrode 1810 may comprise a semicircular screen or plate comprising platinum or one of its alloys. Digestion electrode 1820 may be a wire or metal ribbon which may be straight, twisted, looped in various directions, or helical. In one embodiment, digestion electrode 1820 is a ribbon or flattened wire comprising platinum or one of its alloys. Other compositions, numbers, shapes and arrangements of ablation electrode 1810 and digestion electrode 1820 are also within the scope of the invention. A fluid delivery port 1830 is located proximal to ablation electrode 1810. Port 1830 serves to deliver electrically conductive fluid to tissue at a target site or to ablation electrode 1810 before or during a surgical procedure. Although port 1830 is shown in FIG. 60A as being substantially crescent shaped, other shapes, arrangements, and numbers of port 1830 are also within the scope of the invention.

Figure 61:
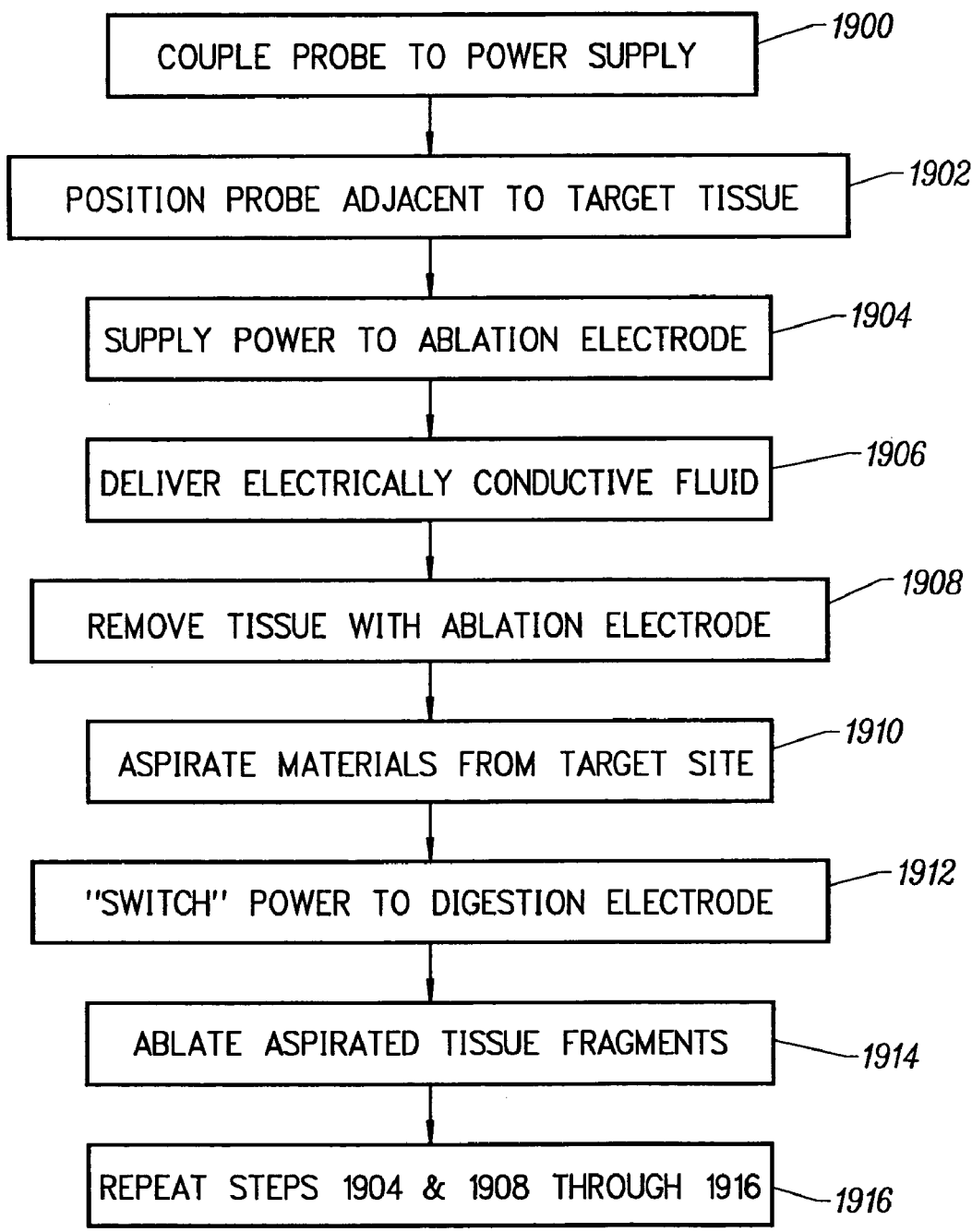
FIG. 61 schematically represents a series of steps involved in a method of aggressively removing tissue during a surgical procedure.

FIG. 61 schematically represents a series of steps involved in a method of removing tissue from a target site to be treated using an electrosurgical system, according to another embodiment of the invention, wherein step 1900 involves coupling an electrosurgical probe to a power supply unit. The probe may be a probe having the elements, structures, features or characteristics described herein, e.g., with reference to FIG. 49 through FIG. 60B. In particular the probe, has two types of electrodes, one or more ablation electrodes and one or more digestion electrodes. The two types of electrodes are independently coupled to opposite poles of the power supply so that current can flow therebetween. In one embodiment, the ablation electrode(s) are adapted for aggressively removing tissue, including cartilage tissue, from a region of tissue to be treated; and the ablation electrode(s) are adapted for breaking down tissue fragments, e.g. resected tissue fragments dislodged by the ablation electrode(s), into smaller fragments or low molecular weight ablation by-products. Both the ablation and digestion electrodes are adapted for performing tissue ablation in a cool ablation process, i.e., a plasma is generated in the presence of an electrically conductive fluid, and the plasma induces molecular dissociation of high molecular weight tissue components into low molecular weight by-products. During such a process, the tissue treated or removed may be exposed to a temperature generally not exceeding 90° C., and typically in the range of from about 45° to 90° C., more typically from about 55° to 75° C.

The power supply may be, for example, power supply 428 (FIG. 7). Preferably, the power supply to which the probe is coupled is capable of providing to the probe a high frequency (e.g., RF) voltage of a selected voltage level and frequency. The selected voltage frequency is typically between about 5 kHz and 20 MHz, essentially as described hereinabove. The RMS voltage will usually be in the range of from about 5 volts to 1000 volts, and the peak-to-peak voltage will be in the range of from about 10 to 2000 volts, again as described hereinabove. Step 1902 involves positioning the probe adjacent to target tissue. For example, the probe distal end may be advanced towards target tissue such that the ablation electrode is in the vicinity of the tissue at the site targeted for treatment. By way of a more specific example, the ablation electrode may be brought adjacent to the meniscus during arthroscopic surgery of the knee. In one aspect, the probe may be positioned with respect to target tissue such that the ablation electrode is in contact with tissue at the target site, while the digestion electrode is not in contact with the tissue at the target site. In one embodiment, the digestion electrode may be located substantially proximal to the ablation electrode, such that when the ablation electrode is in the presence of the tissue at the target site, the digestion electrode is somewhat distant from the tissue at the target site. For example, the ablation electrode may be positioned terminally on the shaft or near the terminus of the shaft, while the digestion electrode may be positioned within the aspiration lumen.

Step 1904 involves supplying power from the power supply to the ablation electrode. Typically, when the ablation electrode is in the presence of tissue, the power supply preferentially supplies power to the ablation electrode, and under these circumstances the ablation electrode generally serves as active electrode. (During a different phase or step of the procedure, the ablation electrode may undergo a reversal of roles to function as a return electrode (step 1912)). Supplying power of a suitable frequency and voltage to the ablation electrode in the presence of an electrically conductive fluid causes a plasma to be generated in the vicinity of the ablation electrode. The plasma generated leads to the localized removal of tissue via a cool ablation mechanism (Coblation®), as described hereinabove. In one embodiment, step 1904 involves preferentially supplying power from the power supply to the ablation electrode, largely to the exclusion of the digestion electrode. That is to say, at any given time point, power from the power supply is supplied preferentially to one or the other of the two types of electrodes, such that the ablation electrode (or the digestion electrode, step 1912) may receive up to about 100% of the power from the power supply. In this way, the power available from the power supply is used efficiently by the electrode which receives the power (i.e., the electrode functioning as the active electrode) for the aggressive generation of a plasma and ablation of tissue.

Optional step 1906 involves delivering an electrically conductive fluid, e.g., isotonic saline, a gel, etc., to the target site or to the ablation electrode. In a wet field procedure, wherein an electrically conductive fluid is already present, step 1906 may be omitted. Step 1906 may be performed before, during, or after the performance of step 1904. Also, step 1906 may be repeated as often as is appropriate during the course of a surgical procedure. Step 1906 may be achieved by delivering an electrically conductive fluid via a fluid delivery device which is integral with the electrosurgical probe, or via an ancillary device. Step 1908 involves removing tissue from the target site with the ablation electrode via a cool ablation mechanism of the invention. Step 1908 leads to molecular dissociation of tissue components and results in the formation of low molecular weight by-products. Depending on the nature of the tissue, the voltage level, and other parameters, step 1908 may also result in the formation of resected tissue fragments. In one embodiment, step 1908 involves aggressively removing tissue from the target site such that tissue fragments may be resected from the target site by the ablation electrode due, at least in part, to the generation of an aggressive plasma in the vicinity of the target site (step 1904).

Step 1910 involves aspirating materials from the target site. Materials thus aspirated may include electrically conductive body fluids (e.g., synovial fluid, blood), extrinsic electrically conductive fluids (e.g., isotonic saline supplied in step 1906), and resected tissue fragments. Such materials may be aspirated from the target site via an aspiration device integral with the electrosurgical probe, as described hereinabove. The aspirated materials which pass from the target site through the aspiration device constitute an aspiration stream.

Step 1912 involves supplying power to the digestion electrode. In one embodiment, step 1912 involves supplying power to the digestion electrode largely to the exclusion of the ablation electrode. That is to say, during step 1912 up to about 100% of the power from the power supply may be supplied to the digestion electrode. Under these circumstances, the digestion electrode serves as an active electrode, and the ablation electrode serves as a return electrode. Typically, the digestion electrode preferentially receives power from the power supply under circumstances where the digestion electrode is in the presence of tissue, for example, one or more resected tissue fragments in the aspiration stream adjacent to the digestion electrode.

Step 1914 involves ablating any resected tissue fragments present in the aspiration stream to form low molecular weight ablation by-products. Typically, the digestion electrode is arranged in relation to the aspiration device such that the aspiration stream contacts the digestion electrode. For example, the digestion electrode may be adjacent to or proximal to an aspiration port, or the digestion electrode may be located within an aspiration lumen. Typically, ablation of resected tissue fragments is accomplished by the digestion electrode in a cool ablation process, as described hereinabove. In one embodiment, the electrosurgical system may be triggered to "switch" power from the ablation electrode to the digestion electrode by changes in electrical impedance in the aspiration stream in the vicinity of the digestion electrode. Such localized changes in impedance may result from the proximity of resected tissue fragments to the digestion electrode. Triggering a switch in the power away from the ablation electrode and to the digestion electrode may be dependent on the surface area ratio of the ablation and digestion electrodes. In one aspect of the invention, steps 1912, 1914 represent a transient, intermittent phase of operation of the electrosurgical system/probe. For example, immediately after the completion of step 1914, the ablation electrode may resume its role as active electrode, and concomitantly therewith the digestion electrode may revert to its role as return electrode. For instance, in the absence of resected tissue fragments in the vicinity of the digestion electrode, the power may be switched away from the digestion electrode and instead the power may be supplied preferentially to the ablation electrode. In this way, once power to the probe has been turned on by the operator (surgeon), steps 1904 and 1908 through 1912 may be repeated numerous times in rapid succession during the course of a surgical procedure, without operator intervention or input. As already noted above, step 1906 may also be repeated as appropriate.

Figure 62A:
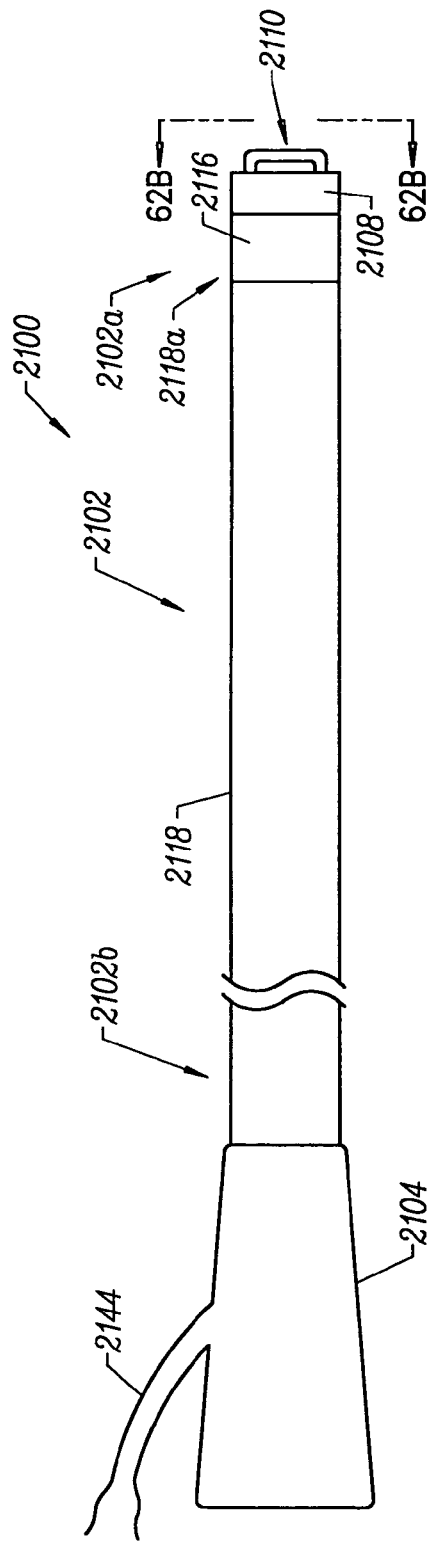
FIGS. 62A and 62B show a side view and an end-view, respectively, of an electrosurgical suction apparatus, according to another embodiment of the invention.
Figure 62B:
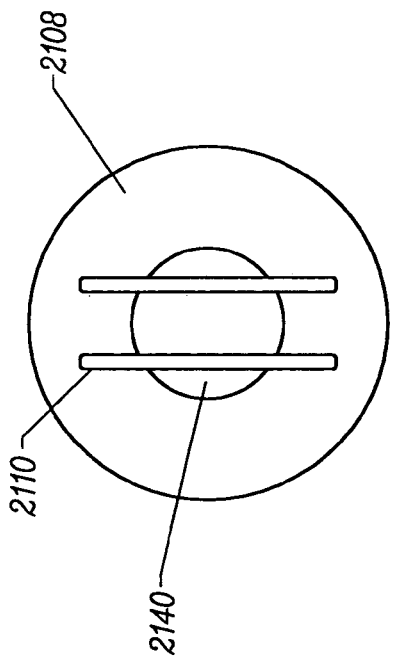

FIGS. 62A and 62B show a side view and an end-view, respectively, of an electrosurgical suction apparatus 2100, according to another embodiment of the invention. Apparatus 2100 generally includes a shaft 2102 having a shaft distal end portion 2102*a* and a shaft proximal end portion 2102*b*, the latter affixed to a handle 2104. An aspiration tube 2144, adapted for coupling apparatus 2100 to a vacuum source, is joined at handle 2104. An electrically insulating electrode support 2108 is disposed on shaft distal end portion 2102*a*. Electrode support 2108 may comprise a durable or refractory material such as a ceramic, a glass, a fluoropolymer, or a silicone rubber. In one embodiment, electrode support 2108 comprises an alumina ceramic. A plurality of active electrodes 2110 are arranged on electrode support 2108.

Shaft 2102 may comprise an electrically conducting material, such as stainless steel alloys, tungsten, platinum or its alloys, titanium or its alloys, molybdenum or its alloys, and nickel or its alloys. An insulating sleeve 2118 covers a portion of shaft 2102. An exposed portion of shaft 2102 located between sleeve distal end 2118*a* and electrode support 2108 defines a return electrode 2116. In an alternative embodiment (not shown), shaft 2102 may comprise an insulating material and a return electrode may be provided on the shaft, for example, in the form of an annulus of an electrically conductive material.

FIG. 62B shows an end-view of apparatus 2100, taken along the lines 62B—62B of FIG. 62A. A plurality of active electrodes 2110 are arranged substantially parallel to each other on electrode support 2108. A void within electrode support 2108 defines an aspiration port 2140. Typically, the plurality of active electrodes 2110 span or traverse aspiration port 2140, wherein the latter is substantially centrally located within electrode support 2108. Aspiration port 2140 is in communication with an aspiration channel 2142 (FIG. 62C) for aspirating unwanted materials from a surgical site.

Figure 62C:
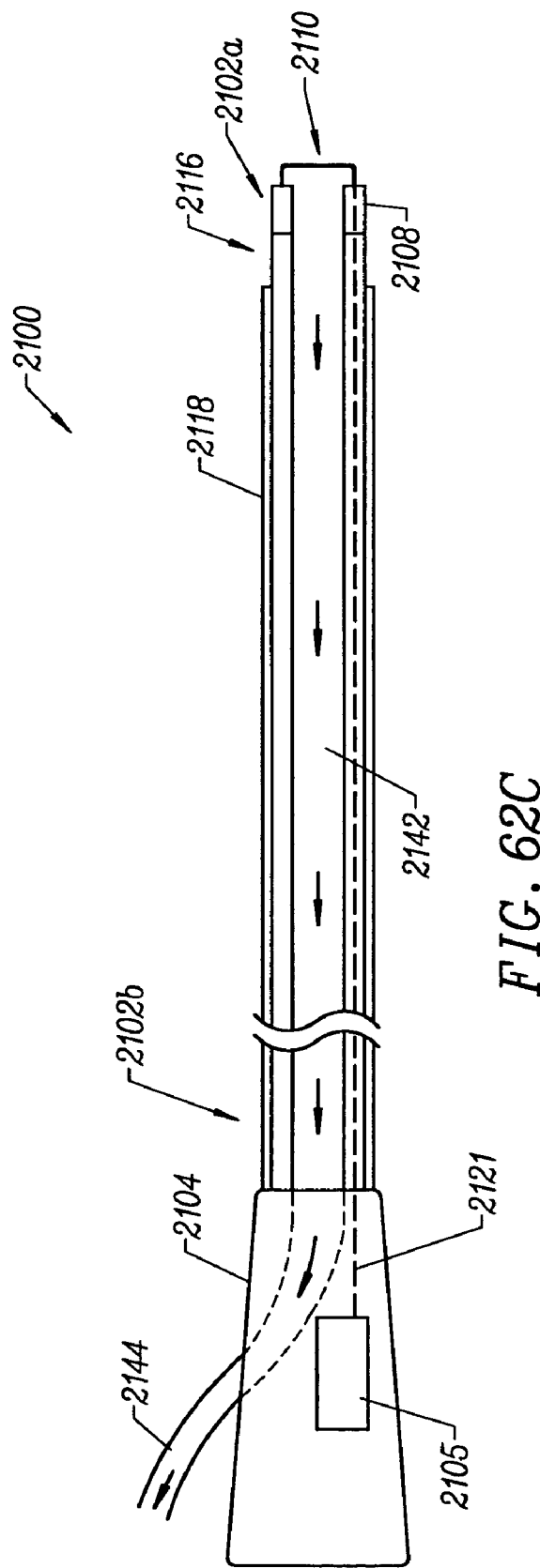
FIG. 62C shows a longitudinal cross-section of the apparatus of FIG. 62A, 62B.

FIG. 62C shows a longitudinal cross-section of the apparatus of FIG. 62A. Aspiration channel 2142 is in communication at its proximal end with aspiration tube 2144. Aspiration port 2140, aspiration channel 2142, and aspiration tube 2144 provide a convenient aspiration unit or element for removing unwanted materials, e.g., ablation by-products, excess saline, from the surgical field during a procedure. The direction of flow of an aspiration stream during use of apparatus 2100 is indicated by the solid arrows. Handle 2104 houses a connection block 2105 adapted for independently coupling active electrodes 2110 and return electrode 2116 to a high frequency power supply (e.g., FIG. 1). An active electrode lead 2121 couples each active electrode 2110 to connection block 2105. Return electrode 2116 is independently coupled to connection block 2105 via a return electrode connector (not shown). Connection block 2105 thus provides a convenient mechanism for independently coupling active electrodes 2110 and return electrode 2116 to a power supply (e.g., power supply 28, FIG. 1).

Figure 63A:
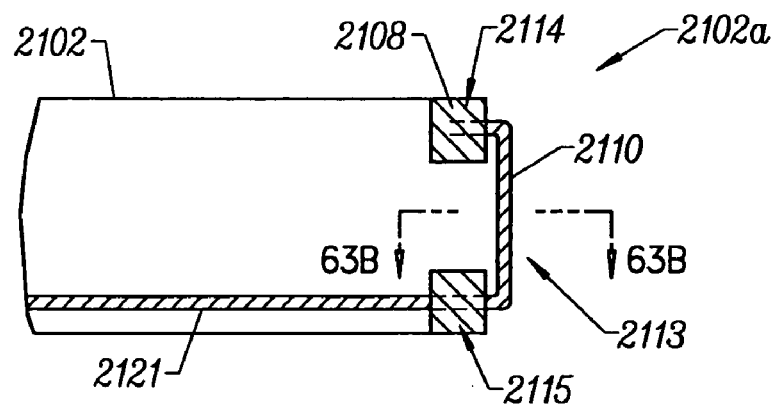
FIG. 63A shows a longitudinal cross-section of the shaft distal end of an electrosurgical suction apparatus, according to the invention.
Figure 63B:
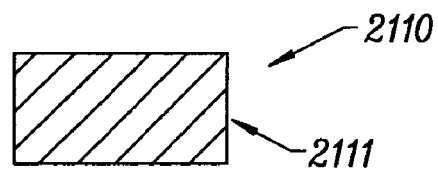
FIG. 63B shows a transverse cross-sectional view of an active electrode of the apparatus of FIG. 63A as taken along the lines 63B—63B.

FIG. 63A is a longitudinal cross-section of the shaft distal end 2102*a* of an electrosurgical suction apparatus 2100, showing the arrangement of active electrode 2110 according to one embodiment. Active electrode 2110 includes a loop portion 2113, a free end 2114, and a connected end 2115. Active electrode 2110 is disposed on electrode support 2108, and is in communication at connected end 2115 with active electrode lead 2121 for coupling active electrode 2110 to connection block 2105. Aspiration channel 2142 is omitted from FIG. 63A for the sake of clarity. FIG. 63B is a cross-section of active electrode 2110 as taken along the lines 63B—63B of FIG. 63A, showing an electrode distal face 2111. Although FIG. 63B shows a substantially rectangular shape for active electrode 2110, other shapes (e.g., those depicted in FIGS. 39A–I) are also possible under the invention.

Figure 63C:
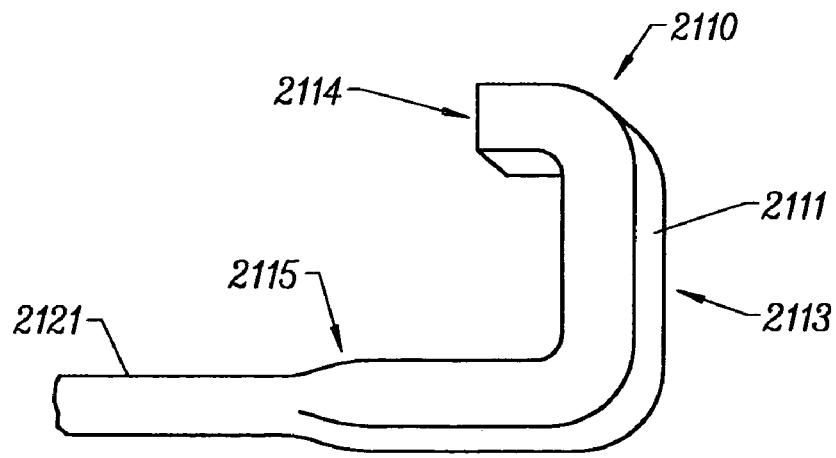
FIG. 63C shows an active electrode in communication with an electrode lead.

FIG. 63C shows in more detail active electrode 2110 in the form of a loop of flattened wire in communication with electrode lead 2121, according to one embodiment of the invention. Typically, free end 2114 terminates within electrode support 2108 or within another electrically insulating material. In this embodiment, electrode lead 2121 is integral with active electrode 2110. Electrode lead 2121 and active electrode 2110 may each comprise a highly conductive, corrosion-resistant metal such as tungsten, stainless steel alloys, platinum or its alloys, titanium or its alloys, molybdenum or its alloys, nickel or its alloys, iridium, aluminum, gold, copper, and the like. In one embodiment, one or both of electrode lead 2121 and active electrode 2110 may each comprise a platinum/iridium alloy, such as an alloy comprising from about 85% to 95% platinum and from about 5% to 15% iridium.

FIG. 64A shows an electrosurgical suction apparatus 2100 having an outer sheath 2152 external to shaft 2102 to provide an annular fluid delivery channel 2150, according to another aspect of the invention. The distal terminus of outer sheath 2152 defines an annular fluid delivery port 2156 at a location proximal to return electrode 2116. Outer sheath 2152 is in communication at its proximal end with a fluid delivery tube 2154 at handle 2104. Fluid delivery port 2156, fluid delivery channel 2150, and tube 2154 provide a convenient fluid delivery unit for providing an electrically conductive fluid (e.g., isotonic saline) to the distal end of the suction apparatus or to a target site undergoing treatment. The direction of flow of an electrically conductive fluid during use of apparatus 2100 is indicated by the solid arrows. An extraneous electrically conductive fluid forms a current flow path between active electrodes 2110 and return electrode 2116, and can facilitate generation of a plasma in the vicinity of active electrodes 2110, as described hereinabove. Provision of an extraneous electrically conductive fluid may be particularly valuable in a dry field situation (e.g., in situations where there is a paucity of native electrically conductive bodily fluids, such as blood, synovial fluid, etc.). In an alternative embodiment, an electrically conductive fluid, such as saline, may be delivered to the distal end of suction apparatus 2100 by a separate device (not shown). FIG. 64B is a transverse cross-section of shaft 2102 of the apparatus of FIG. 64A, and shows the relationship between outer sheath 2152, shaft 2102, and fluid delivery port 2156. Aspiration channel 2142 and electrode lead 2121 are omitted from FIGS. 64A, 64B for the sake of clarity.

Figure 65A:
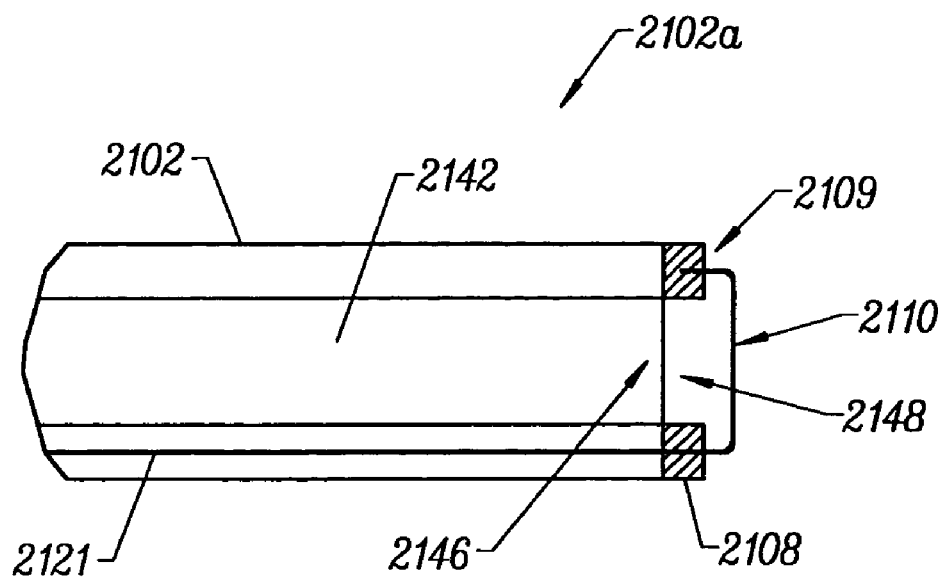
FIG. 65A shows a longitudinal cross-section of the shaft distal end of an electrosurgical suction apparatus having a baffle.
Figure 65B:
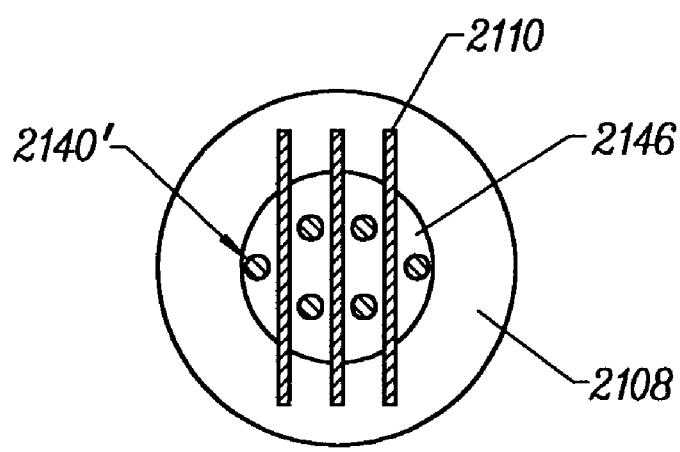
FIG. 65B is an end view of the apparatus of FIG. 65A, according to another embodiment of the invention.

With reference to FIG. 65A there is shown in longitudinal cross-section the shaft distal end 2102a of an electrosurgical suction apparatus 2100 including a baffle or trap 2146, according to another embodiment, wherein baffle 2146 is arranged transversely within shaft 2102 at the distal end of aspiration channel 2142. In the embodiment shown, baffle 2146 is recessed with respect to treatment surface 2109 to define a holding chamber 2148 within the void of electrode support 2108. As seen in the end view of FIG. 65B, baffle 2146 includes a plurality of aspiration ports 2140'. A plurality of active electrodes 2110 are arranged substantially parallel to each other on electrode support 2108. During a procedure involving resection or ablation of tissue, any relatively large resected tissue fragments or other tissue debris drawn by suction to a location proximal to active electrodes 2110 may be retained by baffle 2146 within holding chamber 2148. By relatively large resected tissue fragments is meant those fragments too large to be readily drawn through ports 2140' in an aspiration stream. Such tissue fragments temporarily retained by baffle 2146 are conveniently positioned with respect to active electrodes 2110, and are readily digested by one or more of active electrodes 2110 by a suitable high frequency voltage applied between active electrodes 2110 and return electrode 2116. As an additional advantage, because aspiration channel 2142 is wider than each of aspiration ports 2140', the former is not subject to being clogged by resected tissue fragments or other debris. Using the configuration of FIGS. 65A, 65B only aspirations ports 2140' are subject to (temporary) blockage; as pointed out above, any tissue fragments too large to pass through ports 2140' are rapidly digested by active electrodes 2110. Baffle 2146 may be constructed from an electrically insulating material, such as various plastics. Alternatively, baffle 2146 may comprise an electrically conducting material such as various metals, in which case baffle 2146 is typically electrically isolated.

Figure 66A:
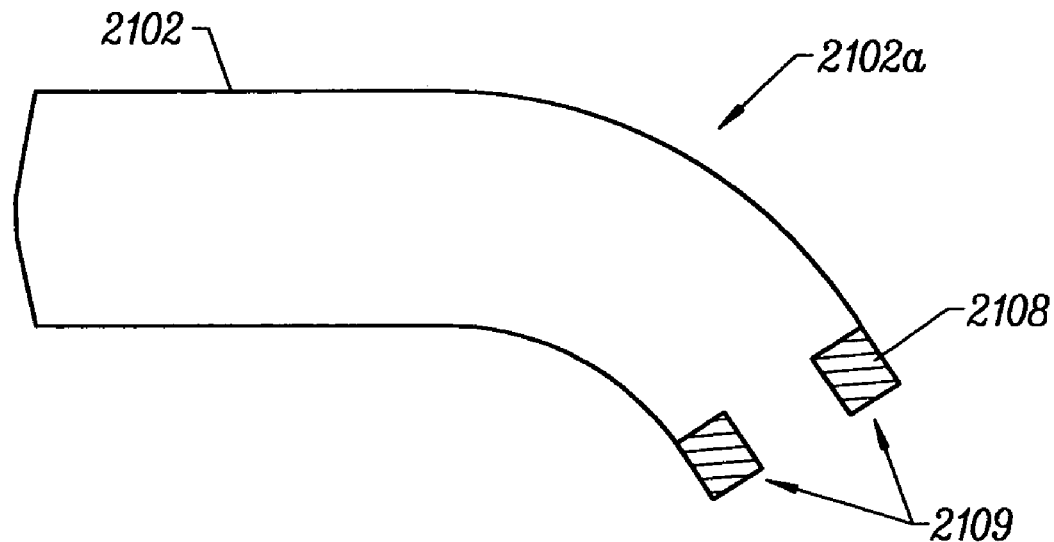
FIGS. 66A and 66B each show a longitudinal cross-section of the shaft distal end of an electrosurgical suction apparatus, according to two different embodiments of the invention.

FIG. 66A is a longitudinal cross-section of a shaft distal end 2102a of a suction apparatus 2100, according to another embodiment, wherein shaft distal end 2102a is curved. The distal end of electrode support 2108 defines a treatment surface 2109 (the latter perhaps best seen in FIG. 67A). A curve in shaft distal end 2102a may facilitate access of treatment surface 2109 to a site targeted for electrosurgical treatment. Active electrodes 2110, which typically protrude from treatment surface 2109 (e.g., FIGS. 67A, 67B), are omitted from FIG. 66A for the sake of clarity.

Figure 66B:
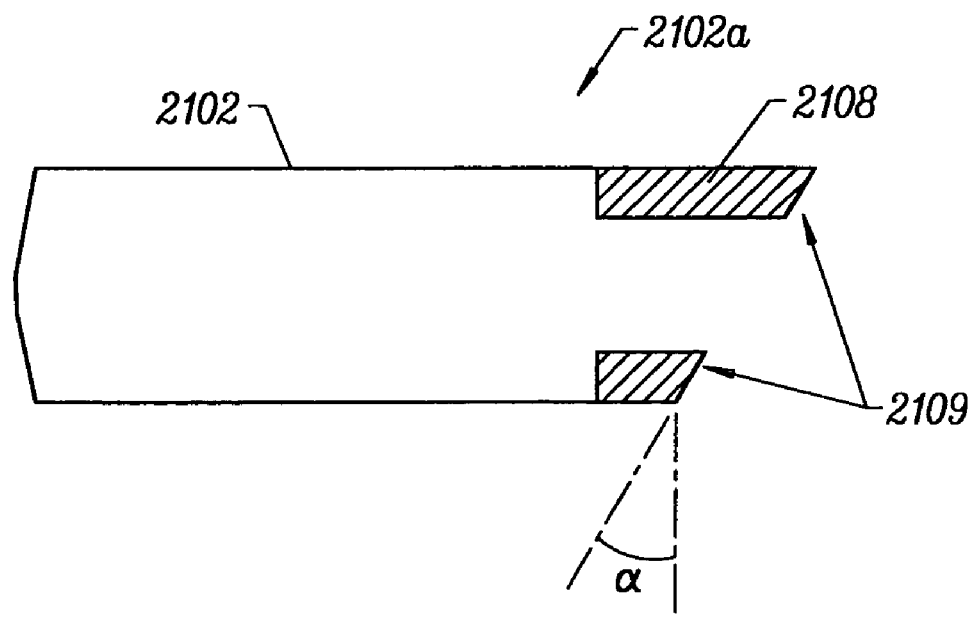

FIG. 66B is a longitudinal cross-section of shaft distal end 2102a of a suction apparatus 2100, according to another embodiment of the invention, wherein the distal end of electrode support 2108 is beveled at an angle, . Typically angle is in the range of from about 15° to 60°, more typically from about 20° to 45°, and usually from about 25° to 35°. Active electrodes 2110 are omitted from FIG. 66B for the sake of clarity. A beveled treatment surface 2109 may facilitate access of shaft distal end portion 2102a to tissue at a target site as well as manipulation of shaft 2102 during treatment.

Figure 67A:
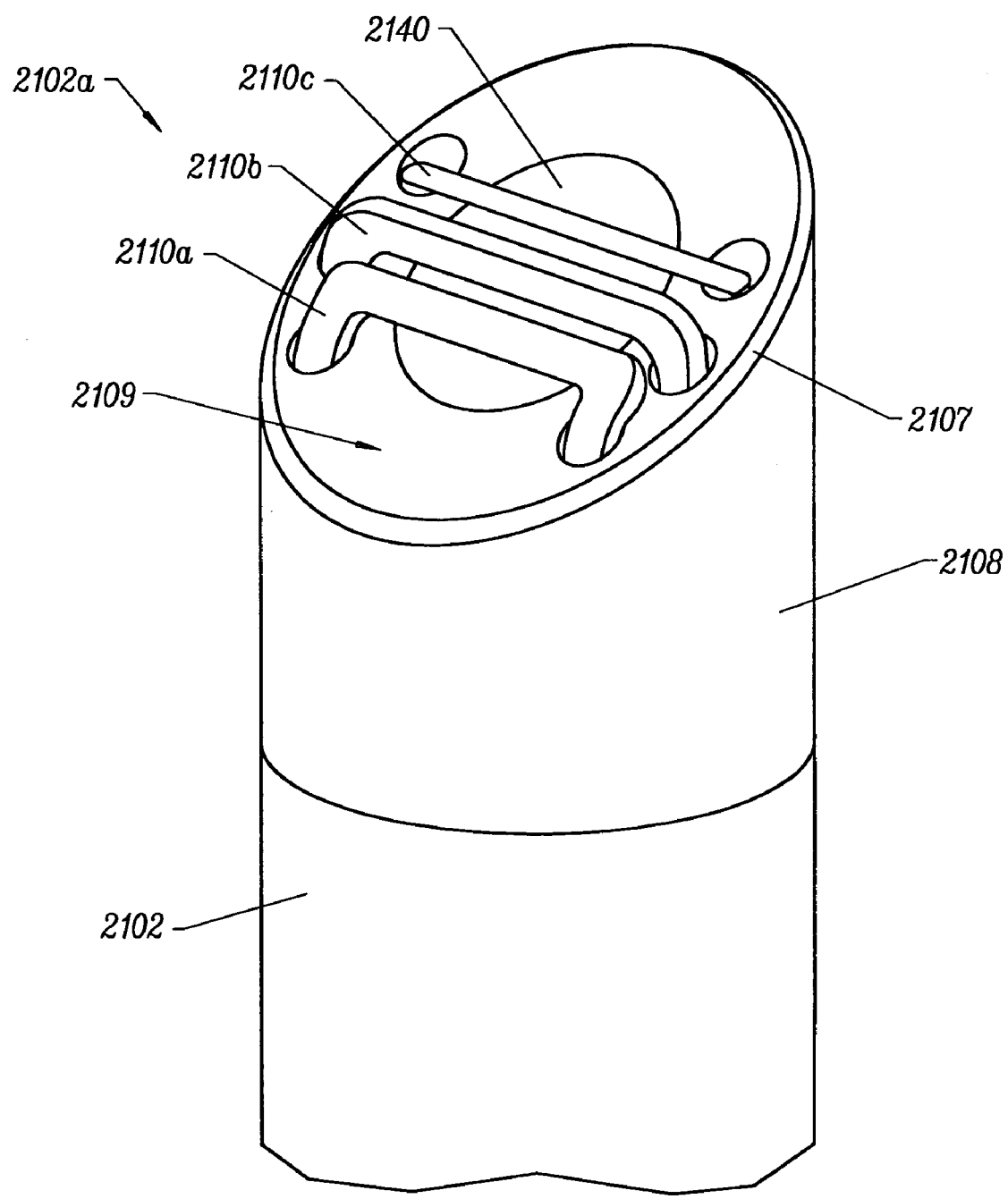
FIGS. 67A and 67B show a perspective view and a side view, respectively, of the shaft distal end of an electrosurgical suction apparatus, according to another embodiment of the invention.

FIG. 67A shows a specific configuration of a shaft distal end 2102a of an electrosurgical suction apparatus 2100, according to one embodiment of the invention. The distal end of electrode support 2108 defines a beveled treatment surface 2109. A first, a second, and a third active electrode 2110a,b,c extend from treatment surface 2109. Treatment surface 2109 includes a rounded perimeter 2107 which serves to eliminate sharp edges from electrode support 2108. The presence of rounded perimeter 2107 prevents mechanical damage to delicate or sensitive tissues during use of apparatus 2100. Electrode support 2108 encircles aspiration port 2140.

Loop portions 2113 (e.g., FIG. 63C) of first, second, and third active electrodes, 2110a, 2110b, 2110c, traverse or bridge aspiration port 2140. First, second, and third active electrodes, 2110a, 2110b, 2110c are arranged substantially parallel to each other, and protrude from treatment surface 2109. In the case of second active electrode 2110b, the orientation with respect to treatment surface 2109 of free end 2114, loop portion 2113, and connected end 2115 is at least substantially the same. In contrast, in the case of first and third active electrodes 2110a, 2110c, the orientation with respect to treatment surface 2109 of loop portion 2113 is different from the orientation of connected end 2115 and free end 2114. That is to say, the orientation of active electrodes 2110a and 2110c with respect to treatment surface 2109 changes from a first direction in the region of connected end 2115 and free end 2114, to a second direction in the region of loop portion 2113.

Furthermore, loop portions 2113 of first, second, and third active electrodes, 2110a, 2110b, 2110c are oriented in different directions. Thus, second electrode 2110b extends substantially in the direction of the longitudinal axis of shaft 2102, and distal face 2111b is also oriented in the direction of the longitudinal axis of shaft 2102. First and third electrodes 2110a, 2110c flank second electrode 2110b, loop portions 2113 of first and second electrodes 2110a, 2110c are oriented towards second electrode 2110b, and distal faces 2111a, 2111c both face towards second electrode 2110b. In other words, first, second, and third electrodes 2110a, 2110b, 2110c all point in different directions.

Figure 67B:
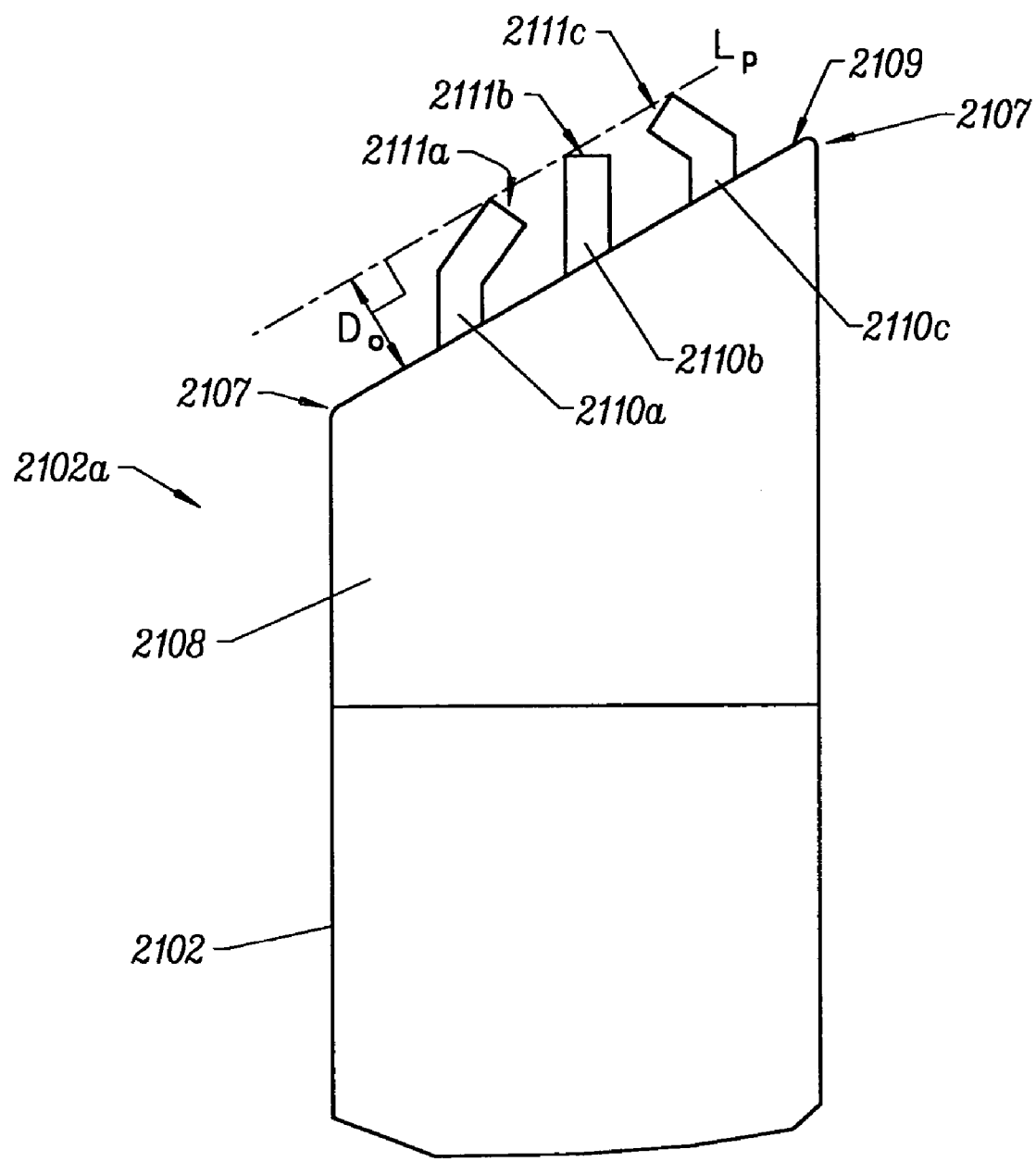

Perhaps as best seen in FIG. 67B, each active electrode 2110a–c includes a distal face 2111a–c. In the embodiment of FIGS. 67A, 67B, each distal face 2111a, 2111b, 2111c faces, or is oriented in, a different direction as described with reference to FIG. 67A. Furthermore, a dashed line $L_p$ drawn parallel to treatment surface 2109 illustrates that the orthogonal distance, $D_o$ from treatment surface 2109 to each distal face 2111a,b,c is substantially the same for each of active electrodes 2110a,b,c.

Electrosurgical suction apparatus 2100 described with reference to FIGS. 62A through 67B can be used for the removal, resection, ablation, and contouring of tissue during a broad range of procedures, including procedures described hereinabove with reference to other apparatus and systems of the invention. Typically during such procedures, the apparatus is advanced towards the target tissue such that treatment surface 2109 and active electrodes 2110 are positioned so as to contact, or be in close proximity to, the target tissue. Each of the plurality of active electrodes includes a loop portion adapted for ablating tissue via molecular dissociation of tissue components upon application of a high frequency voltage to the apparatus. In one embodiment, an electrically conductive fluid may be delivered to the distal end of the apparatus via a fluid delivery channel to provide a convenient current flow path between the active and return electrodes. A high frequency voltage is applied to the apparatus from a high frequency power supply to ablate the tissue at the target site. Suitable values for various voltage parameters are presented hereinabove.

Unwanted materials, such as low molecular weight ablation by-products, excess extraneously supplied fluid, resected tissue fragments, blood, etc., are conveniently removed from the target site via the integral aspiration unit of the invention. Typically, such an aspiration unit comprises an aspiration channel in communication with a distal aspiration port and a proximal aspiration tube, the latter coupled to a suitable vacuum source (not shown). Vacuum sources suitable for use in conjunction with apparatus and systems of the invention are well known in the art.

In one embodiment, the apparatus may be reciprocated or otherwise manipulated during application of the high frequency voltage, such that loop portion 2113 including distal face 2111 of each active electrode moves with respect to the target tissue, and the tissue in the region of each distal face 2111 is ablated via molecular dissociation of tissue components. The apparatus is capable of effectively removing tissue in a highly controlled manner, and is particularly useful in procedures requiring a smooth and/or contoured tissue surface.

Figure 68A:
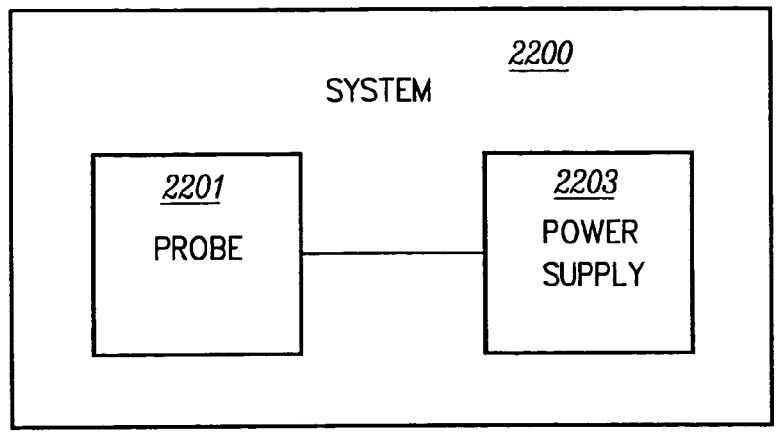
FIG. 68A is a block diagram representing an electrosurgical system, according to another embodiment of the invention.
Figure 68B:
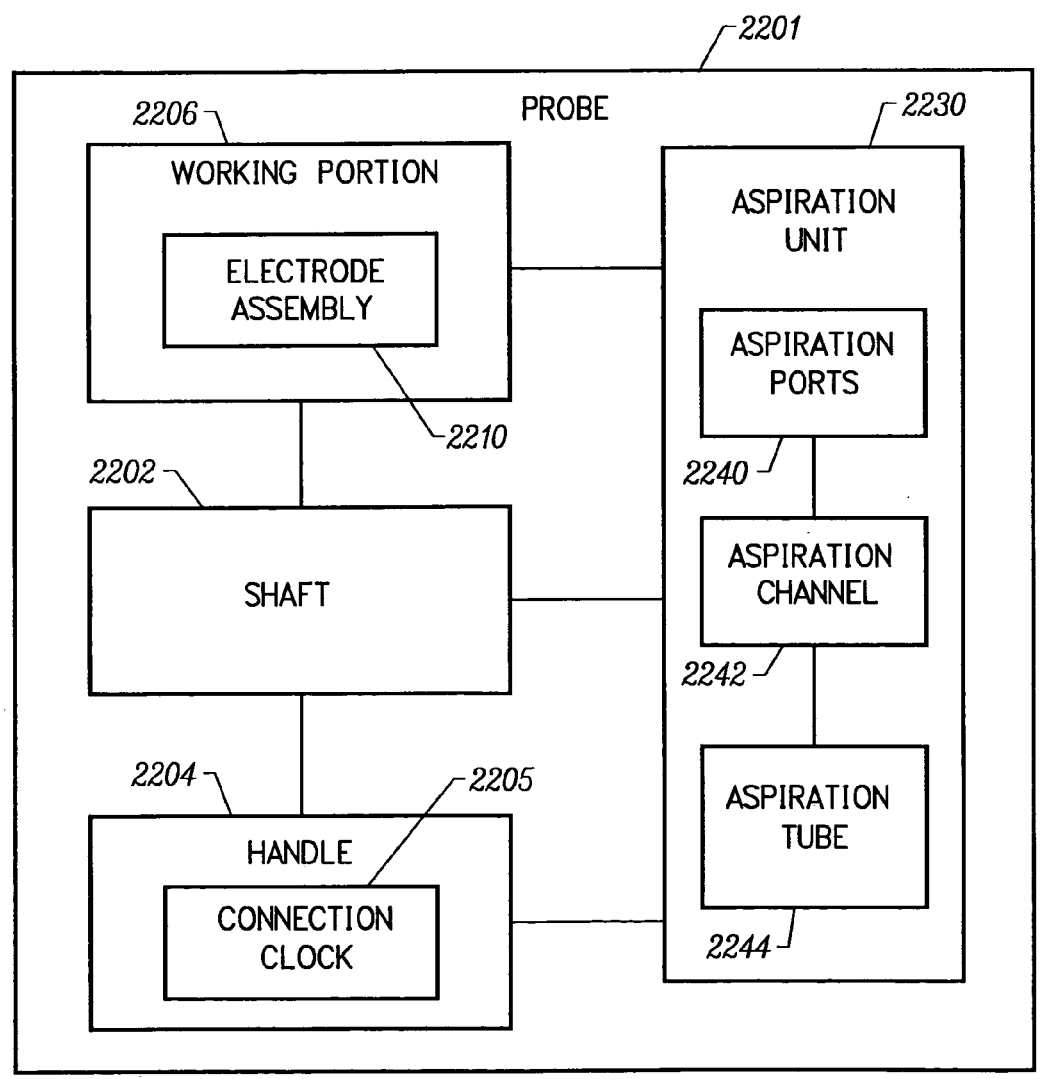
FIG. 68B is a block diagram representing an electrosurgical probe of the system of FIG. 68A, FIGS. 69A–69C each schematically represent a working portion of an electrosurgical probe, according to various embodiments of the invention.

FIG. 68A is a block diagram representing an electrosurgical system 2200, according to another embodiment of the invention. System 2200 generally includes an electrosurgical probe 2201 coupled to a high frequency power supply 2203. FIG. 68B is a block diagram representing electrosurgical probe 2201, including a working portion 2206, a shaft 2202, and a handle 2204. Working portion 2206 includes an electrode assembly 2210 having a plurality of active electrodes (e.g., FIG. 71A). Typically, handle 2204 houses a connection block 2205 by which each of the plurality of active electrodes of electrode assembly 2210 may be conveniently coupled to high frequency power supply 2203. Probe 2201 further includes an aspiration unit 2230, having a plurality of aspiration ports 2240 in communication with an aspiration channel 2242. Typically, channel 2242 is coupled to a suitable vacuum source (not shown) via an aspiration tube 2244. Each of the plurality of aspiration ports 2240 is adapted for aspirating materials, e.g., fluids, from the vicinity of working portion 2206 during a surgical procedure.

Figure 69A:
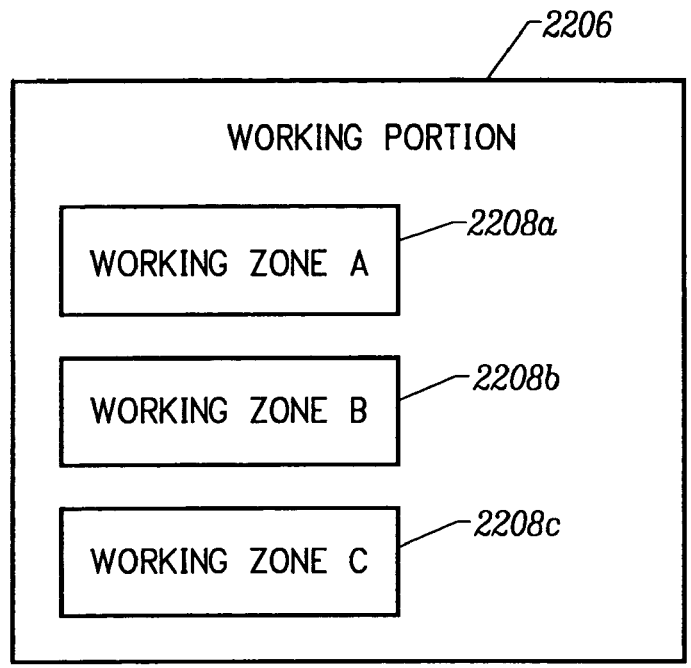
Figure 69B:
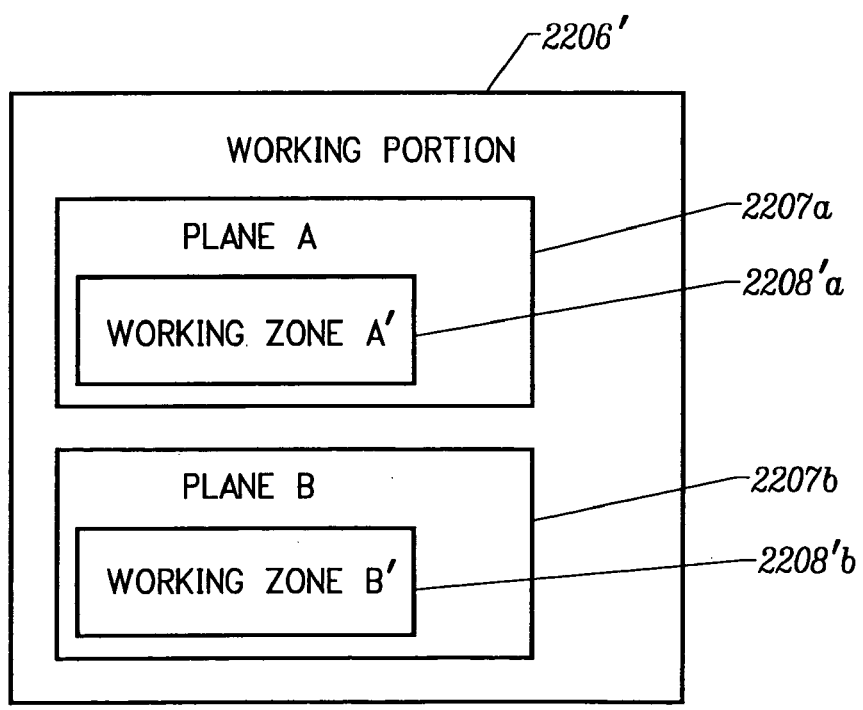
Figure 69C:
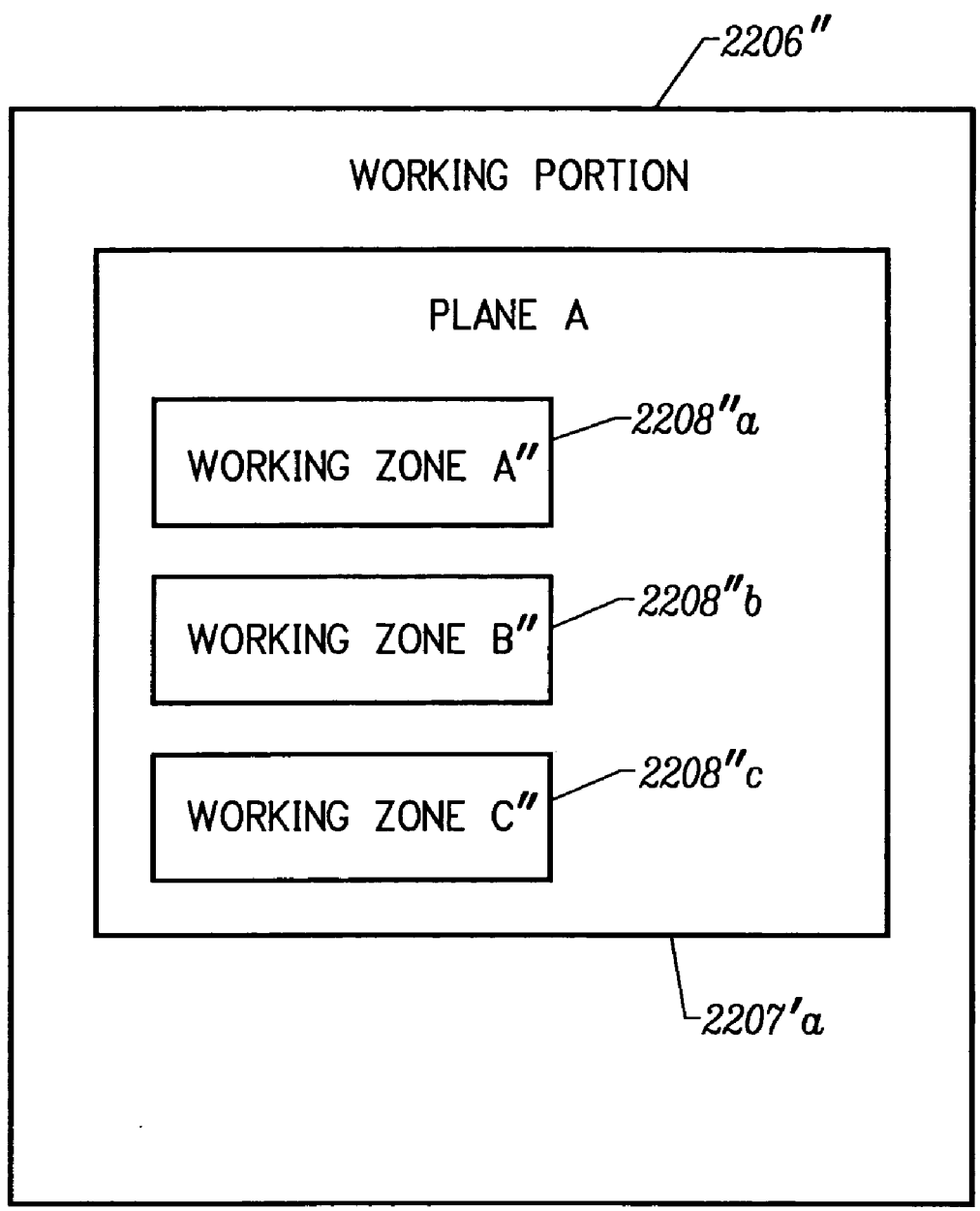

FIGS. 69A–69C each schematically represent a working portion of an electrosurgical probe 2201, according to the instant invention. Each working portion (2206, 2206', 2206") includes a plurality of working zones (e.g., 2208a–n, FIG. 69A). Each working zone typically includes at least one active electrode and at least one aspiration port. In general, the suction pressure in a given working zone is proportional to the aspiration rate via the aspiration ports of that zone. For a situation in which each of the plurality of aspiration ports is coupled to a common aspiration channel 2242, the suction pressure of each working zone is a function of the number and size of the least one aspiration port in that zone. Each active electrode is adapted for generating a plasma, when in the presence of an electrically conductive fluid and upon application of a high frequency voltage between the active electrode and a return electrode. However, the extent to which the active electrode(s) in each zone form a plasma is dependent, in part, on the local environment of that zone, wherein the local environment is determined by the aspiration rate. Thus, according to one aspect of the invention, the propensity for each working zone to initiate and maintain a plasma is a function of the suction pressure in that zone.

While not being bound by theory, applicant has determined that a relatively low suction pressure (low aspiration rate) in a given zone is conducive to the facile initiation and maintenance of a plasma thereat, upon application of the high frequency voltage to the active electrode(s) disposed on that working zone. Thus, a relatively low aspiration rate in a given working zone strongly promotes generation of a plasma at that zone. Conversely, a relatively high suction pressure (high aspiration rate) in a particular zone generally results in relatively weak generation of a plasma thereat. For electrosurgical ablation according to the invention, facile generation of a plasma at a working zone generally results in rapid ablation of tissue; whereas weak generation of a plasma generally results in a relatively slow ablation rate. That is to say, the ablation rate of a working zone is determined, inter alia, by the aspiration rate of that zone. Therefore, by the appropriate selection of the number and/or size of aspiration port(s) of the various working zones of probe 2201, the relative rate of ablation of each working zone of probe 2201 can be controlled. According to one aspect of the invention, during operation of probe 2201, a suction pressure gradient may exist between each working zone of working portion 2206.

FIG. 69A schematically represents a working portion 2206 of an electrosurgical probe, according to one embodiment of the invention. As shown, working portion 2206 includes a plurality of working zones represented as zones 2208a–n. Typically, each working zone, e.g., zone 2208a, of working portion 2206 may be differentiated from other working zones, e.g., zone 2208b and zone 2208n, on the basis of its suction pressure. That is to say, during operation of probe 2201, each working zone 2208a–n typically has a different suction pressure associated therewith. Consequently, each working zone 2208a–n differs in its propensity to form a plasma thereat, and is characterized by a different ablation rate. The plurality of working zones 2208a–n may be located on the same plane, or on different planes of working portion 2206 (e.g., FIGS. 69B, 69C).

FIG. 69B schematically represents a working portion 2206' of an electrosurgical probe, according to another embodiment of the invention. As shown, working portion 2206' includes a plurality of planes, viz. plane A 2207a and plane B 2207b, and a plurality of working zones 2208'a and 2208'b, wherein each working zone 2208'a, 2208'b is located on a different plane of working portion 2206'. Each of working zones 2208'a and 2208'b typically includes at least one aspiration port and at least one active electrode. Typically, working zone 2208'a is distinguishable from working zone 2208'b on the basis of its suction pressure. That is to say, during operation of a probe 2201, working zones 2208'a, 2208'b show different propensities to initiate and maintain a plasma thereat. Accordingly, during operation of probe 2201, working zones 2208'a, 2208'b typically have dissimilar rates of ablation and dissimilar aspiration rates. By careful selection of the number and/or size of aspiration ports of each of working zone 2208'a, 2208'b, the relative rate of ablation of working zones 2208'a and 2208'b can be controlled.

FIG. 69C schematically represents working portion 2206" of an electrosurgical probe, according to another embodiment of the invention. As shown, a single plane, plane A' 2207'a, includes a plurality of working zones 2208"a, 2208"b, and 2208"c. As described hereinabove, each working zone 2208"a, 2208"b, and 2208"c typically includes at least one aspiration port and at least one active electrode. Typically, each working zone, e.g., zone 2208"a, is distinguishable from other working zones, e.g., zones 2208"b, 2208"c, on the basis of its suction pressure. Because of the relationship between suction pressure of a given working zone and its ablation rate, as described hereinabove, working zones 2208"a, 2208"b, and 2208"c may each have a markedly different rate of ablation.

Figure 70A:
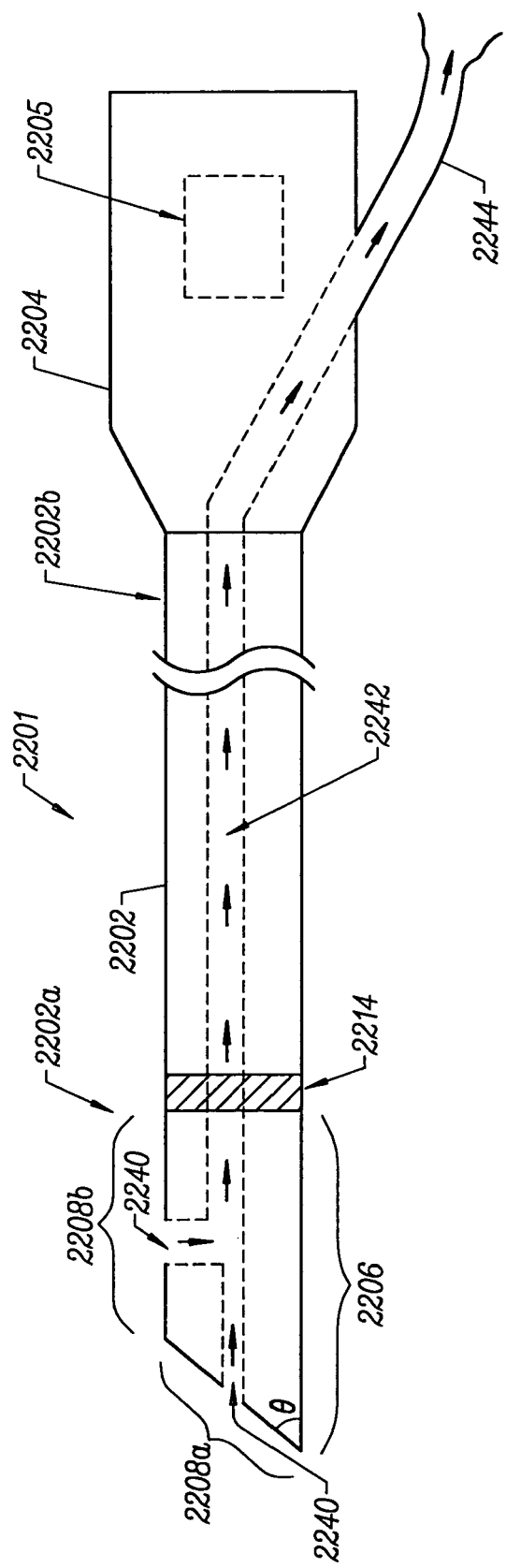
FIG. 70A is a longitudinal sectional view of an electrosurgical probe, according to one embodiment of the invention.
Figure 70B:
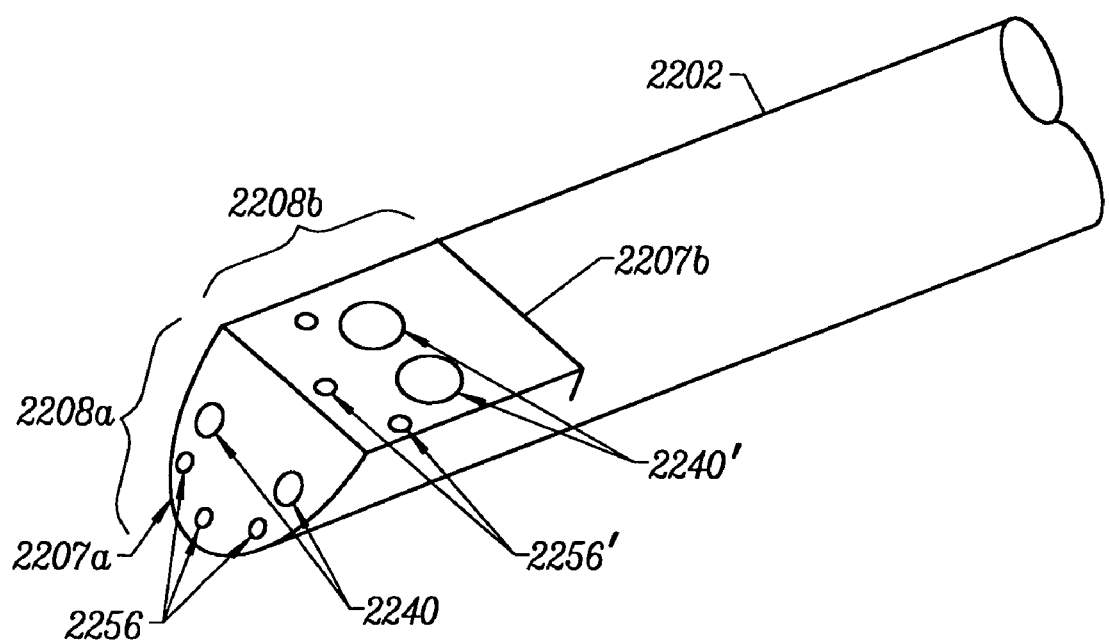
FIG. 70B is a perspective view of the distal portion of the electrosurgical probe of FIG. 70A.

FIG. 70A is a longitudinal sectional view of an electrosurgical probe 2201, according to one embodiment of the invention. Probe 2201 generally includes a shaft 2202 having a shaft distal end 2202a and a shaft proximal end 2202b, a working portion 2206 disposed on shaft distal end 2202a, and a handle 2204 affixed to shaft proximal end 2202b. Working portion 2206 comprises a first working zone 2208a, and a second working zone 2208b. First working zone 2208a lies on a first plane 2207a (FIG. 70B), which is beveled at an acute angle □ with respect to the longitudinal axis of probe 2201. Angle □ is typically in the range of from about 15° to 75°. Typically, each of first working zone 2208a and second working zone 2208b includes at least one active electrode. (Active electrodes are omitted from FIG. 70A for the sake of clarity.) Probe 2201 may further include a return electrode 2214. Handle 2204 may include a connection block 2205 for conveniently coupling probe 2201 to high frequency power supply 2203 (FIG. 68A). Typically, working portion 2206 comprises an electrically insulating support 2220 (e.g., FIG. 71A). Probe 2201 further includes an aspiration unit, which comprises an aspiration channel 2242 in communication at its distal end with a plurality of aspiration ports 2240, 2240' (FIG. 70B). Aspiration channel 2242 is coupled at its proximal end to an aspiration tube 2244. Aspiration tube 2244 may be coupled to a suitable vacuum source (not shown) for aspirating fluids from first and second working zones 2208a, 2208b via aspiration ports 2240, 2240'.

With reference to FIGS. 70A and 70B, the embodiment shown includes a first set of aspiration ports 2240 arranged on first working zone 2208a, and a second set of aspiration ports 2240' arranged on second working zone 2208b. It can be seen, from an examination of FIGS. 70A, 70B, that the combined area of aspiration ports 2240' is greater than the combined area of aspiration ports 2240. Furthermore, aspiration ports 2240' on second working zone 2208b are located proximal to aspiration ports 2240 on first working zone 2208a. Because aspiration ports 2240, 2240' are in communication with a common aspiration channel 2242, the aspiration rate from first working zone 2208a is less than the aspiration rate from second working zone 2208b. As a result, upon application of a high frequency voltage to active electrodes on working portion 2206, first working zone 2208a has a greater ability to initiate and maintain an aggressive plasma as compared with second working zone 2208b. By "aggressive plasma" is meant a plasma which is capable of aggressively ablating target tissue. Consequently, first working zone 2208a typically has a higher ablation rate as compared with second working zone 2208b. Typically, ablation by each working zone 2208a, 2208b is via plasma-induced molecular. dissociation of target tissue components, as described hereinabove.

In one embodiment, the ablation rate of first working zone 2208a is such that ablation of tissue results in production of resected fragments of target tissue, as well as low molecular weight (or gaseous) ablation by-products. The low molecular weight ablation by-products may be removed from the surgical site by aspiration via aspiration ports 2240 and/or 2240', while the resected tissue fragments may be ablated or vaporized by second working zone 2208b. Low molecular weight ablation by-products resulting from the ablation of the resected tissue fragments may be aspirated via aspiration ports 2240' of second working zone 2208b.

Probe 2201 may further include a fluid delivery unit (e.g., FIG. 64A) for delivering an electrically conductive fluid to working portion 2206, wherein the electrically conductive fluid provides a current flow path between at least one active electrode and return electrode 2214. With reference to FIG. 70B, working zone 2208a on first plane 2207a includes a plurality of fluid delivery ports 2256. Similarly, working zone 2208b on second plane 2207b includes a plurality of fluid delivery ports 2256'. Return electrode 2214, as well as a fluid delivery channel (e.g., FIG. 64A), are omitted from FIG. 70B for the sake of clarity.

Figure 71A:
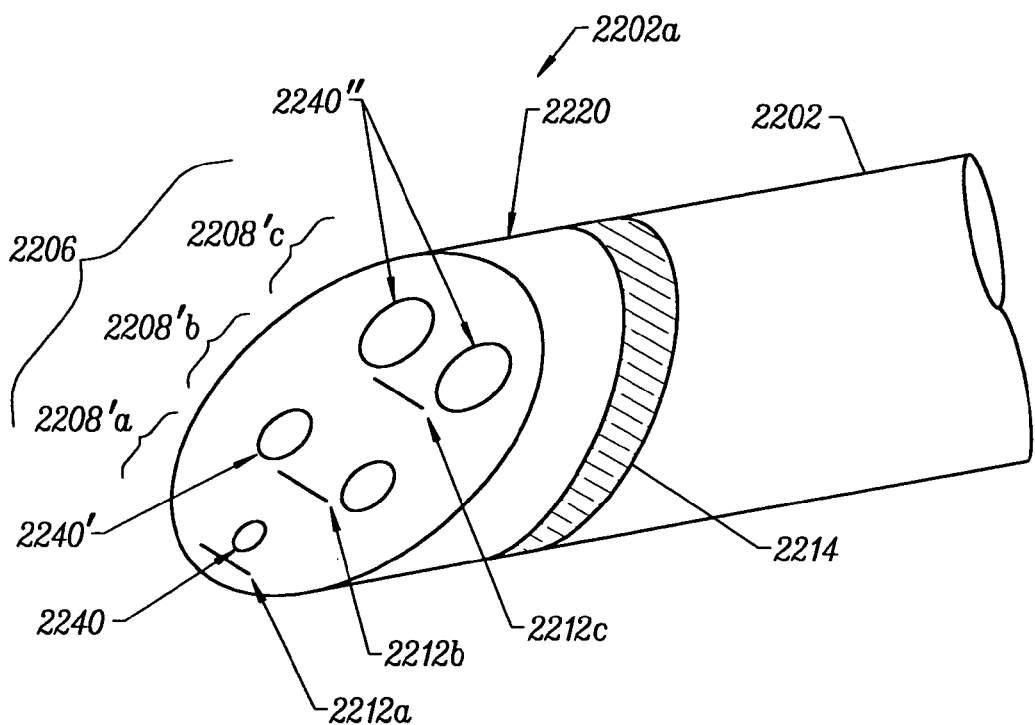
FIG. 71A is a perspective view of the distal portion of an electrosurgical probe, according to another embodiment of the invention.

FIG. 71A shows a perspective view of the distal portion of an electrosurgical probe, according to another embodiment of the invention. An electrically insulating support 2220 is disposed on shaft distal end 2202a. Return electrode 2214 is located proximal to support 2220. Shaft 2202 may comprise an electrically conducting material (e.g., stainless steel or other metal) or an electrically insulating material (e.g., a polyimide or other plastic). In the former situation, return electrode 2214 may comprise an exposed (i.e., non-insulated) portion of shaft 2202, while support 2220 may comprise a material such as a silicone rubber, a ceramic, or a glass.

Figure 71B:
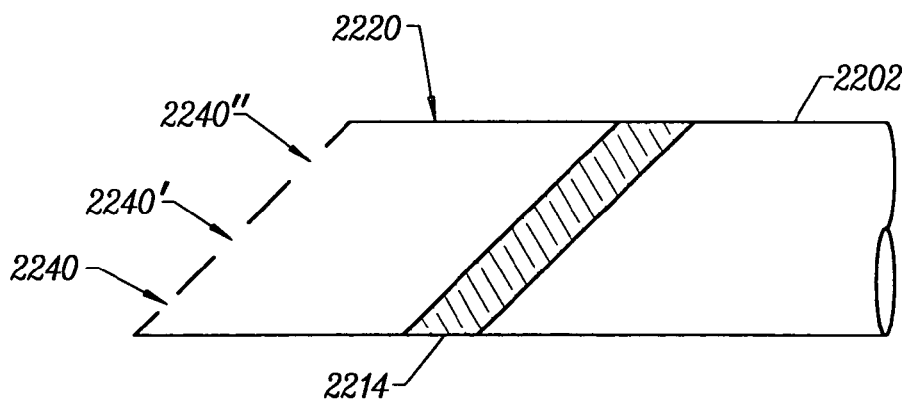
FIG. 71B is a side view of the distal portion of the probe of FIG. 71A.

With reference to FIGS. 71A and 71B, the distal end of support 2220 is beveled to provide a single plane 2207. In the embodiment of FIGS. 71A and 71B, working portion 2206 essentially occupies single plane 2207. As shown, plane 2207 includes first, second, and third working zones 2208'a, 2208'b, and 2208'c, respectively. Plane 2207 has a plurality of active electrodes 2212a–c, and a plurality of aspiration ports 2240, 2240', 2240". First working zone 2208'a includes a distal active electrode 2212a and has a single aspiration port 2240. Second working zone 2208'b is located proximal to first working zone 2208'a, and includes an active electrode 2212b. Second working zone 2208'b has two aspiration ports 2240', wherein aspiration ports 2240' are somewhat larger than aspiration port 2240. Similarly, third working zone 2208'c, which is located proximal to second working zone 2208'b, includes an active electrode 2212c and has two aspiration ports 2240".

Aspiration ports 2240" are significantly larger than aspiration ports 2240', and substantially larger than aspiration port 2240. As a result, the total aspiration port area, and the aspiration rate, progressively increase for working zones 2208'a, 2208'b, 2208'c. Thus, an aspiration gradient (or suction pressure gradient) exists on plane 2207, in which the suction pressure diminishes in a distal direction. Because of the relationship between suction pressure of a given working zone and its ablation rate, as described hereinabove, a gradient of ablation rate exists on plane 2207, in which the rate of ablation diminishes in a proximal direction.

From an examination of FIGS. 71A and 71B, it is apparent that aspiration ports 2240 and 2240" are arranged near the periphery of working portion 2206. Applicant has found that arrangement of aspiration ports around the periphery of the working portion of a probe facilitates removal of ablation by-products, and in particular the removal of gaseous by-products entrapped within a liquid, during a procedure. Of course, other peripheral arrangements for aspiration ports, other than that depicted in FIGS. 71A, 71B, are also within the scope of the invention.

Active electrodes 2112a–c are represented in FIG. 71A as being linear and arranged substantially orthogonal to the longitudinal axis of the probe. However, numerous other configurations and orientations of active electrodes are possible under the invention. For example, the active electrodes may have any of the configurations described hereinabove, e.g., with reference to FIGS. 62A through 67B.

Figure 72:
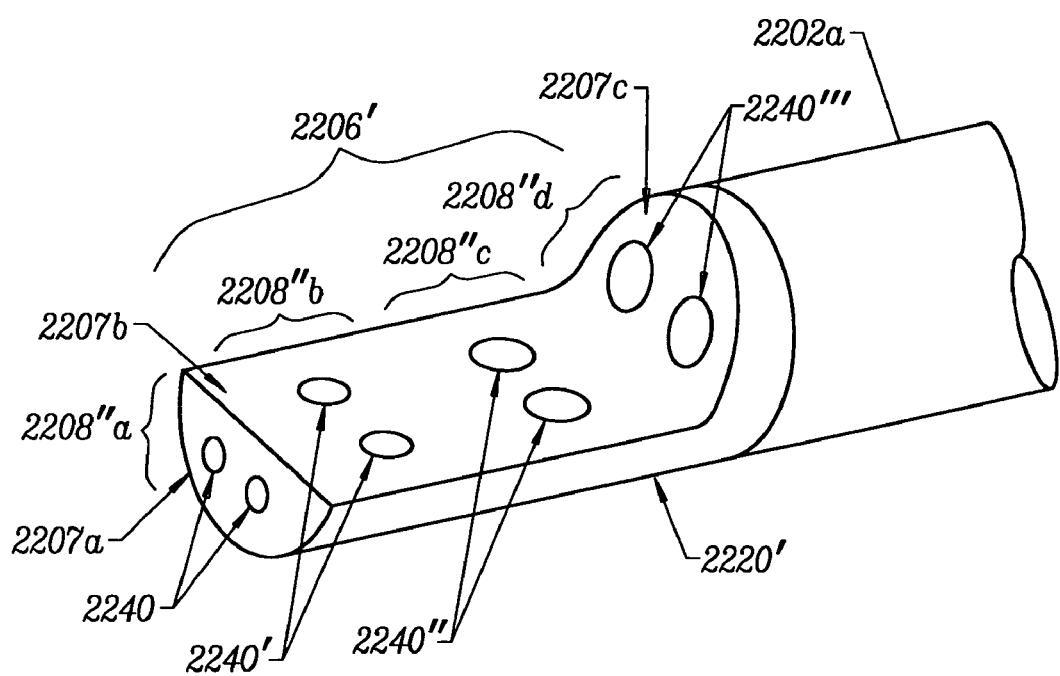
FIG. 72 is a perspective view of the distal portion of an electrosurgical probe, according to another embodiment of the invention.

FIG. 72 is a perspective view of the distal portion of an electrosurgical probe, according to another embodiment of the invention, including electrode support 2220' disposed on shaft distal end 2202a. Electrode support 2220' accommodates a working portion 2206'. Working portion 2206' includes a first, a second, and a third plane 2207a, 2207b, 2207c, respectively. A first working zone 2208"a on first plane 2207a has first aspiration ports 2240. A second working zone 2208"b and a third working zone 2208"c jointly occupy second plane 2207b. Second working zone 2208"b and third working zone 2208"c have second aspiration ports 2240' and third aspiration ports 2240", respectively. A fourth working zone 2208"d lies on third plane 2207c, and has fourth aspiration ports 2240'''.

As shown, first, second, third, and fourth aspiration ports 2240, 2240', 2240", and 2240''', respectively, progressively increase in size. As a result, a suction pressure gradient exists axially within working portion 2206', from the lowest suction pressure of first working zone 2208"a to the highest suction pressure at fourth working zone 2208"d. Because of the relationship between suction pressure of a given working zone and its ablation rate, as described hereinabove, the suction pressure gradient of working portion 2206' translates to a gradient of ablation rate within working portion 2206'. Although the gradient of suction pressure and ablation rate in the embodiment of FIG. 72 is axial, a gradient of both suction pressure and ablation rate in other orientations or directions is also contemplated and is within the scope of the invention. Active electrodes are omitted from FIG. 72 for the sake of clarity.

It should be understood that mechanisms for controlling the relative suction pressure of two or more working zones, other than the size, number, and arrangement of the aspiration port(s), are also possible under the invention. For example, the aspiration port(s) of each working zone may be coupled to a separate aspiration channel, and the flow rate within each aspiration channel may be independently controlled via valves.

Figure 73A:
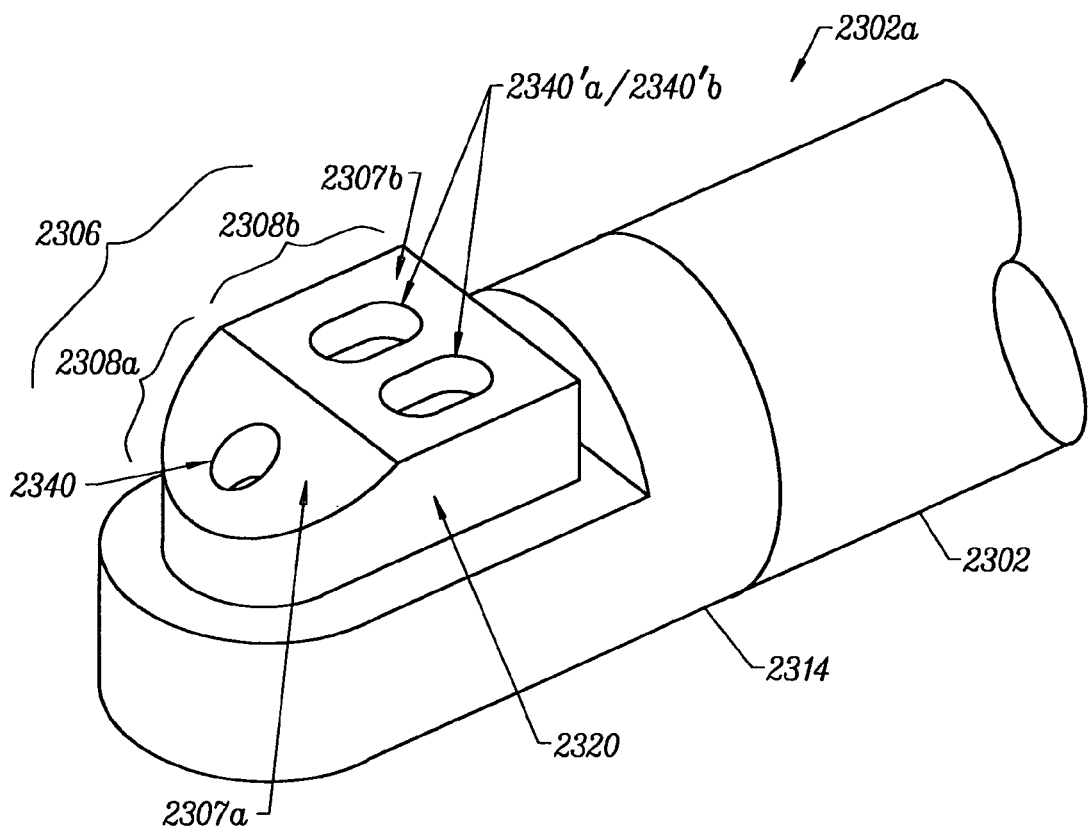
FIG. 73A is a perspective view of the distal portion of an electrosurgical probe, according to another embodiment of the invention.
Figure 73B:
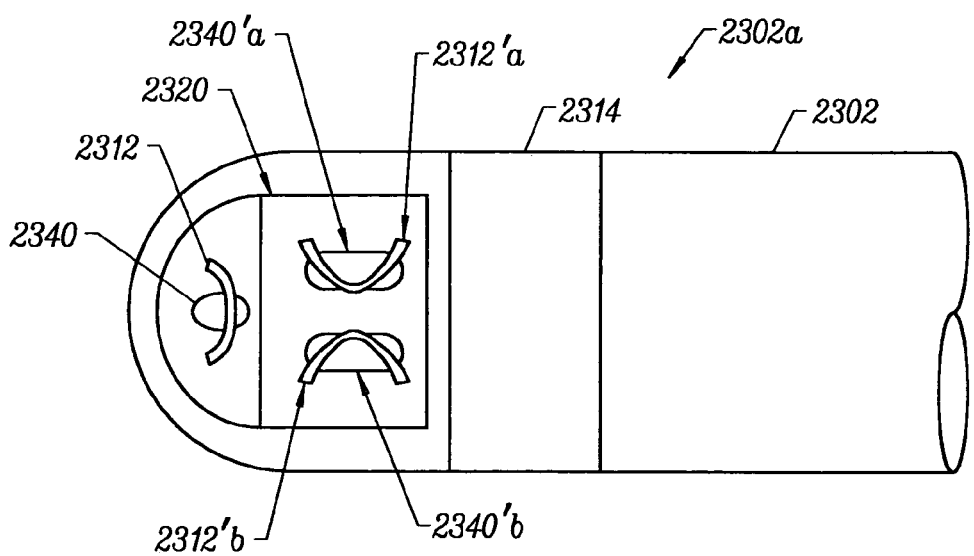
FIG. 73B is a plan view of the distal portion of the probe of FIG. 73A.

FIG. 73A shows a perspective view of the distal end of an electrosurgical probe, according to another embodiment of the invention. An electrode support 2320 is disposed on shaft distal end 2302a, and includes a first distal plane 2307a and a second proximal plane 2307b. First plane 2307a is beveled at an angle, typically in the range of from about 15° to 75°, with respect to the longitudinal axis of shaft 2302. A first working zone 2308a lies on first plane 2307a, while a second working zone 2308b lies on second plane 2307b. First working zone 2308a and second working zone 2308b comprise a working portion 2306. First working zone 2308a includes a single aspiration port 2340, while second working zone 2308b includes two aspiration ports 2340'a, 2340'b. As shown, return electrode 2314 is located proximal and inferior to electrode support 2320. However, other configurations for a return electrode are also within the scope of the invention. Each working zone 2308a, 2308b has one or more active electrodes arranged thereon (FIG. 73B). Active electrodes are omitted from FIG. 73A for the sake of clarity.

FIG. 73B shows the distal portion of the probe of FIG. 73A in plan view. First working zone 2308a includes an active electrode 2312 in the form of a loop. As shown, active electrode 2312 extends across aspiration port 2340. Second working zone 2308b includes two active electrodes 2312'a and 2312'b, each in the form of a loop, which extend across aspiration ports 2340'a and 2340'b, respectively. In this configuration, active electrodes 2312'a, 2312'b are strategically located with respect to aspiration ports 2340'a, 2340'b so as to prevent blockage of ports 2340'a and 2340'b by resected tissue fragments.

Each of active electrodes 2312, 2312'a, 2312'b may comprise a metal, such as tungsten, stainless steel, platinum, titanium, molybdenum, palladium, iridium, nickel, aluminum, gold, or copper, and the like, or their alloys. In one embodiment, one or more of active electrodes 2312, 2312'a, 2312'b may comprise a platinum/iridium alloy, for example, an alloy having from about 80% to 95% platinum and from about 5% to 20% iridium, by weight. Other numbers, arrangements, configurations, and compositions for the active electrodes are also within the scope of the invention.

Figure 74:
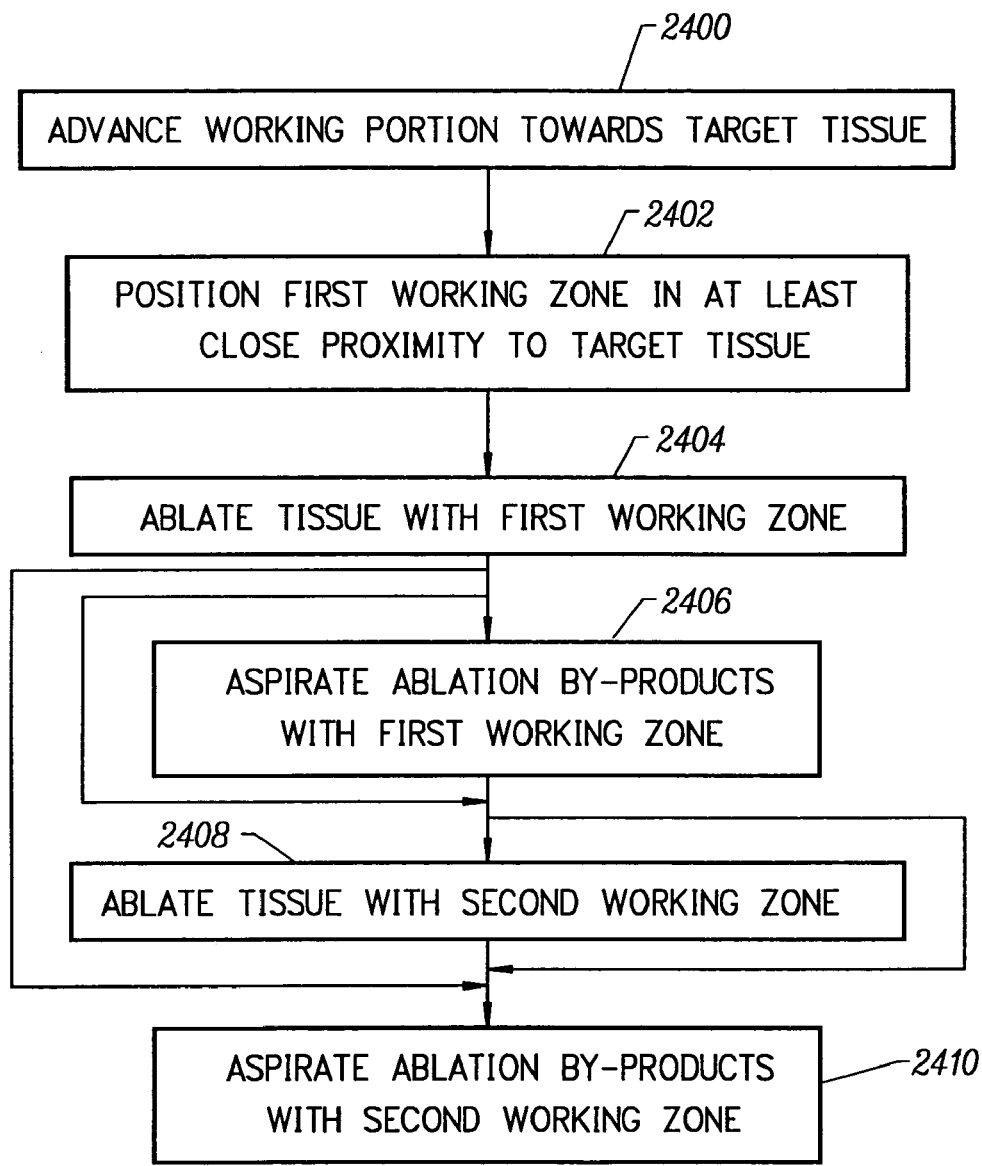
FIG. 74 schematically represents a series of steps involved in a method of ablating tissue, according to another embodiment of the invention.

FIG. 74 schematically represents a series of steps involved in a method of ablating tissue, according to another embodiment of the invention. It should be understood that systems, apparatus, and methods of the invention are not limited to a particular target tissue or surgical procedure, but instead are generally applicable to ablation of a wide variety of different tissues during a broad range of procedures. Regardless, of the particular procedure and target tissue, methods of the instant invention are generally concerned with plasma-induced ablation of tissue via the molecular dissociation of tissue components to form low molecular weight (e.g., gaseous) by-products.

Again with reference to FIG. 74, step 2400 involves advancing the working portion of an electrosurgical probe of the invention towards a target tissue. As was noted hereinabove, the working portion of the probe typically includes a plurality of working zones, each of which may be characterized by a particular ablation rate and aspiration rate. The term "ablation rate" generally refers to an amount of tissue removed or vaporized per unit time; while the term "aspiration rate" usually refers to the rate at which one or more fluids may be aspirated from a given region. Such fluids may include body fluids, such as blood; extraneously supplied electrically conductive fluid, such as saline; a plasma, such as a plasma derived from extraneously supplied saline; gaseous ablation by-products, or mixtures thereof. Typically, the working portion of the probe comprises an electrically insulating electrode support, wherein the electrode support is disposed on the distal end of a shaft, and a plurality of active electrodes are arranged on the electrode support. Each working zone typically has at least one aspiration port and at least one of the plurality of active electrodes. The at least one active electrode of each working zone may be strategically located with respect to the at least one aspiration port.

Step 2402 involves positioning a first working zone of the probe in at least close proximity to the target tissue. Usually, the first working zone is characterized as having a relatively high ablation rate, as compared with other working zones of the probe. As noted hereinabove, according to one aspect of the invention, ablation rate and aspiration rate are generally inversely related. That is to say, in general, a working zone having a relatively low aspiration rate has a relatively high ablation rate, and vice versa. This relationship is due, at least in part, to the fact that a high aspiration rate in a working zone provides a localized (e.g., working zone-specific) environment which is somewhat inimical to the initiation and maintenance of a plasma thereat.

Step 2404 involves ablating at least a portion of the target tissue using the first working zone. The ablation performed in step 2404 may be sufficiently rapid and aggressive that tissue fragments are resected from the target tissue via the molecular dissociation of tissue components, in addition to the formation of low-molecular weight ablation by-products. A portion of the low-molecular weight ablation by-products, together with some smaller resected tissue fragments, may be aspirated directly from the surgical site via one or more aspiration ports of the first working zone, step 2406. Other resected tissue fragments may be vaporized by the at least one active electrode of the first working zone, and the low-molecular weight ablation by-products again removed via one or more aspiration ports of the first working zone.

Alternatively, or additionally, resected tissue fragments may be vaporized by at least one active electrode of the second working zone, step 2408. Thereafter, the low-molecular weight ablation by-products resulting from step 2408 may be removed via one or more aspiration ports of the second working zone, step 2410. The second working zone typically has a relatively high aspiration rate. Typically, the second working zone has an ablation rate which is lower than that of the first working zone, but which is nevertheless sufficient to vaporize resected tissue fragments. In this manner, blockage of the aspiration ports of the second working zone by tissue fragments is prevented.

Other modifications and variations can be made to the disclosed embodiments without departing from the subject invention. For example, other numbers and arrangements of the aspiration channel(s), aspiration ports, and active electrodes on the working portion of the probe are possible. Similarly, numerous other methods of ablating or otherwise treating tissue using electrosurgical probes of the invention will be apparent to the skilled artisan. Thus, while the exemplary embodiments of the present invention have been described in detail, by way of example and for clarity of understanding, a variety of changes, adaptations, and modifications will be obvious to those of skill in the art. Therefore, the scope of the present invention is limited solely by the appended claims.

What is claimed is:

1. An electrosurgical instrument for removing tissue from a target site within or on a patient's body comprising:

(a) a shaft having a proximal end portion and a distal end portion, and an active electrode comprising a substantially flat active screen electrode disposed on the distal end portion of the shaft;

(b) a return electrode arranged on the shaft, and spaced from the active screen electrode;

(c) at least one electrical connector extending through the shaft and having an end that is proximal to the flat screen;

(d) at least one electrical coupling member adapted to secure the active screen electrode to the shaft and to electrically couple the active screen electrode to said at least one electrical connector; and (e) an aspiration lumen disposed within the shaft and having a distal opening coupled to the active screen electrode wherein the active screen electrode inhibits clogging of the aspiration lumen.

2. The instrument of claim 1 wherein the active screen electrode comprises at least one aperture for passage of tissue fragments and fluid therethrough.

3. The instrument of claim 2 wherein said at least one aperture comprises a plurality of apertures.

4. The instrument of claim 3 wherein said apertures are circular.

5. The instrument of claim 3 wherein said apertures comprise corners.

6. The instrument of claim 5 wherein said apertures are rectangular.

7. The instrument of claim 1 wherein the active screen electrode is disposed on a lateral side of the shaft.

8. The instrument of claim 1 further comprising an electrically insulating support member upon which the active screen electrode is mounted.

9. The instrument of claim 8 wherein the support member defines an axial opening in communication with the aspiration lumen, and a lateral opening in contact with the active screen electrode.

10. The instrument of claim 8 further comprising a cap arranged on the distal end portion of the shaft wherein said cap comprises an opening that receives said insulating support member.

11. The instrument of claim 10 wherein said cap is adhered to the return electrode.

12. The instrument of claim 1 wherein the return electrode is comprised of an annular member.

13. The instrument of claim 1 wherein the return electrode is spaced from the active screen electrode such that, when the active screen electrode is brought adjacent to a tissue structure immersed in an electrically conductive fluid, the active screen electrode is positioned between the return electrode and the tissue structure, and the electrically conductive fluid completes a conduction path between the active screen electrode and the return electrode.

14. The instrument of claim 13 wherein the active and return electrodes are configured, upon the application of a sufficiently high frequency voltage therebetween, to vaporize the conductive fluid in a thin layer over at least a portion of the active electrode, and to induce the discharge of energy from the vapor layer.

15. The instrument of claim 1 wherein said at least one electrical coupling member comprises a ballwire.

16. The instrument of claim 1 wherein said at least one electrical coupling member comprises a plurality of electrical coupling members.

17. The instrument of claim 1 wherein the return electrode is arranged on said distal end portion and is ring shaped.

18. The instrument of claim 1 further comprising a liquid supply lumen adapted to supply liquid to the distal end portion of the shaft.

19. A method for treating target tissue whereby a portion of the target tissue is removed, comprising the steps of:

advancing a probe comprising a proximal end, a shaft, a distal end portion, and a substantially flat active screen electrode secured on the distal end portion of the probe such that the active electrode is positioned in close proximity to the target tissue, said probe further comprising at least one electrical connector extending through said shaft and terminating proximal to said screen electrode, and wherein said screen electrode is electrically coupled and mechanically affixed to said probe by a coupling agent;

delivering to the target tissue an electrically conductive fluid;

applying suction to an aspiration lumen disposed within the probe to remove ablated material from the target site, the aspiration lumen being in fluid communication with openings in the screen of the active electrode; and applying a high frequency voltage between the active electrode and a return electrode to ablate tissue at the target site, whereby the screen electrode inhibits clogging of the aspiration lumen.

20. The method of claim 19 wherein said target tissue is within a joint.

21. The method of claim 20 wherein said tissue is selected from the group consisting of meniscus, synovial tissue, and articular cartilage.

22. The method of claim 19 wherein said aspiration lumen is connected with a vacuum source to aspirate material through said aspiration lumen.

23. The method of claim 19 wherein said tissue is a tissue selected from the group consisting of the tonsils and adenoids.

24. The method of claim 19 wherein said screen is attached to said distal end without a press-fit.

25. A method for treating target tissue whereby a portion of the target tissue is removed, comprising the steps of:

advancing a probe comprising a proximal end, a shaft, a distal end portion, and a substantially flat active screen electrode secured on the distal end portion of the probe such that the active electrode is positioned in close proximity to the target tissue, said probe further comprising at least one electrical connector extending through said shaft and coupled to said screen electrode, and wherein said screen electrode is electrically coupled and mechanically affixed to said probe without a press-fit;

delivering to the target tissue an electrically conductive fluid;

applying suction to an aspiration lumen disposed within the probe to remove ablated material from the target site, the aspiration lumen being in fluid communication with openings in the screen of the active electrode; and applying a high frequency voltage between the active electrode and a return electrode to ablate tissue at the target site, whereby the screen electrode inhibits clogging of the aspiration lumen.

* * * * *